United States Patent
Danz et al.

(10) Patent No.: US 12,312,338 B2
(45) Date of Patent: May 27, 2025

(54) ORGANIC MOLECULES FOR USE IN OPTOELECTRONIC DEVICES

(71) Applicant: SAMSUNG DISPLAY CO., LTD., Yongin-si (KR)

(72) Inventors: Michael Danz, Eggenstein-Leopoldshafen (DE); Alhama Arjona Esteban, Stuttgart (DE)

(73) Assignee: Samsung Display Co., Ltd., Yongin-si (KR)

( * ) Notice: Subject to any disclaimer, the term of this patent is extended or adjusted under 35 U.S.C. 154(b) by 761 days.

(21) Appl. No.: 16/181,106

(22) Filed: Nov. 5, 2018

(65) Prior Publication Data

US 2019/0177303 A1    Jun. 13, 2019

(30) Foreign Application Priority Data

Nov. 8, 2017  (DE) ..................... 10 2017 126 064.1
Jun. 6, 2018  (DE) ..................... 10 2018 113 459.2

(51) Int. Cl.
  *C07D 403/14*   (2006.01)
  *C07D 471/04*   (2006.01)
  (Continued)

(52) U.S. Cl.
  CPC ......... *C07D 403/14* (2013.01); *C07D 471/04* (2013.01); *C07D 491/048* (2013.01); *C07D 495/04* (2013.01); *C07D 519/00* (2013.01); *C09K 11/06* (2013.01); *H10K 30/80* (2023.02); *H10K 50/18* (2023.02); *H10K 50/30* (2023.02);
  (Continued)

(58) Field of Classification Search
  CPC .. H10K 85/654; H10K 85/6572; H10K 50/11; H10K 50/15; H10K 50/16; H10K 50/18; H10K 50/30; H10K 30/80; H01L 51/0067; H01L 51/0072; H01L 51/5012; H01L 51/5056; H01L 51/5072; H01L 51/5096; H01L 51/5296; C07D 403/14; C07D 471/04; C07D 491/048; C07D 495/04; C07D 519/00; C09K 11/06; C09K 2211/1007; C09K 2211/1029; C09K 2211/1033; C09K 2211/1037; C09K 2211/1044; C09K 2211/1059
  See application file for complete search history.

(56) References Cited

U.S. PATENT DOCUMENTS 8,609,257 B2   12/2013   Ise et al.
9,972,795 B2   5/2018    Aspuru-Guzik et al.
(Continued)

FOREIGN PATENT DOCUMENTS

CN   105051014 A   11/2015
CN   107074765 A   8/2017
(Continued)

OTHER PUBLICATIONS

Hiroki Uoyama et al. "Highly efficient organic light-emitting diodes from delayed fluorescence", Nature, 2012, vol. 492, p. 234-240 (Year: 2012).*

(Continued)

*Primary Examiner* — Seokmin Jeon
(74) *Attorney, Agent, or Firm* — Womble Bond Dickinson (US) LLP

(57) ABSTRACT

The invention relates to an organic molecule for the use in optoelectronic devices. According to the invention, the organic molecule has
  a first chemical moiety with a structure of formula I,

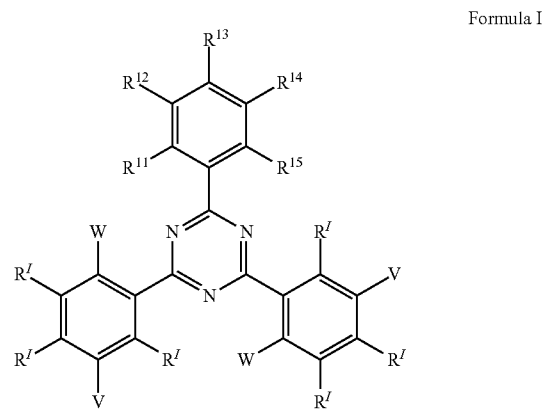

Formula I and
  two second chemical moieties with a structure of formula II,

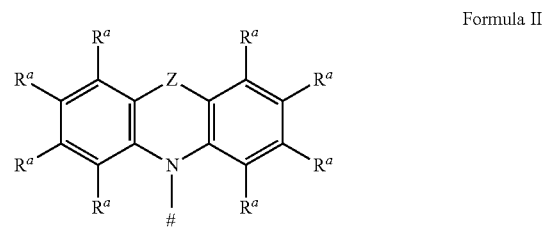

Formula II wherein
  # represents the binding site of a single bond linking the first chemical moiety to the second chemical moiety;
  V is selected from the group consisting of CN and $CF_3$; and (Continued)

W is the bond linking the first chemical moiety to one of the two second chemical moieties.

15 Claims, 2 Drawing Sheets

(51) Int. Cl.
| | |
|---|---|
| *C07D 491/048* | (2006.01) |
| *C07D 495/04* | (2006.01) |
| *C07D 519/00* | (2006.01) |
| *C09K 11/06* | (2006.01) |
| *H10K 30/80* | (2023.01) |
| *H10K 50/11* | (2023.01) |
| *H10K 50/15* | (2023.01) |
| *H10K 50/16* | (2023.01) |
| *H10K 50/18* | (2023.01) |
| *H10K 50/30* | (2023.01) |
| *H10K 85/60* | (2023.01) |

(52) U.S. Cl.
CPC ....... *H10K 85/654* (2023.02); *H10K 85/6572* (2023.02); *C09K 2211/1007* (2013.01); *C09K 2211/1029* (2013.01); *C09K 2211/1033* (2013.01); *C09K 2211/1037* (2013.01); *C09K 2211/1044* (2013.01); *C09K 2211/1059* (2013.01); *H10K 50/11* (2023.02); *H10K 50/15* (2023.02); *H10K 50/16* (2023.02)

(56) References Cited

U.S. PATENT DOCUMENTS

| | | |
|---|---|---|
| 10,193,079 B2 | 1/2019 | Stoessel et al. |
| 10,263,196 B2 | 4/2019 | Danz et al. |
| 2006/0103298 A1* | 5/2006 | Lee ............................. 313/504 |
| 2012/0126221 A1 | 5/2012 | Kitamura et al. |
| 2016/0285007 A1* | 9/2016 | Swager ............... H01L 51/0071 |
| 2017/0352816 A1* | 12/2017 | Jeon ................... H01L 51/0072 |
| 2018/0123049 A1 | 5/2018 | Lee et al. |
| 2018/0198075 A1 | 7/2018 | Danz et al. |

FOREIGN PATENT DOCUMENTS

| | | |
|---|---|---|
| JP | 2011-49511 A | 3/2011 |
| JP | 2016-516085 A | 6/2016 |
| JP | 2017-518281 A | 7/2017 |
| KR | 10-2016-0116297 A | 10/2016 |
| KR | 10 2017 0 113 808 A | 10/2017 |
| WO | 2011/013681 A1 | 2/2011 |
| WO | 2016/159479 A1 | 10/2016 |
| WO | 2017/005699 A1 | 1/2017 |

OTHER PUBLICATIONS

John C. de Mello et al. "An improved experimental determination of external photoluminescence quantum efficiency" Adv. Mater. 1997, vol. 9, p. 230-232 (Year: 1997).*

Pamela Schrogel et al. "A series of CBP-derivatives as host materials for blue phosphorescent organic light-emitting diodes", J. Mater. Chem. 2011, vol. 21, p. 2266 (Year: 2011).*

Dongdong Zhang et al. "Sterically shielded blue thermally activated delayed fluorescence emitters with improved efficiency and stability" Mater. Horiz. 2016, vol. 3, p. 145-151 (Year: 2016).*

Mallesham Godumala et al. "Thermally activated delayed fluorescence blue dopants and hosts: from the design strategy to organic light-emitting diode applications" J. Mater. Chem. 2016, vol. 4, p. 11355-11381 (Year: 2016).*

* cited by examiner

ORGANIC MOLECULES FOR USE IN OPTOELECTRONIC DEVICES

CROSS-REFERENCE TO RELATED APPLICATIONS

This application claims priority to German Application No. 102017126064.1 filed on Nov. 8, 2017, and to German Application No. 102018113459.2 filed on Jun. 6, 2018, the disclosures of which are incorporated by reference herein in their entireties.

FIELD OF INVENTION

The invention relates to light-emitting organic molecules and their use in organic light-emitting diodes (OLEDs) and in other optoelectronic devices.

BRIEF DESCRIPTION OF THE DRAWINGS

Exemplary embodiments of the present invention will be described below in more detail, with reference to the accompanying drawings, of which.

DETAILED DESCRIPTION OF EXEMPLARY EMBODIMENTS OF THE INVENTION

Figure 1:
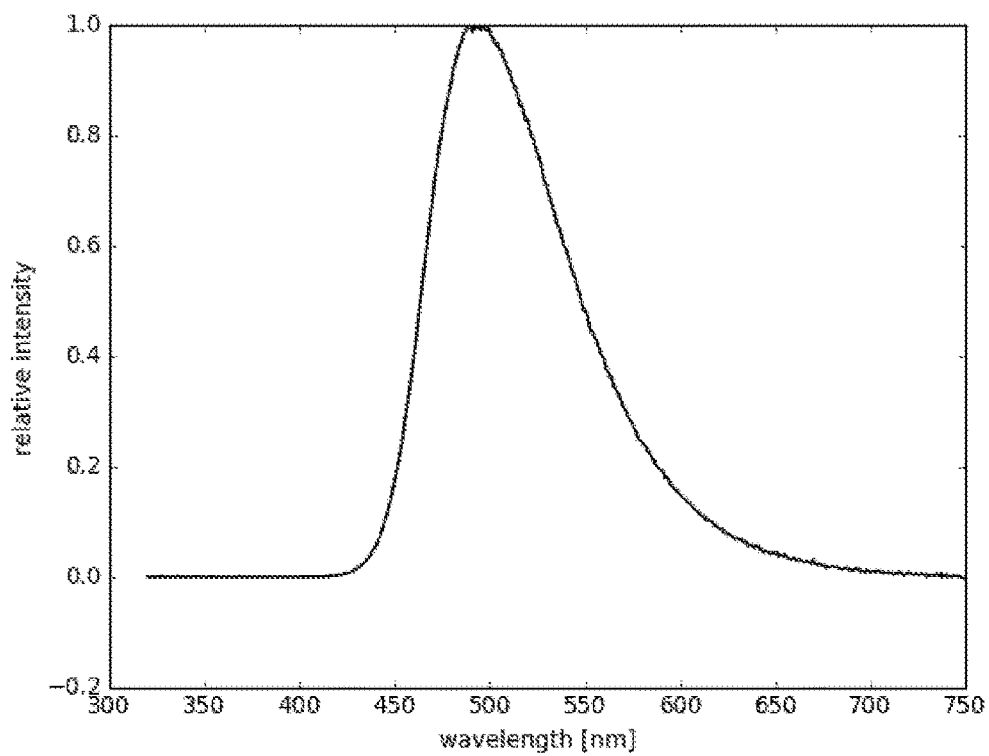
FIG. 1 shows the emission spectrum of example 1 (10% by weight) in PMMA.

Exemplary embodiments of the invention will now be discussed in further detail. This invention may, however, be embodied in many different forms and should not be construed as limited to the embodiments set forth herein.

The object of the present invention is to provide molecules which are suitable for use in optoelectronic devices.

This object is achieved by the invention which provides a new class of organic molecules.

The organic molecules of the invention are purely organic molecules, i.e. they do not contain any metal ions in contrast to metal complexes known for use in optoelectronic devices.

The organic molecules exhibit emission maxima in the blue, sky-blue or green spectral range.

The photoluminescence quantum yields of the organic molecules according to the invention are, in particular, 26% or more. The molecules of the invention exhibit in particular thermally activated delayed fluorescence (TADF). The use of the molecules according to the invention in an optoelectronic device, for example, an organic light-emitting diode (OLED), leads to higher efficiencies of the device. Corresponding OLEDs have a higher stability than OLEDs with known emitter materials and comparable color. In particular, the molecules can be used in combination with a fluorescence emitter to enable so-called hyperfluorescence.

The organic molecules according to the invention comprise or consist of one first chemical moiety comprising or consisting of a structure of formula I, Formula I and
two second chemical moieties comprising or consisting of a structure of formula II, Formula II wherein the first chemical moiety is linked to the second chemical moiety via a single bond.
  # represents the binding site of a single bond linking the first chemical moiety to the second chemical moiety.
  W is the bond linking the first chemical moiety to one of the two second chemical moieties.
  V is selected from the group consisting of CN and $CF_3$.
  Z is at each occurrence independently from another selected from the group consisting of: a direct bond, $CR^3R^4$, $C=CR^3R^4$, $C=O$, $C=NR^3$, $NR^3$, O, $SiR^3R^4$, S, S(O) and $S(O)_2$.
  $R^I$ is at each occurrence independently from another selected from the group consisting of: hydrogen, deuterium, $C_1$-$C_5$-alkyl,
    wherein one or more hydrogen atoms are optionally substituted by deuterium; $C_2$-$C_8$-alkenyl,
    wherein one or more hydrogen atoms are optionally substituted by deuterium; $C_2$-$C_8$-alkynyl,
    wherein one or more hydrogen atoms are optionally substituted by deuterium; and $C_6$-$C_{18}$-aryl.
  $R^{11}$, $R^{12}$, $R^{13}$, $R^{14}$ and $R^{15}$ is at each occurrence independently from another selected from the group consisting of: hydrogen, deuterium, CN, $CF_3$, phenyl, $C_1$-$C_5$-alkyl,
    wherein one or more hydrogen atoms are optionally substituted by deuterium;
  $C_2$-$C_8$-alkenyl,
    wherein one or more hydrogen atoms are optionally substituted by deuterium;
  $C_2$-$C_8$-alkynyl,
    wherein one or more hydrogen atoms are optionally substituted by deuterium;

$C_6$-$C_{18}$-aryl,
  which is optionally substituted with one or more substituents $R^6$; and
$C_3$-$C_{17}$-heteroaryl,
  which is optionally substituted with one or more substituents $R^6$.

$R^a$, $R^3$ and $R^4$ is at each occurrence independently from another selected from the group consisting of: hydrogen, deuterium, $N(R^5)_2$, $OR^5$, $Si(R^5)_3$, $B(OR^5)_2$, $OSO_2R^5$, $CF_3$, CN, F, Br, I,
$C_1$-$C_{40}$-alkyl,
  which is optionally substituted with one or more substituents $R^5$ and
  wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;
$C_1$-$C_{40}$-alkoxy,
  which is optionally substituted with one or more substituents $R^5$ and
  wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;
$C_1$-$C_{40}$-thioalkoxy,
  which is optionally substituted with one or more substituents $R^5$ and
  wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;
$C_2$-$C_{40}$-alkenyl,
  which is optionally substituted with one or more substituents $R^5$ and
  wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;
$C_2$-$C_{40}$-alkynyl,
  which is optionally substituted with one or more substituents $R^5$ and
  wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;
$C_6$-$C_{60}$-aryl,
  which is optionally substituted with one or more substituents $R^5$; and
$C_3$-$C_{57}$-heteroaryl,
  which is optionally substituted with one or more substituents $R^5$.

$R^5$ is at each occurrence independently from another selected from the group consisting of: hydrogen, deuterium, $N(R^6)_2$, $OR^6$, $Si(R^6)_3$, $B(OR^6)_2$, $OSO_2R^6$, $CF_3$, CN, F, Br, I,
$C_1$-$C_{40}$-alkyl,
  which is optionally substituted with one or more substituents $R^6$ and
  wherein one or more non-adjacent $CH_2$-groups are optionally substituted by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$;
$C_1$-$C_{40}$-alkoxy,
  which is optionally substituted with one or more substituents $R^6$ and
  wherein one or more non-adjacent $CH_2$-groups are optionally substituted by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$;
$C_1$-$C_{40}$-thioalkoxy,
  which is optionally substituted with one or more substituents $R^6$ and
  wherein one or more non-adjacent $CH_2$-groups are optionally substituted by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$;
$C_2$-$C_{40}$-alkenyl,
  which is optionally substituted with one or more substituents $R^6$ and
  wherein one or more non-adjacent $CH_2$-groups are optionally substituted by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$;
$C_2$-$C_{40}$-alkynyl,
  which is optionally substituted with one or more substituents $R^6$ and
  wherein one or more non-adjacent $CH_2$-groups are optionally substituted by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$;
$C_6$-$C_{60}$-aryl,
  which is optionally substituted with one or more substituents $R^6$; and
$C_3$-$C_{57}$-heteroaryl,
  which is optionally substituted with one or more substituents $R^6$.

$R^6$ is at each occurrence independently from another selected from the group consisting of hydrogen, deuterium, OPh, $CF_3$, CN, F,
$C_1$-$C_5$-alkyl,
  wherein optionally one or more hydrogen atoms are independently from each other substituted by deuterium, CN, $CF_3$, or F;
$C_1$-$C_5$-alkoxy,
  wherein optionally one or more hydrogen atoms are independently from each other substituted by deuterium, CN, $CF_3$, or F;
$C_1$-$C_5$-thioalkoxy,
  wherein optionally one or more hydrogen atoms are independently from each other substituted by deuterium, CN, $CF_3$, or F;
$C_2$-$C_5$-alkenyl,
  wherein optionally one or more hydrogen atoms are independently from each other substituted by deuterium, CN, $CF_3$, or F;
$C_2$-$C_5$-alkynyl,
  wherein optionally one or more hydrogen atoms are independently from each other substituted by deuterium, CN, $CF_3$, or F;
$C_6$-$C_{18}$-aryl,
  which is optionally substituted with one or more $C_1$-$C_5$-alkyl substituents;
$C_3$-$C_{17}$-heteroaryl,
  which is optionally substituted with one or more $C_1$-$C_5$-alkyl substituents;
$N(C_6$-$C_{18}$-aryl$)_2$;
$N(C_3$-$C_{17}$-heteroaryl$)_2$; and
$N(C_3$-$C_{17}$-heteroaryl)($C_6$-$C_{18}$-aryl).

The substituents $R^a$, $R^3$, $R^4$ or $R^5$, independently from each other, optionally form a mono- or polycyclic, aliphatic, aromatic and/or benzo-fused ring system with one or more other substituents $R^a$, $R^3$, $R^4$ or $R^5$.

In one embodiment, $R^{11}$, $R^{12}$, $R^{13}$, $R^{14}$ and $R^{15}$ is independently from each other selected from the group consisting of H, methyl, CN, $CF_3$ and phenyl.

In one embodiment, $R^I$ is at each occurrence independently from each other selected from the group consisting of H, methyl and phenyl.

In one embodiment, $R^{11}$ and $R^{15}$ is independently from each other at each occurrence selected from the group consisting of H, CN, $CF_3$ and phenyl.

In one embodiment, $R^{11}$ is selected from the group consisting of H, CN, $CF_3$ and phenyl.

In one embodiment, $R^{13}$ is selected from the group consisting of H, CN, $CF_3$ and phenyl.

In one embodiment, $R^{15}$ is selected from the group consisting of H, CN, $CF_3$ and phenyl.

In one embodiment, $R^{11}$, $R^{12}$, $R^{13}$, $R^{14}$, and $R^{15}$ is H.

In one embodiment, $R^I$ is H.

In one embodiment, $R^{11}$, $R^{12}$, $R^{13}$, $R^{14}$, $R^{15}$ and $R^I$ is H.

In one embodiment, V is CN. In another embodiment, V is $CF_3$.

In a further embodiment of the invention, the second chemical moiety comprises or consists of a structure of formula IIa:

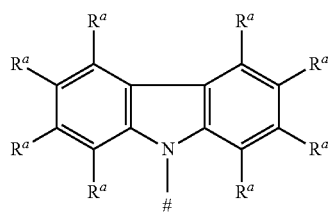

Formula IIa wherein # and $R^a$ are defined as above.

In a further embodiment of the invention, $R^a$ is at each occurrence independently from another selected from the group consisting of:
hydrogen,
Me,
$^iPr$,
$^tBu$,
CN,
$CF_3$,
Ph, which is optionally substituted with one or more substituents independently from each other selected from the group consisting of Me, $^iPr$, $^tBu$, ON, $CF_3$, and Ph,
pyridinyl, which is optionally substituted with one or more substituents independently from each other selected from the group consisting of Me, $^iPr$, $^tBu$, ON, $CF_3$, and Ph,
pyrimidinyl, which is optionally substituted with one or more substituents independently from each other selected from the group consisting of Me, $^iPr$, $^tBu$, ON, $CF_3$, and Ph,
carbazolyl, which is optionally substituted with one or more substituents independently from each other selected from the group consisting of Me, $^iPr$, $^tBu$, ON, $CF_3$, and Ph,
triazinyl, which is optionally substituted with one or more substituents independently from each other selected from the group consisting of Me, $^iPr$, $^tBu$, ON, $CF_3$, and Ph,
and $N(Ph)_2$.

In a further embodiment of the invention, $R^a$ is at each occurrence independently from another selected from the group consisting of:
hydrogen,
Me,
$^iPr$,
$^tBu$,
CN,
$CF_3$,
Ph, which is optionally substituted with one or more substituents independently from each other selected from the group consisting of Me, $^iPr$, $^tBu$, ON, $CF_3$, and Ph,
pyridinyl, which is optionally substituted with one or more substituents independently from each other selected from the group consisting of Me, $^iPr$, $^tBu$, CN, $CF_3$, and Ph,
pyrimidinyl, which is optionally substituted with one or more substituents independently from each other selected from the group consisting of Me, $^iPr$, $^tBu$, CN, $CF_3$, and Ph, and
triazinyl, which is optionally substituted with one or more substituents independently from each other selected from the group consisting of Me, $^iPr$, $^tBu$, CN, $CF_3$, and Ph.

In a further embodiment of the invention, the second chemical moiety comprises or consists of a structure of formula IIb, a structure of formula IIb-2, a structure of formula IIb-3 or a structure of formula IIb-4:

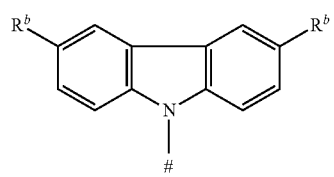

Formula IIb

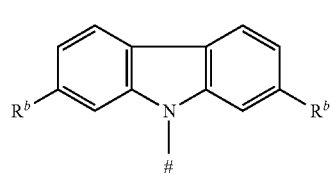

Formula IIb-2

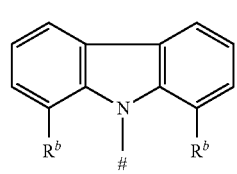

Formula IIb-3

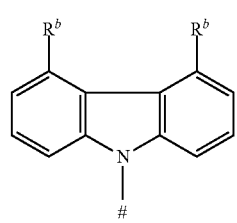

Formula IIb-4 wherein
$R^b$ is at each occurrence independently from another selected from the group consisting of deuterium, $N(R^5)_2$, $OR^5$, $Si(R^5)_3$, $B(OR^5)_2$, $OSO_2R^5$, $CF_3$, CN, F, Br, I, $C_1$-$C_{40}$-alkyl,
  which is optionally substituted with one or more substituents $R^5$ and
  wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, $SO$, $SO_2$, $NR^5$, $O$, $S$ or $CONR^5$;

$C_1$-$C_{40}$-alkoxy,
  which is optionally substituted with one or more substituents $R^5$ and
  wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, $SO$, $SO_2$, $NR^5$, $O$, $S$ or $CONR^5$;

$C_1$-$C_{40}$-thioalkoxy,
  which is optionally substituted with one or more substituents $R^5$ and
  wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, $SO$, $SO_2$, $NR^5$, $O$, $S$ or $CONR^5$;

$C_2$-$C_{40}$-alkenyl,
  which is optionally substituted with one or more substituents $R^5$ and
  wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, $SO$, $SO_2$, $NR^5$, $O$, $S$ or $CONR^5$;

$C_2$-$C_{40}$-alkynyl,
  which is optionally substituted with one or more substituents $R^5$ and
  wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, $SO$, $SO_2$, $NR^5$, $O$, $S$ or $CONR^5$;

$C_6$-$C_{60}$-aryl,
  which is optionally substituted with one or more substituents $R^5$; and $C_3$-$C_{57}$-heteroaryl,
  which is optionally substituted with one or more substituents $R^5$.

Apart from that, the aforementioned definitions apply.

In an additional embodiment of the invention, the second chemical moiety comprises or consists of a structure of formula IIc, a structure of formula IIc-2, a structure of formula IIc-3 or a structure of formula IIc-4:

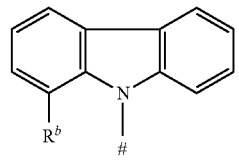

Formula IIc

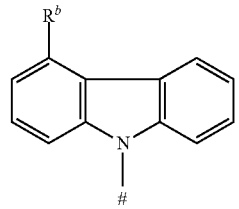

Formula IIc-2

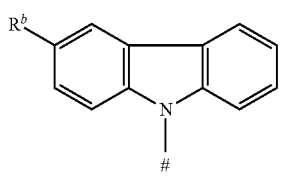

Formula IIc-3

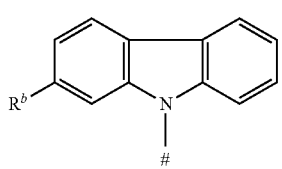

Formula IIc-4 wherein the aforementioned definitions apply.

In a further embodiment of the invention, $R^b$ is at each occurrence independently from another selected from the group consisting of:

Me, $^i$Pr, $^t$Bu, CN, $CF_3$,

Ph, which is optionally substituted with one or more substituents independently from each other selected from the group consisting of Me, $^i$Pr, $^t$Bu, ON, $CF_3$, and Ph, pyridinyl, which is optionally substituted with one or more substituents independently from each other selected from the group consisting of Me, $^i$Pr, $^t$Bu, CN, $CF_3$, and Ph, carbazolyl, which is optionally substituted with one or more substituents independently from each other selected from the group consisting of Me, $^i$Pr, $^t$Bu, CN, $CF_3$, and Ph, triazinyl, which is optionally substituted with one or more substituents independently from each other selected from the group consisting of Me, $^i$Pr, $^t$Bu, CN, $CF_3$, and Ph, and $N(Ph)_2$.

In a further embodiment of the invention, $R^b$ is at each occurrence independently from another selected from the group consisting of:

Me, $^i$Pr, $^t$Bu,

CN, $CF_3$,

Ph, which is optionally substituted with one or more substituents independently from each other selected from the group consisting of Me, $^i$Pr, $^t$Bu, ON, $CF_3$, and Ph, pyridinyl, which is optionally substituted with one or more substituents independently from each other selected from the group consisting of Me, $^i$Pr, $^t$Bu, ON, $CF_3$, and Ph, pyrimidinyl, which is optionally substituted with one or more substituents independently from each other selected from the group consisting of Me, $^i$Pr, $^t$Bu, ON, $CF_3$, and Ph, and triazinyl, which is optionally substituted with one or more substituents independently from each other selected from the group consisting of Me, $^i$Pr, $^t$Bu, ON, $CF_3$, and Ph.

Below, examples for the second chemical moiety are shown:
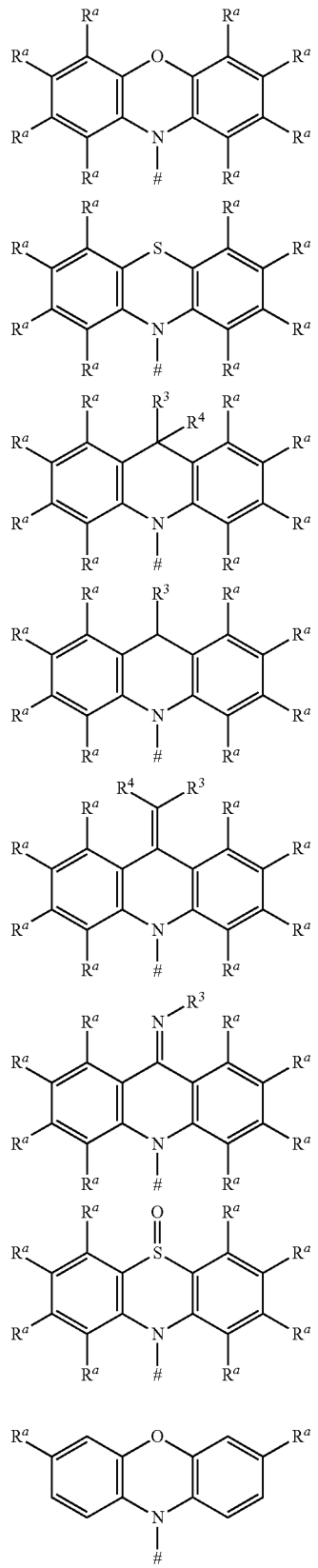
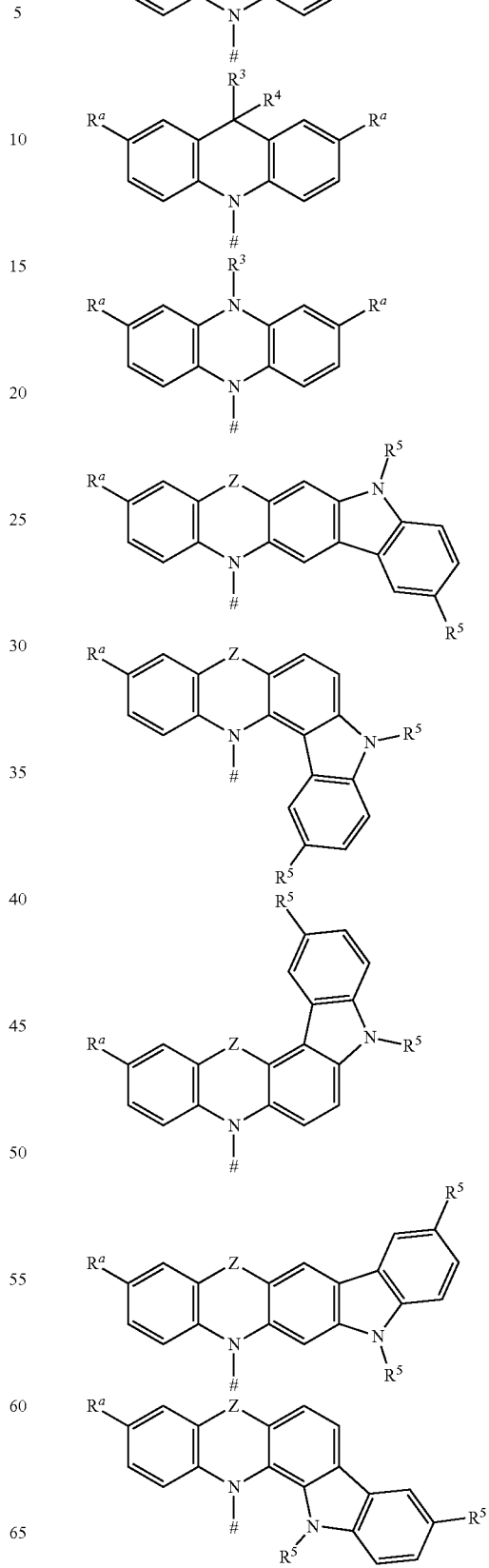

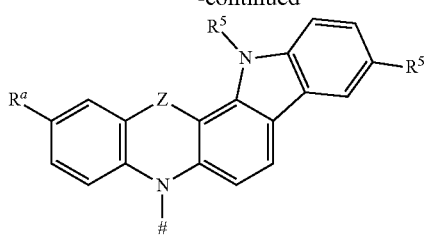
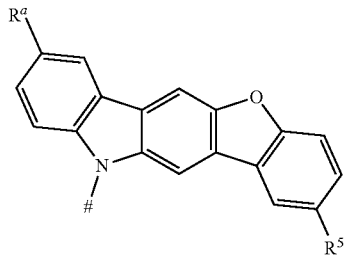
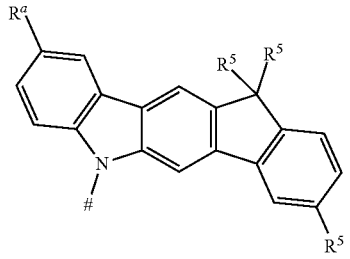
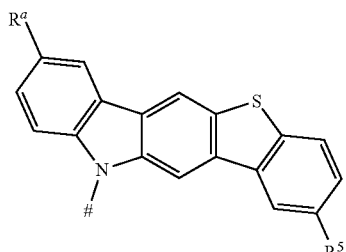
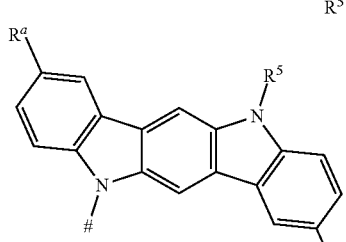
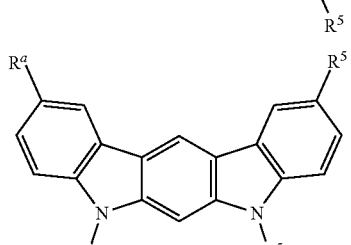
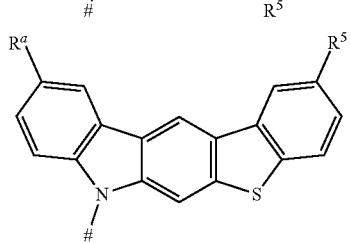
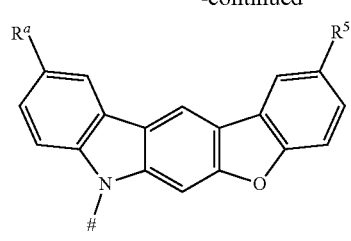
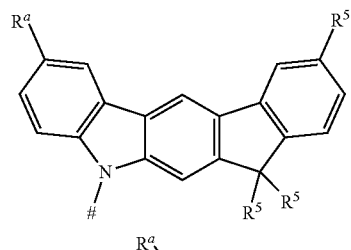
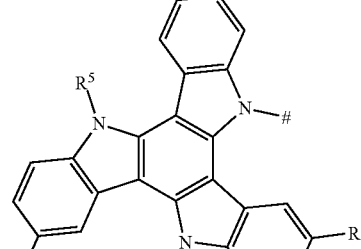
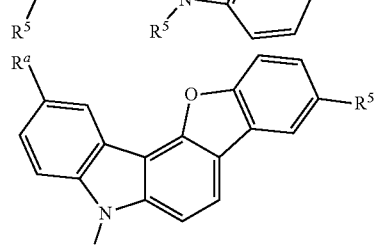
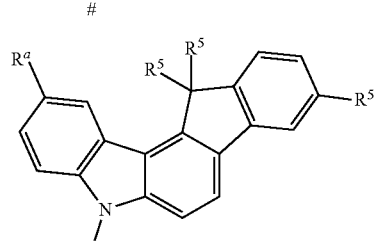
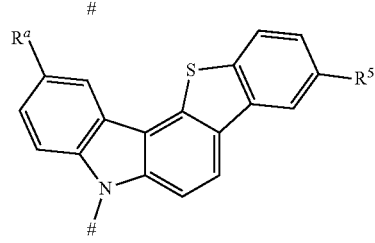
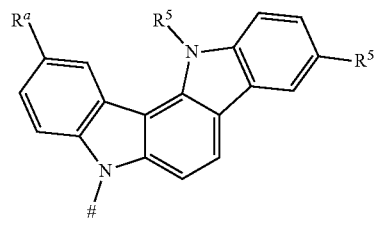

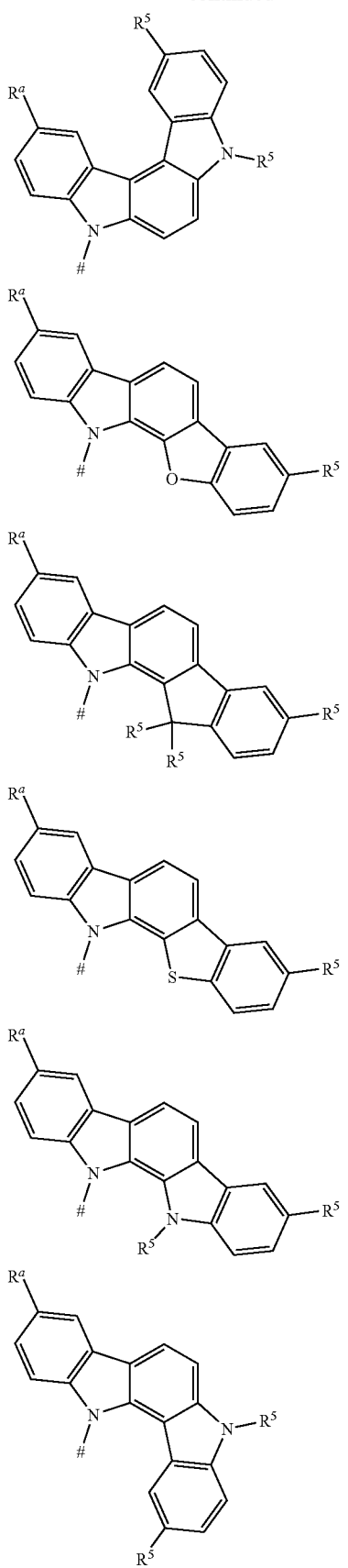
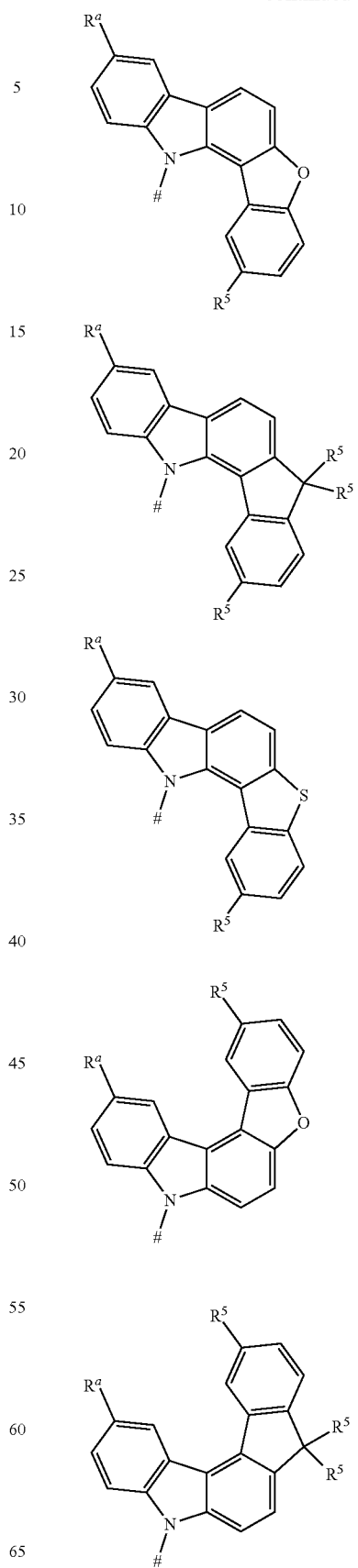

-continued

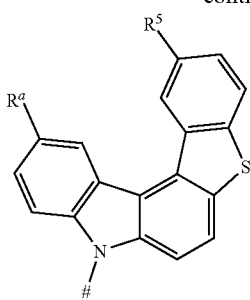

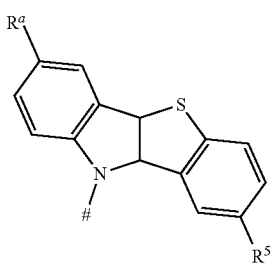

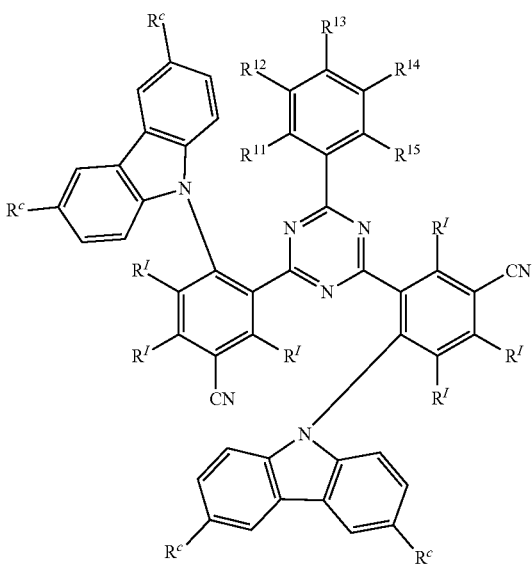

wherein for #, Z, R$^a$, R$^3$, R$^4$ and R$^5$ the aforementioned definitions apply.

In one embodiment, R$^a$ and R$^5$ is at each occurrence independently from another selected from the group consisting of hydrogen (H), methyl (Me), i-propyl (CH(CH$_3$)$_2$) ($^i$Pr), t-butyl ($^t$Bu), phenyl (Ph), CN, CF$_3$, and diphenylamine (NPh$_2$).

In one embodiment of the invention, the organic molecules comprise or consist of a structure of formula III:

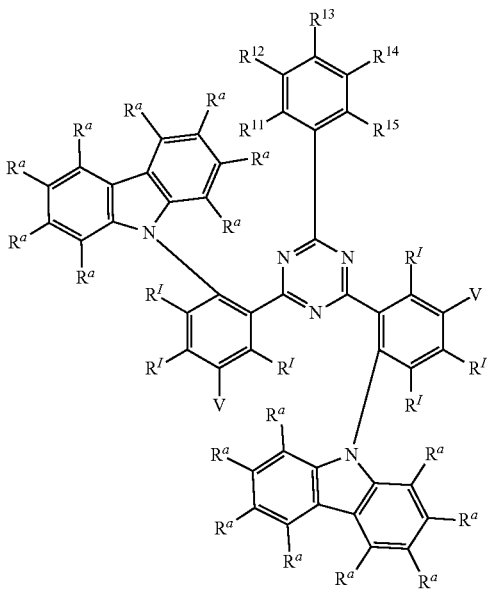

Formula III wherein the aforementioned definitions apply.

In a further embodiment of the invention, the organic molecules comprise or consist of a structure of formula IIIa-I or formula IIIa-II:

Formula IIIa-I

-continued

Formula IIIa-II

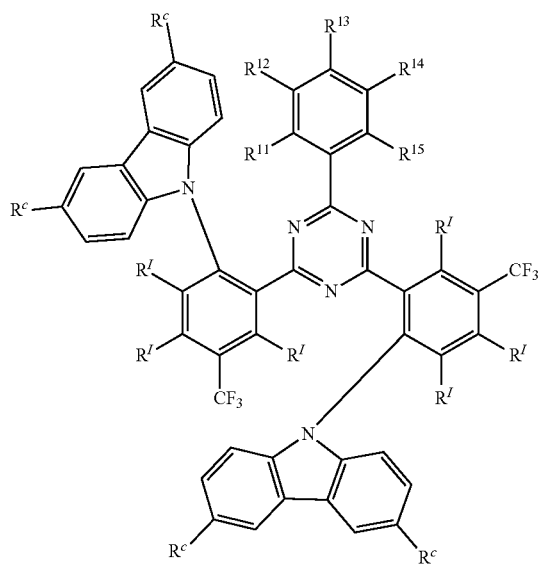

wherein $R^c$ is at each occurrence independently from another selected from the group consisting of:

Me, $^i$Pr, $^t$Bu,

Ph, which is optionally substituted with one or more substituents independently from each other selected from the group consisting of Me, $^i$Pr, $^t$Bu, ON, $CF_3$, and Ph, pyridinyl, which is optionally substituted with one or more substituents independently from each other selected from the group consisting of Me, $^i$Pr, $^t$Bu, CN, $CF_3$, and Ph, pyrimidinyl, which is optionally substituted with one or more substituents independently from each other selected from the group consisting of Me, $^i$Pr, $^t$Bu, CN, $CF_3$, and Ph, carbazolyl, which is optionally substituted with one or more substituents independently from each other selected from the group consisting of Me, $^i$Pr, $^t$Bu, CN, $CF_3$, and Ph, triazinyl, which is optionally substituted with one or more substituents independently from each other selected from the group consisting of Me, $^i$Pr, $^t$Bu, CN, $CF_3$, and Ph, and $N(Ph)_2$, and wherein $R^{11}$, $R^{12}$, $R^{13}$, $R^{14}$, $R^{15}$ and $R^I$ are defined as above.

In further embodiments of the invention, the organic molecule comprises or consists of a structure of formula IIIb-I or formula IIIb-II:

Formula IIIb-I

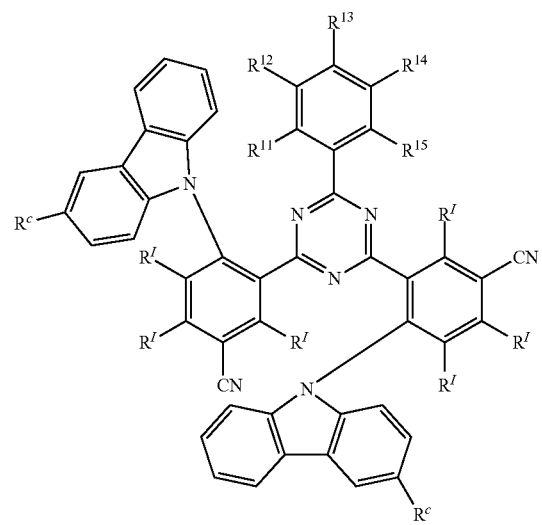

Formula IIIb-II

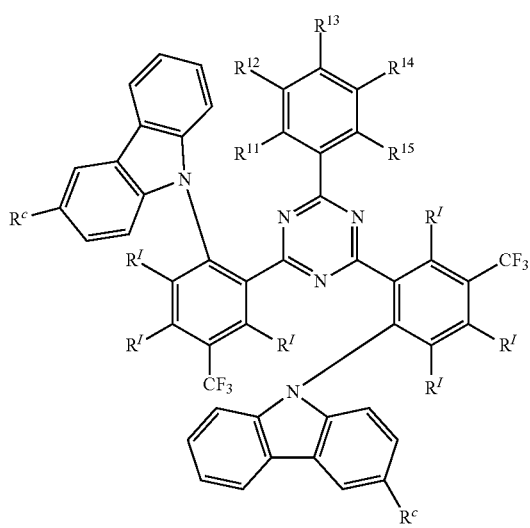

wherein the aforementioned definitions apply.

In further embodiments of the invention, the organic molecules comprise or consist of a structure of formula IIIc-I or formula IIIc-II:

Formula IIIc-I

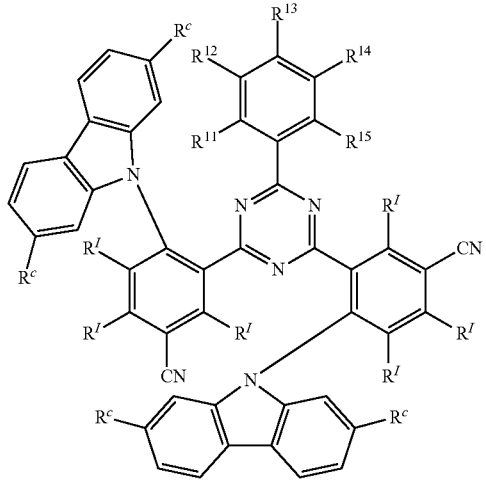

Formula IIIc-II

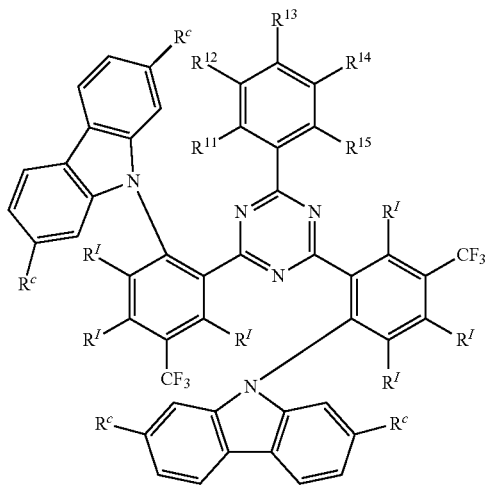

wherein the aforementioned definitions apply.

In further embodiments of the invention, the organic molecules comprise or consist of a structure of formula IIId-I or formula IIId-II:

Formula IIId-I

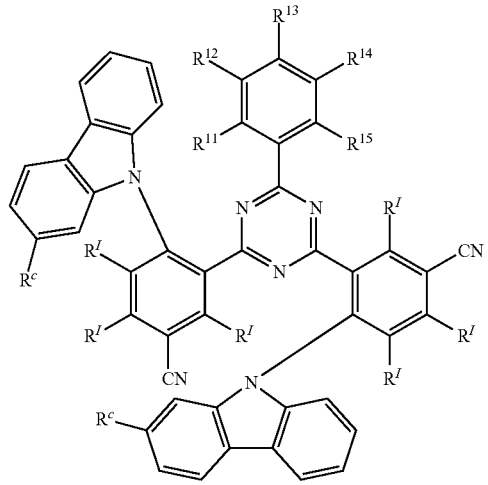

Formula IIId-II

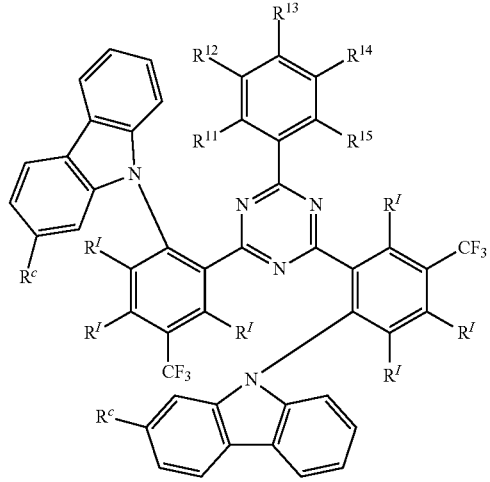

wherein the aforementioned definitions apply.

In further embodiments of the invention, the organic molecules comprise or consist of a structure of formula IIIe-I or formula IIIe-II:

Formula IIIe-I

Formula IIIe-II wherein the aforementioned definitions apply.

In further embodiments of the invention, the organic molecules comprise or consist of a structure of formula IIIf-I or formula IIIf-II:

Formula IIIf-I

Formula IIIf-II wherein the aforementioned definitions apply.

In further embodiments of the invention, the organic molecules comprise or consist of a structure of formula IIIg-I or formula IIIg-II:

Formula IIIg-I

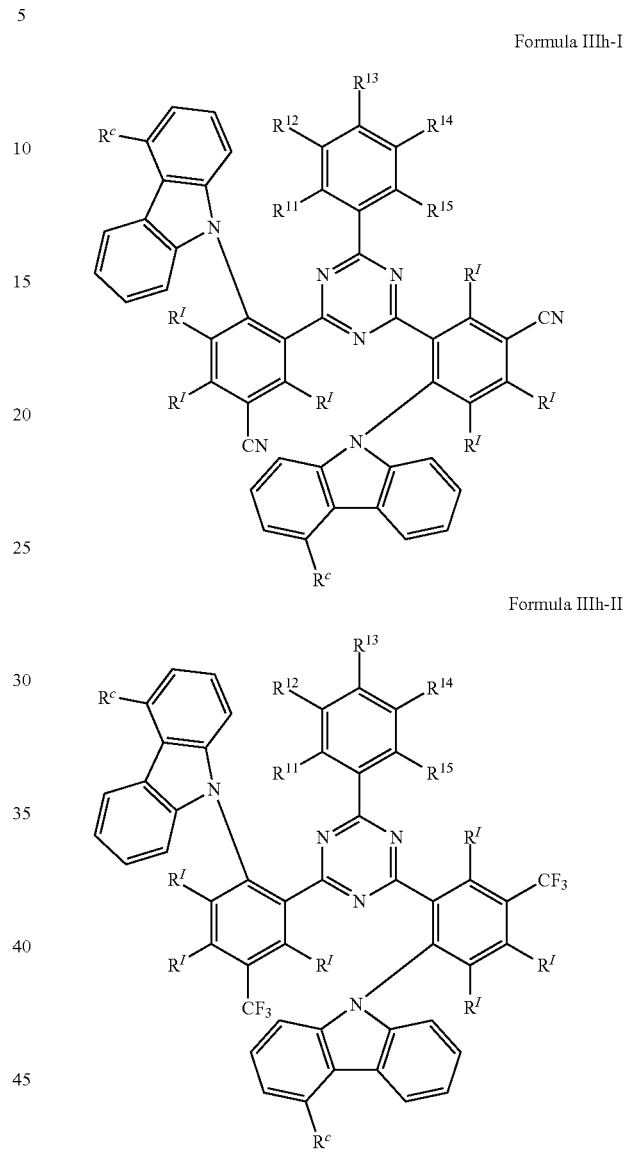

Formula IIIg-II

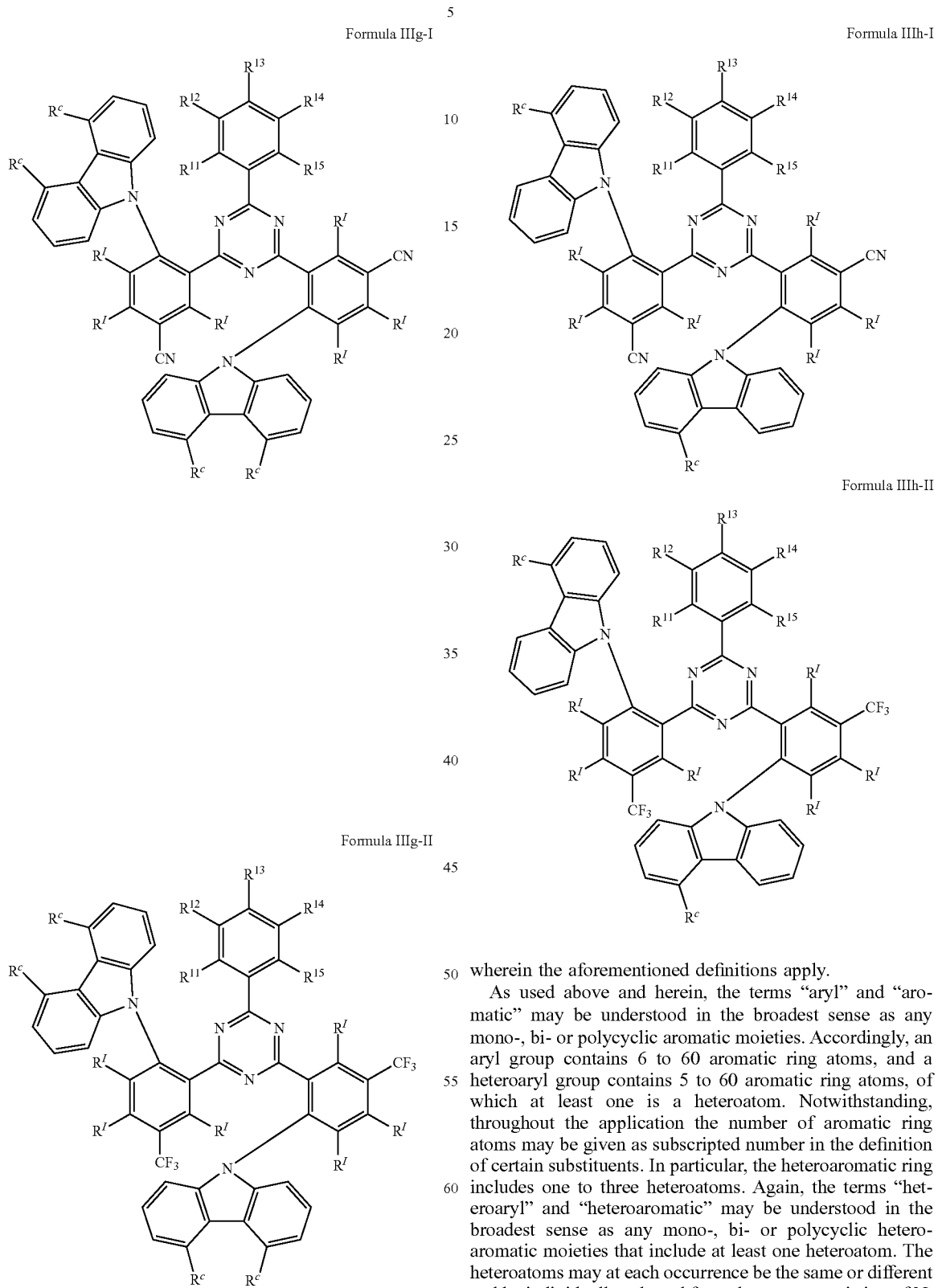

wherein the aforementioned definitions apply.

In further embodiments of the invention, the organic molecules comprise or consist of a structure of formula IIIh-I or formula IIIh-II:

Formula IIIh-I

Formula IIIh-II wherein the aforementioned definitions apply.

As used above and herein, the terms "aryl" and "aromatic" may be understood in the broadest sense as any mono-, bi- or polycyclic aromatic moieties. Accordingly, an aryl group contains 6 to 60 aromatic ring atoms, and a heteroaryl group contains 5 to 60 aromatic ring atoms, of which at least one is a heteroatom. Notwithstanding, throughout the application the number of aromatic ring atoms may be given as subscripted number in the definition of certain substituents. In particular, the heteroaromatic ring includes one to three heteroatoms. Again, the terms "heteroaryl" and "heteroaromatic" may be understood in the broadest sense as any mono-, bi- or polycyclic heteroaromatic moieties that include at least one heteroatom. The heteroatoms may at each occurrence be the same or different and be individually selected from the group consisting of N, O and S. Accordingly, the term "arylene" refers to a divalent substituent that bears two binding sites to other molecular structures and thereby serving as a linker structure. In case, a group in the exemplary embodiments is defined differently from the definitions given here, for example, the number of aromatic ring atoms or number of heteroatoms differs from the given definition, the definition in the exemplary embodiments is to be applied. According to the invention, a condensed (annulated) aromatic or heteroaromatic polycycle is built of two or more single aromatic or heteroaromatic cycles, which formed the polycycle via a condensation reaction.

In particular, as used throughout the present application the term aryl group or heteroaryl group comprises groups which can be bound via any position of the aromatic or heteroaromatic group, derived from benzene, naphthaline, anthracene, phenanthrene, pyrene, dihydropyrene, chrysene, perylene, fluoranthene, benzanthracene, benzphenanthrene, tetracene, pentacene, benzpyrene, furan, benzofuran, isobenzofuran, dibenzofuran, thiophene, benzothiophene, isobenzothiophene, dibenzothiophene; pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthoimidazole, phenanthroimidazole, pyridoimidazole, pyrazinoimidazole, quinoxalinoimidazole, oxazole, benzoxazole, napthooxazole, anthroxazol, phenanthroxazol, isoxazole, 1,2-thiazole, 1,3-thiazole, benzothiazole, pyridazine, benzopyridazine, pyrimidine, benzopyrimidine, 1,3,5-triazine, quinoxaline, pyrazine, phenazine, naphthyridine, carboline, benzocarboline, phenanthroline, 1,2,3-triazole, 1,2,4-triazole, benzotriazole, 1,2,3-oxadiazole, 1,2,4-oxadiazole, 1,2,5-oxadiazole, 1,2,3,4-tetrazine, purine, pteridine, indolizine and benzothiadiazole or combinations of the abovementioned groups.

As used throughout the present application the term cyclic group may be understood in the broadest sense as any mono-, bi- or polycyclic moieties.

As used above and herein, the term alkyl group may be understood in the broadest sense as any linear, branched, or cyclic alkyl substituent. In particular, the term alkyl comprises the substituents methyl (Me), ethyl (Et), n-propyl ($^n$Pr), i-propyl ($^i$Pr), cyclopropyl, n-butyl ($^n$Bu), i-butyl ($^i$Bu), s-butyl ($^s$Bu), t-butyl ($^t$Bu), cyclobutyl, 2-methylbutyl, n-pentyl, s-pentyl, t-pentyl, 2-pentyl, neo-pentyl, cyclopentyl, n-hexyl, s-hexyl, t-hexyl, 2-hexyl, 3-hexyl, neo-hexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2,2,2]octyl, 2-bicyclo[2,2,2]-octyl, 2-(2,6-dimethyl) octyl, 3-(3,7-dimethyl)octyl, adamantyl, 2,2,2-trifluorethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyln-n-hexadec-1-yl, 1,1-diethyl-n-octadec-1-yl, 1-(n-propyl)-cyclohex-1-yl, 1-(n-butyl)-cyclohex-1-yl, 1-(n-hexyl)-cyclohex-1-yl, 1-(n-octyl)-cyclohex-1-yl and 1-(n-decyl)-cyclohex-1-yl.

As used above and herein, the term alkenyl comprises linear, branched, and cyclic alkenyl substituents. The term alkenyl group exemplarily comprises the substituents ethenyl, propenyl, butenyl, pentenyl, cyclopentenyl, hexenyl, cyclohexenyl, heptenyl, cycloheptenyl, octenyl, cyclooctenyl or cyclooctadienyl.

As used above and herein, the term alkynyl comprises linear, branched, and cyclic alkynyl substituents. The term alkynyl group exemplarily comprises ethynyl, propynyl, butynyl, pentynyl, hexynyl, heptynyl or octynyl.

As used above and herein, the term alkoxy comprises linear, branched, and cyclic alkoxy substituents. The term alkoxy group exemplarily comprises methoxy, ethoxy, n-propoxy, i-propoxy, n-butoxy, i-butoxy, s-butoxy, t-butoxy and 2-methylbutoxy.

As used above and herein, the term thioalkoxy comprises linear, branched, and cyclic thioalkoxy substituents, in which the O of the exemplarily alkoxy groups is replaced by S.

As used above and herein, the terms "halogen" and "halo" may be understood in the broadest sense as being preferably fluorine, chlorine, bromine or iodine.

Whenever hydrogen (H) is mentioned herein, it could also be replaced by deuterium at each occurrence.

It is understood that when a molecular fragment is described as being a substituent or otherwise attached to another moiety, its name may be written as if it were a fragment (e.g. naphtyl, dibenzofuryl) or as if it were the whole molecule (e.g. naphthalene, dibenzofuran). As used herein, these different ways of designating a substituent or attached fragment are considered to be equivalent.

In one embodiment, the organic molecules according to the invention have an excited state lifetime of not more than 150 μs, of not more than 100 μs, in particular of not more than 50 μs, more preferably of not more than 10 μs or not more than 7 μs in a film of poly(methyl methacrylate) (PMMA) with 10% by weight of organic molecule at room temperature.

In one embodiment of the invention, the organic molecules according to the invention represent thermally-activated delayed fluorescence (TADF) emitters, which exhibit a $\Delta E_{ST}$ value, which corresponds to the energy difference between the first excited singlet state (Si) and the first excited triplet state (T1), of less than 5000 cm$^{-1}$, preferably less than 3000 cm$^{-1}$, more preferably less than 1500 cm$^{-1}$, even more preferably less than 1000 cm$^{-1}$ or even less than 500 cm$^{-1}$.

In a further embodiment of the invention, the organic molecules according to the invention have an emission peak in the visible or nearest ultraviolet range, i.e., in the range of a wavelength of from 380 to 800 nm, with a full width at half maximum of less than 0.50 eV, preferably less than 0.48 eV, more preferably less than 0.45 eV, even more preferably less than 0.43 eV or even less than 0.40 eV in a film of poly(methyl methacrylate) (PMMA) with 10% by weight of organic molecule at room temperature.

In a further embodiment of the invention, the organic molecules according to the invention have an emission peak in the visible or nearest ultraviolet range, i.e., in the range of a wavelength of from 380 to 800 nm, with a full width at half maximum of less than 0.40 eV in a film of poly(methyl methacrylate) (PMMA) with 10% by weight of organic molecule at room temperature.

In a further embodiment of the invention, the organic molecules according to the invention have a "blue material index" (BMI), calculated by dividing the photoluminescence quantum yield (PLQY) in % by the CIEy color coordinate of the emitted light, of more than 150, in particular more than 200, preferably more than 250, more preferably of more than 300 or even more than 500.

Orbital and excited state energies can be determined either by means of experimental methods or by calculations employing quantum-chemical methods, in particular density functional theory calculations. The energy of the highest occupied molecular orbital $E^{HOMO}$ is determined by methods known to the person skilled in the art from cyclic voltammetry measurements with an accuracy of 0.1 eV. The energy of the lowest unoccupied molecular orbital $E^{LUMO}$ is determined as the onset of the absorption spectrum.

The onset of an absorption spectrum is determined by computing the intersection of the tangent to the absorption spectrum with the x-axis. The tangent to the absorption spectrum is set at the low-energy side of the absorption band and at the point at half maximum of the maximum intensity of the absorption spectrum.

The energy of the first excited triplet state T1 is determined from the onset of the emission spectrum at low temperature, typically at 77 K. For host compounds, where the first excited singlet state and the lowest triplet state are energetically separated by >0.4 eV, the phosphorescence is usually visible in a steady-state spectrum in 2-Me-THF. The triplet energy can thus be determined as the onset of the phosphorescence spectrum. For TADF emitter molecules, the energy of the first excited triplet state T1 is determined from the onset of the delayed emission spectrum at 77 K, if not otherwise stated measured in a film of PMMA with 10% by weight of emitter. Both for host and emitter compounds, the energy of the first excited singlet state S1 is determined from the onset of the emission spectrum, if not otherwise stated measured in a film of PMMA with 10% by weight of host or emitter compound.

The onset of an emission spectrum is determined by computing the intersection of the tangent to the emission spectrum with the x-axis. The tangent to the emission spectrum is set at the high-energy side of the emission band and at the point at half maximum of the maximum intensity of the emission spectrum.

A further aspect of the invention relates to a process for preparing the organic molecules (with an optional subsequent reaction) of the invention, wherein a $R^{11}$-$R^{15}$-substituted 2,4-dichloro-6-phenyltriazine is used as reactant:

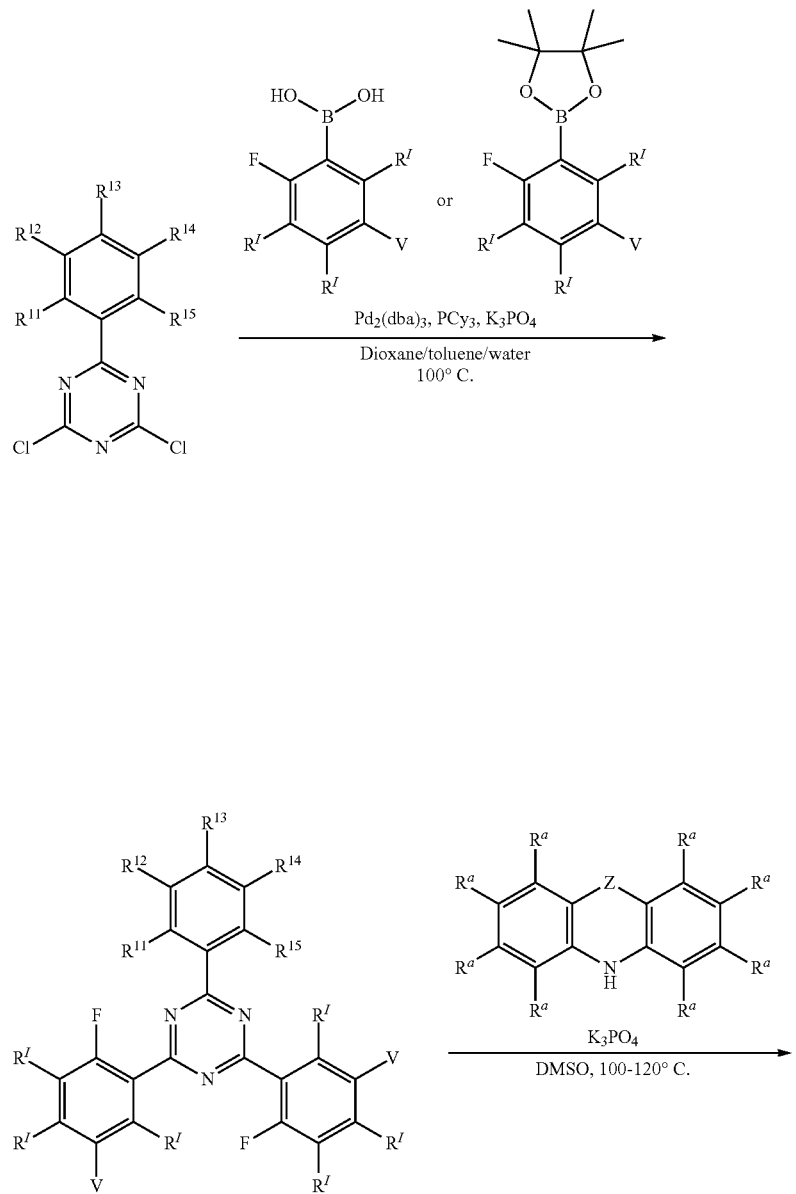

-continued

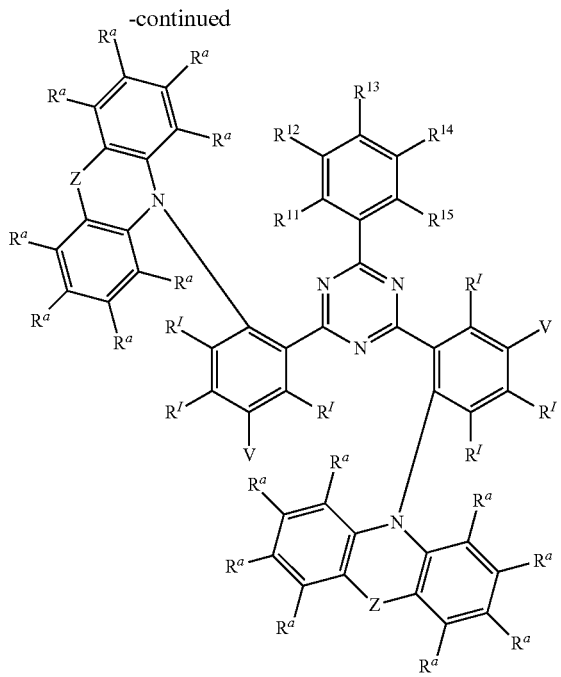

For the reaction of a nitrogen heterocycle in a nucleophilic aromatic substitution with an aryl halide, preferably an aryl fluoride, typical conditions include the use of a base, such as tribasic potassium phosphate for example, in an aprotic polar solvent, such as dimethyl sulfoxide (DMSO) or N,N-dimethylformamide (DMF), for example.

A further aspect of the invention relates to the use of an organic molecule according to the invention as a luminescent emitter or as an absorber, and/or as host material and/or as electron transport material, and/or as hole injection material, and/or as hole blocking material in an optoelectronic device.

The optoelectronic device may be understood in the broadest sense as any device based on organic materials that is suitable for emitting light in the visible or nearest ultraviolet (UV) range, i.e., in the range of a wavelength of from 380 to 800 nm. More preferably, the optoelectronic device may be able to emit light in the visible range, i.e., of from 400 to 800 nm.

In the context of such use, the optoelectronic device is more particularly selected from the group consisting of:
   organic light-emitting diodes (OLEDs),
   light-emitting electrochemical cells,
   OLED sensors, especially in gas and vapor sensors not hermetically externally shielded,
   organic diodes,
   organic solar cells,
   organic transistors,
   organic field-effect transistors,
   organic lasers and
   down-conversion elements.

A light-emitting electrochemical cell consists of three layers, namely a cathode, an anode, and an active layer, which contains the organic molecule according to the invention.

In a preferred embodiment in the context of such use, the optoelectronic device is a device selected from the group consisting of an organic light emitting diode (OLED), a light emitting electrochemical cell (LEC), an organic laser, and a light-emitting transistor.

In one embodiment, the light-emitting layer of an organic light-emitting diode comprises not only the organic molecules according to the invention but also a host material whose triplet (T1) and singlet (Si) energy levels are energetically higher than the triplet (T1) and singlet (Si) energy levels of the organic molecule.

A further aspect of the invention relates to a composition comprising or consisting of:
   (a) the organic molecule of the invention, in particular in the form of an emitter and/or a host, and
   (b) one or more emitter and/or host materials, which differ from the organic molecule of the invention, and
   (c) optionally, one or more dyes and/or one or more solvents.

In a further embodiment of the invention, the composition has a photoluminescence quantum yield (PLQY) of more than 26%, preferably more than 40%, more preferably more than 60%, even more preferably more than 80% or even more than 90% at room temperature.

Compositions with at Least One Further Emitter

One embodiment of the invention relates to a composition comprising or consisting of:
   (i) 1-50% by weight, preferably 5-40% by weight, in particular 10-30% by weight, of the organic molecule according to the invention;
   (ii) 5-98% by weight, preferably 30-93.9% by weight, in particular 40-88% by weight, of one host compound H;
   (iii) 1-30% by weight, in particular 1-20% by weight, preferably 1-5% by weight, of at least one further emitter molecule F with a structure differing from the structure of the molecules according to the invention; and
   (iv) optionally 0-94% by weight, preferably 0.1-65% by weight, in particular 1-50% by weight, of at least one further host compound D with a structure differing from the structure of the molecules according to the invention; and
   (v) optionally 0-94% by weight, preferably 0-65% by weight, in particular 0-50% by weight, of a solvent.

The components or the compositions are chosen such that the sum of the weight of the components add up to 100%.

In a further embodiment of the invention, the composition has an emission peak in the visible or nearest ultraviolet range, i.e., in the range of a wavelength of from 380 to 800 nm.

In one embodiment of the invention, the at least one further emitter molecule F is a purely organic emitter.

In one embodiment of the invention, the at least one further emitter molecule F is a purely organic TADF emitter. Purely organic TADF emitters are known from the state of the art, e.g. Wong and Zysman-Colman ("Purely Organic Thermally Activated Delayed Fluorescence Materials for Organic Light-Emitting Diodes.", Adv. Mater. 2017 June; 29(22)).

In one embodiment of the invention, the at least one further emitter molecule F is a fluorescence emitter, in particular a blue, a green or a red fluorescence emitter.

In a further embodiment of the invention, the composition, containing the at least one further emitter molecule F shows an emission peak in the visible or nearest ultraviolet range, i.e., in the range of a wavelength of from 380 to 800 nm, with a full width at half maximum of less than 0.30 eV, in particular less than 0.25 eV, preferably less than 0.22 eV, more preferably less than 0.19 eV or even less than 0.17 eV at room temperature, with a lower limit of 0.05 eV.

Composition Wherein the at Least One Further Emitter Molecule F is a Blue Fluorescence Emitter In one embodiment of the invention, the at least one further emitter molecule F is a fluorescence emitter, in particular a blue fluorescence emitter.

In one embodiment, the at least one further emitter molecule F is a blue fluorescence emitter selected from the following group:

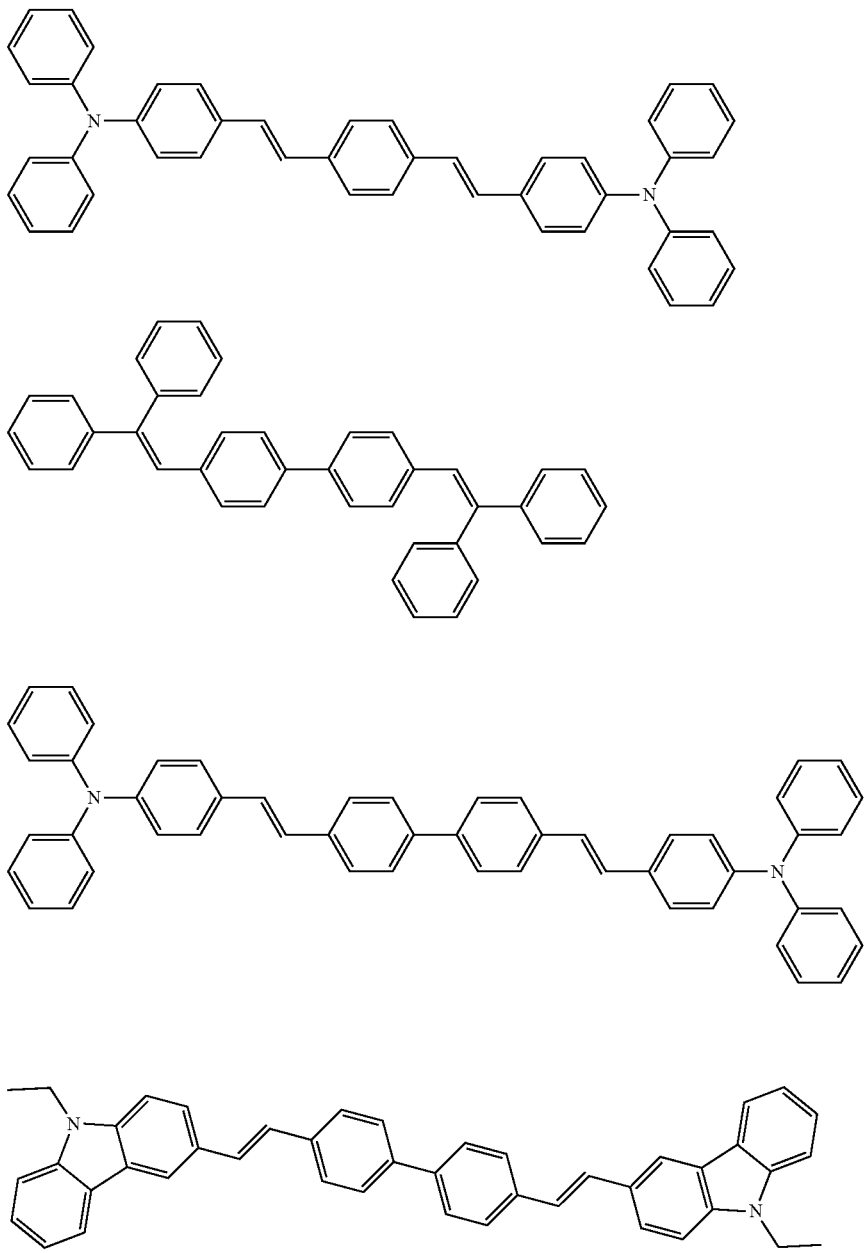

-continued
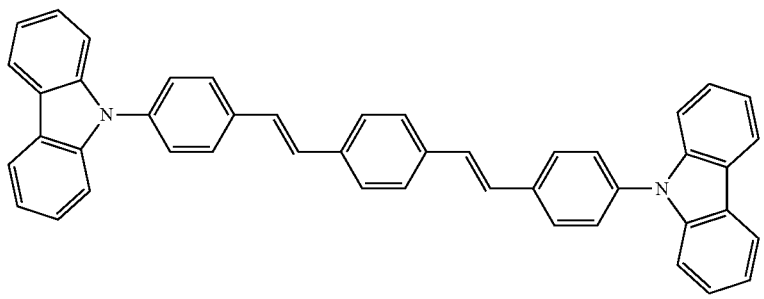
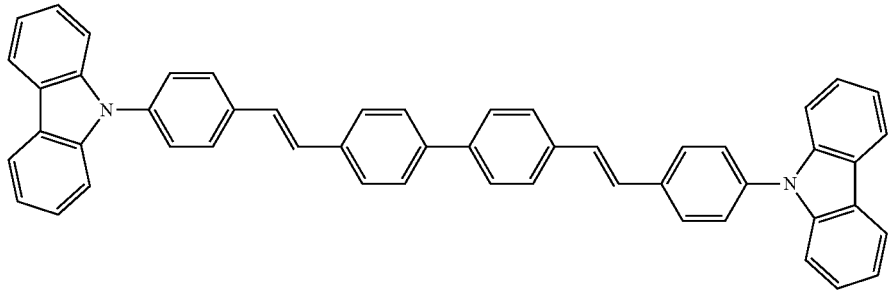
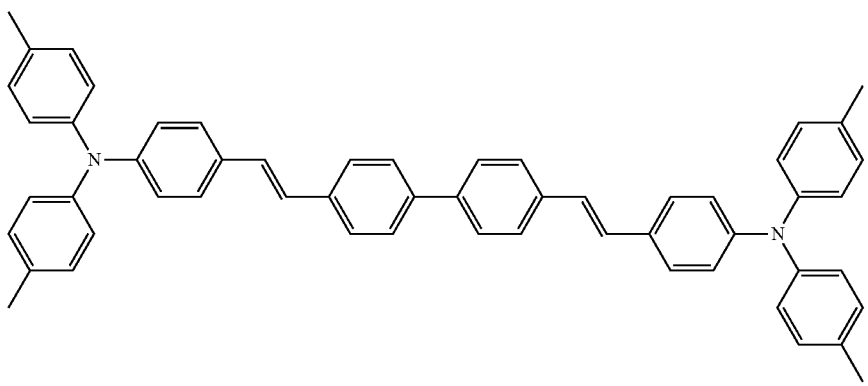
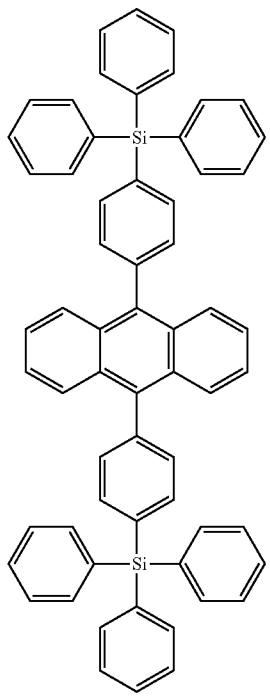

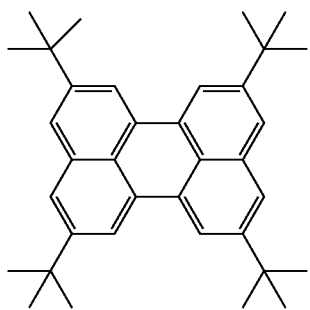
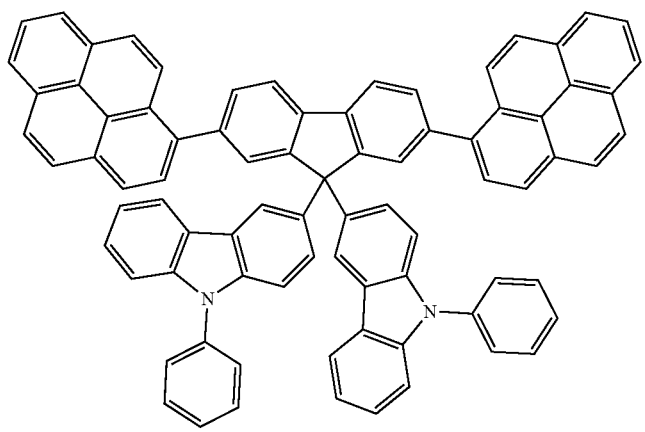
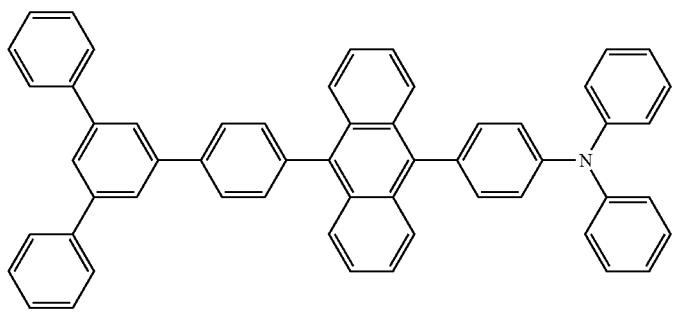

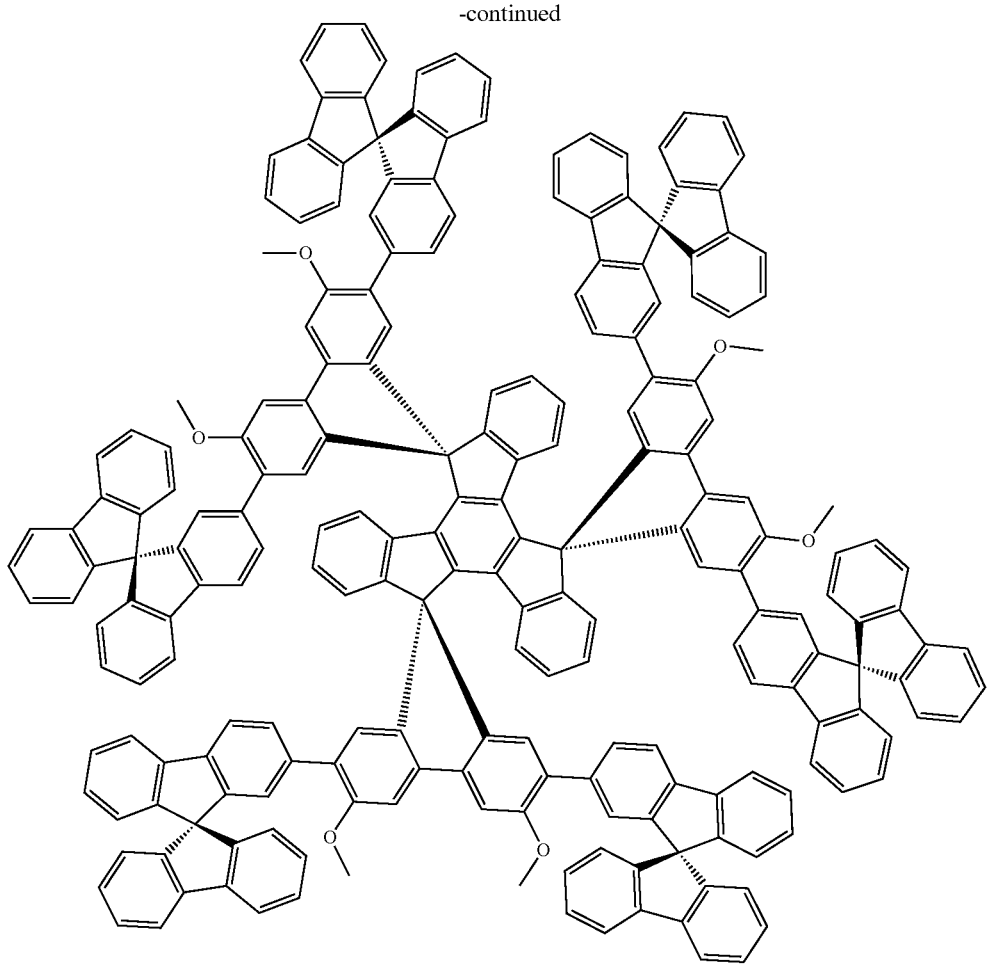
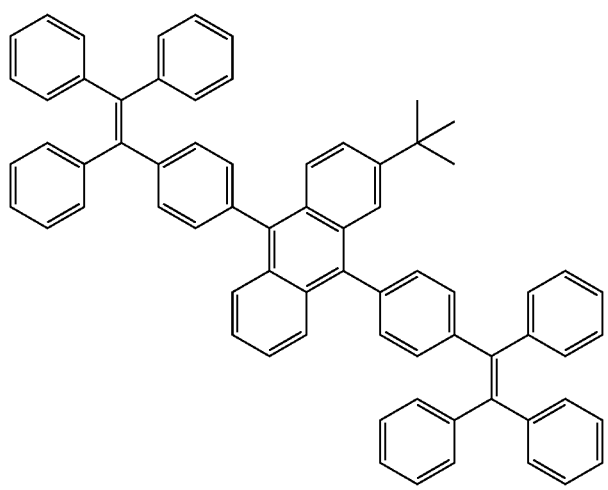

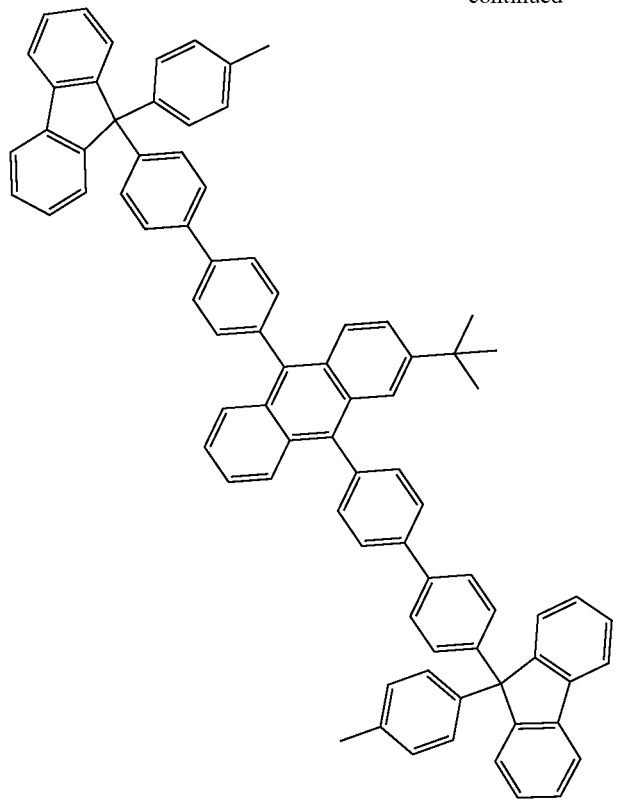
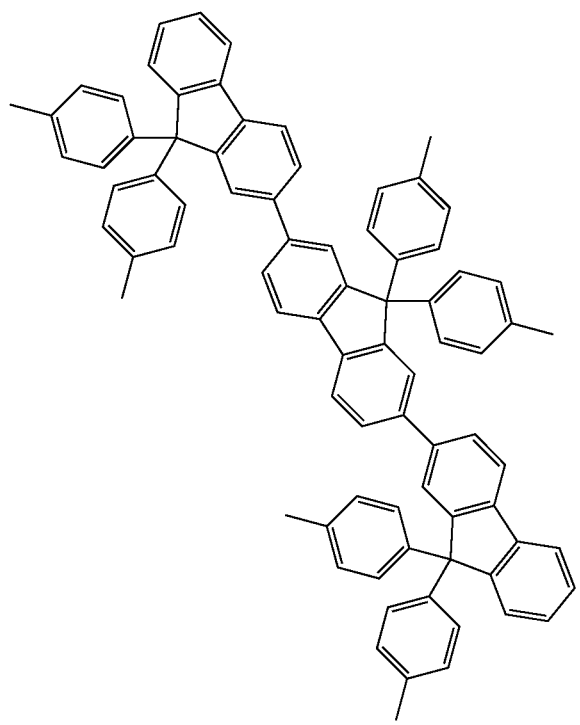

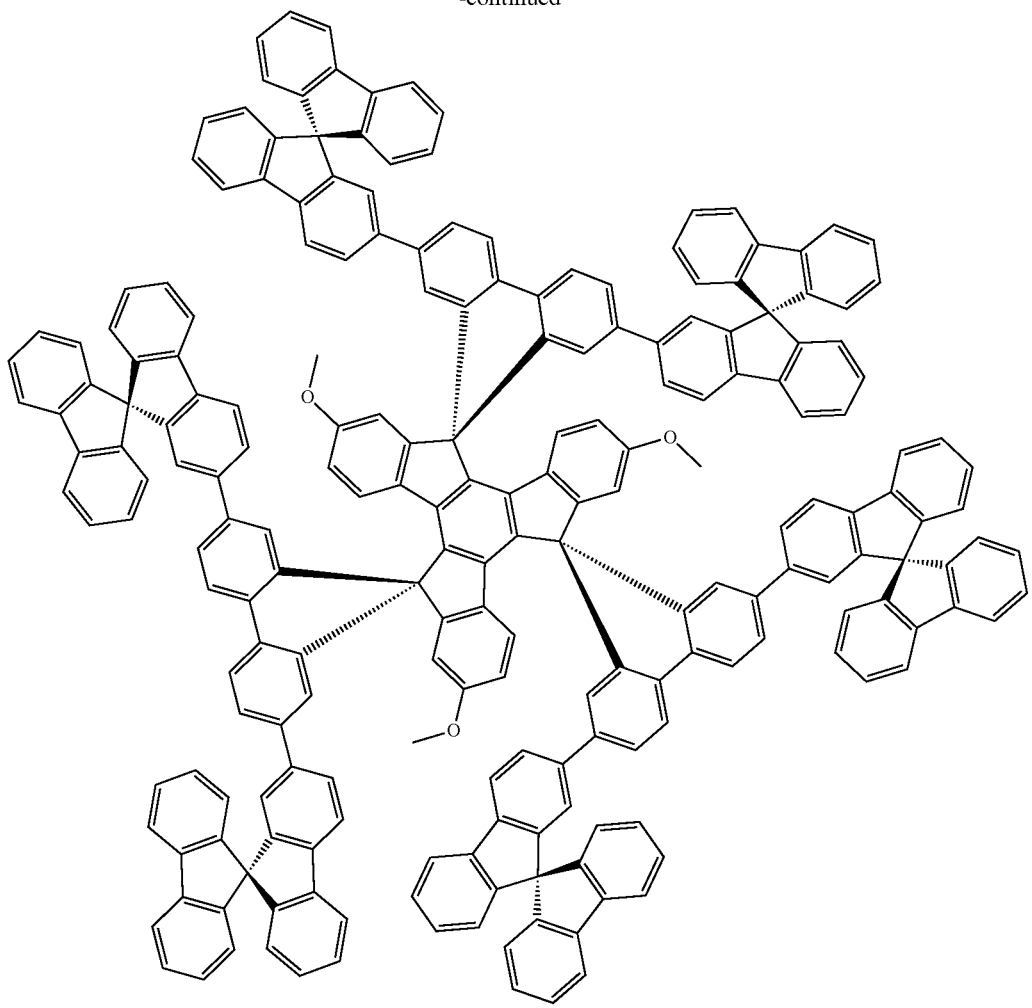
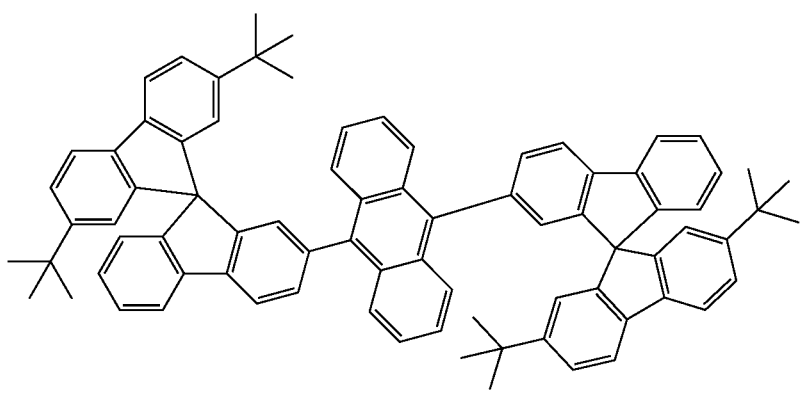

-continued
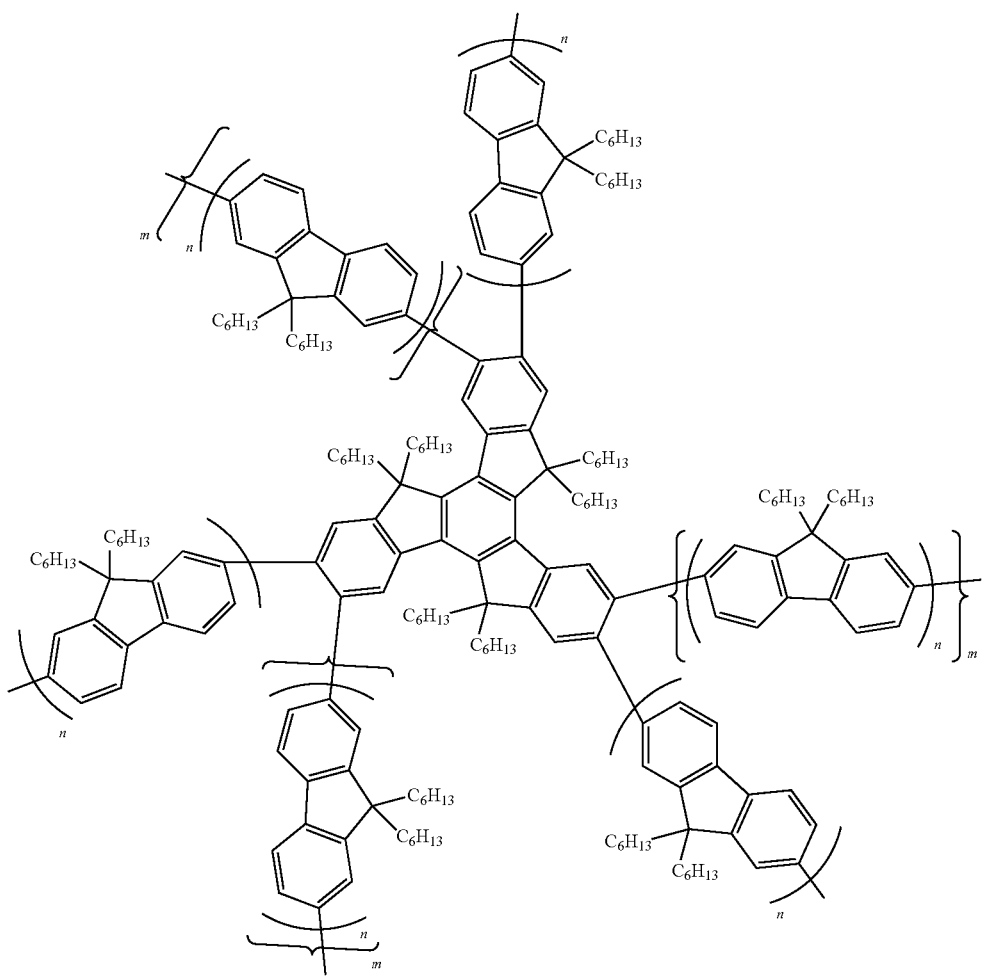
n = 1,2,3,4
m = 0,1
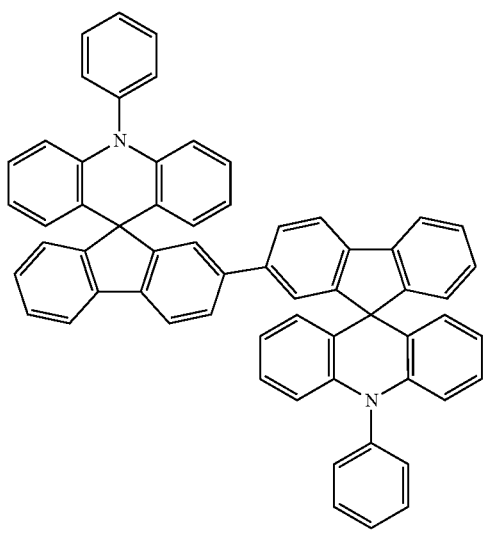

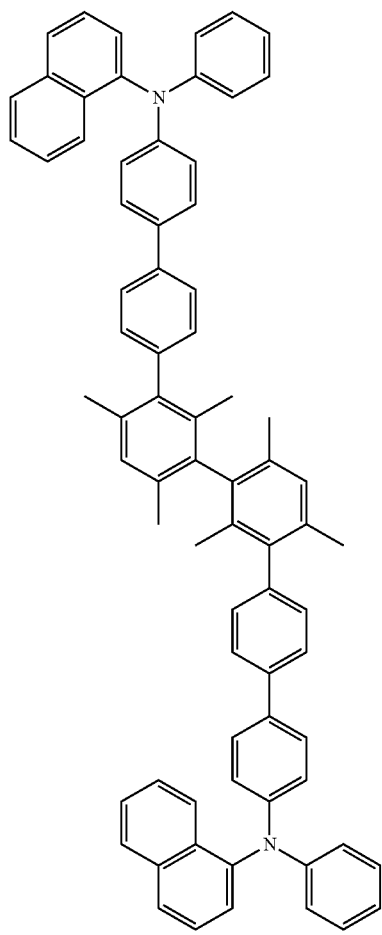
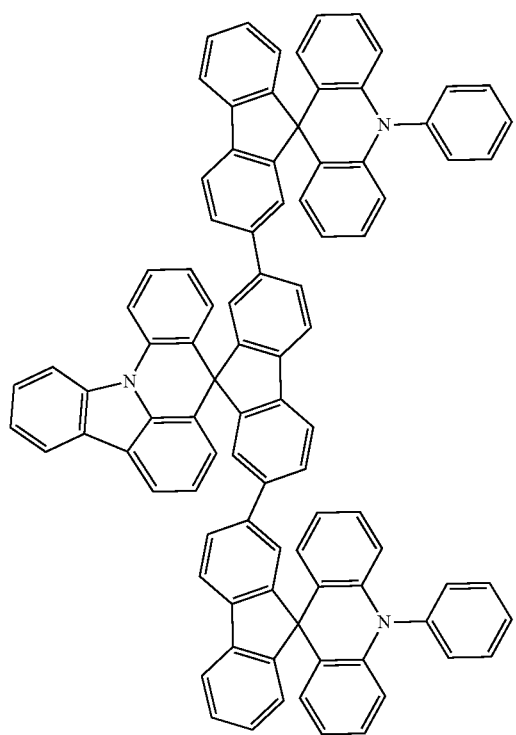

-continued
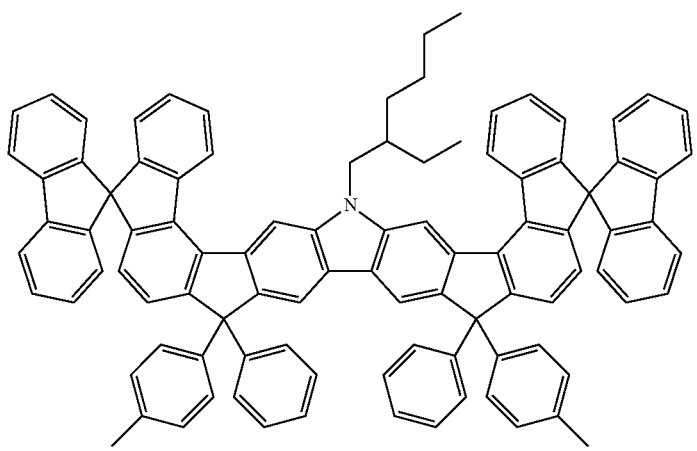
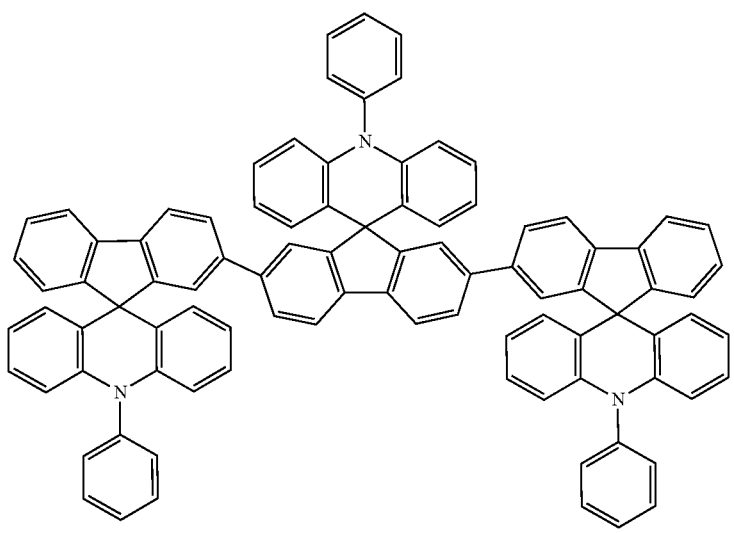

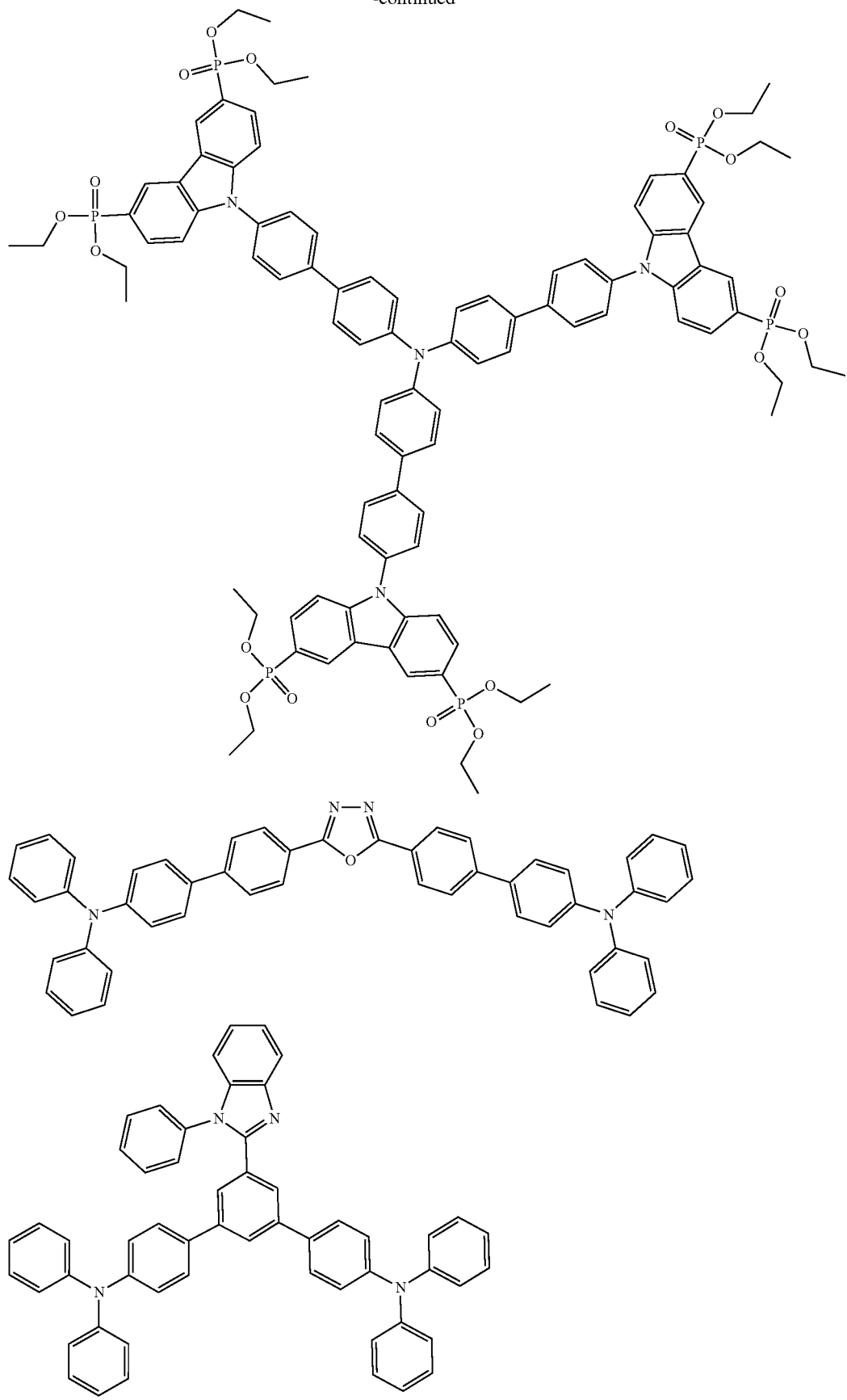

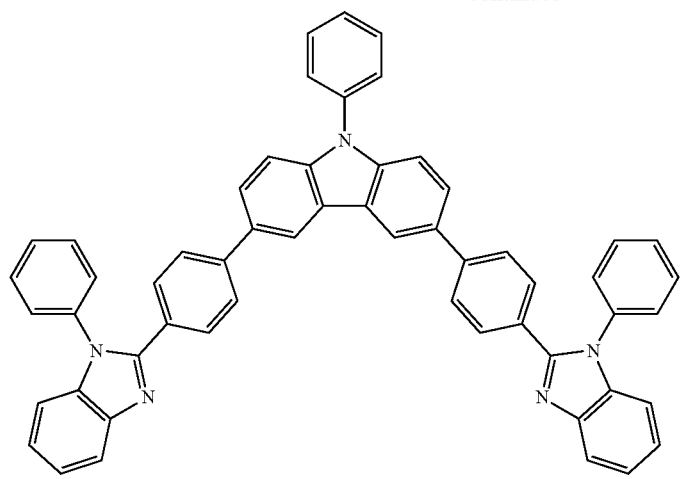
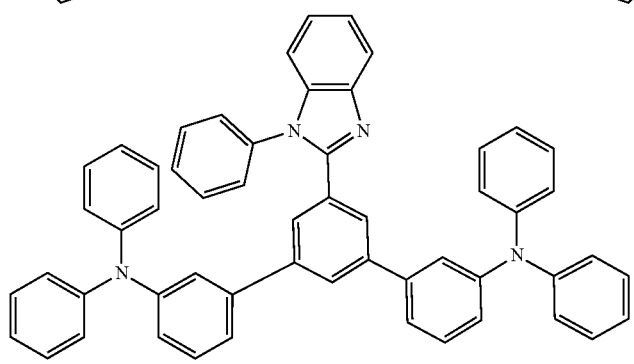
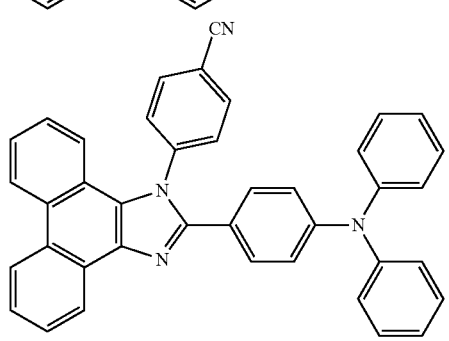
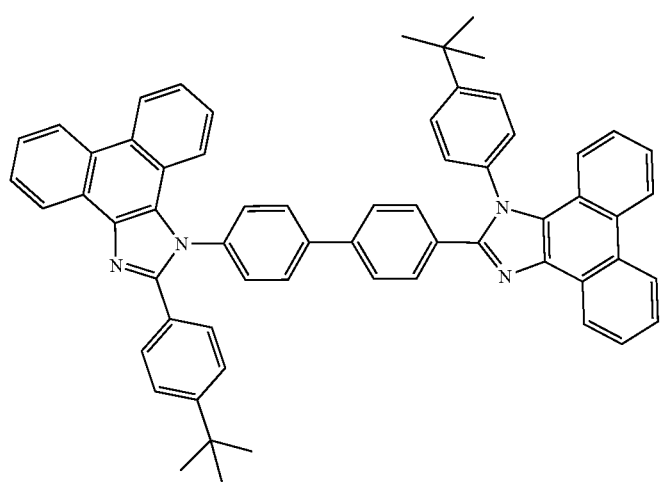

-continued
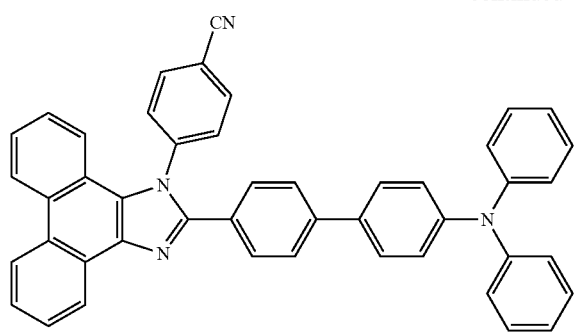
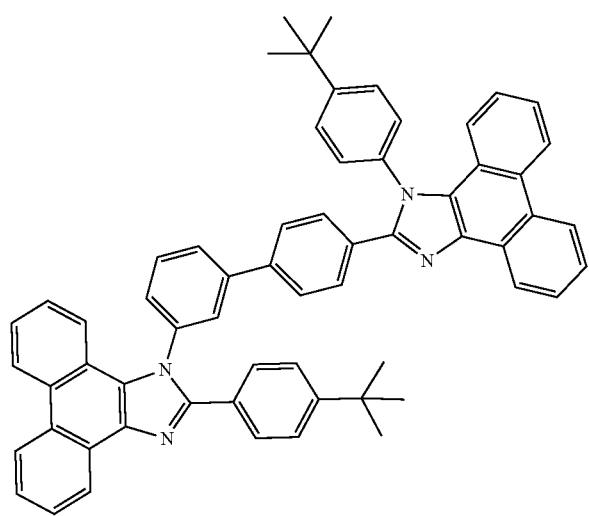

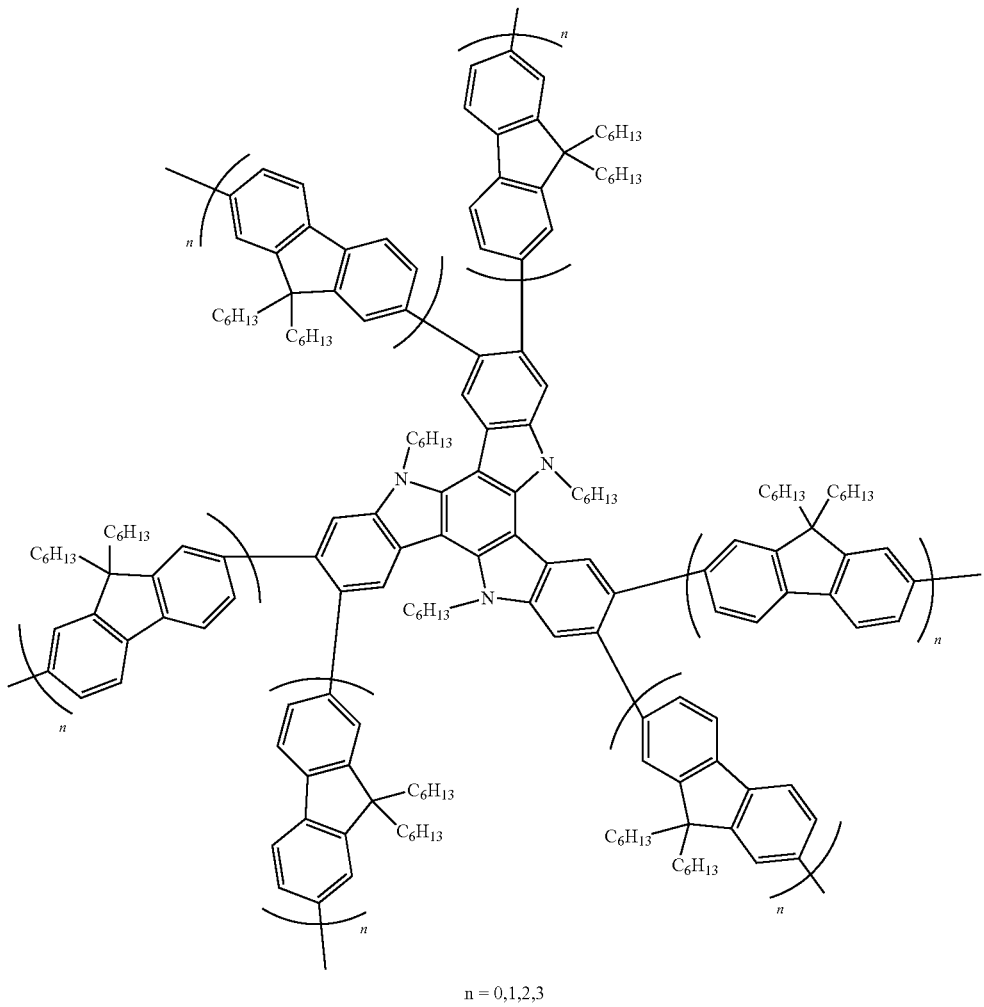
n = 0,1,2,3

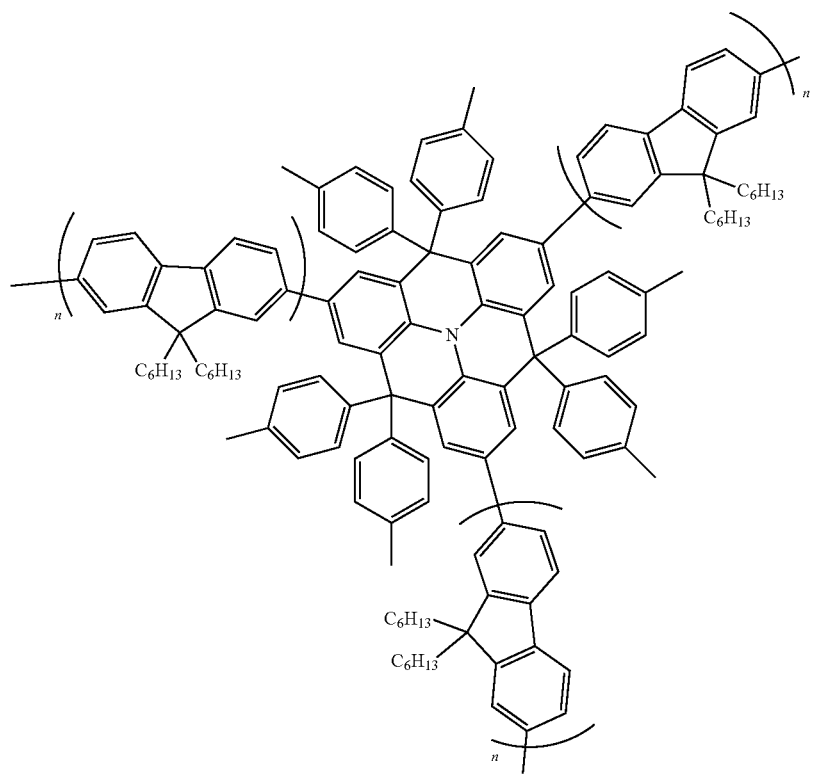
n = 2,3

-continued
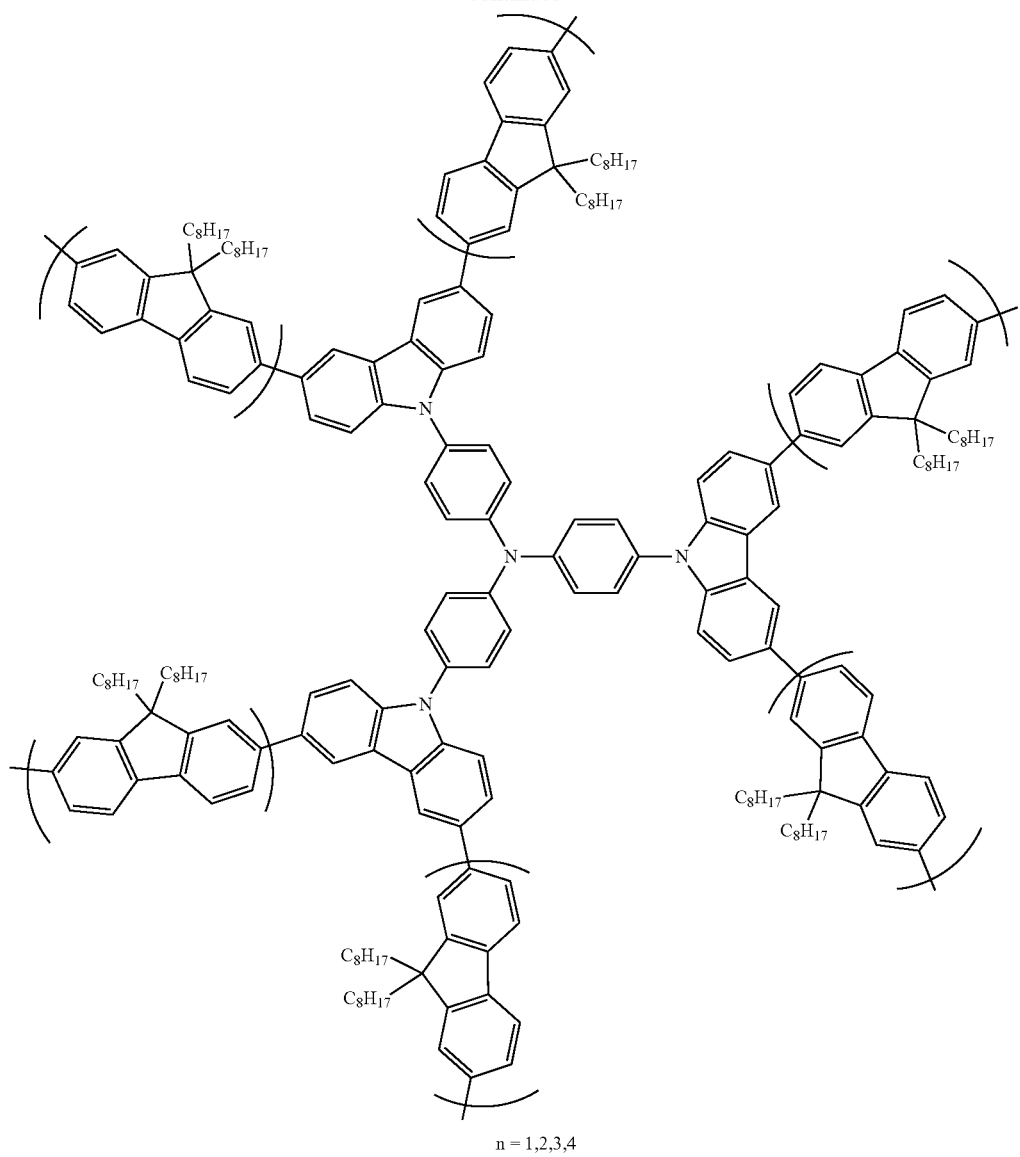
n = 1,2,3,4
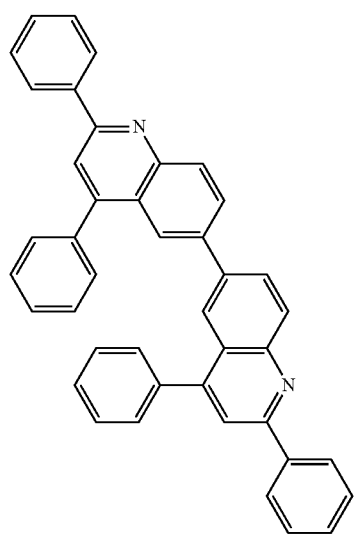

-continued
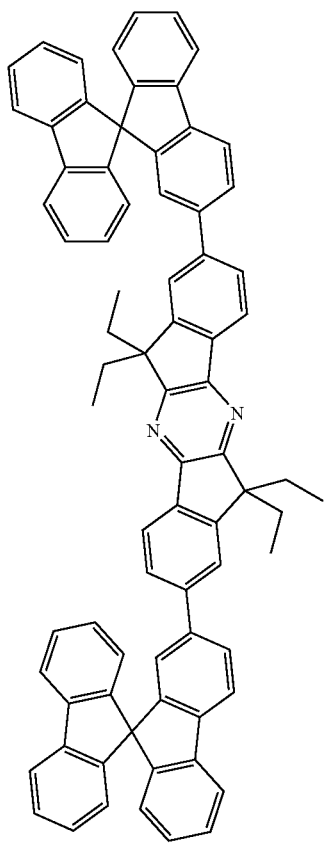
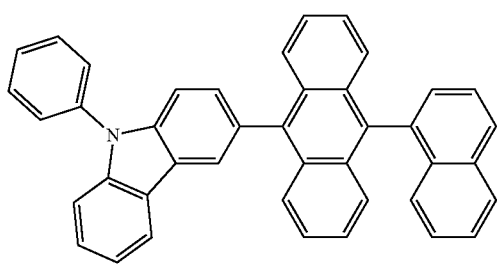

-continued
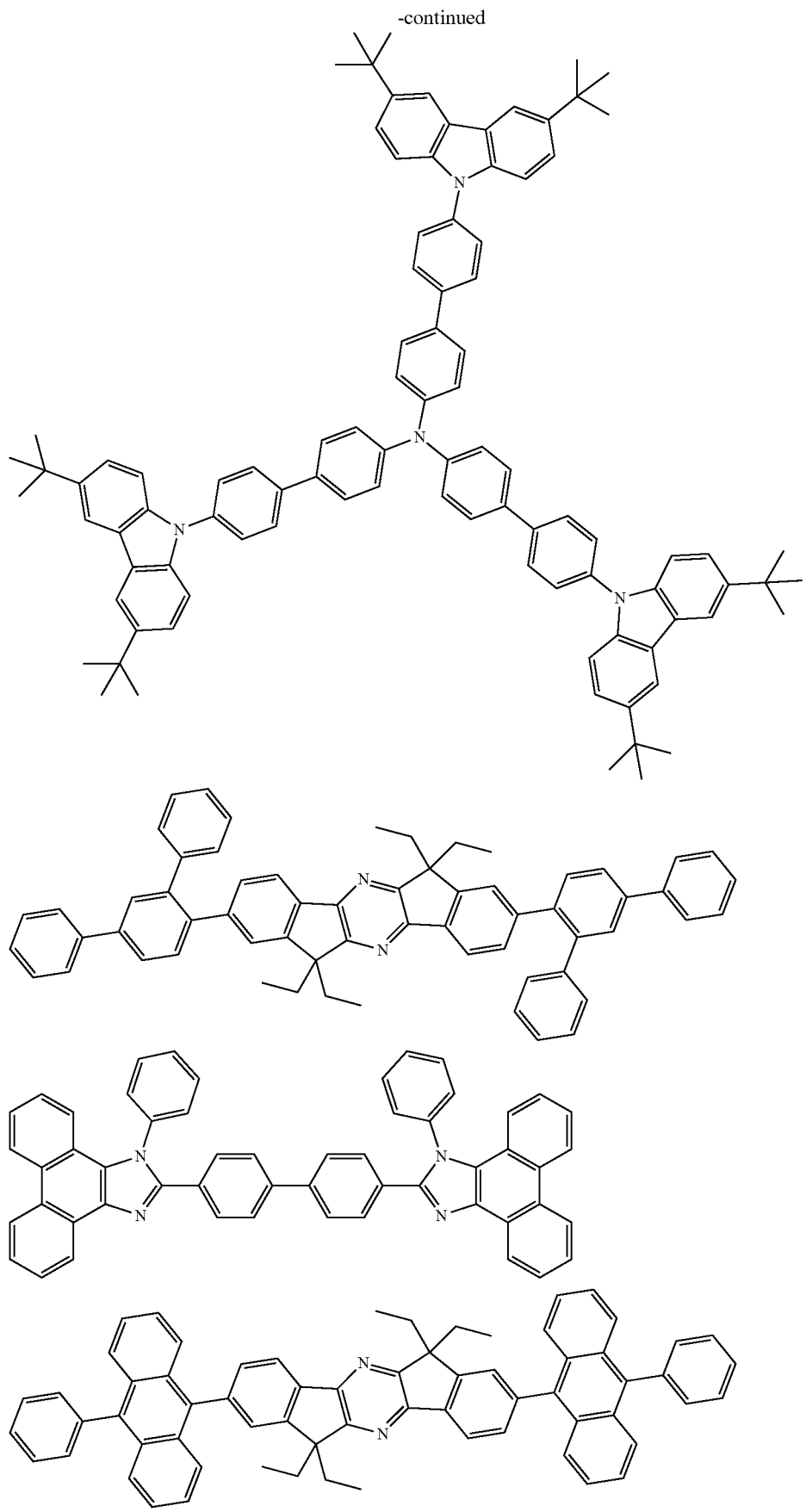

-continued
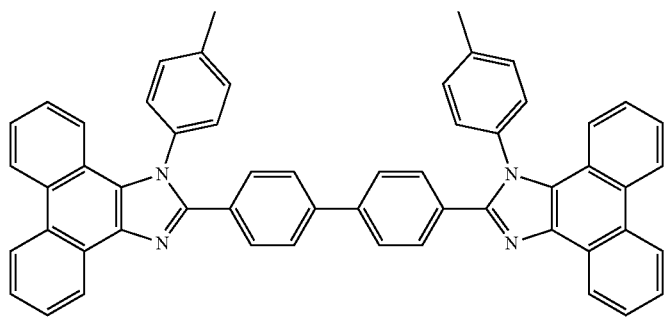
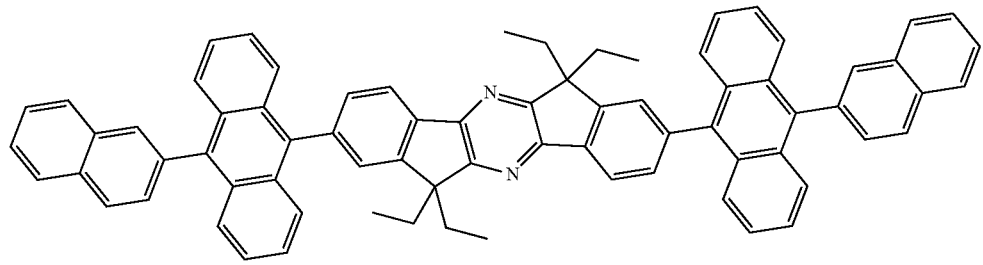
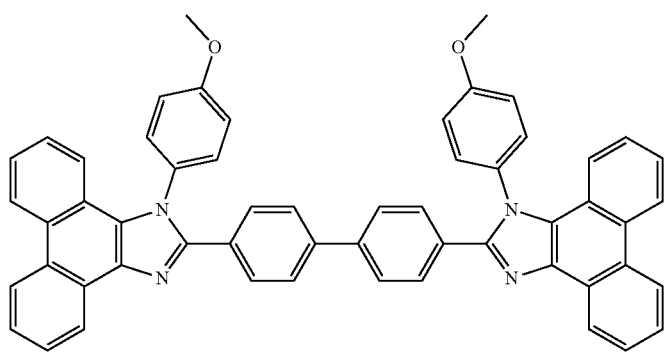
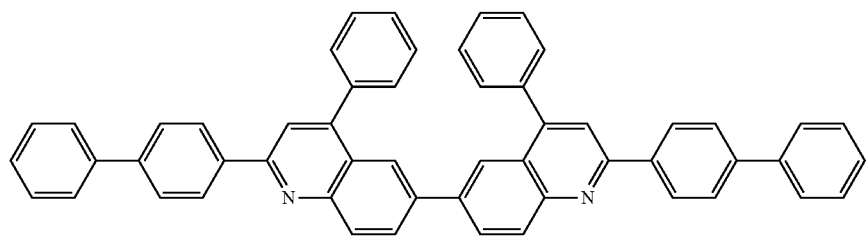
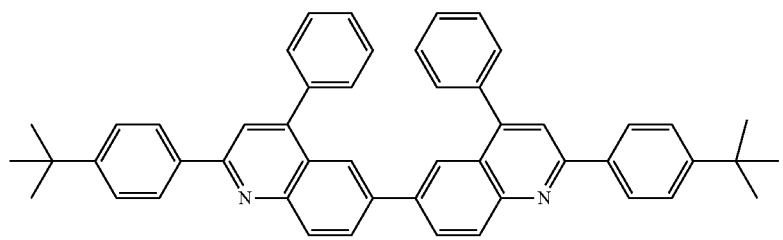
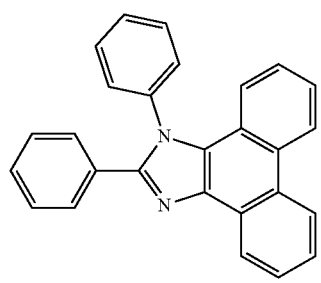

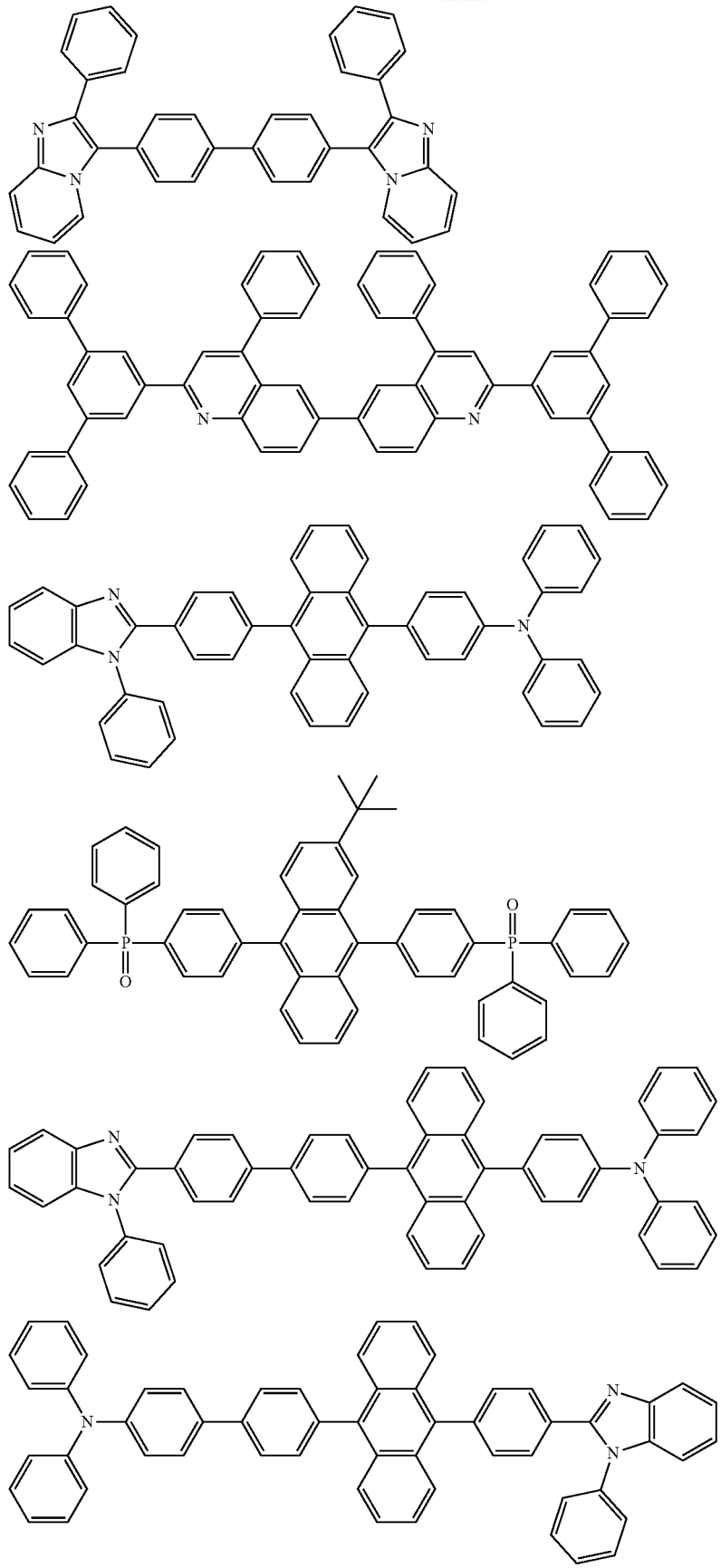

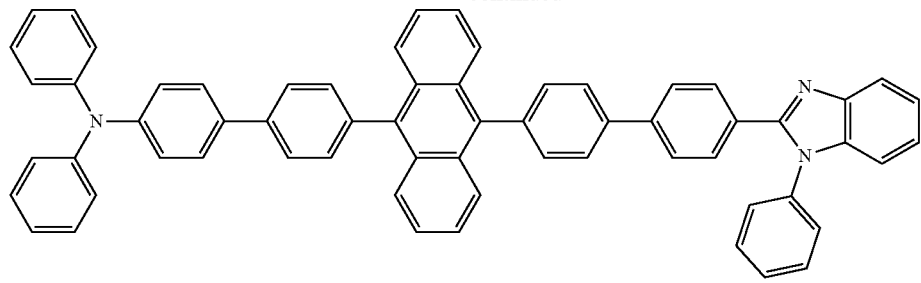
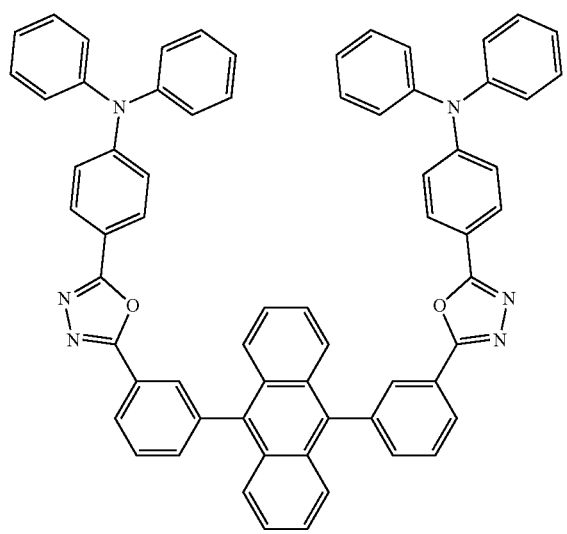
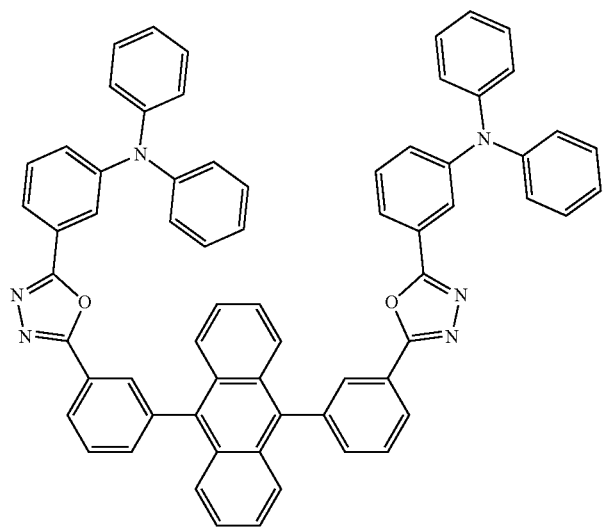

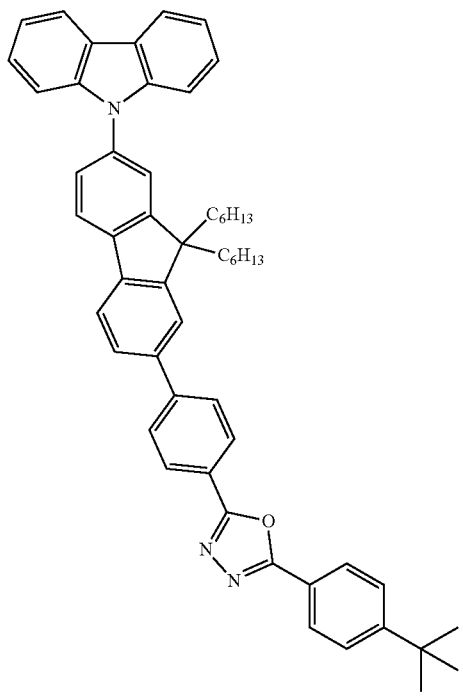
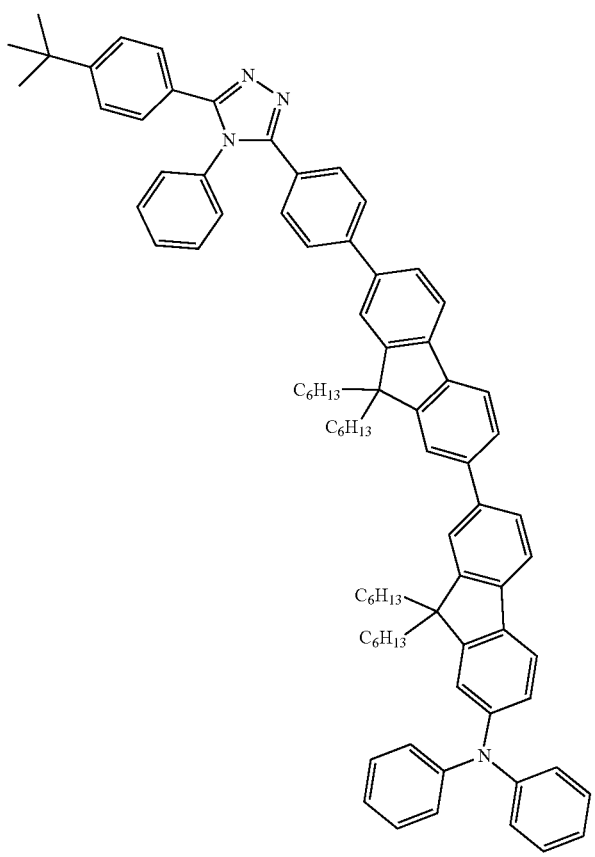

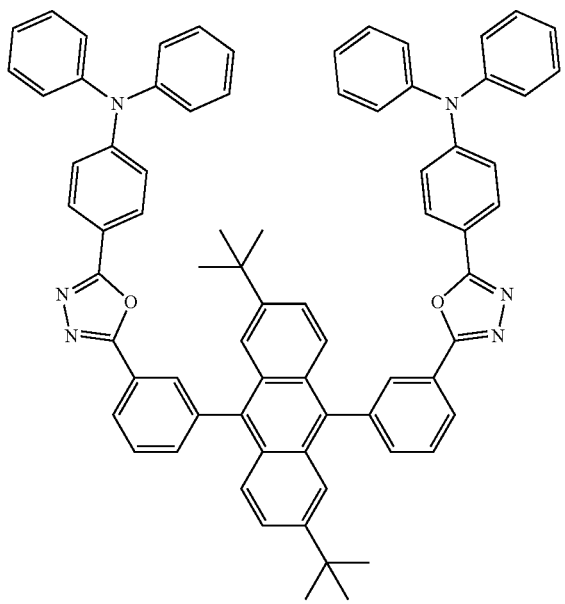
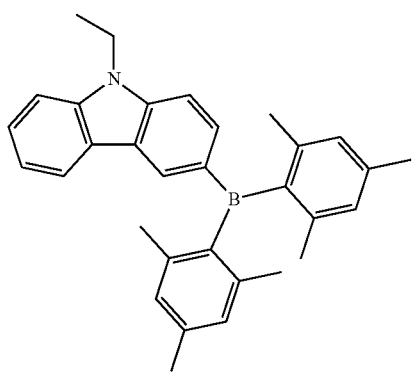

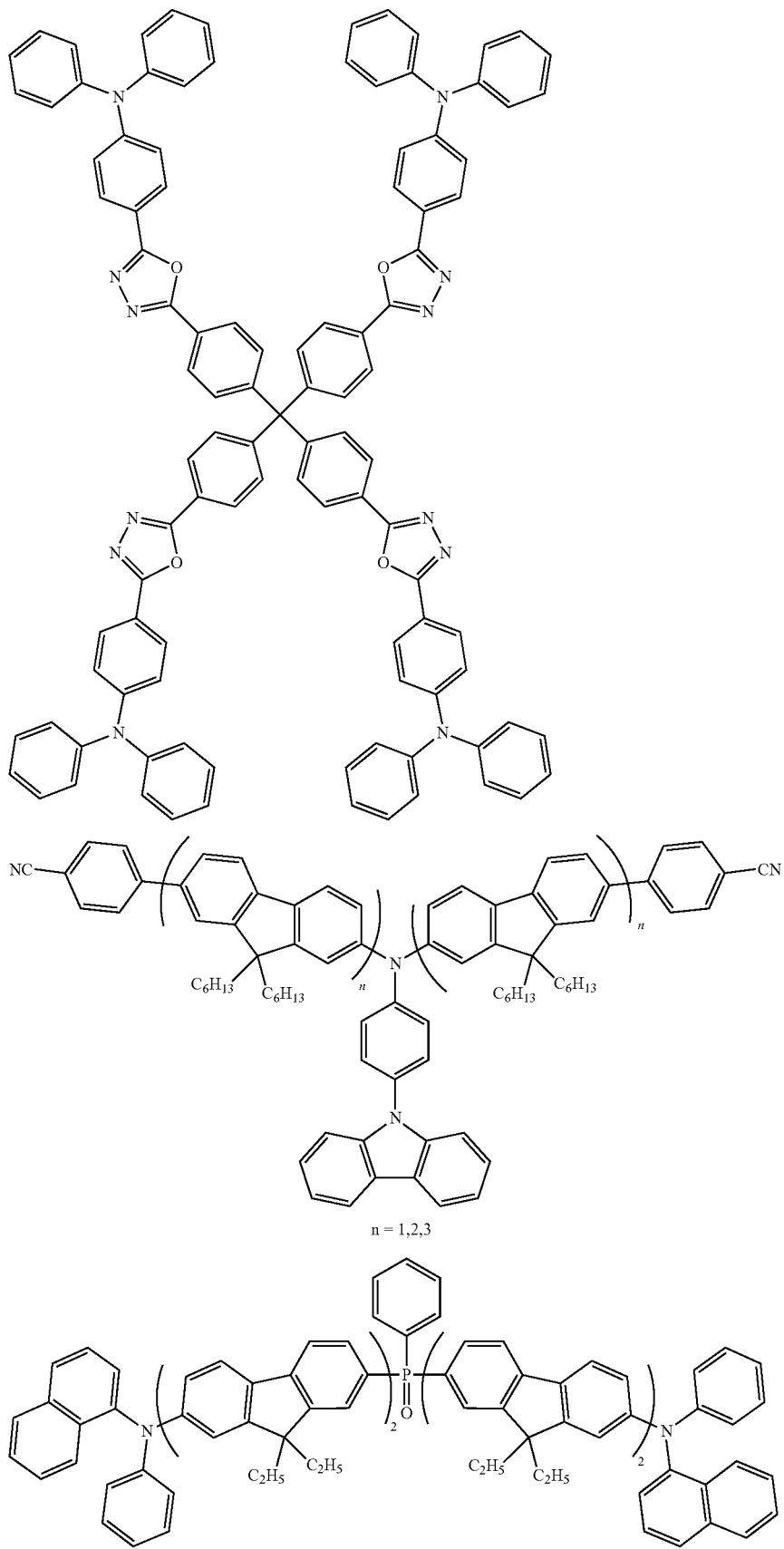
n = 1,2,3

-continued
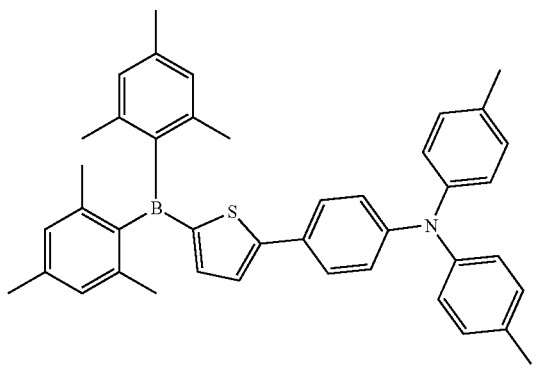
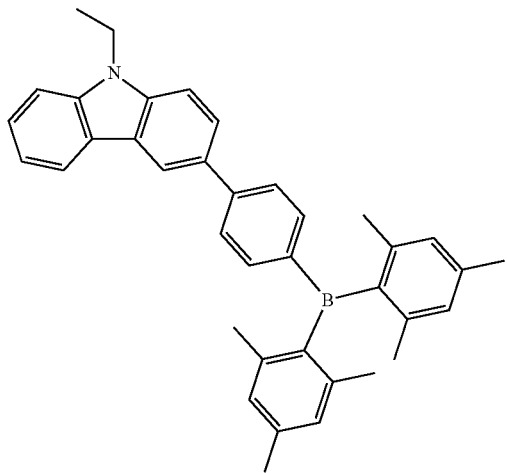
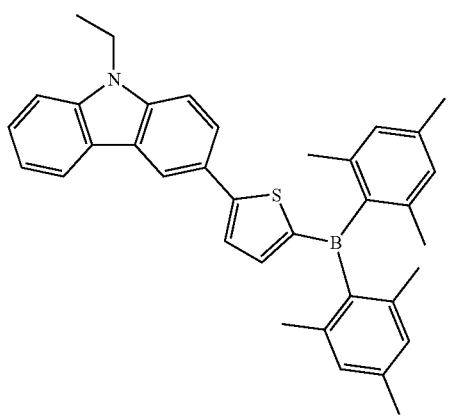
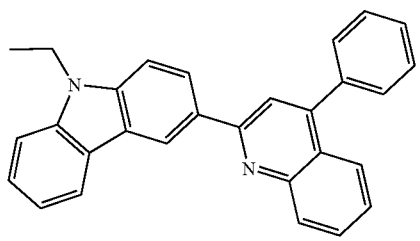

-continued
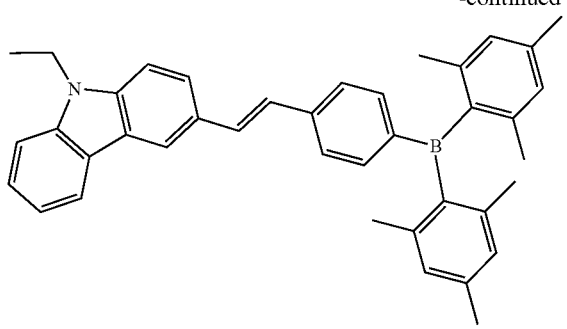
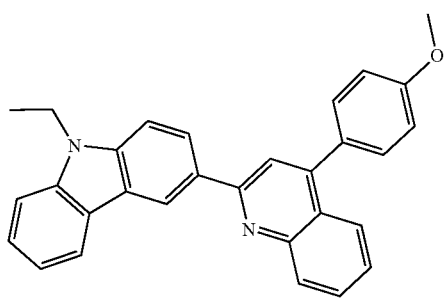
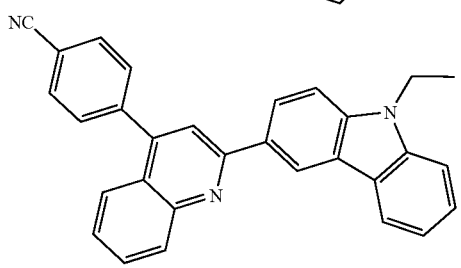
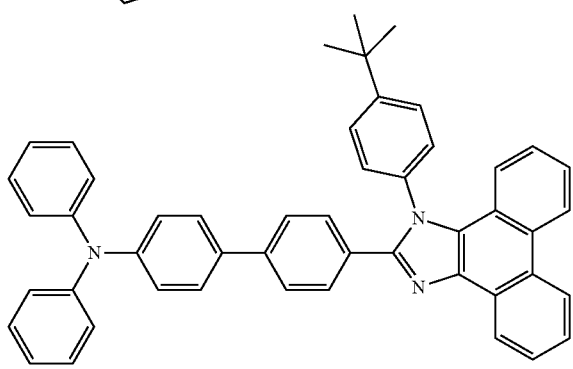
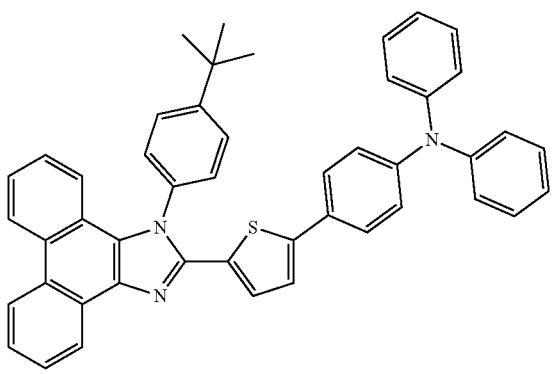

-continued
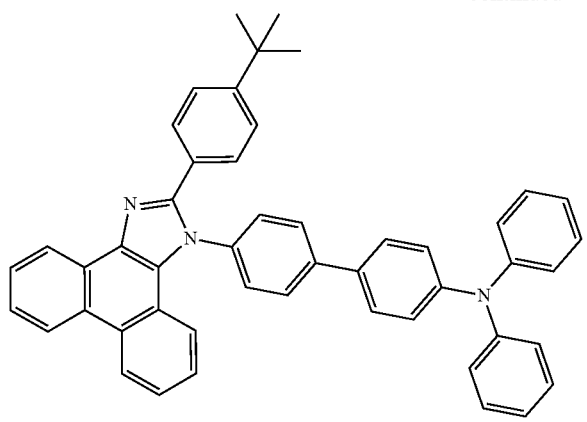
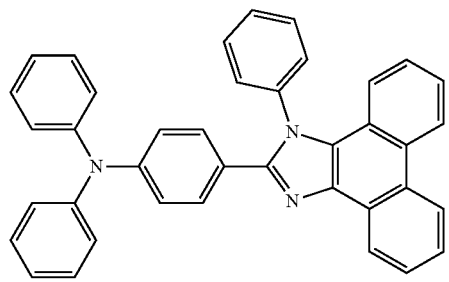
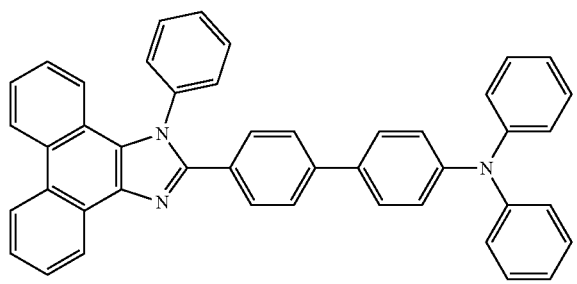
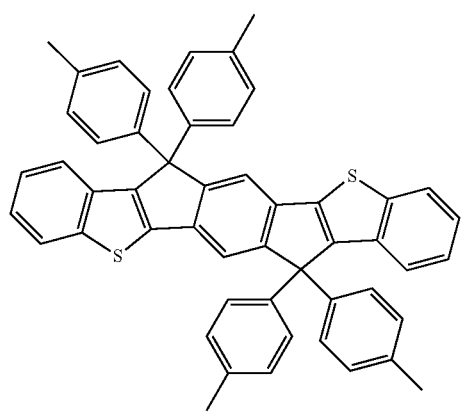

-continued
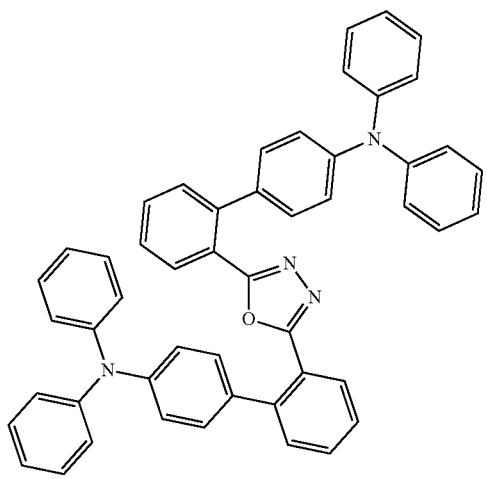
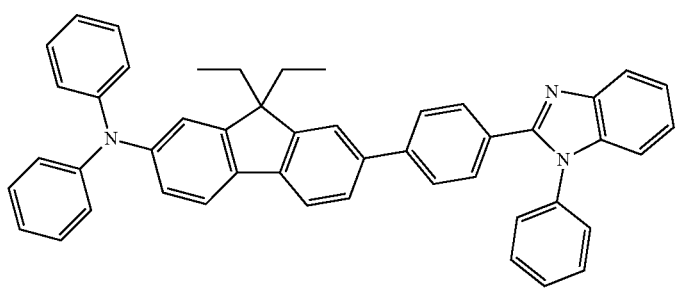
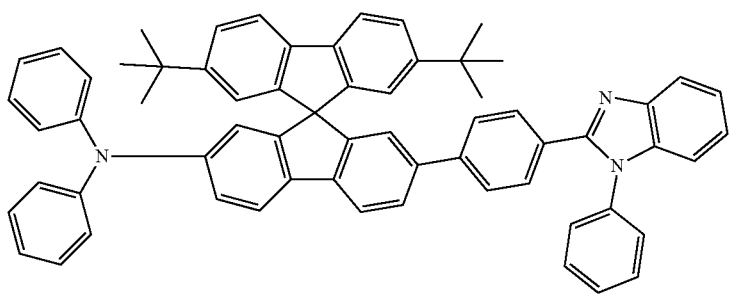

-continued
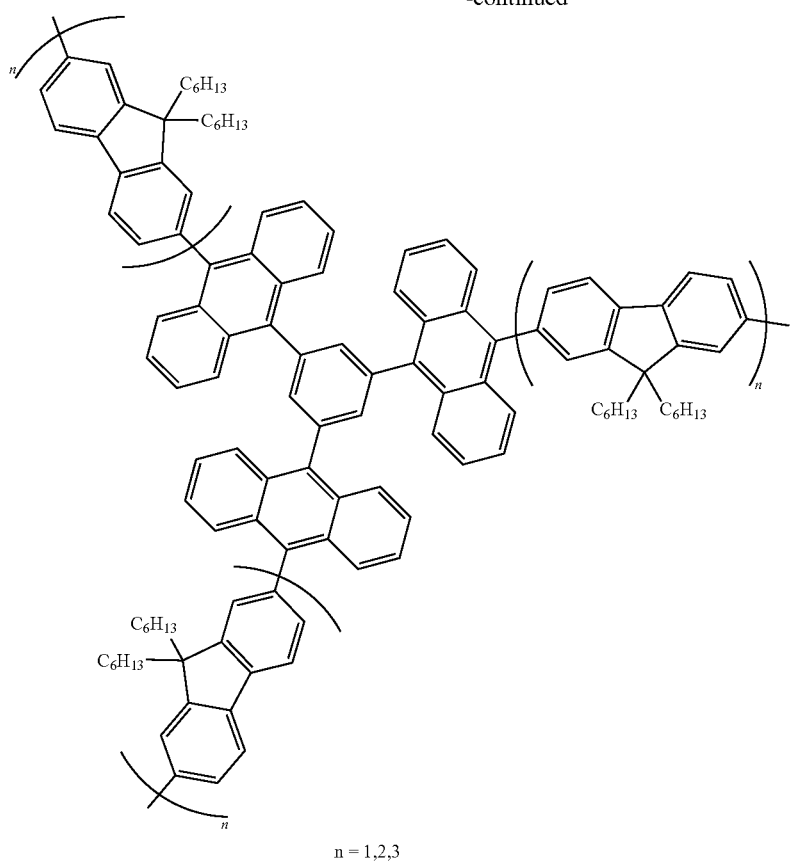
n = 1,2,3
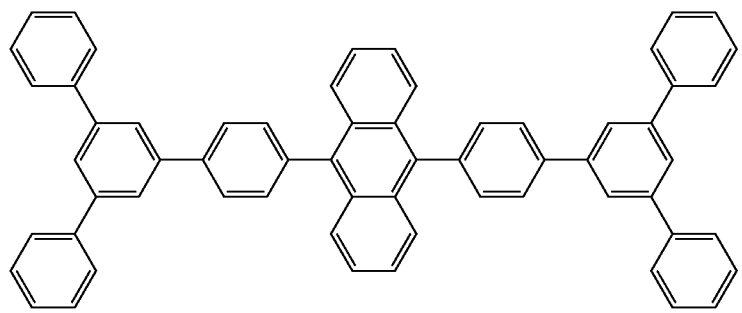
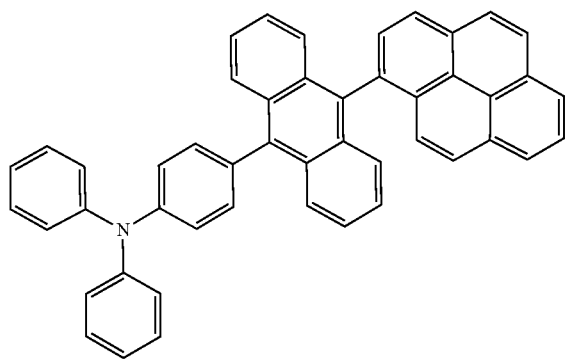

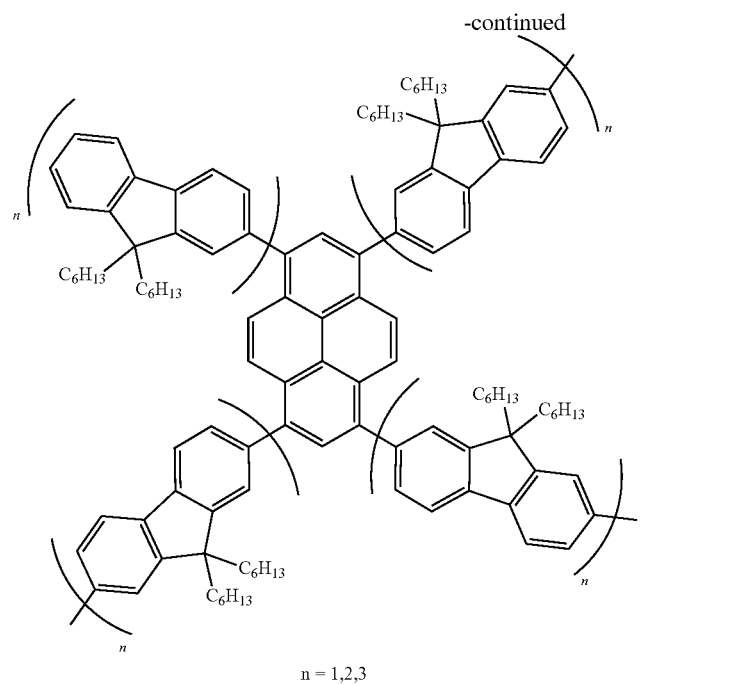
n = 1,2,3
In certain embodiments, the one further emitter molecule F is a blue fluorescence emitter selected from the following group:
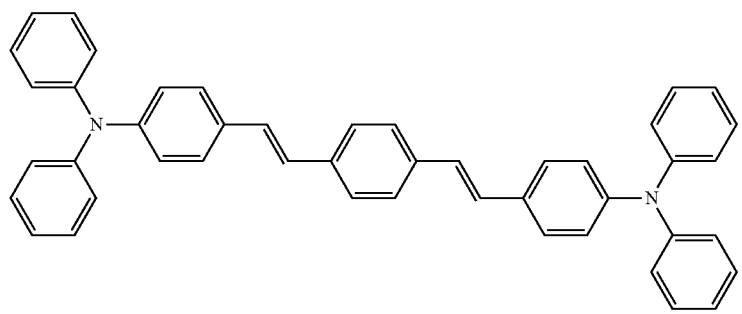
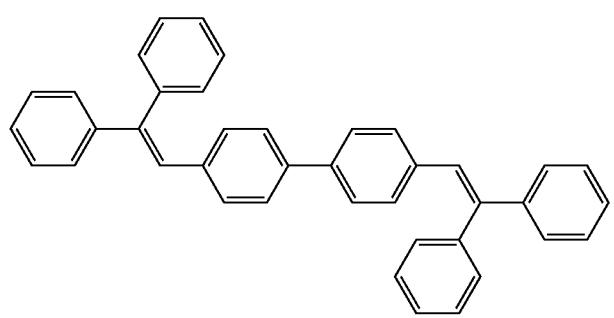

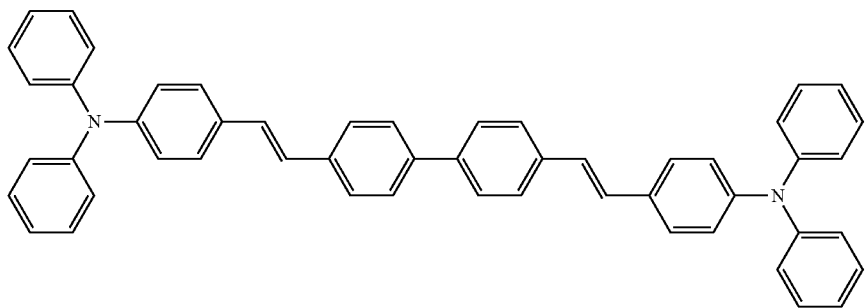
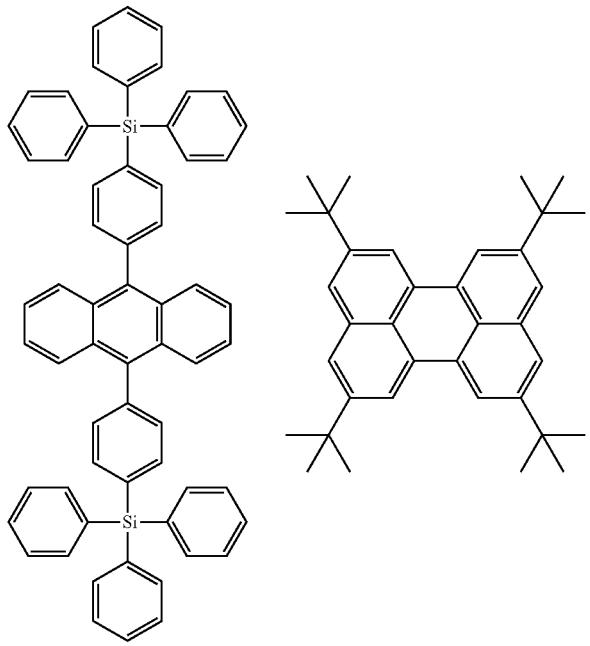
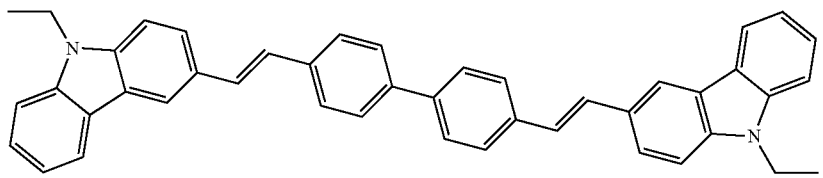
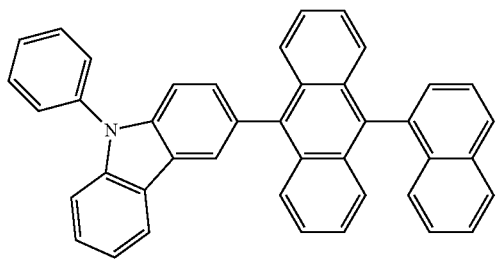
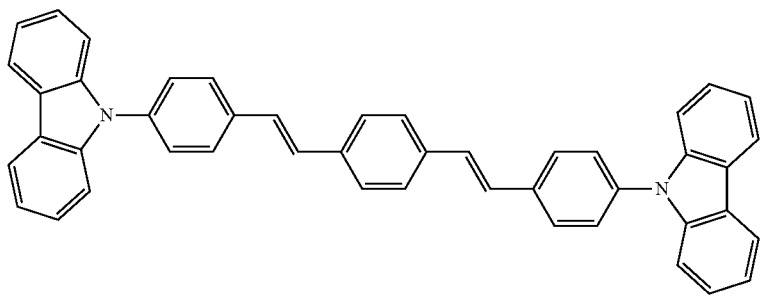

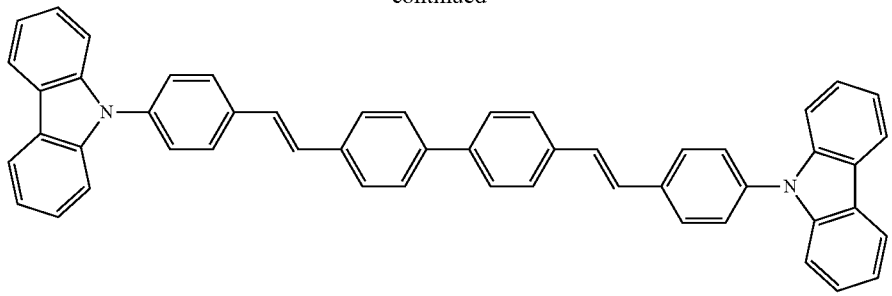

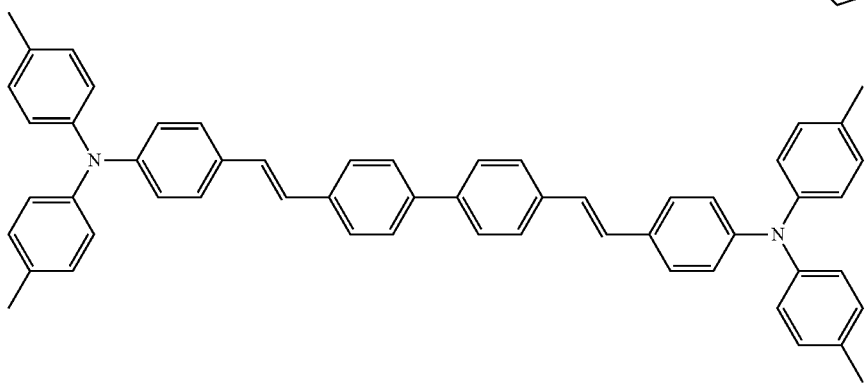

Composition Wherein the at Least One Further Emitter Molecule F is a Triplet-Triplet Annihilation (TTA) Fluorescence Emitter In one embodiment of the invention, the at least one further emitter molecule F is a triplet-triplet annihilation (TTA) emitter. In one embodiment, F is a blue TTA emitter selected from the following group:

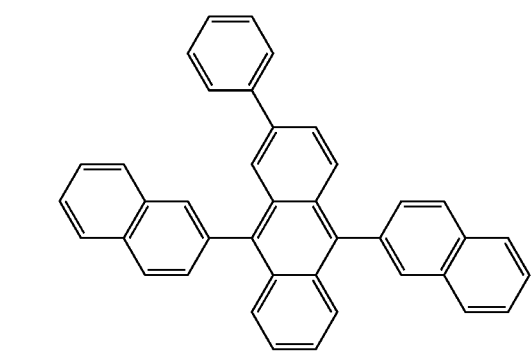

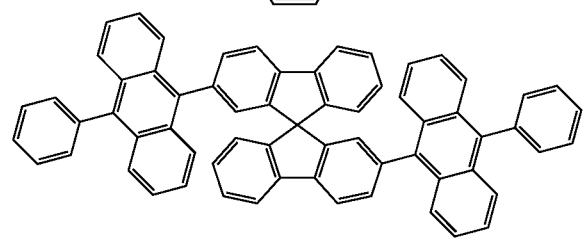

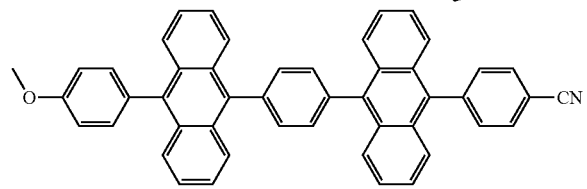

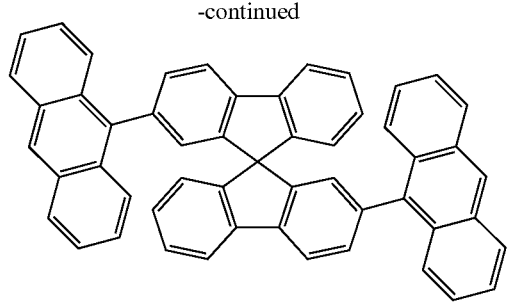

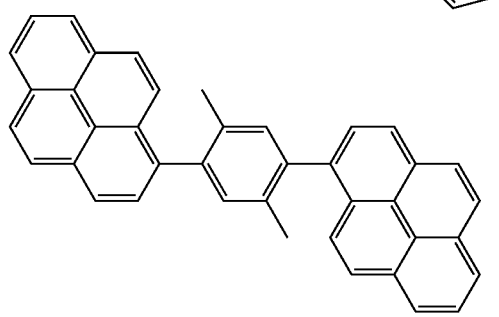

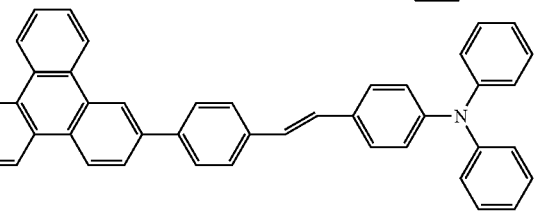

Composition Wherein the at Least One Further Emitter Molecule F is a Green Fluorescence Emitter In a further embodiment of the invention, the at least one further emitter molecule F is a fluorescence emitter, in particular a green fluorescence emitter.

In one embodiment, the at least one further emitter molecule F is a fluorescence emitter selected from the following group:
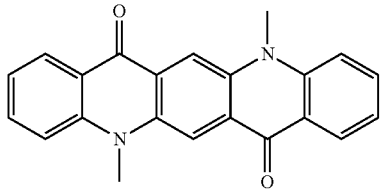
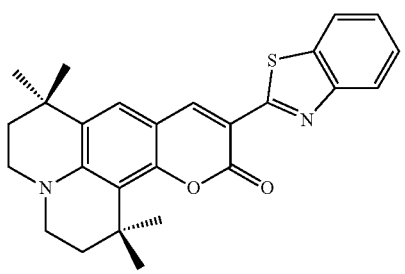
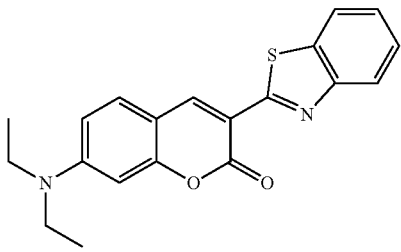
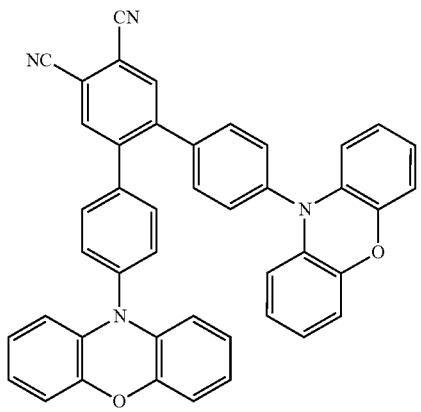
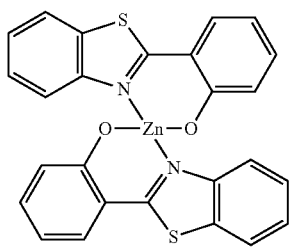
-continued
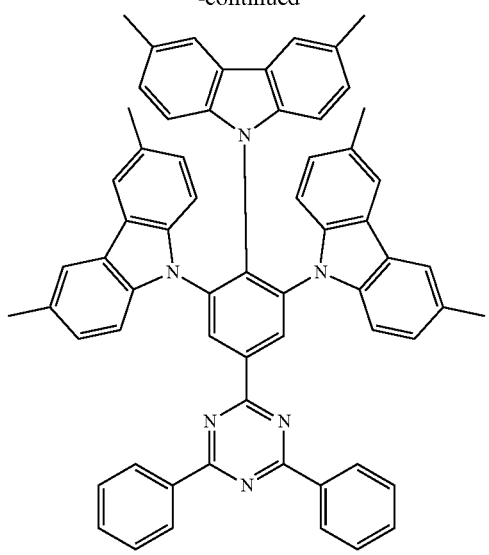
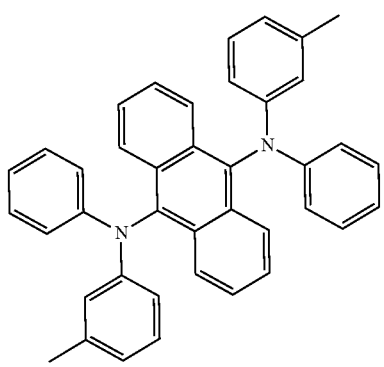
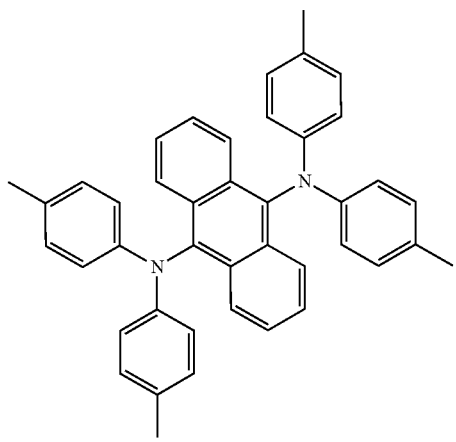

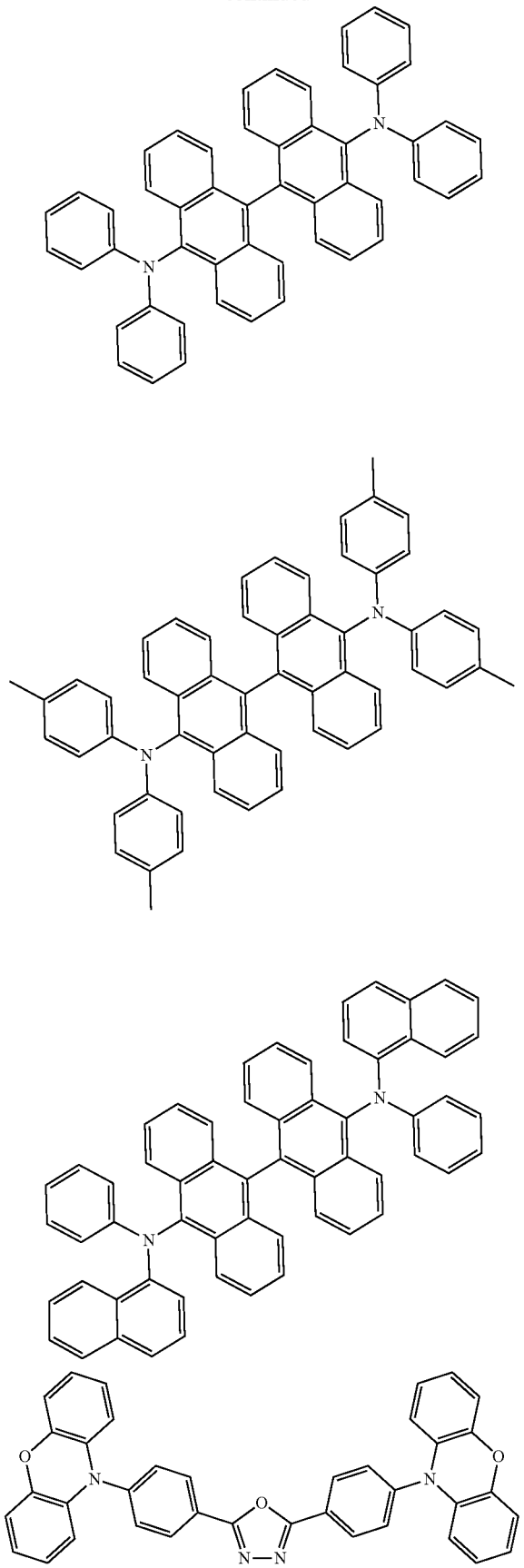

97
-continued
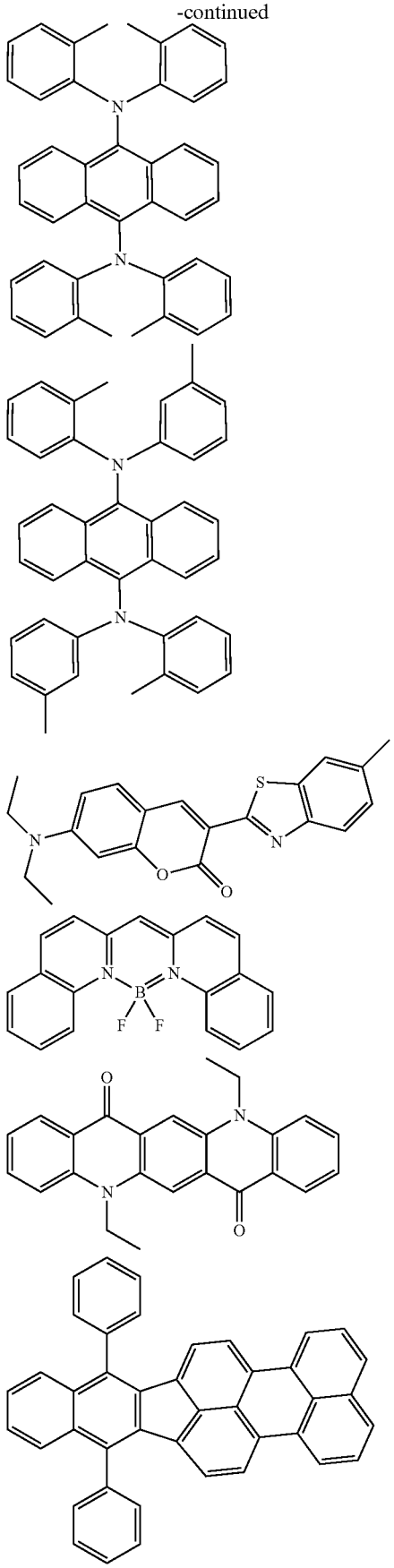
98
-continued
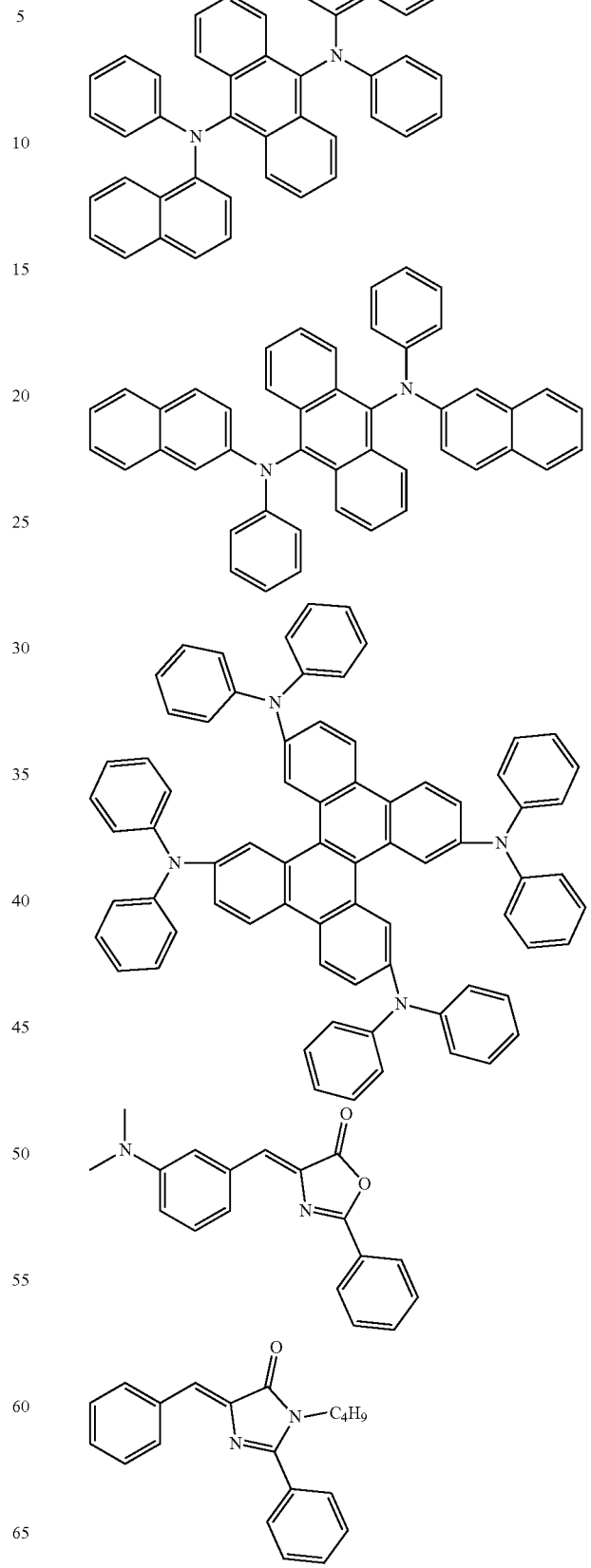

99
-continued

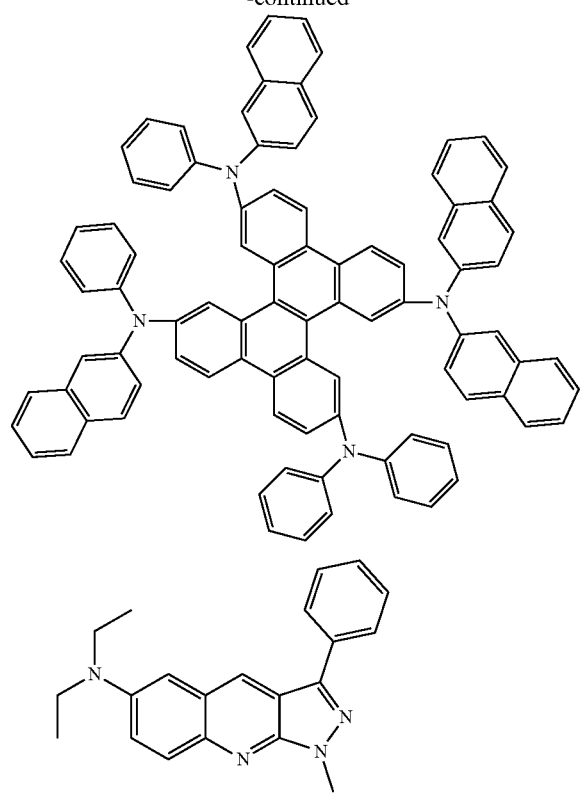

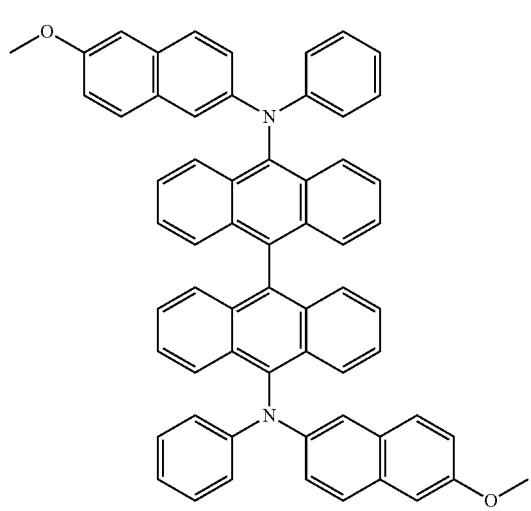

100
-continued

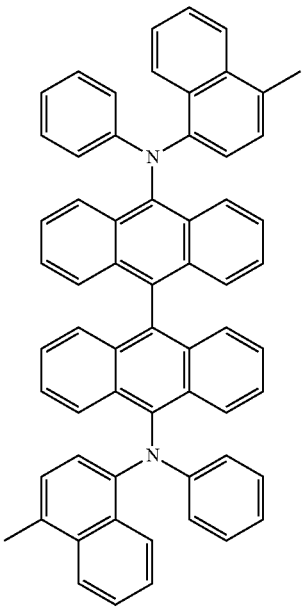

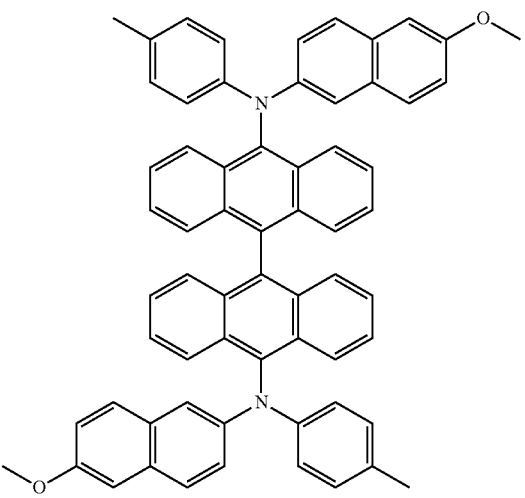

In a further embodiment of the invention, the composition has an emission peak in the visible or nearest ultraviolet range, i.e., in the range of a wavelength of from 380 to 800 nm, in particular between 485 nm and 590 nm, preferably between 505 nm and 565 nm, even more preferably between 515 nm and 545 nm.

Composition Wherein the at Least One Further Emitter Molecule F is a Red Fluorescence Emitter In a further embodiment of the invention, the at least one further emitter molecule F is a fluorescence emitter, in particular a red fluorescence emitter.

In one embodiment, the at least one further emitter molecule F is a fluorescence emitter selected from the following group:
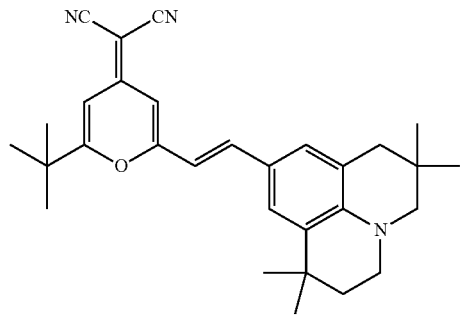
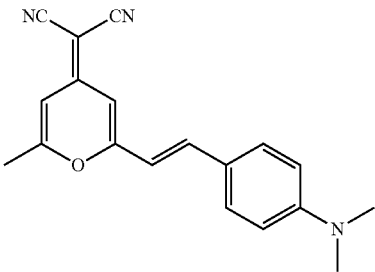
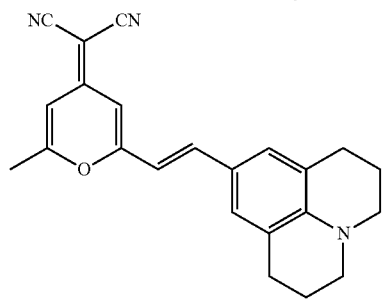
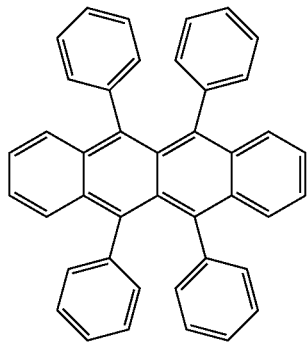
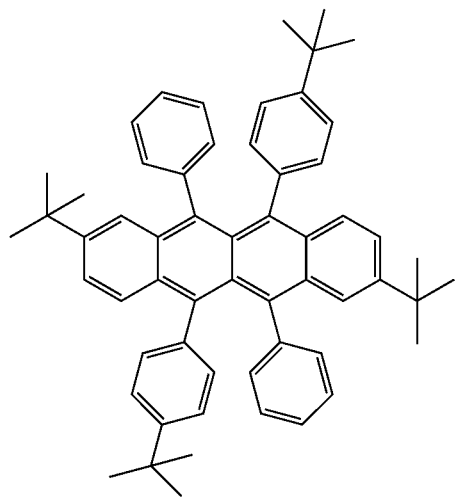
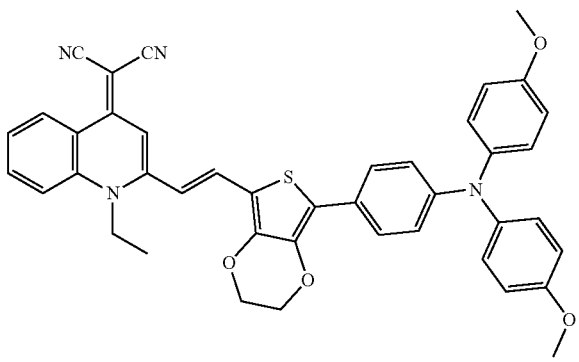
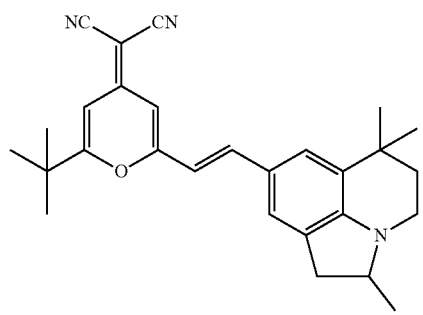
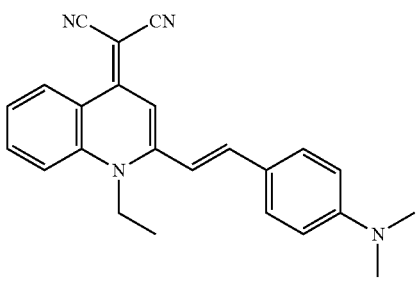

103
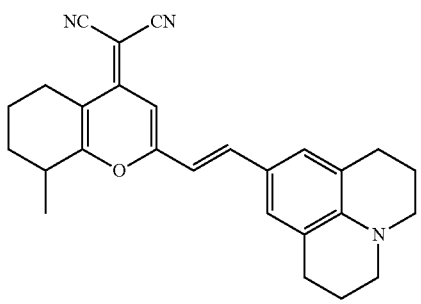
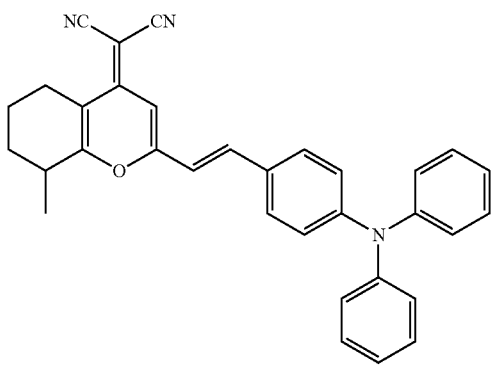
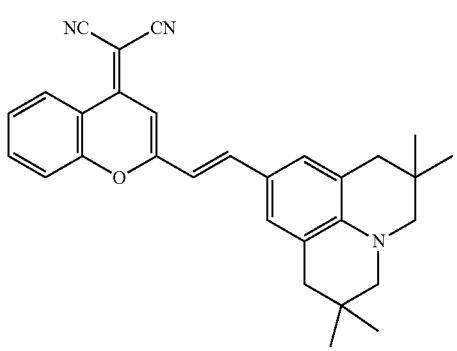
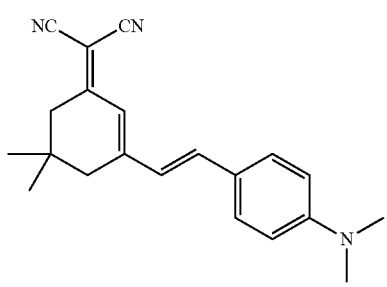
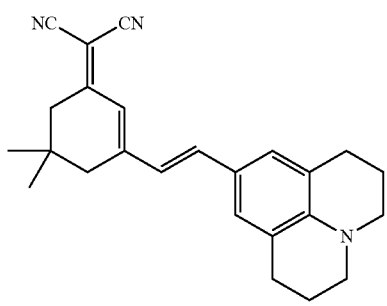
104
-continued
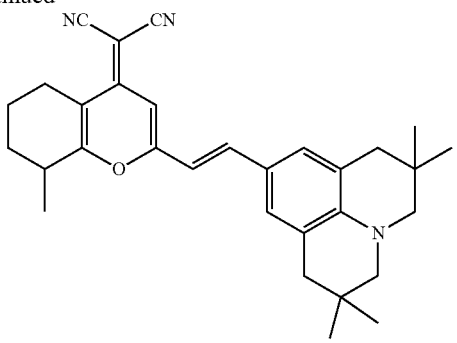
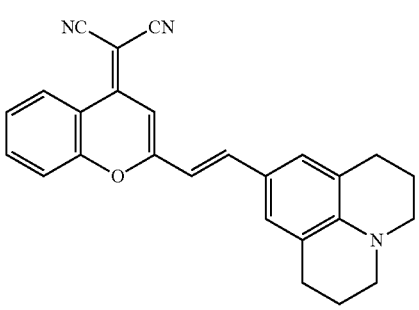
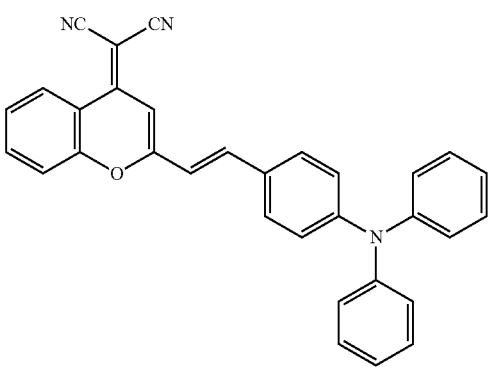
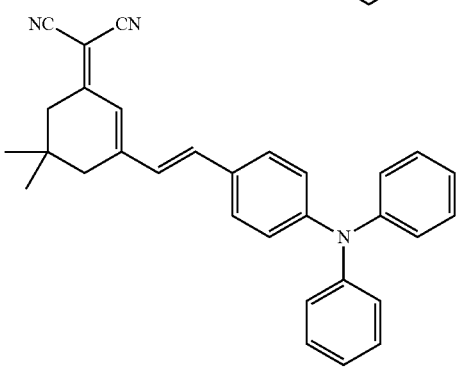
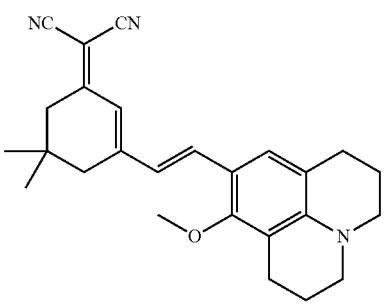

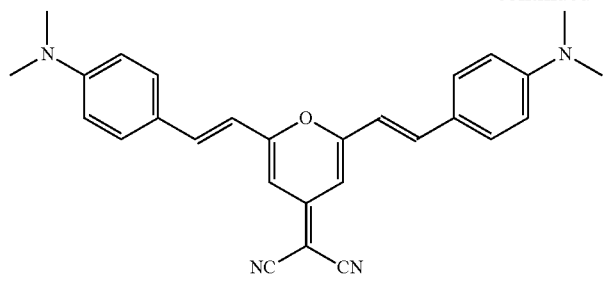
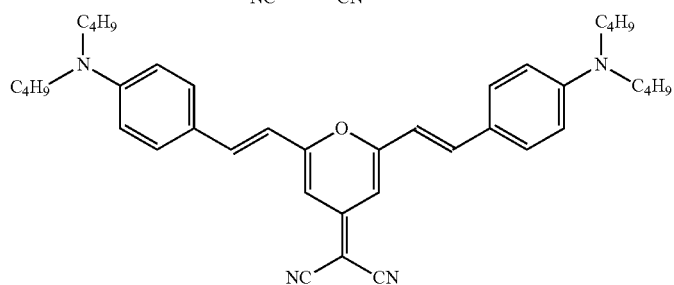
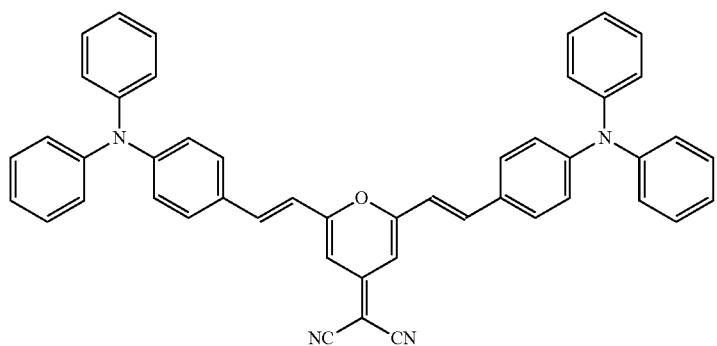
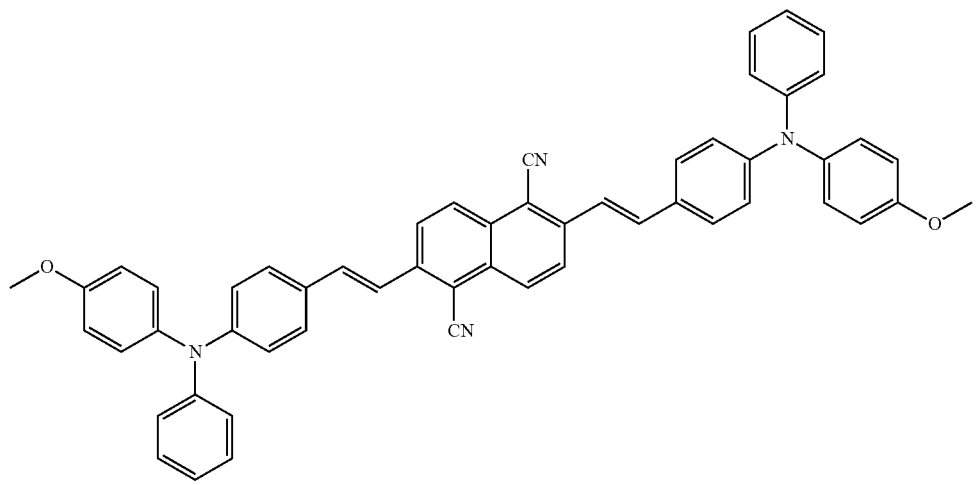
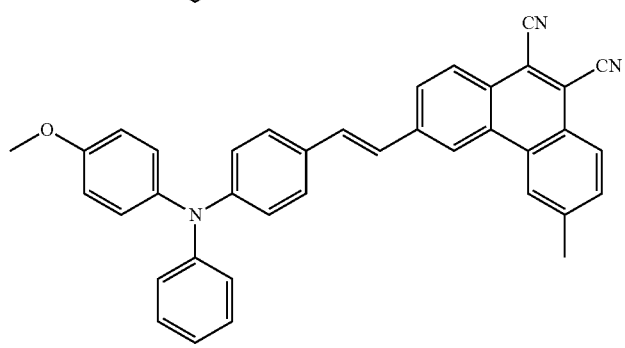

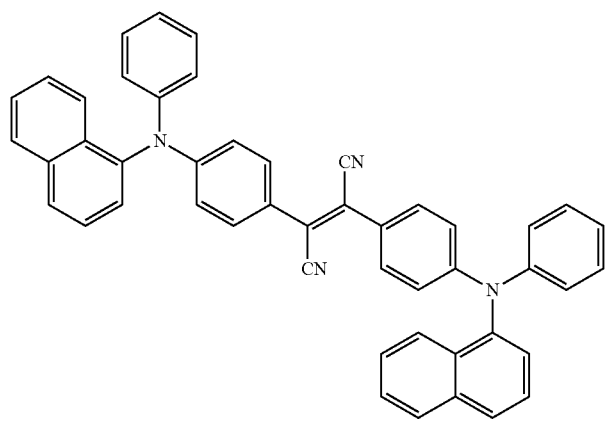
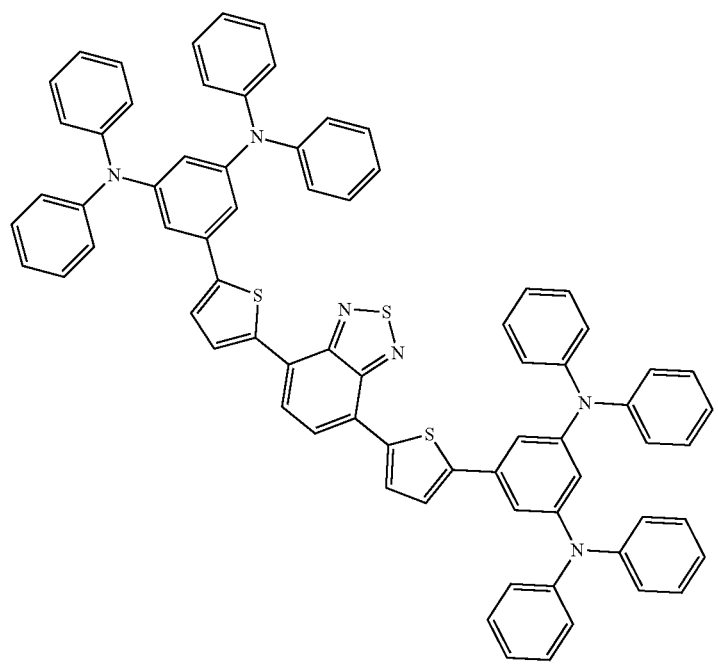
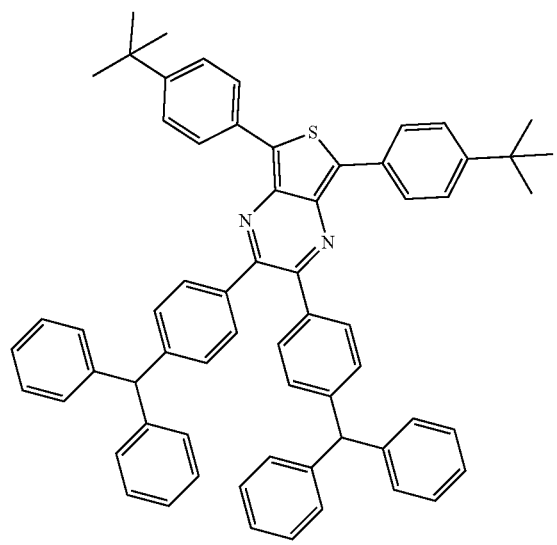

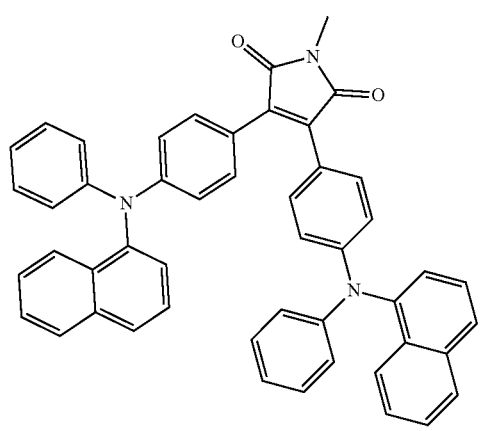
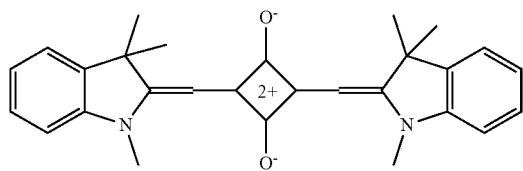
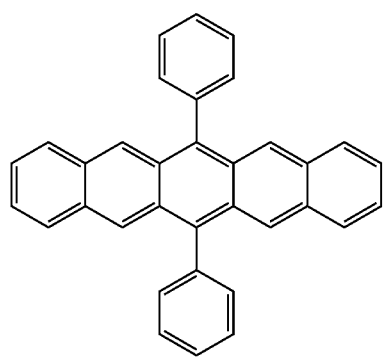
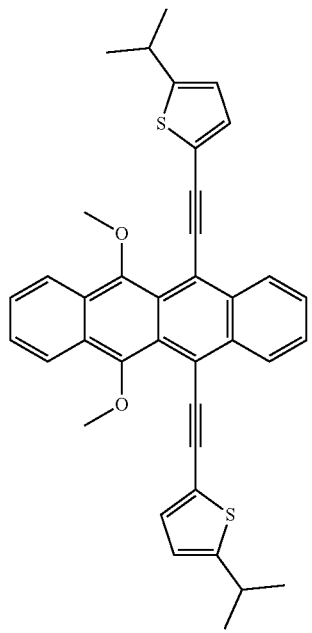

111
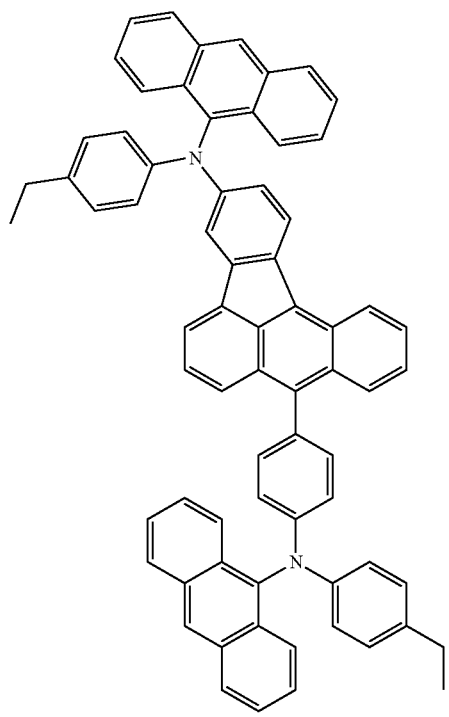
-continued
112
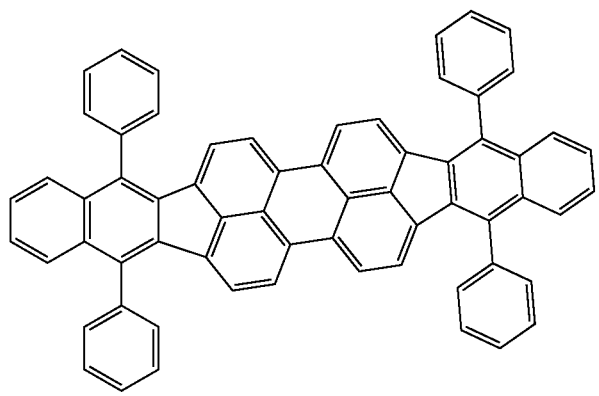
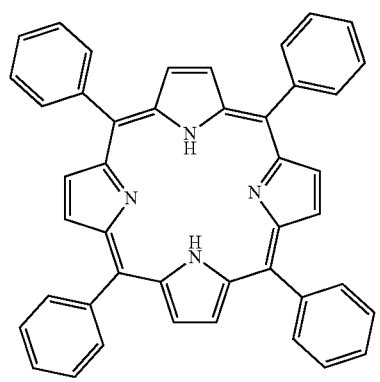
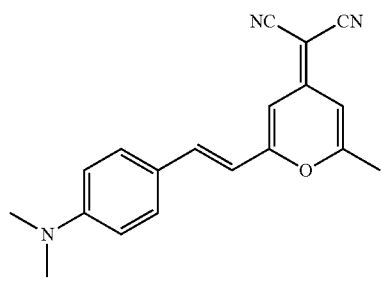
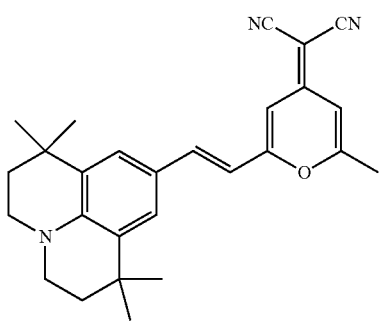

-continued
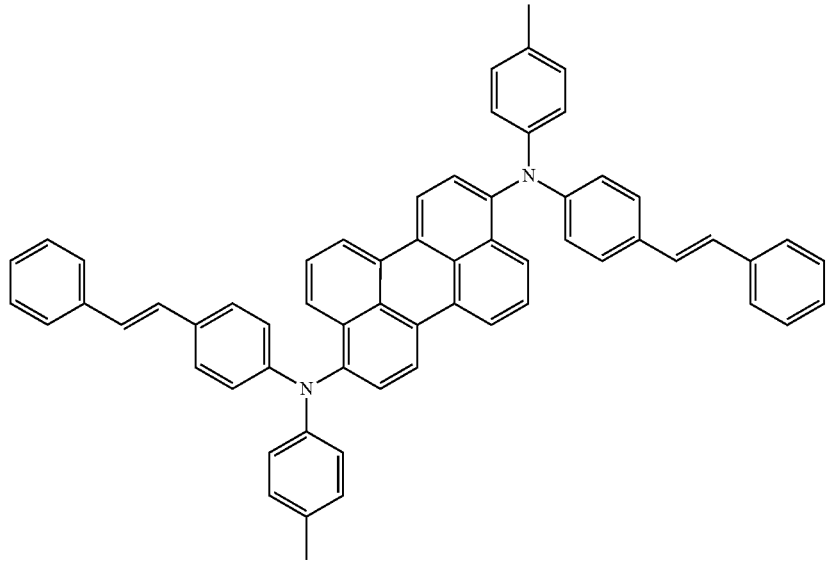
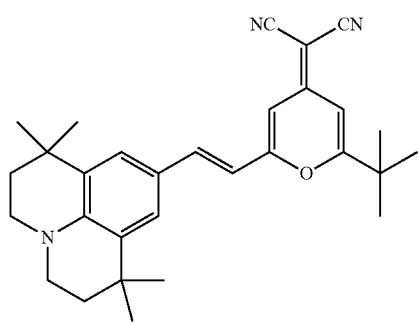
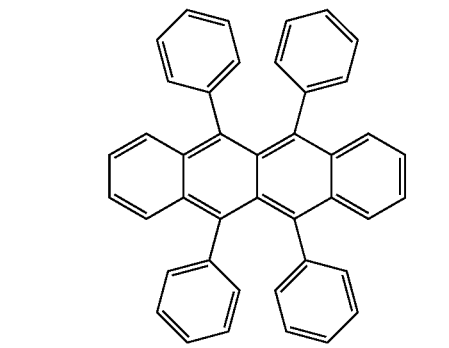
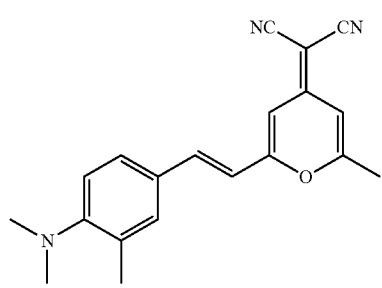
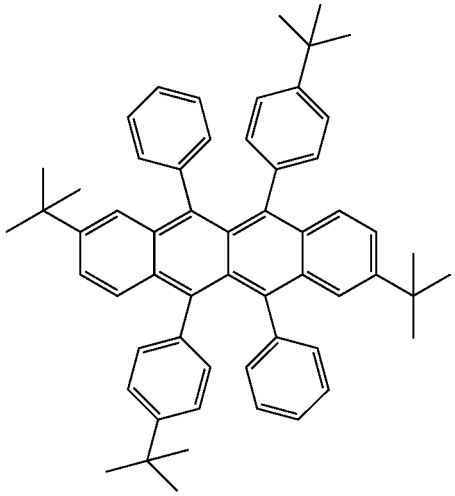
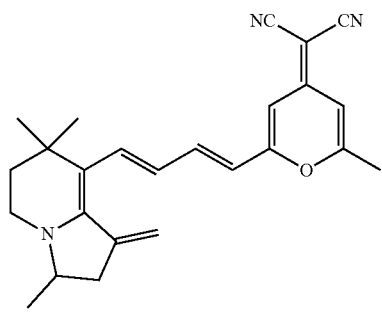

In a further embodiment of the invention, the composition has an emission peak in the visible or nearest ultraviolet range, i.e., in the range of a wavelength of from 380 to 800 nm, in particular between 590 nm and 690 nm, preferably between 610 nm and 665 nm, even more preferably between 620 nm and 640 nm.

Light-Emitting Layer EML

In one embodiment, the light-emitting layer EML of an organic light-emitting diode of the invention comprises (or essentially consists of) a composition comprising or consisting of:
(i) 1-50% by weight, preferably 5-40% by weight, in particular 10-30% by weight, of one or more organic molecules according to the invention;
(ii) 5-99% by weight, preferably 30-94.9% by weight, in particular 40-89% by weight, of at least one host compound H; and
(iii) optionally 0-94% by weight, preferably 0.1-65% by weight, in particular 1-50% by weight, of at least one further host compound D with a structure differing from the structure of the molecules according to the invention; and
(iv) optionally 0-94% by weight, preferably 0-65% by weight, in particular 0-50% by weight, of a solvent; and
(v) optionally 0-30% by weight, in particular 0-20% by weight, preferably 0-5% by weight, of at least one further emitter molecule F with a structure differing from the structure of the molecules according to the invention.

Preferably, energy can be transferred from the host compound H to the one or more organic molecules of the invention, in particular transferred from the first excited triplet state T1(H) of the host compound H to the first excited triplet state T1(E) of the one or more organic molecules according to the invention and/or from the first excited singlet state S1(H) of the host compound H to the first excited singlet state S1(E) of the one or more organic molecules according to the invention.

In one embodiment, the host compound H has a highest occupied molecular orbital HOMO(H) having an energy $E^{HOMO}(H)$ in the range of from −5 eV to −6.5 eV and one organic molecule according to the invention E has a highest occupied molecular orbital HOMO(E) having an energy $E^{HOMO}(E)$, wherein $E^{HOMO}(H) > E^{HOMO}(E)$.

In a further embodiment, the host compound H has a lowest unoccupied molecular orbital LUMO(H) having an energy $E^{LUMO}(H)$ and the one organic molecule according to the invention E has a lowest unoccupied molecular orbital LUMO(E) having an energy $E^{LUMO}(E)$, wherein $E^{LUMO}(H) > E^{LUMO}(E)$.

Light-Emitting Layer EML Comprising at Least One Further Host Compound D

In a further embodiment, the light-emitting layer EML of an organic light-emitting diode of the invention comprises (or essentially consists of) a composition comprising or consisting of:
(i) 1-50% by weight, preferably 5-40% by weight, in particular 10-30% by weight, of one organic molecule according to the invention;
(ii) 5-99% by weight, preferably 30-94.9% by weight, in particular 40-89% by weight, of one host compound H; and
(iii) 0-94% by weight, preferably 0.1-65% by weight, in particular 1-50% by weight, of at least one further host compound D with a structure differing from the structure of the molecules according to the invention; and
(iv) optionally 0-94% by weight, preferably 0-65% by weight, in particular 0-50% by weight, of a solvent; and
(v) optionally 0-30% by weight, in particular 0-20% by weight, preferably 0-5% by weight, of at least one further emitter molecule F with a structure differing from the structure of the molecules according to the invention.

In one embodiment of the organic light-emitting diode of the invention, the host compound H has a highest occupied molecular orbital HOMO(H) having an energy $E^{HOMO}(H)$ in the range of from −5 eV to −6.5 eV and the at least one further host compound D has a highest occupied molecular orbital HOMO(D) having an energy $E^{HOMO}(D)$, wherein $E^{HOMO}(H) > E^{HOMO}(D)$. The relation $E^{HOMO}(H) > E^{HOMO}(D)$ favors an efficient hole transport.

In a further embodiment, the host compound H has a lowest unoccupied molecular orbital LUMO(H) having an energy $E^{LUMO}(H)$ and the at least one further host compound D has a lowest unoccupied molecular orbital LUMO(D) having an energy $E^{LUMO}(D)$, wherein $E^{LUMO}(H) > E^{LUMO}(D)$. The relation $E^{LUMO}(H) > E^{LUMO}(D)$ favors an efficient electron transport.

In one embodiment of the organic light-emitting diode of the invention, the host compound H has a highest occupied molecular orbital HOMO(H) having an energy $E^{HOMO}(H)$ and a lowest unoccupied molecular orbital LUMO(H) having an energy $E^{LUMO}(H)$, and
the at least one further host compound D has a highest occupied molecular orbital HOMO(D) having an energy $E^{HOMO}(D)$ and a lowest unoccupied molecular orbital LUMO(D) having an energy $E^{LUMO}(D)$,
the organic molecule E of the invention has a highest occupied molecular orbital HOMO(E) having an energy $E^{HOMO}(E)$ and a lowest unoccupied molecular orbital LUMO(E) having an energy $E^{LUMO}(E)$,
wherein
$E^{HOMO}(H) > E^{HOMO}(D)$ and the difference between the energy level of the highest occupied molecular orbital HOMO(E) of organic molecule according to the invention ($E^{HOMO}(E)$) and the energy level of the highest occupied molecular orbital HOMO(H) of the host compound H ($E^{HOMO}(H)$) is between −0.5 eV and 0.5 eV, more preferably between −0.3 eV and 0.3 eV, even more preferably between −0.2 eV and 0.2 eV or even between −0.1 eV and 0.1 eV; and
$E^{LUMO}(H) > E^{LUMO}(D)$ and the difference between the energy level of the lowest unoccupied molecular orbital LUMO(E) of organic molecule according to the invention ($E^{LUMO}(E)$) and the lowest unoccupied molecular orbital LUMO(D) of the at least one further host compound D ($E^{LUMO}(D)$) is between −0.5 eV and 0.5 eV, more preferably between −0.3 eV and 0.3 eV, even more preferably between −0.2 eV and 0.2 eV or even between −0.1 eV and 0.1 eV.

Light-Emitting Layer EML Comprising at Least One Further Emitter Molecule F

In a further embodiment, the light-emitting layer EML comprises (or (essentially) consists of) a composition comprising or consisting of:
(i) 1-50% by weight, preferably 5-40% by weight, in particular 10-30% by weight, of one organic molecule according to the invention;
(ii) 5-98% by weight, preferably 30-93.9% by weight, in particular 40-88% by weight, of one host compound H;
(iii) 1-30% by weight, in particular 1-20% by weight, preferably 1-5% by weight, of at least one further emitter molecule F with a structure differing from the structure of the molecules according to the invention; and (iv) optionally 0-94% by weight, preferably 0.1-65% by weight, in particular 1-50% by weight, of at least one further host compound D with a structure differing from the structure of the molecules according to the invention; and (v) optionally 0-94% by weight, preferably 0-65% by weight, in particular 0-50% by weight, of a solvent.

In a further embodiment, the light-emitting layer EML comprises (or (essentially) consists of) a composition as described in Compositions with at least one further emitter, with the at least one further emitter molecule F as defined in Composition wherein the at least one further emitter molecule F is a blue fluorescence emitter.

In a further embodiment, the light-emitting layer EML comprises (or (essentially) consists of) a composition as described in Compositions with at least one further emitter, with the at least one further emitter molecule F as defined in Composition wherein the at least one further emitter molecule F is a triplet-triplet annihilation (TTA) fluorescence emitter.

In a further embodiment, the light-emitting layer EML comprises (or (essentially) consists of) a composition as described in Compositions with at least one further emitter, with the at least one further emitter molecule F as defined in Composition wherein the at least one further emitter molecule F is a green fluorescence emitter.

In a further embodiment, the light-emitting layer EML comprises (or (essentially) consists of) a composition as described in Compositions with at least one further emitter, with the at least one further emitter molecule F as defined in Composition wherein the at least one further emitter molecule F is a red fluorescence emitter.

In one embodiment of the light-emitting layer EML comprising at least one further emitter molecule F, energy can be transferred from the one or more organic molecules of the invention E to the at least one further emitter molecule F, in particular transferred from the first excited singlet state S1(E) of one or more organic molecules of the invention E to the first excited singlet state S1(F) of the at least one further emitter molecule F.

In one embodiment, the first excited singlet state S1(H) of one host compound H of the light-emitting layer is higher in energy than the first excited singlet state S1(E) of the one or more organic molecules of the invention E: S1(H)>S1(E), and the first excited singlet state S1(H) of one host compound H is higher in energy than the first excited singlet state S1(F) of the at least one emitter molecule F: S1(H)>S1(F).

In one embodiment, the first excited triplet state T1(H) of one host compound H is higher in energy than the first excited triplet state T1(E) of the one or more organic molecules of the invention E: T1(H)>T1(E), and the first excited triplet state T1(H) of one host compound H is higher in energy than the first excited triplet state T1(F) of the at least one emitter molecule F: T1(H)>T1(F).

In one embodiment, the first excited singlet state S1(E) of the one or more organic molecules of the invention E is higher in energy than the first excited singlet state S1(F) of the at least one emitter molecule F: S1(E)>S1(F).

In one embodiment, the first excited triplet state T1(E) of the one or more organic molecules E of the invention is higher in energy than the first excited singlet state T1(F) of the at least one emitter molecule F: T1(E)>T1(F).

In one embodiment, the first excited triplet state T1(E) of the one or more organic molecules E of the invention is higher in energy than the first excited singlet state T1(F) of the at least one emitter molecule F: T1(E)>T1(F), wherein the absolute value of the energy difference between T1(E) and T1(F) is larger than 0.3 eV, preferably larger than 0.4 eV, or even larger than 0.5 eV.

In one embodiment, the host compound H has a highest occupied molecular orbital HOMO(H) having an energy $E^{HOMO}(H)$ and a lowest unoccupied molecular orbital LUMO(H) having an energy $E^{LUMO}(H)$, and the one organic molecule according to the invention E has a highest occupied molecular orbital HOMO(E) having an energy $E^{HOMO}(E)$ and a lowest unoccupied molecular orbital LUMO(E) having an energy $E^{LUMO}(E)$, the at least one further emitter molecule F has a highest occupied molecular orbital HOMO(F) having an energy $E^{HOMO}(F)$ and a lowest unoccupied molecular orbital LUMO(E) having an energy $E^{LUMO}(F)$, wherein $E^{HOMO}(H) > E^{HOMO}(E)$ and the difference between the energy level of the highest occupied molecular orbital HOMO(F) of the at least one further emitter molecule ($E^{HOMO}(F)$) and the energy level of the highest occupied molecular orbital HOMO(H) of the host compound H ($E^{HOMO}(H)$) is between −0.5 eV and 0.5 eV, more preferably between −0.3 eV and 0.3 eV, even more preferably between −0.2 eV and 0.2 eV or even between −0.1 eV and 0.1 eV; and $E^{LUMO}(H) > E^{LUMO}(E)$ and the difference between the energy level of the lowest unoccupied molecular orbital LUMO(F) of the at least one further emitter molecule ($E^{LUMO}(F)$) and the lowest unoccupied molecular orbital LUMO(E) of the one organic molecule according to the invention ($E^{LUMO}(E)$) is between −0.5 eV and 0.5 eV, more preferably between −0.3 eV and 0.3 eV, even more preferably between −0.2 eV and 0.2 eV or even between −0.1 eV and 0.1 eV.

Optoelectronic Devices

In a further aspect, the invention relates to an optoelectronic device comprising an organic molecule or a composition as described herein, more particularly in the form of a device selected from the group consisting of organic light-emitting diode (OLED), light-emitting electrochemical cell, OLED sensor, more particularly gas and vapour sensors not hermetically externally shielded, organic diode, organic solar cell, organic transistor, organic field-effect transistor, organic laser and down-conversion element.

In a preferred embodiment, the optoelectronic device is a device selected from the group consisting of an organic light emitting diode (OLED), a light emitting electrochemical cell (LEC), and a light-emitting transistor.

In one embodiment of the optoelectronic device of the invention, the organic molecule according to the invention is used as emission material in a light-emitting layer EML.

In one embodiment of the optoelectronic device of the invention, the light-emitting layer EML consists of the composition according to the invention described herein.

When the optoelectronic device is an OLED, it may, for example, exhibit the following layer structure:

1. substrate
2. anode layer A
3. hole injection layer, HIL
4. hole transport layer, HTL
5. electron blocking layer, EBL
6. emitting layer, EML
7. hole blocking layer, HBL 8. electron transport layer, ETL
9. electron injection layer, EIL
10. cathode layer, wherein the OLED comprises each layer only optionally, different layers may be merged and the OLED may comprise more than one layer of each layer type defined above.

Furthermore, the optoelectronic device may optionally comprise one or more protective layers protecting the device from damaging exposure to harmful species in the environment including, exemplarily moisture, vapor and/or gases.

In one embodiment of the invention, the optoelectronic device is an OLED, which exhibits the following inverted layer structure:
1. substrate
2. cathode layer
3. electron injection layer, EIL
4. electron transport layer, ETL
5. hole blocking layer, HBL
6. emitting layer, B
7. electron blocking layer, EBL
8. hole transport layer, HTL
9. hole injection layer, HIL
10. anode layer A wherein the OLED with an inverted layer structure comprises each layer only optionally, different layers may be merged and the OLED may comprise more than one layer of each layer types defined above.

In one embodiment of the invention, the optoelectronic device is an OLED, which may exhibit stacked architecture. In this architecture, contrary to the typical arrangement, where the OLEDs are placed side by side, the individual units are stacked on top of each other. Blended light may be generated with OLEDs exhibiting a stacked architecture, in particular white light may be generated by stacking blue, green and red OLEDs. Furthermore, the OLED exhibiting a stacked architecture may optionally comprise a charge generation layer (CGL), which is typically located between two OLED subunits and typically consists of a n-doped and p-doped layer with the n-doped layer of one CGL being typically located closer to the anode layer.

In one embodiment of the invention, the optoelectronic device is an OLED, which comprises two or more emission layers between anode and cathode. In particular, this so-called tandem OLED comprises three emission layers, wherein one emission layer emits red light, one emission layer emits green light and one emission layer emits blue light, and optionally may comprise further layers such as charge generation layers, blocking or transporting layers between the individual emission layers. In a further embodiment, the emission layers are adjacently stacked. In a further embodiment, the tandem OLED comprises a charge generation layer between each two emission layers. In addition, adjacent emission layers or emission layers separated by a charge generation layer may be merged.

The substrate may be formed by any material or composition of materials. Most frequently, glass slides are used as substrates. Alternatively, thin metal layers (e.g., copper, gold, silver or aluminum films) or plastic films or slides may be used. This may allow a higher degree of flexibility. The anode layer A is mostly composed of materials allowing to obtain an (essentially) transparent film. As at least one of both electrodes should be (essentially) transparent in order to allow light emission from the OLED, either the anode layer A or the cathode layer C is transparent. Preferably, the anode layer A comprises a large content or even consists of transparent conductive oxides (TCOs). Such anode layer A may exemplarily comprise indium tin oxide, aluminum zinc oxide, fluorine doped tin oxide, indium zinc oxide, PbO, SnO, zirconium oxide, molybdenum oxide, vanadium oxide, wolfram oxide, graphite, doped Si, doped Ge, doped GaAs, doped polyaniline, doped polypyrrol and/or doped polythiophene.

Preferably, the anode layer A (essentially) consists of indium tin oxide (ITO) (e.g., (InO3)0.9(SnO2)0.1). The roughness of the anode layer A caused by the transparent conductive oxides (TCOs) may be compensated by using a hole injection layer (HIL). Further, the HIL may facilitate the injection of quasi charge carriers (i.e., holes) in that the transport of the quasi charge carriers from the TCO to the hole transport layer (HTL) is facilitated. The hole injection layer (HIL) may comprise poly-3,4-ethylendioxy thiophene (PEDOT), polystyrene sulfonate (PSS), $MoO_2$, $V_2O_5$, CuPC or CuI, in particular a mixture of PEDOT and PSS. The hole injection layer (HIL) may also prevent the diffusion of metals from the anode layer A into the hole transport layer (HTL). The HIL may exemplarily comprise PEDOT:PSS (poly-3,4-ethylendioxy thiophene: polystyrene sulfonate), PEDOT (poly-3,4-ethylendioxy thiophene), mMTDATA (4,4',4"-tris[phenyl(m-tolyl)amino]triphenylamine), Spiro-TAD (2,2',7,7'-tetrakis(n,n-diphenylamino)-9,9'-spirobifluorene), DNTPD (N1,N1'-(biphenyl-4,4'-diyl)bis(N1-phenyl-N4,N4-di-m-tolylbenzene-1,4-diamine), NPB (N,N'-nis-(1-naphthalenyl)-N,N'-bis-phenyl-(1,1'-biphenyl)-4,4'-diamine), NPNPB (N,N'-diphenyl-N,N'-di-[4-(N,N-diphenyl-amino)phenyl]benzidine), MeO-TPD (N,N,N',N'-tetrakis(4-methoxyphenyl)benzidine), HAT-CN (1,4,5,8,9,11-hexaazatriphenylen-hexacarbonitrile) and/or Spiro-NPD (N,N'-diphenyl-N,N'-bis-(1-naphthyl)-9,9'-spirobifluorene-2,7-diamine).

Adjacent to the anode layer A or hole injection layer (HIL) typically a hole transport layer (HTL) is located. Herein, any hole transport compound may be used. Exemplarily, electron-rich heteroaromatic compounds such as triarylamines and/or carbazoles may be used as hole transport compound. The HTL may decrease the energy barrier between the anode layer A and the light-emitting layer EML. The hole transport layer (HTL) may also be an electron blocking layer (EBL). Preferably, hole transport compounds bear comparably high energy levels of their triplet states T1. Exemplarily the hole transport layer (HTL) may comprise a star-shaped heterocycle such as tris(4-carbazoyl-9-ylphenyl)amine (TCTA), poly-TPD (poly(4-butylphenyl-diphenyl-amine)), [alpha]-NPD (poly(4-butylphenyl-diphenyl-amine)), TAPC (4,4'-cyclohexyliden-bis[N, N-bis(4-methylphenyl)benzenamine]), 2-TNATA (4,4',4"-tris[2-naphthyl(phenyl)amino]triphenylamine), Spiro-TAD, DNTPD, NPB, NPNPB, MeO-TPD, HAT-CN and/or TrisPcz (9,9'-diphenyl-6-(9-phenyl-9H-carbazol-3-yl)-9H,9'H-3,3'-bicarbazole). In addition, the HTL may comprise a p-doped layer, which may be composed of an inorganic or organic dopant in an organic hole-transporting matrix. Transition metal oxides such as vanadium oxide, molybdenum oxide or tungsten oxide may exemplarily be used as inorganic dopant. Tetrafluorotetracyanoquinodimethane (F4-TCNQ), copper-pentafluorobenzoate (Cu(I)pFBz) or transition metal complexes may exemplarily be used as organic dopant.

The EBL may exemplarily comprise mCP (1,3-bis(carbazol-9-yl)benzene), TCTA, 2-TNATA, mCBP (3,3-di(9H-carbazol-9-yl) biphenyl), tris-Pcz, CzSi (9-(4-tert-Butylphenyl)-3,6-bis(triphenylsilyl)-9H-carbazole), and/or DCB (N,N'-dicarbazolyl-1,4-dimethylbenzene).

Adjacent to the hole transport layer (HTL), typically, the light-emitting layer EML is located. The light-emitting layer EML comprises at least one light emitting molecule. Particular, the EML comprises at least one light emitting molecule according to the invention. Typically, the EML additionally comprises one or more host material. Exemplarily, the host material is selected from CBP (4,4'-Bis-(N-carbazolyl)-biphenyl), mCP, mCBP Sif87 (dibenzo[b,d]thiophen-2-yltriphenylsilane), CzSi, Sif88 (dibenzo[b,d]thiophen-2-yl)diphenylsilane), DPEPO (bis[2-(diphenylphosphino)phenyl] ether oxide), 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole, 9-[3,5-bis(2-dibenzothiophenyl)phenyl]-9H-carbazole, T2T (2,4,6-tris(biphenyl-3-yl)-1,3,5-triazine), T3T (2,4,6-tris(triphenyl-3-yl)-1,3,5-triazine) and/or TST (2,4,6-tris(9,9'-spirobifluorene-2-yl)-1,3,5-triazine). The host material typically should be selected to exhibit first triplet (T1) and first singlet (Si) energy levels, which are energetically higher than the first triplet (T1) and first singlet (Si) energy levels of the organic molecule.

In one embodiment of the invention, the EML comprises a so-called mixed-host system with at least one hole-dominant host and one electron-dominant host. In a particular embodiment, the EML comprises exactly one light emitting molecule species according to the invention and a mixed-host system comprising T2T as electron-dominant host and a host selected from CBP, mCP, mCBP, 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole and 9-[3,5-bis(2-dibenzothiophenyl)phenyl]-9H-carbazole as hole-dominant host. In a further embodiment the EML comprises 50-80% by weight, preferably 60-75% by weight of a host selected from CBP, mCP, mCBP, 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole and 9-[3,5-bis(2-dibenzothiophenyl)phenyl]-9H-carbazole; 10-45% by weight, preferably 15-30% by weight of T2T and 5-40% by weight, preferably 10-30% by weight of light emitting molecule according to the invention.

Adjacent to the light-emitting layer EML an electron transport layer (ETL) may be located. Herein, any electron transporter may be used. Exemplarily, compounds poor of electrons such as, e.g., benzimidazoles, pyridines, triazoles, oxadiazoles (e.g., 1,3,4-oxadiazole), phosphinoxides and sulfone, may be used. An electron transporter may also be a star-shaped heterocycle such as 1,3,5-tri(1-phenyl-1H-benzo[d]imidazol-2-yl)phenyl (TPBi). The ETL may comprise NBphen (2,9-bis(naphthalen-2-yl)-4,7-diphenyl-1,10-phenanthroline), Alq3 (Aluminum-tris(8-hydroxyquinoline)), TSPO1 (diphenyl-4-triphenylsilylphenyl-phosphinoxide), BPyTP2 (2,7-di(2,2'-bipyridin-5-yl)triphenyle), Sif87 (dibenzo[b,d]thiophen-2-yltriphenylsilane), Sif88 (dibenzo[b,d]thiophen-2-yl)diphenylsilane), BmPyPhB (1,3-bis[3,5-di(pyridin-3-yl)phenyl]benzene) and/or BTB (4,4'-bis-[2-(4,6-diphenyl-1,3,5-triazinyl)]-1,1'-biphenyl). Optionally, the ETL may be doped with materials such as Liq. The electron transport layer (ETL) may also block holes or a holeblocking layer (HBL) is introduced.

The HBL may, for example, comprise BCP (2,9-dimethyl-4,7-diphenyl-1,10-phenanthroline=Bathocuproine), BAlq (bis(8-hydroxy-2-methylquinoline)-(4-phenylphenoxy)aluminum), NBphen (2,9-bis(naphthalen-2-yl)-4,7-diphenyl-1,10-phenanthroline), Alq3 (Aluminum-tris(8-hydroxyquinoline)), TSPO1 (diphenyl-4-triphenylsilylphenyl-phosphinoxide), T2T (2,4,6-tris(biphenyl-3-yl)-1,3,5-triazine), T3T (2,4,6-tris(triphenyl-3-yl)-1,3,5-triazine), TST (2,4,6-tris(9,9'-spirobifluorene-2-yl)-1,3,5-triazine), and/or TCB/TCP (1,3,5-tris(N-carbazolyl)benzol/1,3,5-tris (carbazol)-9-yl) benzene).

A cathode layer C may be located adjacent to the electron transport layer (ETL). For example, the cathode layer C may comprise or may consist of a metal (e.g., Al, Au, Ag, Pt, Cu, Zn, Ni, Fe, Pb, LiF, Ca, Ba, Mg, In, W, or Pd) or a metal alloy. For practical reasons, the cathode layer may also consist of (essentially) non-transparent metals such as Mg, Ca or Al. Alternatively or additionally, the cathode layer C may also comprise graphite and or carbon nanotubes (CNTs). Alternatively, the cathode layer C may also consist of nanoscalic silver wires.

An OLED may further, optionally, comprise a protection layer between the electron transport layer (ETL) and the cathode layer C (which may be designated as electron injection layer (EIL)). This layer may comprise lithium fluoride, cesium fluoride, silver, Liq (8-hydroxyquinolinolatolithium), $Li_2O$, $BaF_2$, MgO and/or NaF.

Optionally, also the electron transport layer (ETL) and/or a hole blocking layer (HBL) may comprise one or more host compounds.

In order to modify the emission spectrum and/or the absorption spectrum of the light-emitting layer EML further, the light-emitting layer EML may further comprise one or more further emitter molecule F. Such an emitter molecule F may be any emitter molecule known in the art. Preferably such an emitter molecule F is a molecule with a structure differing from the structure of the molecules according to the invention. The emitter molecule F may optionally be a TADF emitter. Alternatively, the emitter molecule F may optionally be a fluorescent and/or phosphorescent emitter molecule which is able to shift the emission spectrum and/or the absorption spectrum of the light-emitting layer EML. For example, the triplet and/or singlet excitons may be transferred from the emitter molecule according to the invention to the emitter molecule F before relaxing to the ground state S0 by emitting light typically red-shifted in comparison to the light emitted by emitter molecule E. Optionally, the emitter molecule F may also provoke two-photon effects (i.e., the absorption of two photons of half the energy of the absorption maximum).

Optionally, an optoelectronic device (e.g., an OLED) may, for example, be an essentially white optoelectronic device. Exemplarily such white optoelectronic device may comprise at least one (deep) blue emitter molecule and one or more emitter molecules emitting green and/or red light. Then, there may also optionally be energy transmittance between two or more molecules as described above.

As used herein, if not defined more specifically in the particular context, the designation of the colors of emitted and/or absorbed light is as follows:
  violet: wavelength range of >380-420 nm;
  deep blue: wavelength range of >420-480 nm;
  sky blue: wavelength range of >480-500 nm;
  green: wavelength range of >500-560 nm;
  yellow: wavelength range of >560-580 nm;
  orange: wavelength range of >580-620 nm;
  red: wavelength range of >620-800 nm.

With respect to emitter molecules, such colors refer to the emission maximum. Therefore, exemplarily, a deep blue emitter has an emission maximum in the range of from >420 to 480 nm, a sky-blue emitter has an emission maximum in the range of from >480 to 500 nm, a green emitter has an emission maximum in a range of from >500 to 560 nm, a red emitter has an emission maximum in a range of from >620 to 800 nm.

A further embodiment of the present invention relates to an OLED, which emits light with CIEx and CIEy color coordinates close to the CIEx (=0.131) and CIEy (=0.046) color coordinates of the primary color blue (CIEx=0.131 and CIEy=0.046) as defined by ITU-R Recommendation BT.2020 (Rec. 2020) and thus is suited for the use in Ultra High Definition (UHD) displays, e.g. UHD-TVs. In this context, the term "close to" refers to the ranges of CIEx and CIEy coordinates provided at the end of this paragraph. In commercial applications, typically top-emitting (top-electrode is transparent) devices are used, whereas test devices as described throughout the present application represent bottom-emitting devices (bottom-electrode and substrate are transparent). The CIEy color coordinate of a blue device can be reduced by up to a factor of two, when changing from a bottom- to a top-emitting device, while the CIEx remains nearly unchanged (Okinaka et al. doi:10.1002/sdtp.10480). Accordingly, a further embodiment of the present invention relates to an OLED, whose emission exhibits a CIEx color coordinate of between 0.02 and 0.30, preferably between 0.03 and 0.25, more preferably between 0.05 and 0.20 or even more preferably between 0.08 and 0.18 or even between 0.10 and 0.15 and/or a CIEy color coordinate of between 0.00 and 0.45, preferably between 0.01 and 0.30, more preferably between 0.02 and 0.20 or even more preferably between 0.03 and 0.15 or even between 0.04 and 0.10.

A further embodiment of the present invention relates to an OLED, which emits light with CIEx and CIEy color coordinates close to the CIEx (=0.170) and CIEy (=0.797) color coordinates of the primary color green (CIEx=0.170 and CIEy=0.797) as defined by ITU-R Recommendation BT.2020 (Rec. 2020) and thus is suited for the use in Ultra High Definition (UHD) displays, e.g. UHD-TVs. In this context, the term "close to" refers to the ranges of CIEx and CIEy coordinates provided at the end of this paragraph. In commercial applications, typically top-emitting (top-electrode is transparent) devices are used, whereas test devices as used throughout the present application represent bottom-emitting devices (bottom-electrode and substrate are transparent). The CIEy color coordinate of a blue device can be reduced by up to a factor of two, when changing from a bottom- to a top-emitting device, while the CIEx remains nearly unchanged (Okinaka et al. doi:10.1002/sdtp.10480). Accordingly, a further aspect of the present invention relates to an OLED, whose emission exhibits a CIEx color coordinate of between 0.06 and 0.34, preferably between 0.07 and 0.29, more preferably between 0.09 and 0.24 or even more preferably between 0.12 and 0.22 or even between 0.14 and 0.19 and/or a CIEy color coordinate of between 0.75 and 1.20, preferably between 0.76 and 1.05, more preferably between 0.77 and 0.95 or even more preferably between 0.78 and 0.90 or even between 0.79 and 0.85.

A further embodiment of the present invention relates to an OLED, which emits light with CIEx and CIEy color coordinates close to the CIEx (=0.708) and CIEy (=0.292) color coordinates of the primary color red (CIEx=0.708 and CIEy=0.292) as defined by ITU-R Recommendation BT.2020 (Rec. 2020) and thus is suited for the use in Ultra High Definition (UHD) displays, e.g. UHD-TVs. In this context, the term "close to" refers to the ranges of CIEx and CIEy coordinates provided at the end of this paragraph. In commercial applications, typically top-emitting (top-electrode is transparent) devices are used, whereas test devices as used throughout the present application represent bottom-emitting devices (bottom-electrode and substrate are transparent). The CIEy color coordinate of a blue device can be reduced by up to a factor of two, when changing from a bottom- to a top-emitting device, while the CIEx remains nearly unchanged (Okinaka et al. doi:10.1002/sdtp.10480). Accordingly, a further aspect of the present invention relates to an OLED, whose emission exhibits a CIEx color coordinate of between 0.60 and 0.88, preferably between 0.61 and 0.83, more preferably between 0.63 and 0.78 or even more preferably between 0.66 and 0.76 or even between 0.68 and 0.73 and/or a CIEy color coordinate of between 0.25 and 0.70, preferably between 0.26 and 0.55, more preferably between 0.27 and 0.45 or even more preferably between 0.28 and 0.40 or even between 0.29 and 0.35.

Accordingly, a further aspect of the present invention relates to an OLED, which exhibits an external quantum efficiency at 1000 $cd/m^2$ of more than 8%, more preferably of more than 10%, more preferably of more than 13%, even more preferably of more than 15% or even more than 20% and/or exhibits an emission maximum between 420 nm and 500 nm, preferably between 430 nm and 490 nm, more preferably between 440 nm and 480 nm, even more preferably between 450 nm and 470 nm and/or exhibits a LT80 value at 500 $cd/m^2$ of more than 100 h, preferably more than 200 h, more preferably more than 400 h, even more preferably more than 750 h or even more than 1000 h.

The optoelectronic device, in particular the OLED according to the present invention can be manufactured by any means of vapor deposition and/or liquid processing. Accordingly, at least one layer is
- prepared by means of a sublimation process,
- prepared by means of an organic vapor phase deposition process,
- prepared by means of a carrier gas sublimation process,
- solution processed or
- printed.

The methods used to manufacture the optoelectronic device, in particular the OLED according to the present invention are known in the art. The different layers are individually and successively deposited on a suitable substrate by means of subsequent deposition processes. The individual layers may be deposited using the same or differing deposition methods.

Vapor deposition processes exemplarily comprise thermal (co)evaporation, chemical vapor deposition and physical vapor deposition. For active matrix OLED display, an AMO-LED backplane is used as substrate. The individual layer may be processed from solutions or dispersions employing adequate solvents. Solution deposition process exemplarily comprise spin coating, dip coating and jet printing. Liquid processing may optionally be carried out in an inert atmosphere (e.g., in a nitrogen atmosphere) and the solvent may optionally be completely or partially removed by means known in the state of the art.

EXAMPLES
General synthesis scheme I
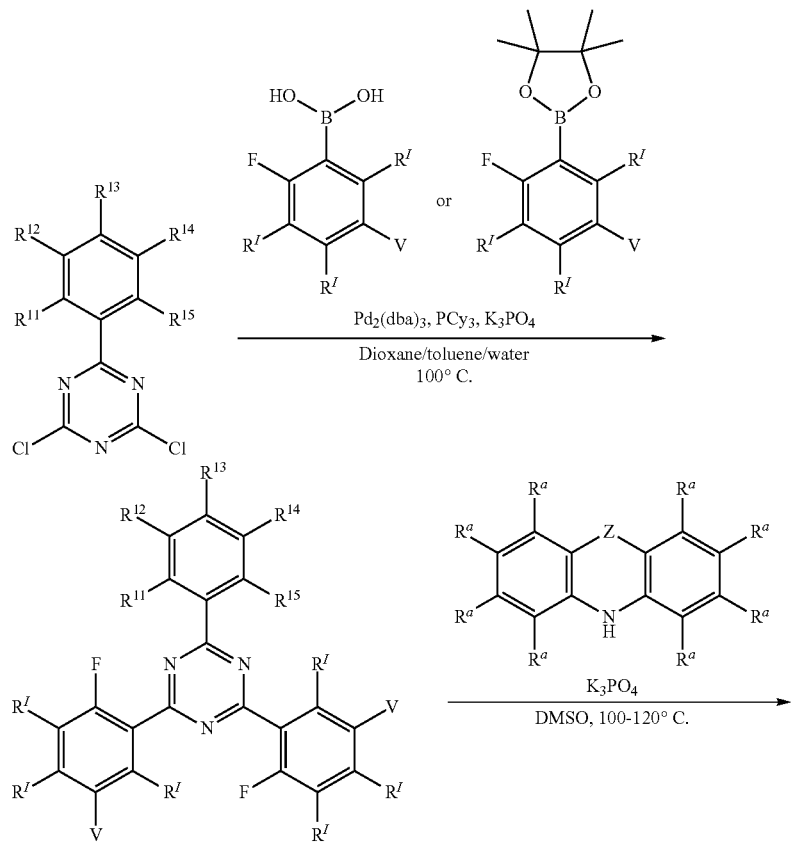
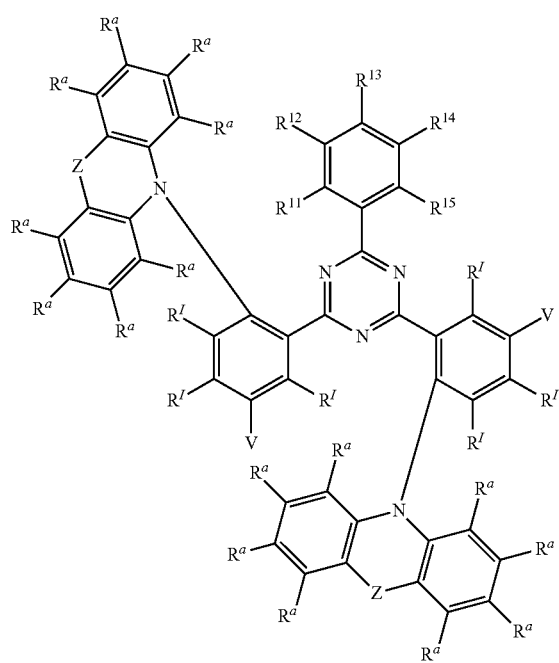

General Procedure for Synthesis AAV1:

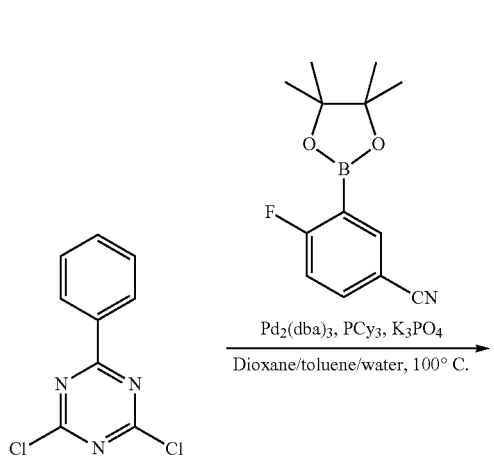

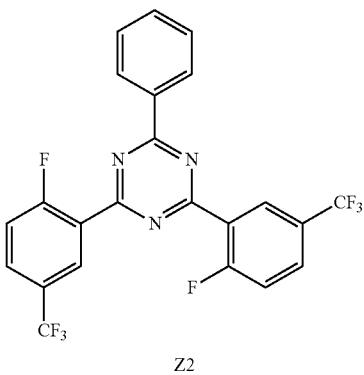

Z2

The synthesis of Z2 is carried out according to AAV1, wherein 2,4-Dichloro-6-phenyl-1,3,5-triazine reacts with 2-fluoro-5-(trifluoromethyl)phenylboronic acid.

General Procedure for Synthesis AAV3:

2,4-Dichloro-6-phenyl-1,3,5-triazine (1.0 equivalents), 2-fluoro-5-cyanophenylboronic acid pinacol ester (2.4 equivalents), tris(dibenzylideneacetone)dipalladium(0) [$Pd_2(dba)_3$; 0.05 equivalents], tricyclohexylphosphine ($PCy_3$, 0.1 equivalents) and tribasic potassium phosphate (3.5 equivalents) are suspended under nitrogen atmosphere in dioxane/toluene/water and stirred at 100° C. (12-15 h). Subsequently, the reaction mixture is filtered and the solvent is evaporated under reduced pressure to obtain the crude product. The product is purified by recrystallization in toluene.

General Procedure for Synthesis AAV2:

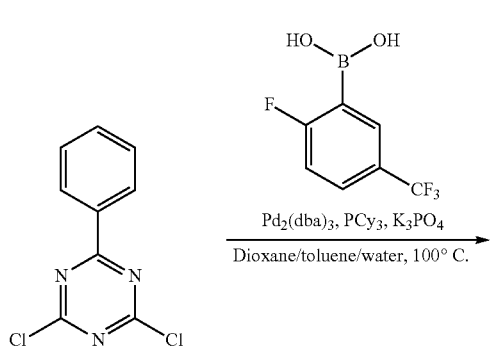

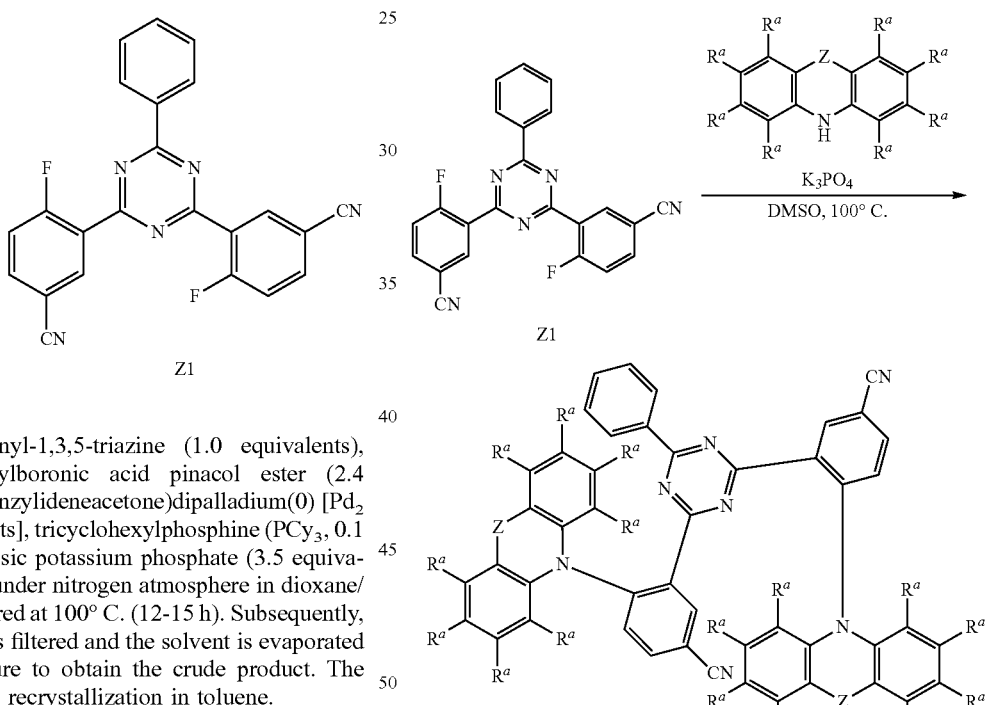

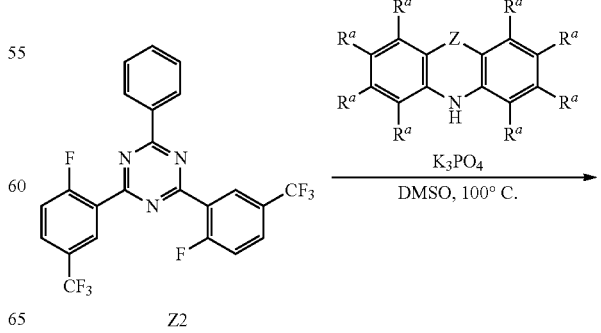

-continued

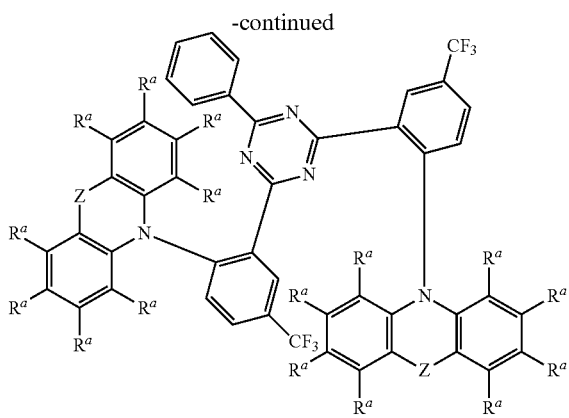

| solvent A: | H₂O (90%) | MeCN (10%) |
| solvent B: | H₂O (10%) | MeCN (90%) |
| solvent C: | THF (100%) | |

From a solution with a concentration of 0.5 mg/ml an injection volume of 15 μL is taken for the measurements. The following gradient is used:

| Flow rate [ml/min] | time [min] | A[%] | B[%] | D[%] |
|---|---|---|---|---|
| 3 | 0 | 40 | 50 | 10 |
| 3 | 10 | 10 | 15 | 75 |
| 3 | 16 | 10 | 15 | 75 |
| 3 | 16.01 | 40 | 50 | 10 |
| 3 | 20 | 40 | 50 | 10 |

Z1 or Z2 (1 equivalent each), the corresponding donor molecule D-H (2.20 equivalents) and tribasic potassium phosphate (4.40 equivalents) are suspended under nitrogen atmosphere in DMSO and stirred at 100-120° C. (20 h). Subsequently, the reaction mixture is poured into a saturated sodium chloride solution and the precipitate is filtered and washed with water. The solid is then dissolved in dichloromethane, dried over MgSO₄ and the solvent is evaporated under reduced pressure. The crude product is purified by recrystallization or by flash chromatography. The product is obtained as a solid.

In particular, the donor molecule D-H is a 3,6-substituted carbazole (e.g., 3,6-dimethylcarbazole, 3,6-diphenylcarbazole, 3,6-di-tert-butylcarbazole), a 2,7-substituted carbazole (e.g., 2,7-dimethylcarbazole, 2,7-diphenylcarbazole, 2,7-di-tert-butylcarbazole), a 1,8-substituted carbazole (e.g., 1,8-dimethylcarbazole, 1,8-diphenylcarbazole, 1,8-di-tert-butyl-carbazole), a 1-substituted carbazole (e.g., 1-methylcarbazole, 1-phenylcarbazole, 1-tert-butylcarbazole), a 2-substituted carbazole (e.g., 2-methylcarbazole, 2-phenylcarbazole, 2-tert-butylcarbazole), or a 3-substituted carbazole (e.g., 3-methylcarbazole, 3-phenylcarbazole, 3-tert-butylcarbazole).

Exemplarily a halogen-substituted carbazole, particularly 3-bromocarbazole, can be used as D-H.

In a subsequent reaction a boronic acid ester functional group or boronic acid functional group may be exemplarily introduced at the position of the one or more halogen substituents, which was introduced via D-H, to yield the corresponding carbazol-3-ylboronic acid ester or carbazol-3-ylboronic acid, e.g., via the reaction with bis(pinacolato) diboron (CAS No. 73183-34-3). Subsequently, one or more substituents $R^a$ may be introduced in place of the boronic acid ester group or the boronic acid group via a coupling reaction with the corresponding halogenated reactant $R^a$-Hal, preferably $R^a$—Cl and $R^a$—Br.

Alternatively, one or more substituents $R^a$ may be introduced at the position of the one or more halogen substituents, which was introduced via D-H, via the reaction with a boronic acid of the substituent $R^a$ [$R^a$—B(OH)₂] or a corresponding boronic acid ester.

HPLC-MS:

HPLC-MS spectroscopy is performed on a HPLC by Agilent (1100 series) with MS-detector (Thermo LTQ XL). A reverse phase column 4.6 mm×150 mm, particle size 5.0 μm from Waters (without pre-column) is used in the HPLC. The HPLC-MS measurements are performed at room temperature (rt) with the solvents acetonitrile, water and THF in the following concentrations:

Ionisation of the probe is performed by atmospheric pressure chemical ionization (APCI).

Cyclic Voltammetry

Cyclic voltammograms are measured from solutions having concentration of $10^{-3}$ mol/l of the organic molecules in dichloromethane or a suitable solvent and a suitable supporting electrolyte (e.g. 0.1 mol/l of tetrabutylammonium hexafluorophosphate). The measurements are conducted at room temperature under nitrogen atmosphere with a three-electrode assembly (Working and counter electrodes: Pt wire, reference electrode: Pt wire) and calibrated using $FeCp_2/FeCp_2^+$ as internal standard. The HOMO data was corrected using ferrocene as internal standard against a SCE (saturated calomel electrode).

Density Functional Theory Calculation

Molecular structures are optimized employing the BP86 functional and the resolution of identity approach (RI). Excitation energies are calculated using the (BP86) optimized structures employing Time-Dependent DFT (TD-DFT) methods. Orbital and excited state energies are calculated with the B3LYP functional. Def2-SVP basis sets (and a m4-grid for numerical integration are used. The Turbomole program package was used for all calculations.

Photophysical Measurements

Sample Pretreatment: Spin-Coating

Apparatus: Spin150, Sps Euro.

The sample concentration is 10 mg/ml, dissolved in a suitable solvent.

Program: 1) 3 s at 400 U/min; 20 s at 1000 U/min at 1000 Upm/s. 3) 10 s at 4000 U/min at 1000 Upm/s. After coating, the films are tried at 70° C. for 1 min.

Photoluminescence Spectroscopy and TCSPC (Time-Correlated Single-Photon Counting)

Steady-state emission spectroscopy is measured by a Horiba Scientific, Modell FluoroMax-4 equipped with a 150 W Xenon-Arc lamp, excitation- and emissions monochromators and a Hamamatsu R928 photomultiplier and a time-correlated single-photon counting option. Emissions and excitation spectra are corrected using standard correction fits.

Excited state lifetimes are determined employing the same system using the TCSPC method with FM-2013 equipment and a Horiba Yvon TCSPC hub.

Excitation Sources:

NanoLED 370 (wavelength: 371 nm, puls duration: 1.1 ns)

NanoLED 290 (wavelength: 294 nm, puls duration: <1 ns)

SpectraLED 310 (wavelength: 314 nm)

SpectraLED 355 (wavelength: 355 nm).

Data analysis (exponential fit) is done using the software suite DataStation and DAS6 analysis software. The fit is specified using the chi-squared-test.

Photoluminescence Quantum Yield Measurements

For photoluminescence quantum yield (PLQY) measurements an Absolute PL Quantum Yield Measurement C9920-03G system (Hamamatsu Photonics) is used. Quantum yields and CIE coordinates are determined using the software U6039-05 version 3.6.0.

Emission maxima are given in nm, quantum yields Φ in % and CIE coordinates as x,y values. PLQY is determined using the following protocol:

1) Quality assurance: Anthracene in ethanol (known concentration) is used as reference
2) Excitation wavelength: the absorption maximum of the organic molecule is determined and the molecule is excited using this wavelength
3) Measurement
   Quantum yields are measured for sample of solutions or films under nitrogen atmosphere. The yield is calculated using the equation:

$$\Phi_{PL} = \frac{n_{photon}, \text{emitted}}{n_{photon}, \text{absorbed}} = \frac{\int \frac{\lambda}{hc}\left[Int_{emitted}^{sample}(\lambda) - Int_{absorbed}^{sample}(\lambda)\right]d\lambda}{\int \frac{\lambda}{hc}\left[Int_{emitted}^{reference}(\lambda) - Int_{absorbed}^{reference}(\lambda)\right]d\lambda}$$

wherein $n_{photon}$ denotes the photon count and Int. the intensity.

Production and Characterization of Optoelectronic Devices

OLED devices comprising organic molecules according to the invention can be produced via vacuum-deposition methods. If a layer contains more than one compound, the weight-percentage of one or more compounds is given in %. The total weight-percentage values amount to 100%, thus if a value is not given, the fraction of this compound equals to the difference between the given values and 100%.

The not fully optimized OLEDs are characterized using standard methods and measuring electroluminescence spectra, the external quantum efficiency (in %) in dependency on the intensity, calculated using the light detected by the photodiode, and the current. The OLED device lifetime is extracted from the change of the luminance during operation at constant current density. The LT50 value corresponds to the time, where the measured luminance decreased to 50% of the initial luminance, analogously LT80 corresponds to the time point, at which the measured luminance decreased to 80% of the initial luminance, LT 95 to the time point, at which the measured luminance decreased to 95% of the initial luminance etc.

Accelerated lifetime measurements are performed (e.g. applying increased current densities). For example, LT80 values at 500 cd/m² are determined using the following equation:

$$LT80\left(500\frac{cd^2}{m^2}\right) = LT80(L_0)\left(\frac{L_0}{500\frac{cd^2}{m^2}}\right)^{1.6}$$

wherein $L_0$ denotes the initial luminance at the applied current density.

The values correspond to the average of several pixels (typically two to eight), the standard deviation between these pixels is given. The figures show the data series for one OLED pixel.

Example 1

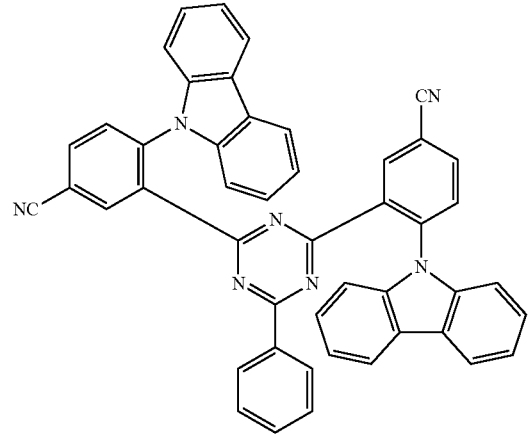 [SMILES: N#Cc1ccc(-n2c3ccccc3c3ccccc32)c(-c2nc(-c3ccccc3)nc(-c3cc(C#N)ccc3-n3c4ccccc4c4ccccc43)n2)c1]

Example 1 was synthesized according to AAV1 (yield 19%) and AAV3 (yield 22%)

FIG. 1 depicts the emission spectrum of example 1(10% by weight in PMMA). The emission maximum ($\lambda_{max}$) is at 489 nm. The photoluminescence quantum yield (PLQY) is 80%, the full width at half maximum (FWHM) is 0.41 eV and the emission lifetime is 6 μs. The resulting $CIE_x$ coordinate is 0.22 and the $CIE_y$ coordinate is 0.44.

MS (HPLC-MS), m/z (retention time): 689.33 (8.13 min).

Example 2

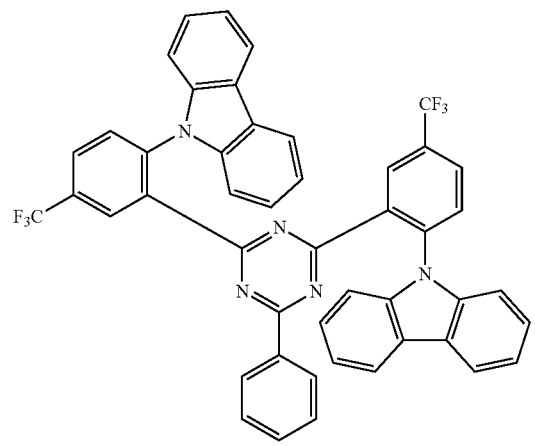 [SMILES: FC(F)(F)c1ccc(-n2c3ccccc3c3ccccc32)c(-c2nc(-c3ccccc3)nc(-c3cc(C(F)(F)F)ccc3-n3c4ccccc4c4ccccc43)n2)c1]

Example 2 was synthesized according to AAV2 (yield 68%) and AAV3 (yield 51%)

Figure 2:
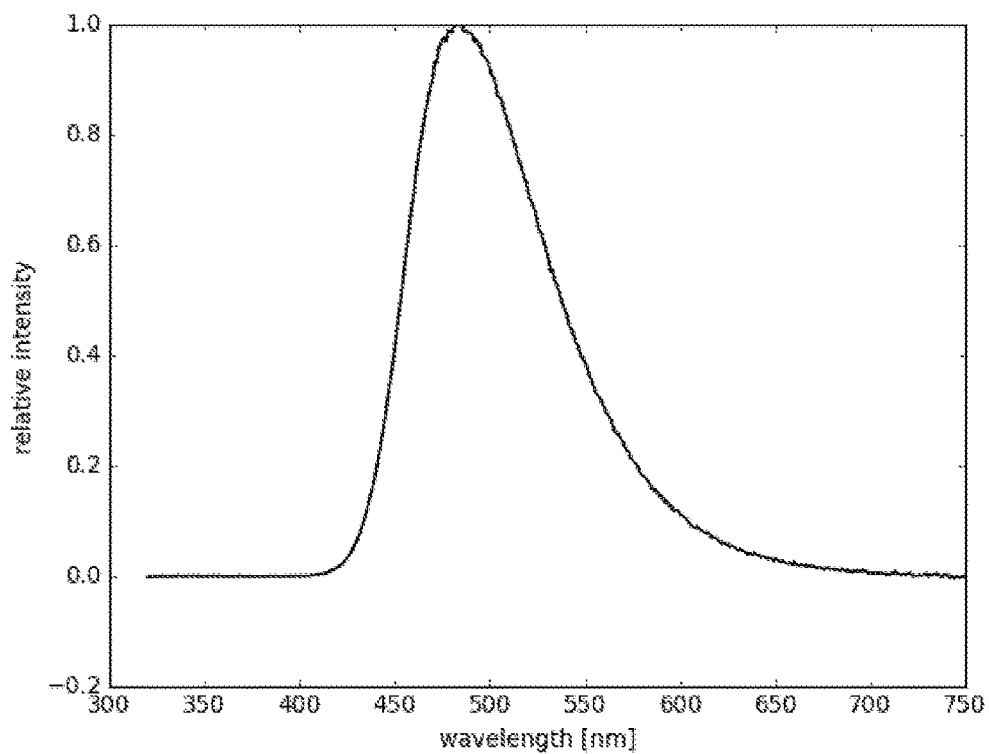
FIG. 2 shows the emission spectrum of example 2 (10% by weight) in PMMA.

FIG. 2 depicts the emission spectrum of example 2 (10% by weight in PMMA). The emission maximum ($\lambda_{max}$) is at 484 nm. The photoluminescence quantum yield (PLQY) is 79%, the full width at half maximum (FWHM) is 0.43 eV and the emission lifetime is 5 μs. The resulting $CIE_x$ coordinate is 0.19 and the $CIE_y$ coordinate is 0.35.

MS (HPLC-MS), m/z (retention time): 775.35 (10.85 min).

Example 3

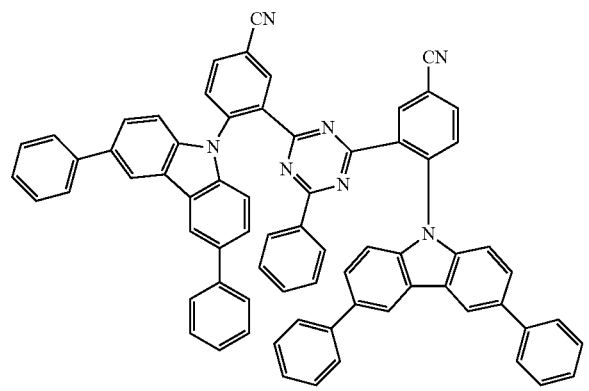 [SMILES: N#Cc1ccc(-n2c3ccc(-c4ccccc4)cc3c3cc(-c4ccccc4)ccc32)c(-c2nc(-c3ccccc3)nc(-c3cc(C#N)ccc3-n3c4ccc(-c5ccccc5)cc4c4cc(-c5ccccc5)ccc43)n2)c1]

Example 3 was synthesized according to AAV1 (yield 84%) and AAV3 (yield 80%)

Figure 3:
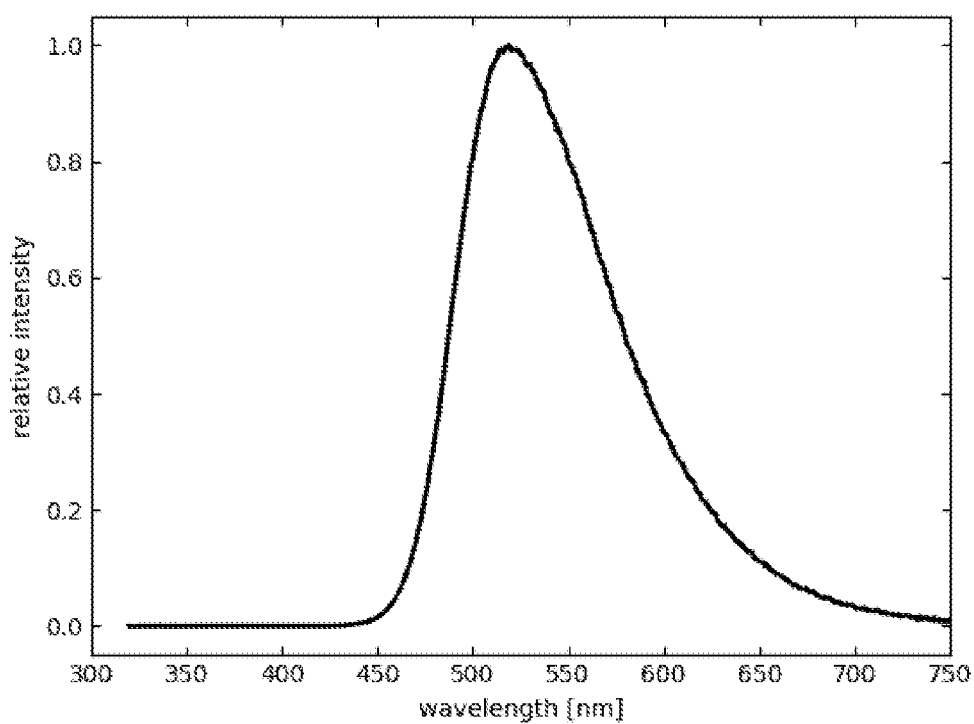
FIG. 3 shows the emission spectrum of example 3 (10% by weight) in PMMA.

FIG. 3 depicts the emission spectrum of example 3 (10% by weight in PMMA). The emission maximum ($\lambda_{max}$) is at 519 nm. The photoluminescence quantum yield (PLQY) is 52%, the full width at half maximum (FWHM) is 0.40 eV and the emission lifetime is 4 μs. The resulting $CIE_x$ coordinate is 0.32 and the $CIE_y$ coordinate is 0.57.

MS (HPLC-MS), m/z: 993.40.

Device D1

Example 3 was tested in an OLED-device D1 with the following layer structure:

| Layer | Thickness | |
|---|---|---|
| 9 | 100 nm | Al |
| 8 | 2 nm | Liq |
| 7 | 35 nm | NBphen |
| 6 | 40 nm | 3 (30%):mCBP (70%) |
| 5 | 5 nm | mCBP |
| 4 | 5 nm | TCTA |
| 3 | 145 nm | NPB |
| 2 | 5 nm | HAT-CN |
| 1 | 50 nm | ITO |
| Substrate | | Glass |

For D1, an external quantum efficiency (EQE) at 1000 cd/m² of 12.6±0.1%, a LT80-value at 500 cd/m² of 10032 h and a LT97-value at 1200 cd/m² of 198 h from accelerated lifetime measurements were determined. The emission maximum is at 528 nm, CIEx is 0.37 and CIEy: 0.57 at 4.5 V.

Device D2

Example 3 was tested in an OLED-device D2 with the following layer structure:

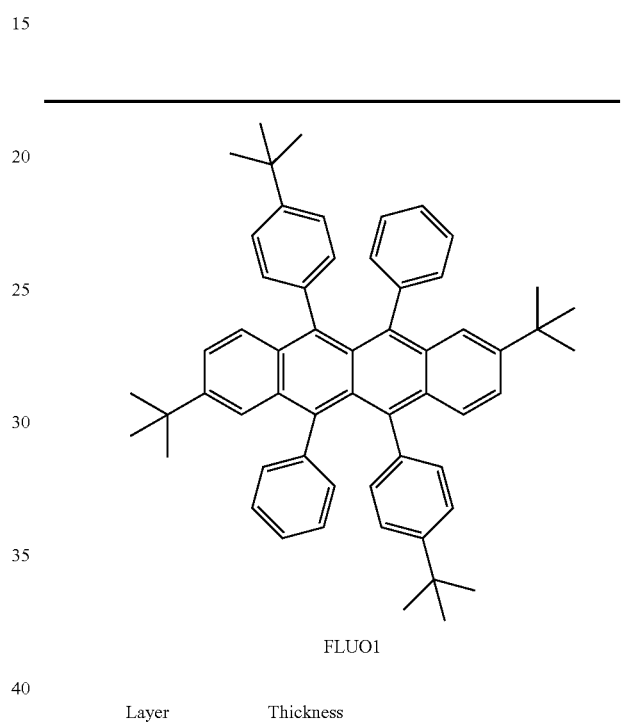

FLUO1

| Layer | Thickness | |
|---|---|---|
| 9 | 100 nm | Al |
| 8 | 2 nm | Liq |
| 7 | 65 nm | NBphen |
| 6 | 30 nm | 3 (11%): mCBP (88%): FLUO1 (1%) |
| 5 | 5 nm | mCBP |
| 4 | 5 nm | TCTA |
| 3 | 20 nm | NPB |
| 2 | 10 nm | HAT-CN |
| 1 | 50 nm | ITO |
| Substrate | | Glass |

For D2, an external quantum efficiency (EQE) at 1000 cd/m² of 9.6±0.2% and a LT97-value at 1200 cd/m² of 306 h from accelerated lifetime measurements were determined. The emission maximum is at 561 nm, CIEx is 0.46 and CIEy: 0.51 at 6.4 V.

Additional Examples of Organic Molecules According to the Invention
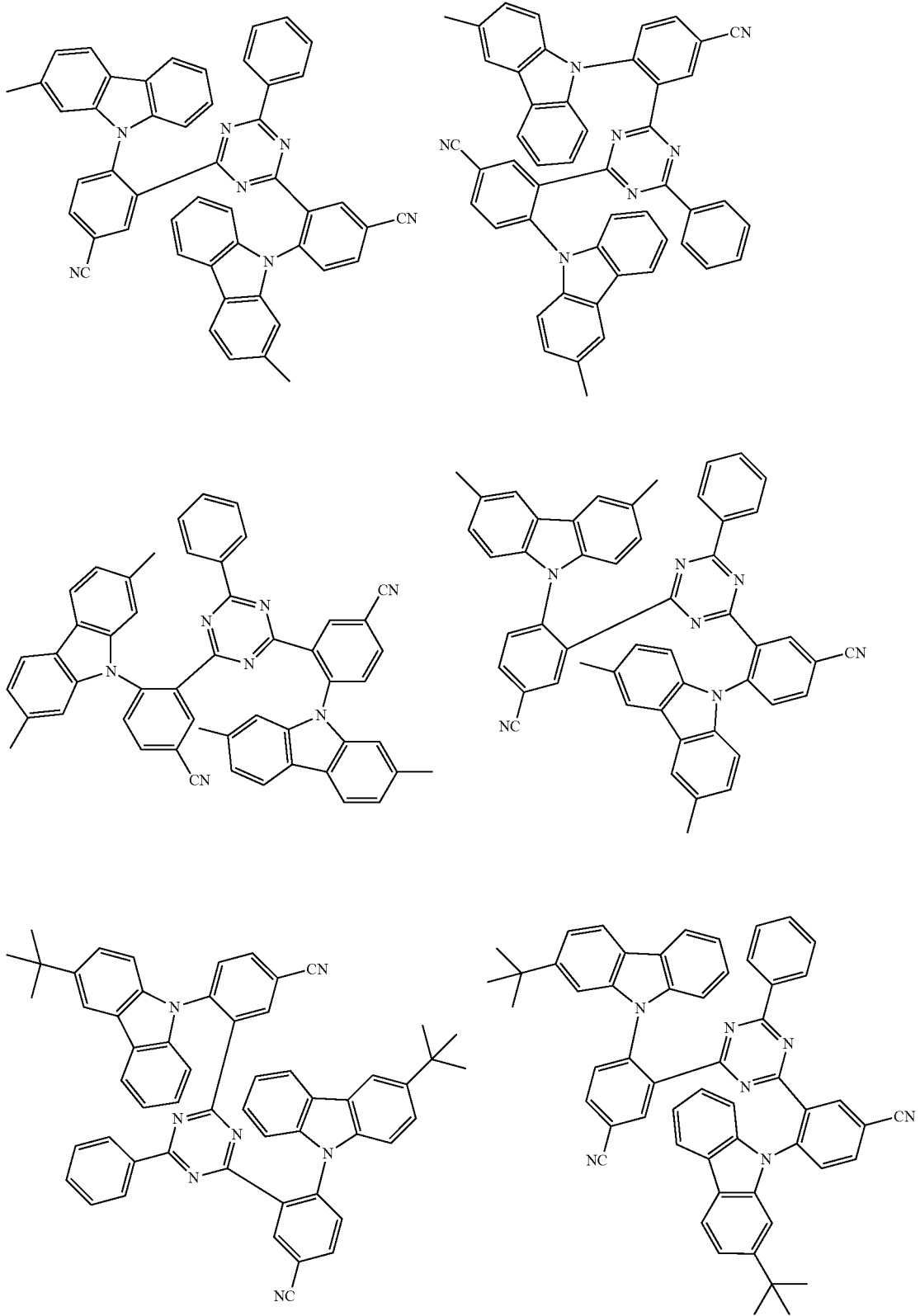

-continued
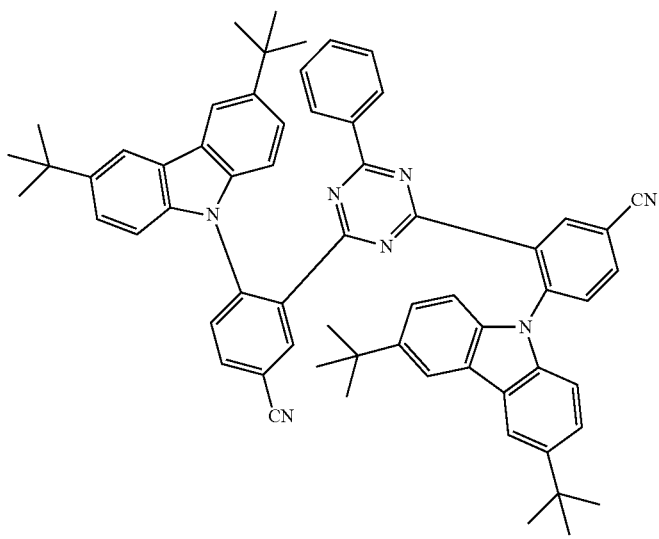
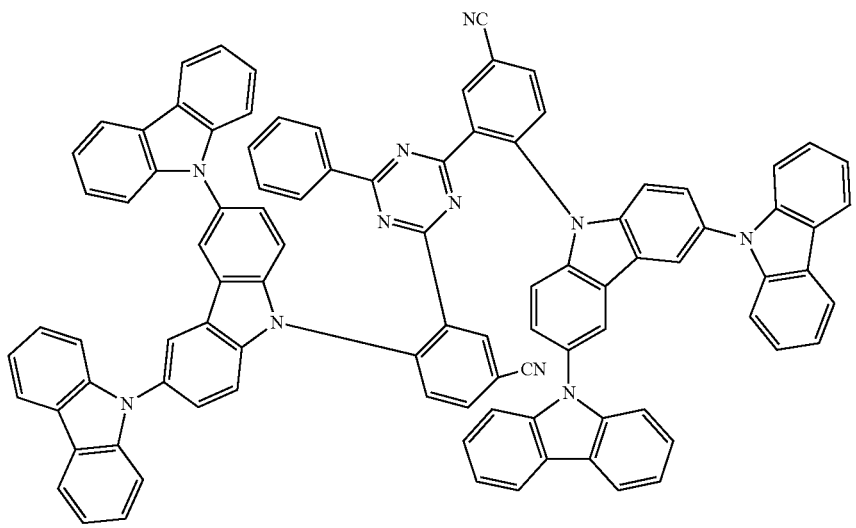
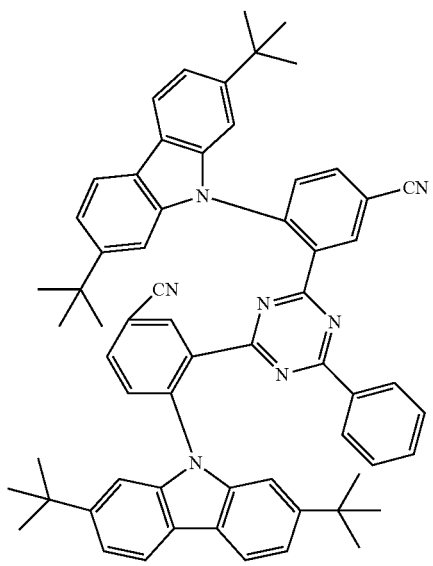
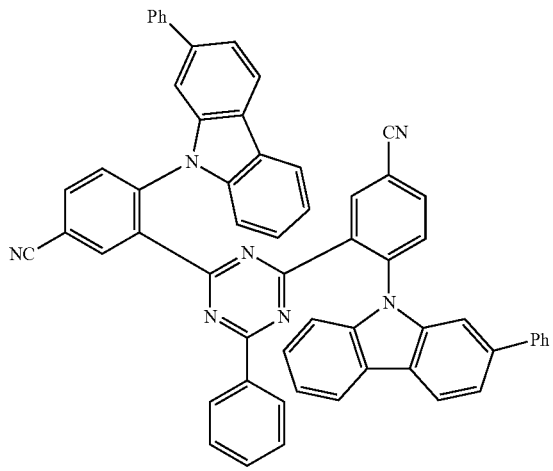

-continued
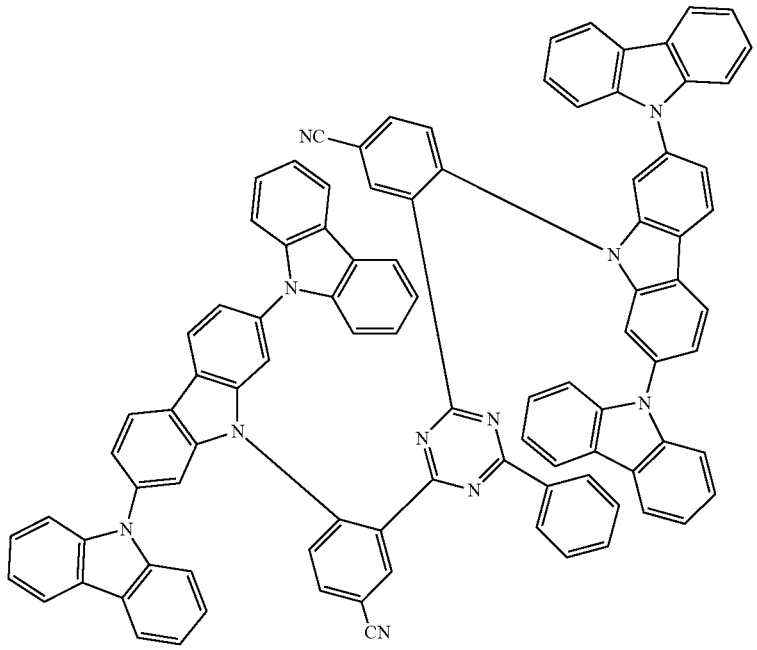
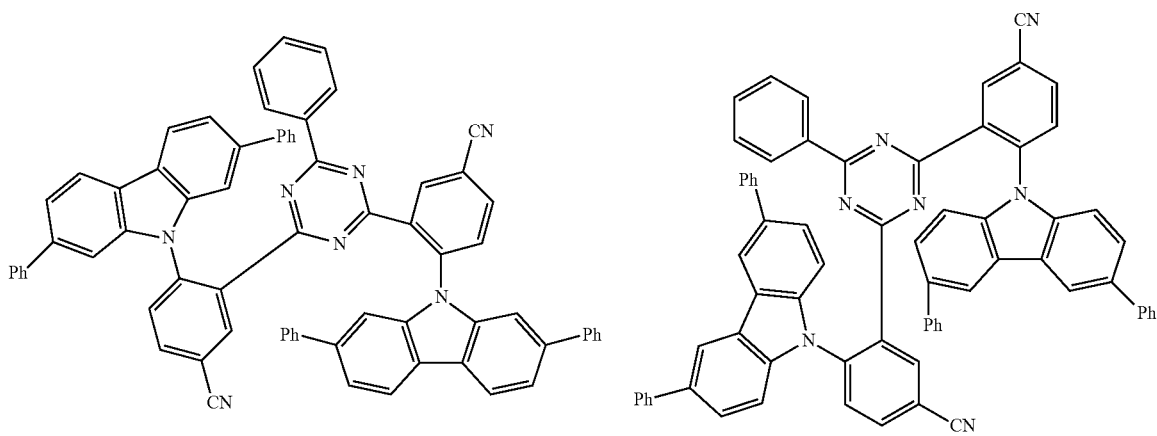
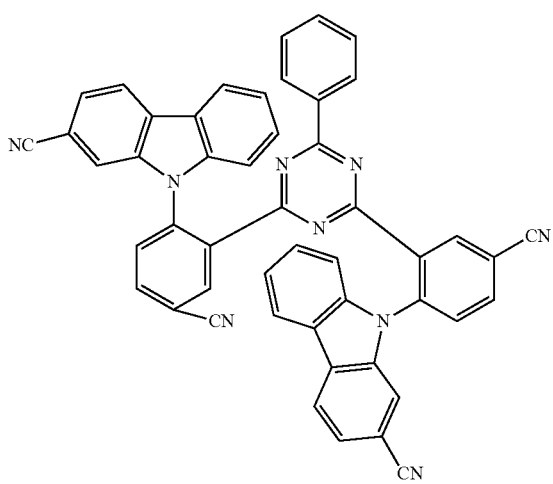
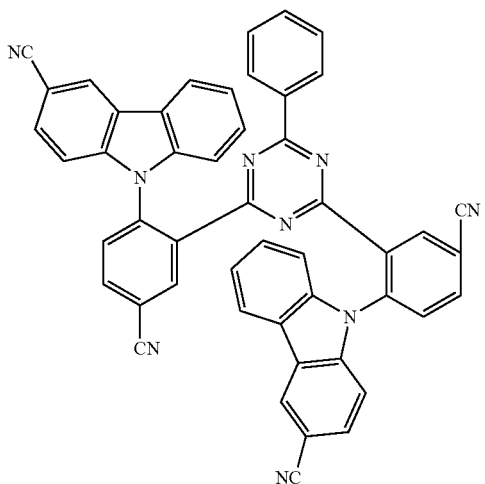

-continued
141 142
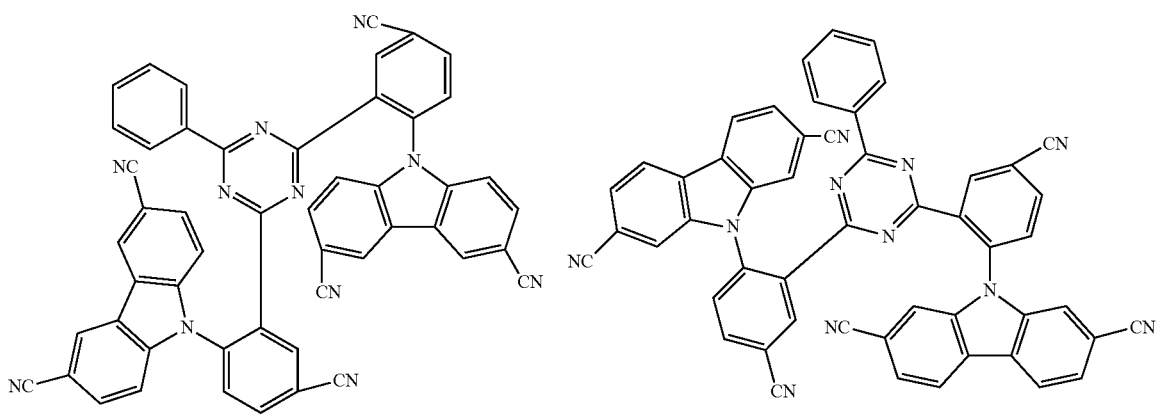
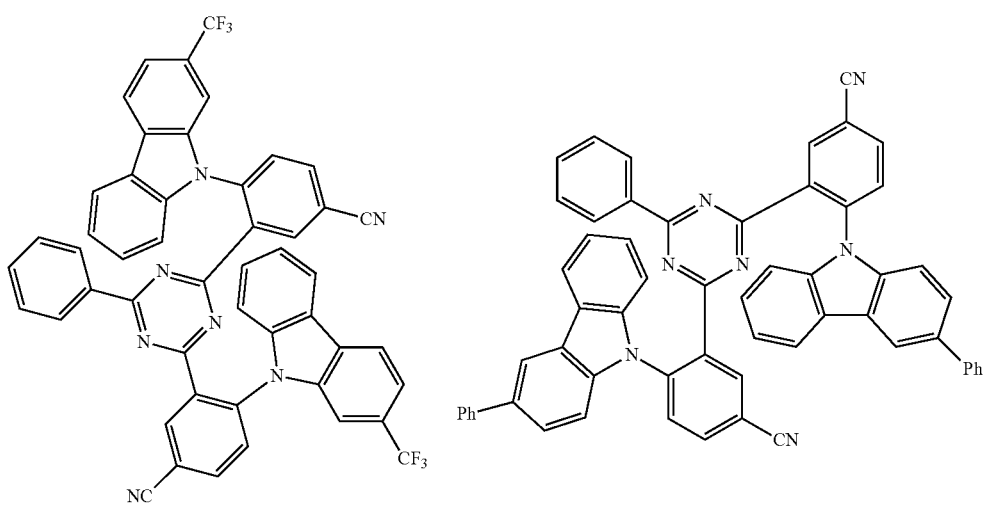
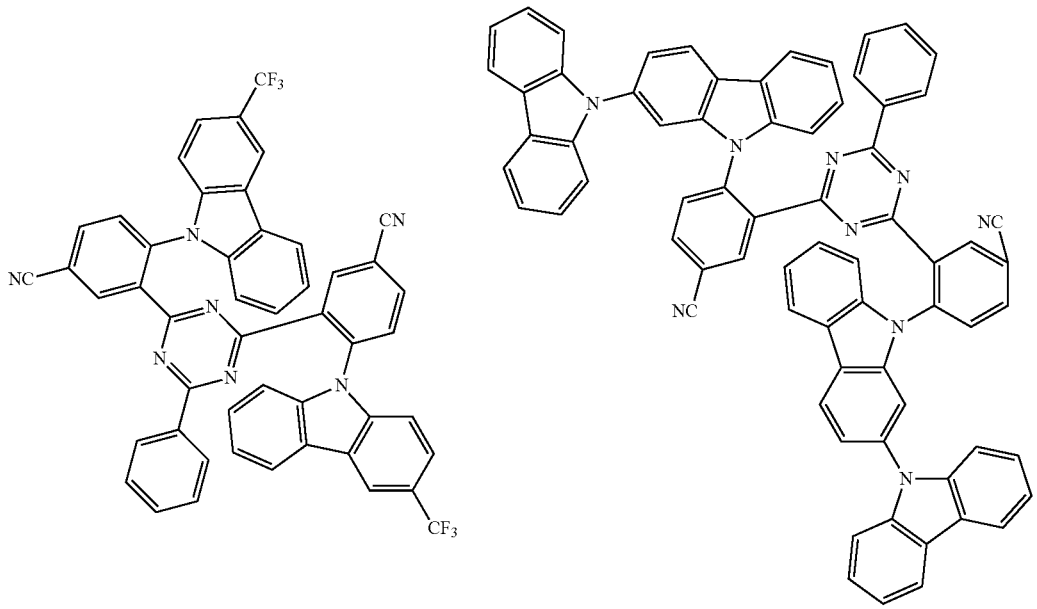

143
-continued
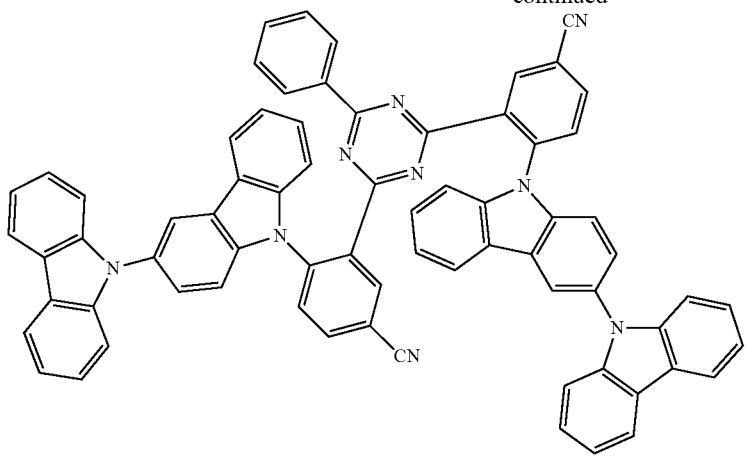
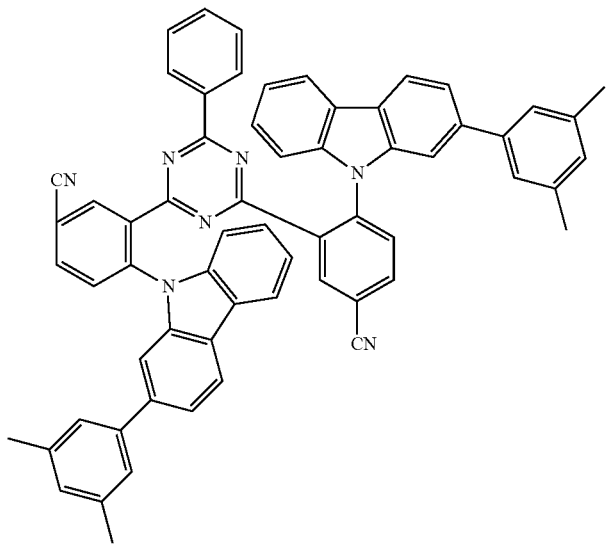
144
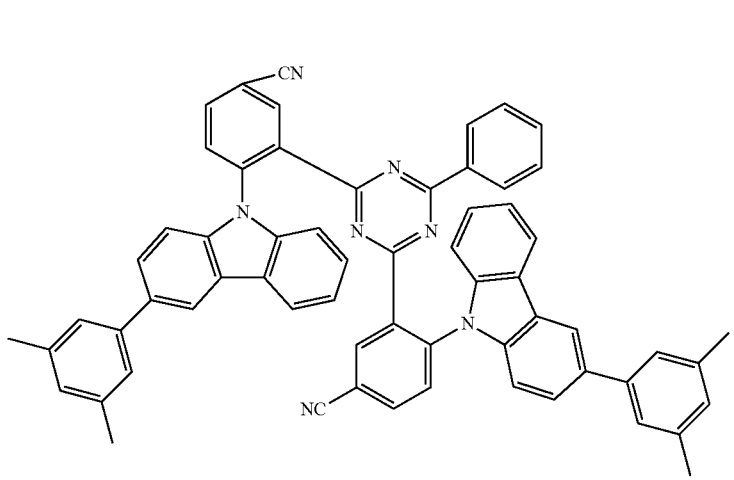
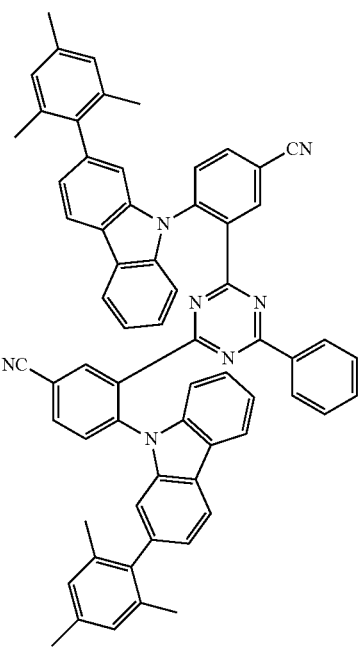

-continued
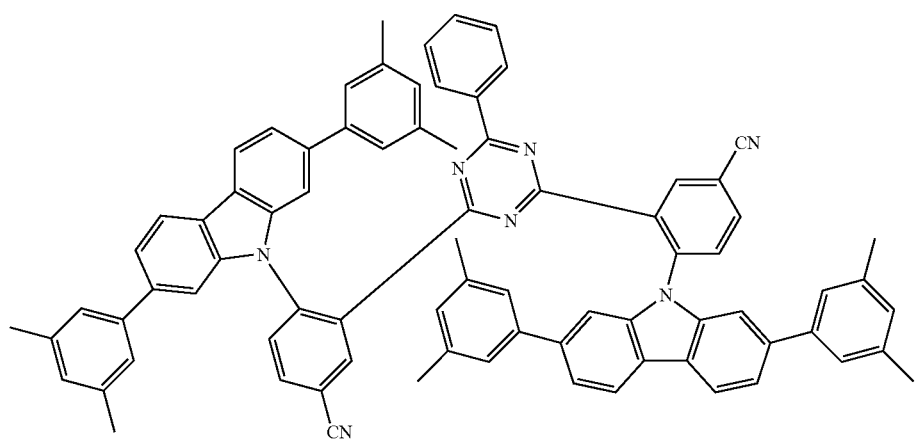
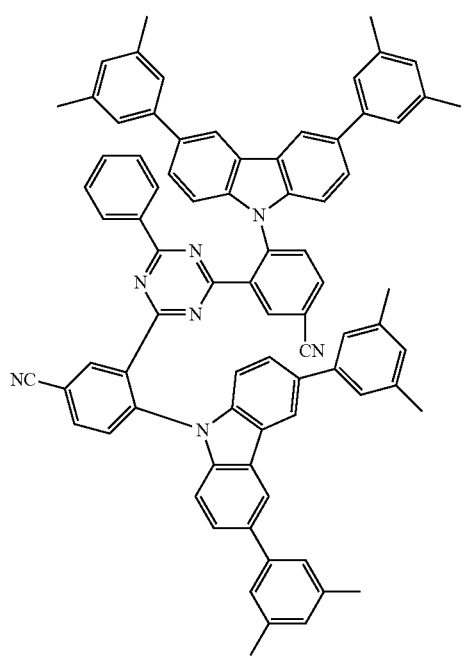
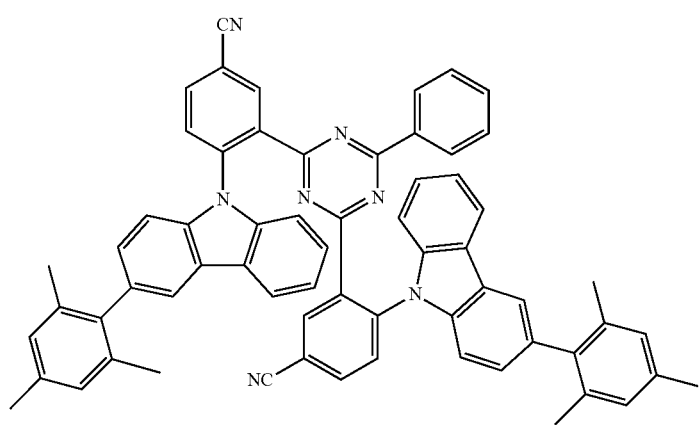

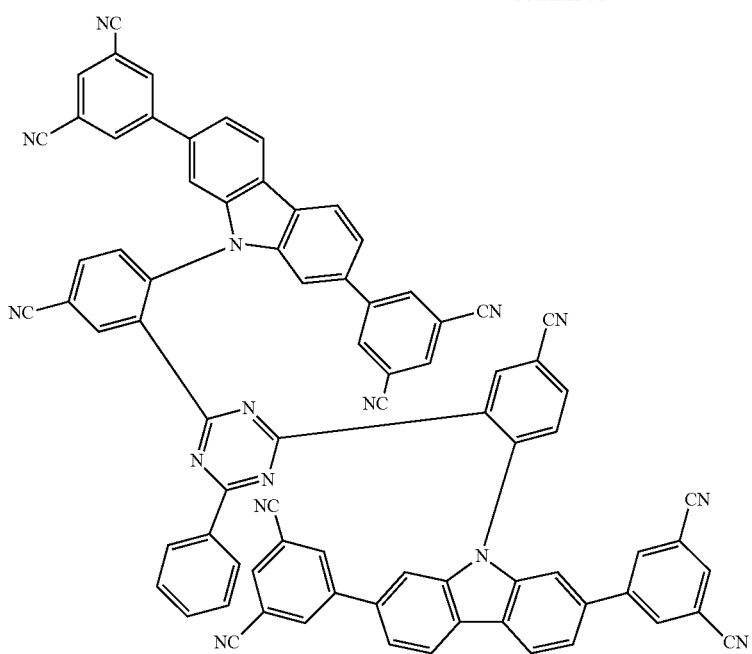
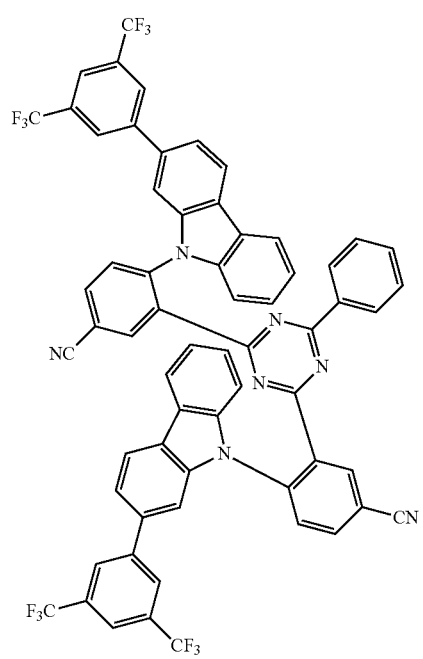

-continued
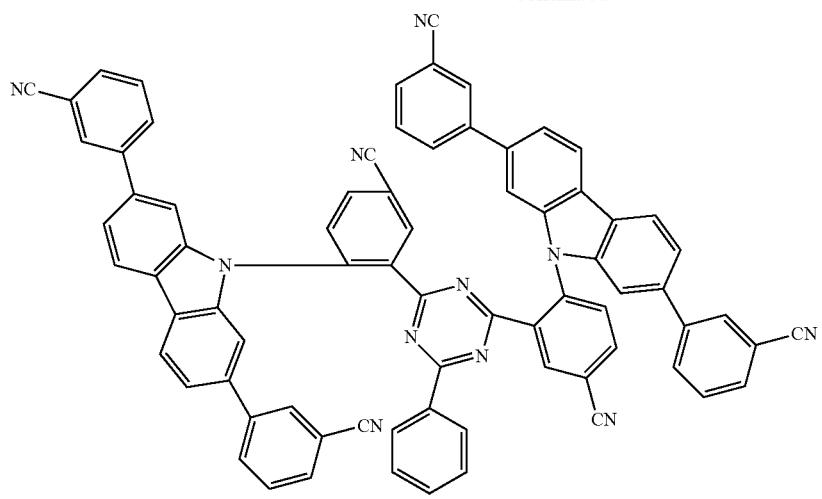
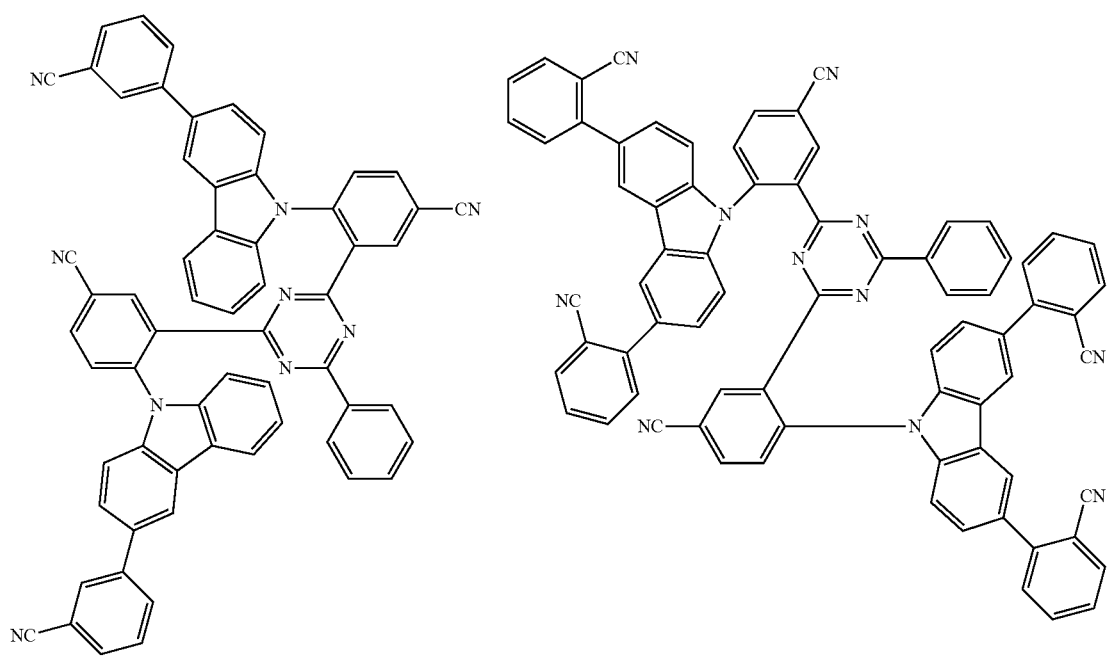

-continued
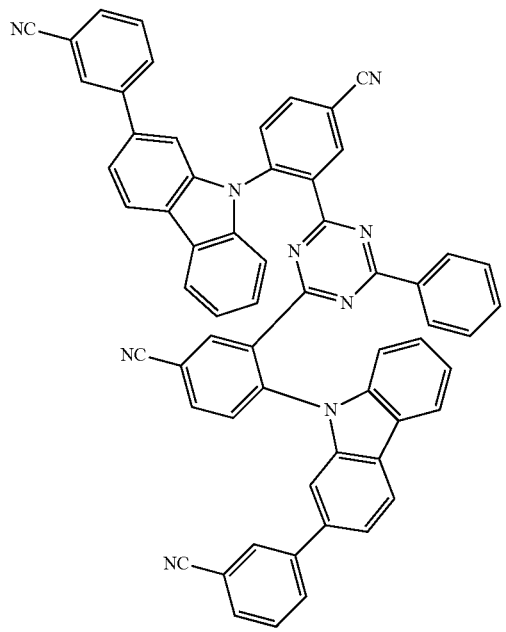
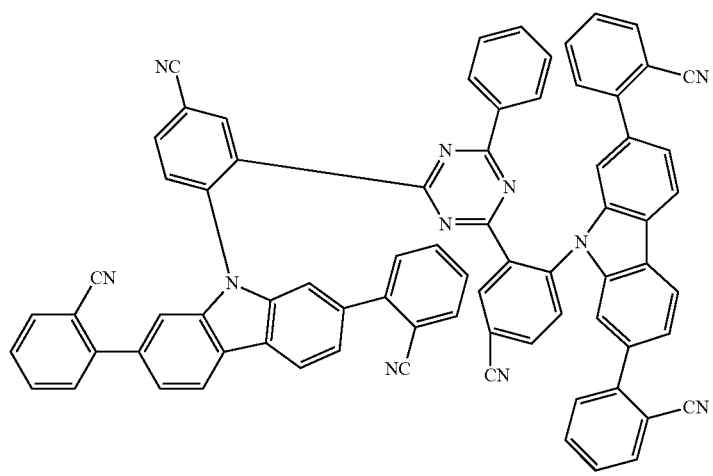
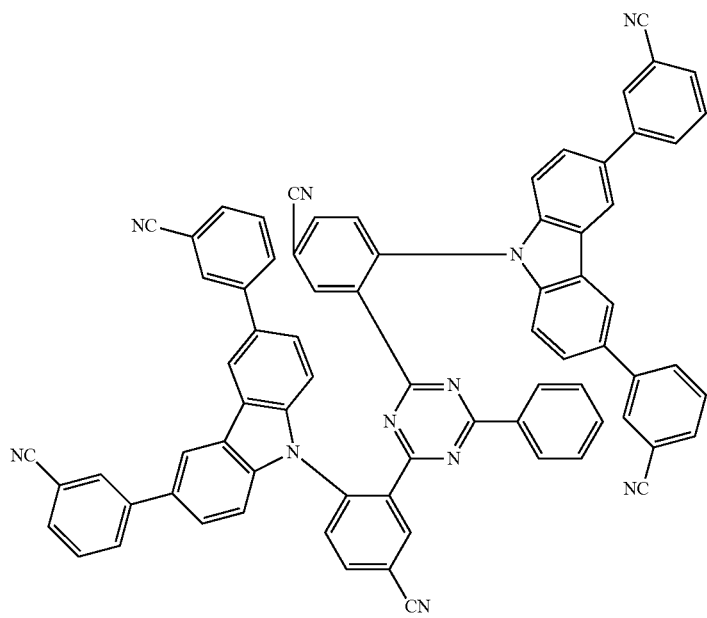

-continued
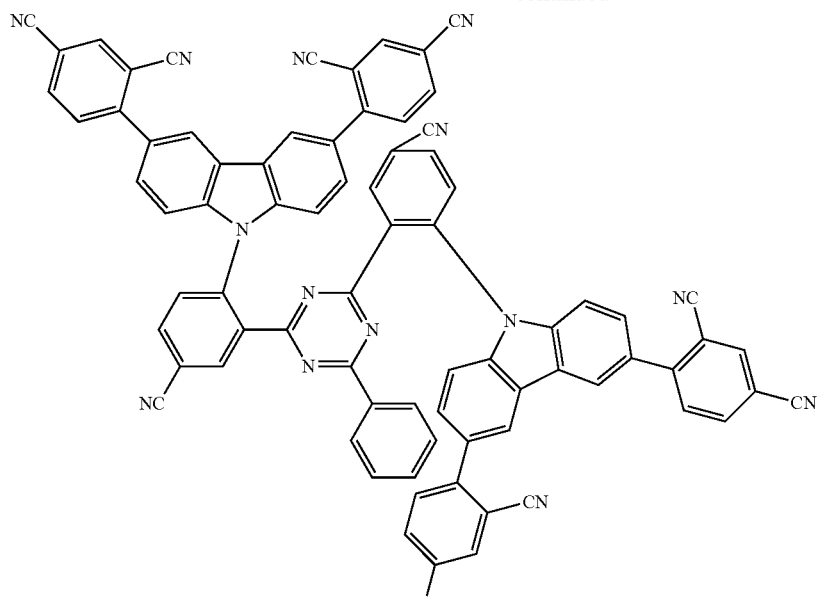
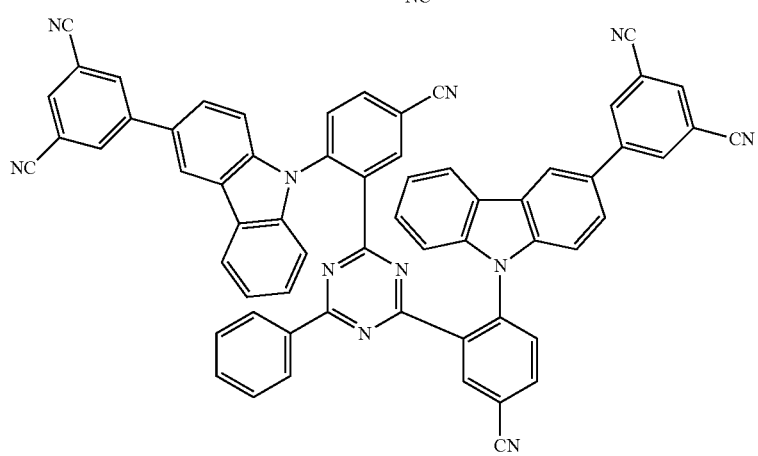
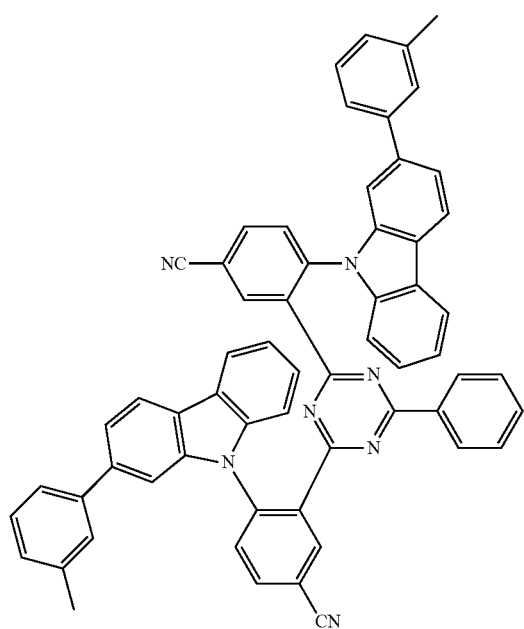

-continued
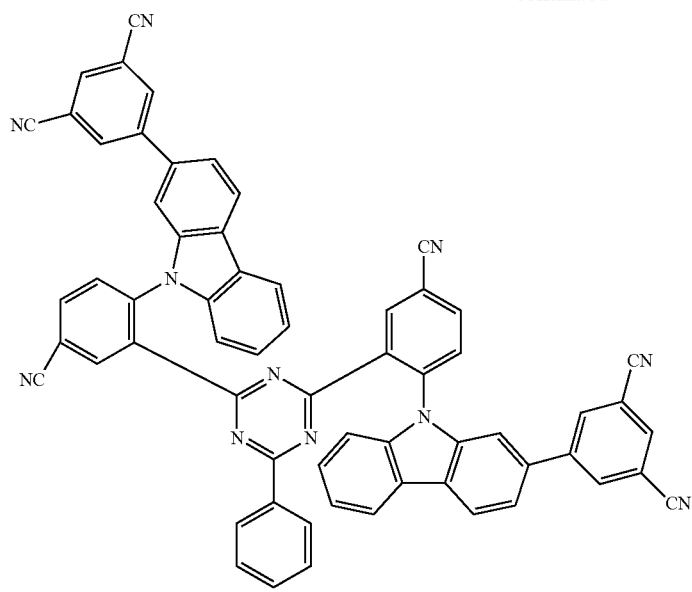
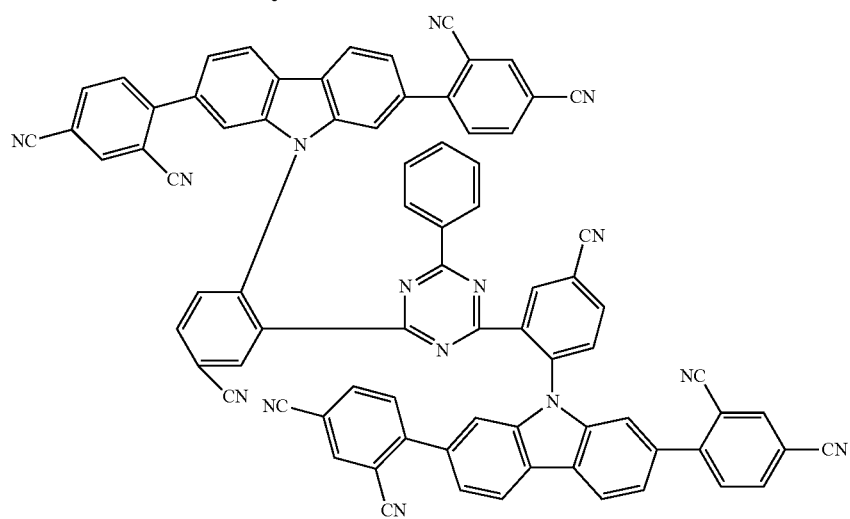
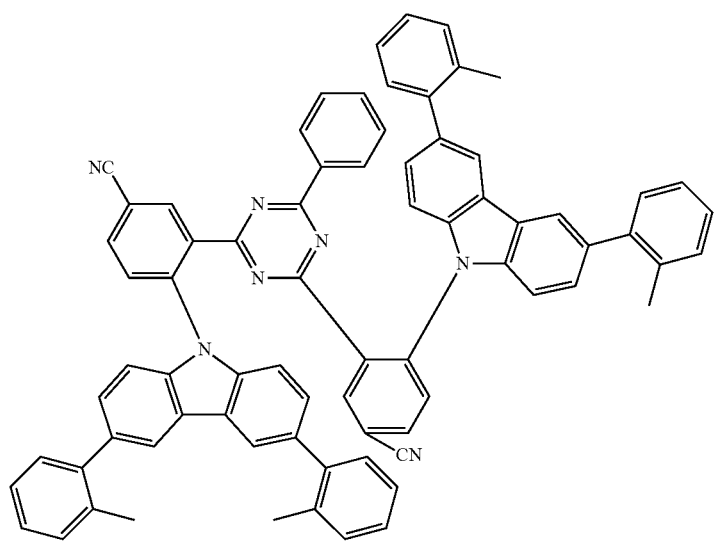

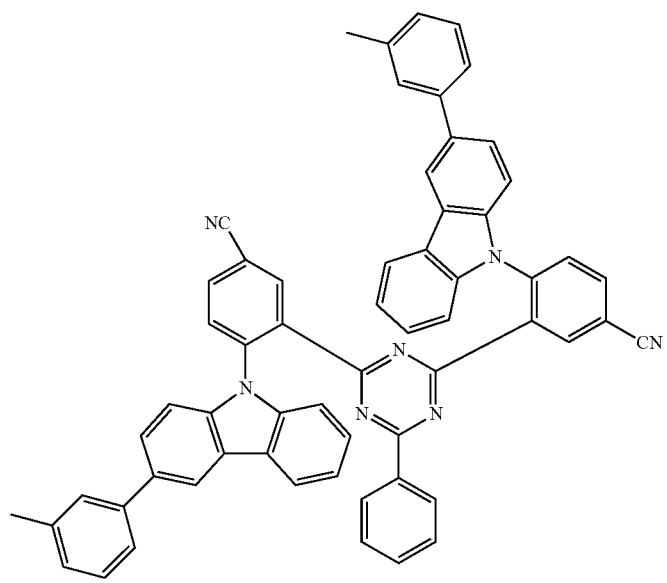
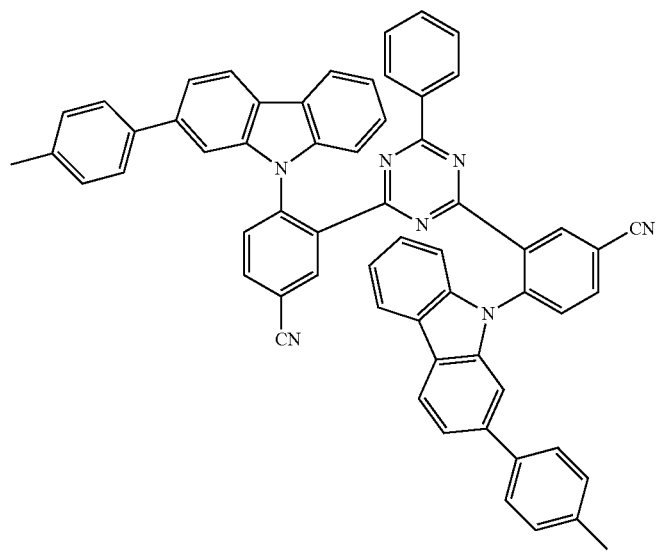

-continued
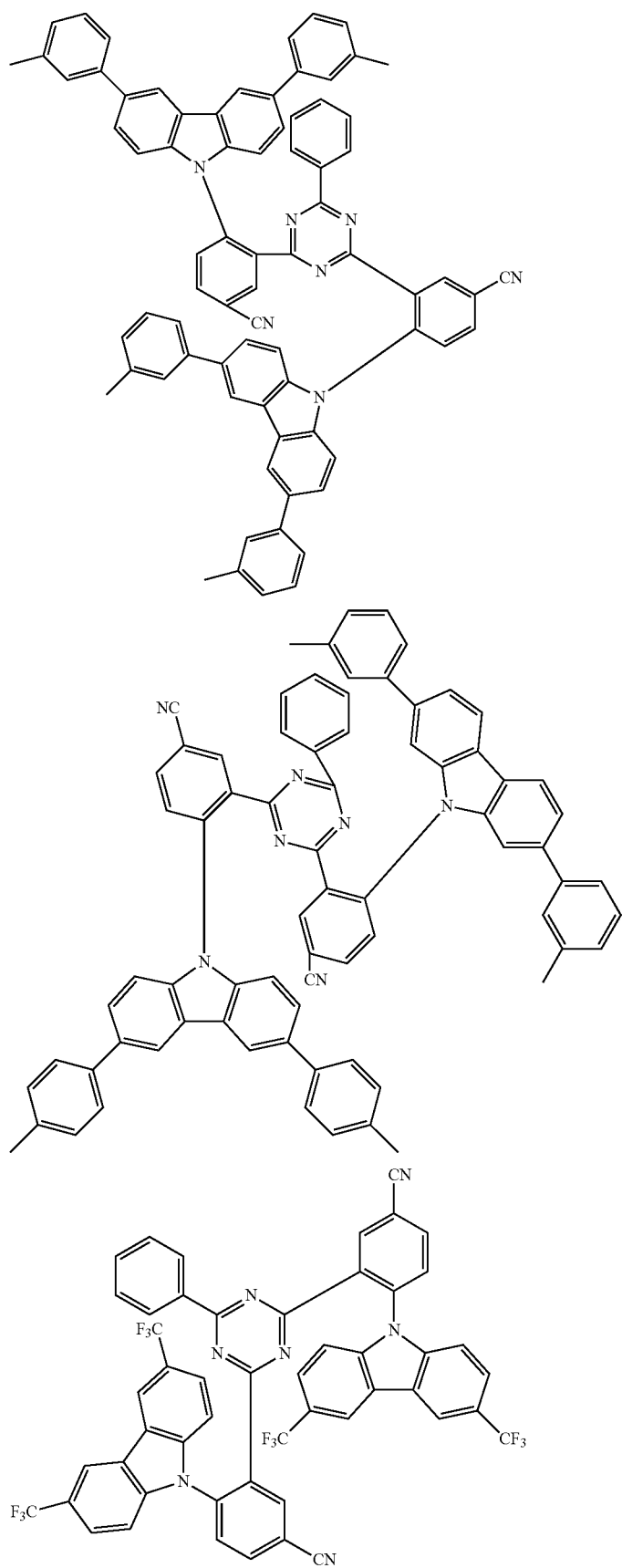

-continued
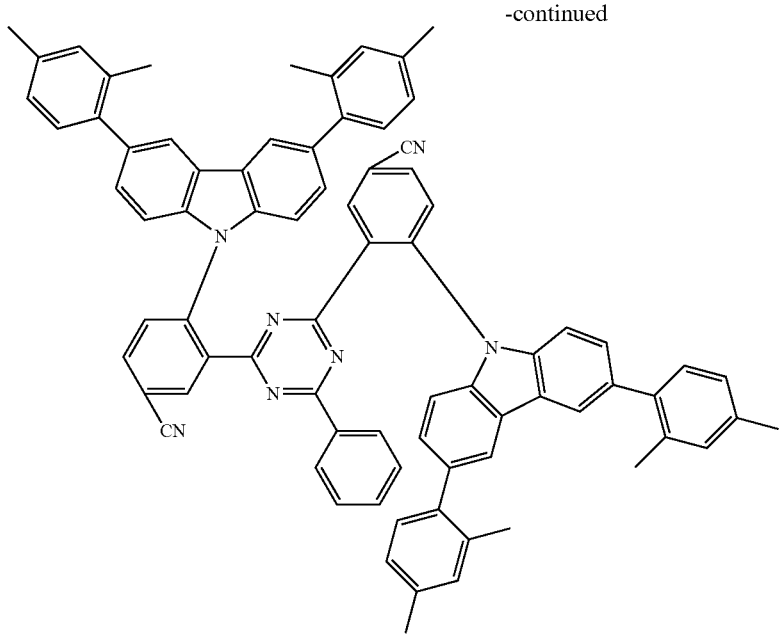
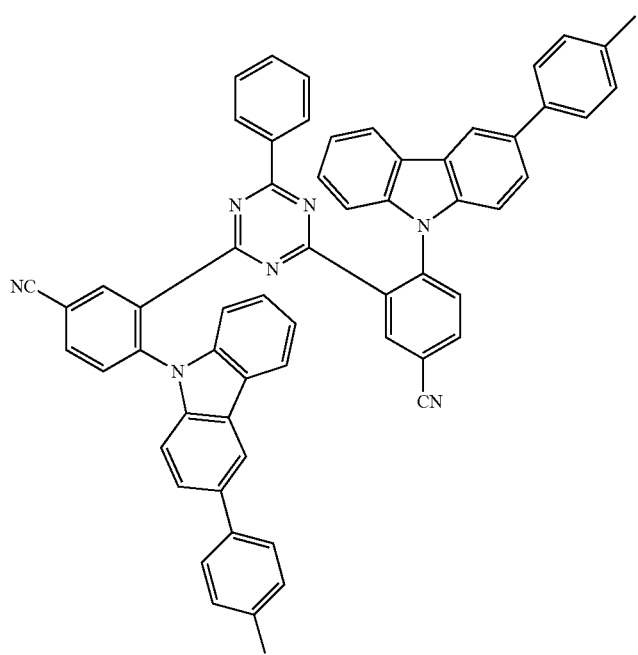

-continued
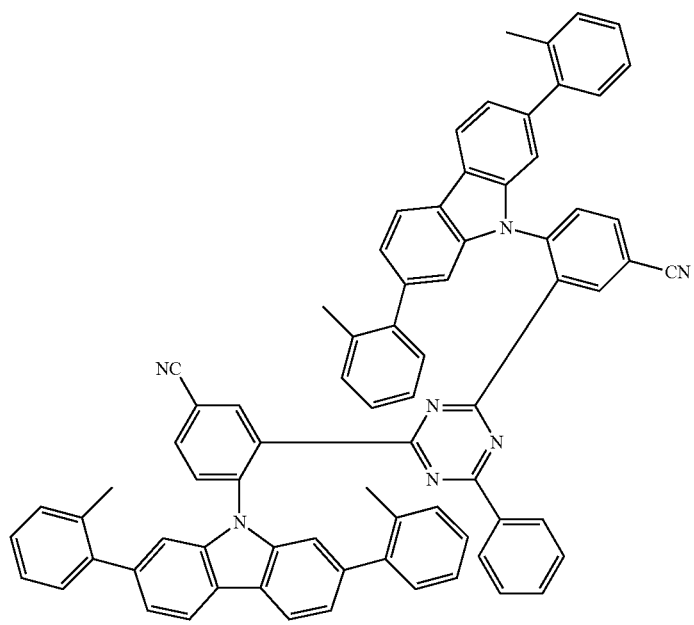
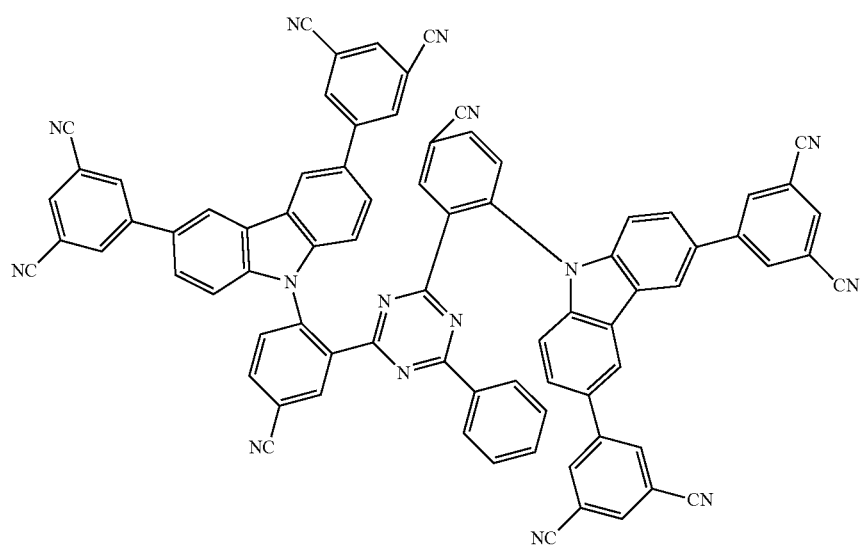

-continued
165
166
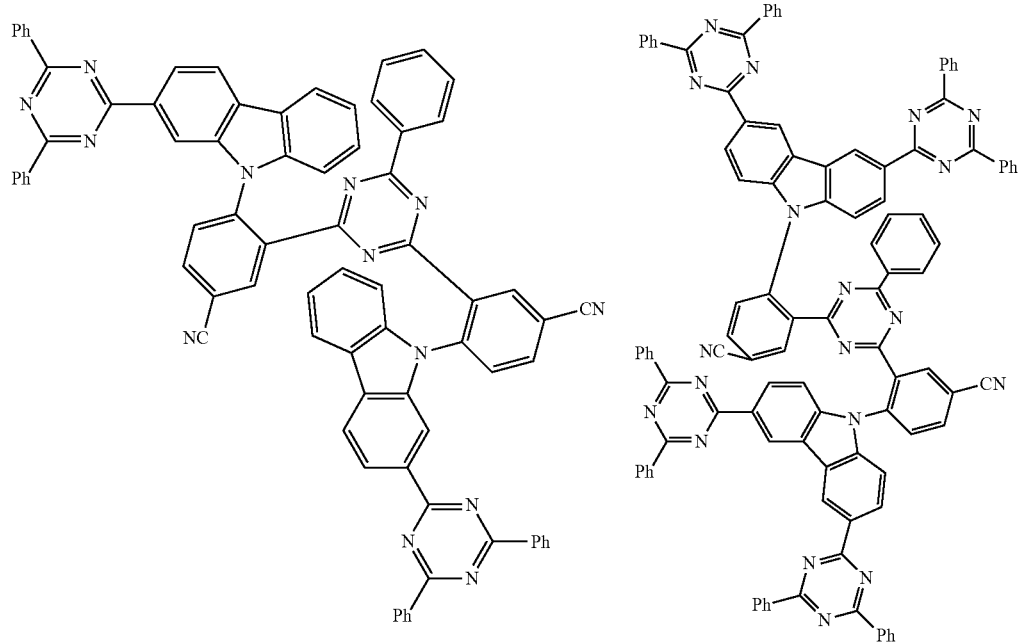
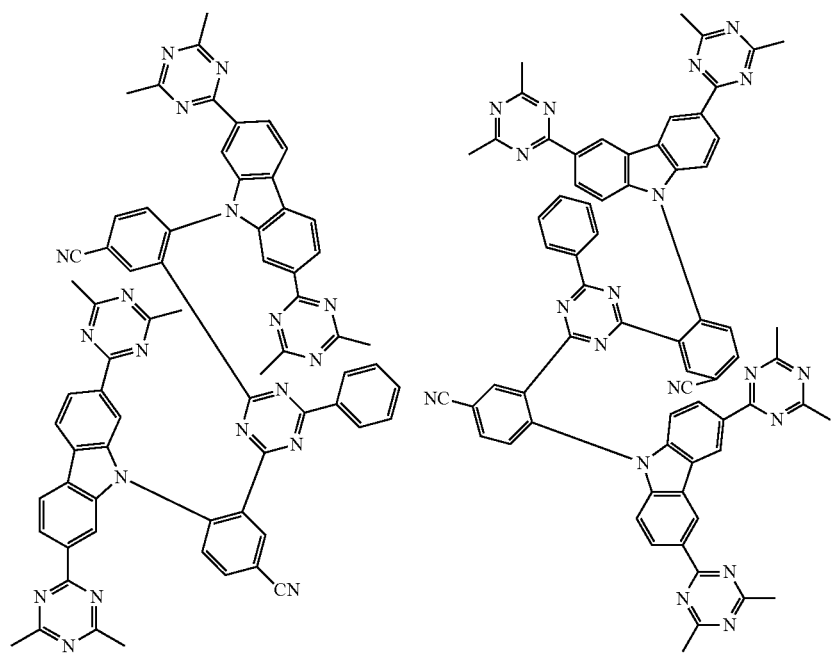
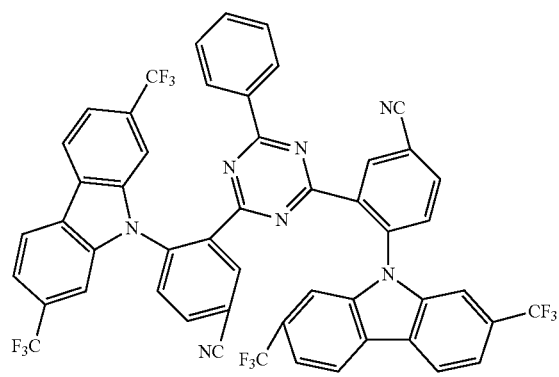

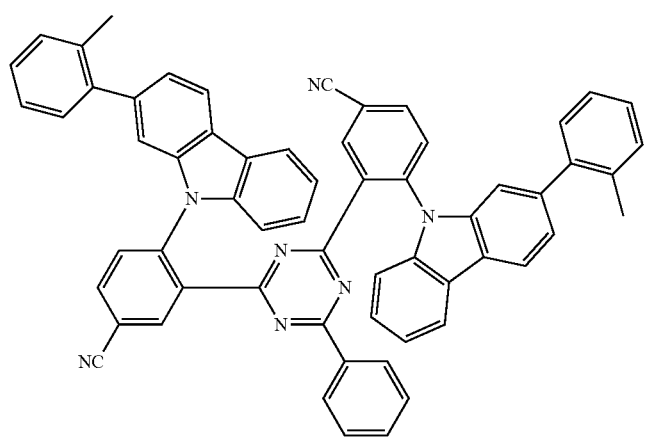
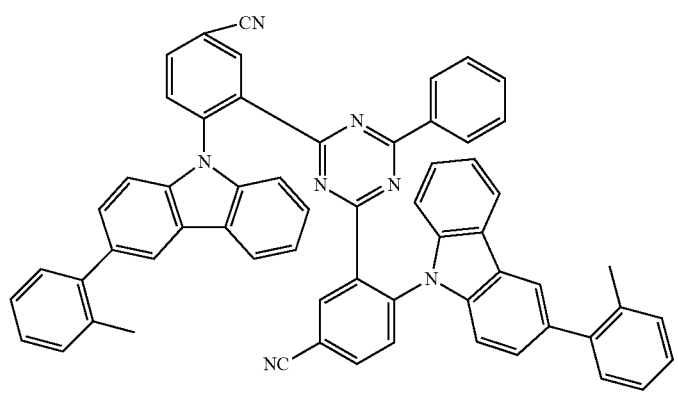
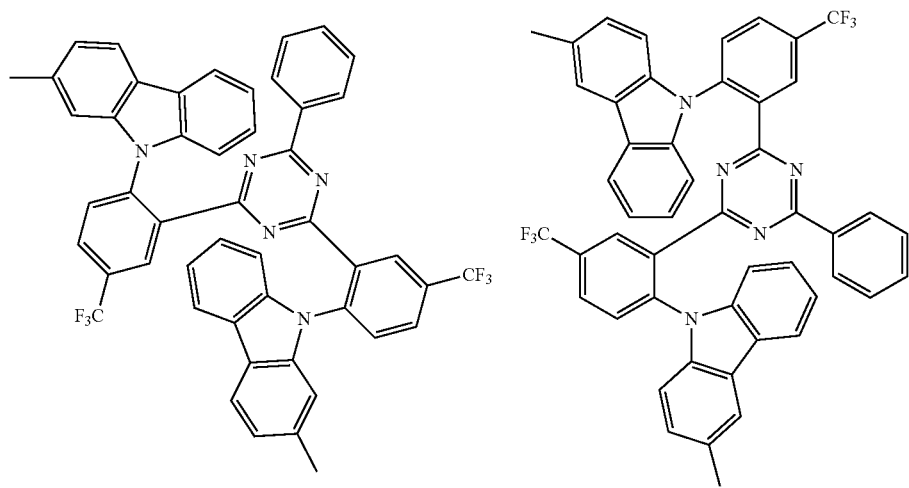

169
170
-continued
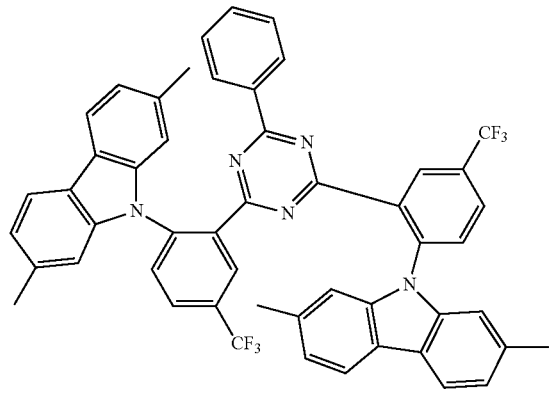
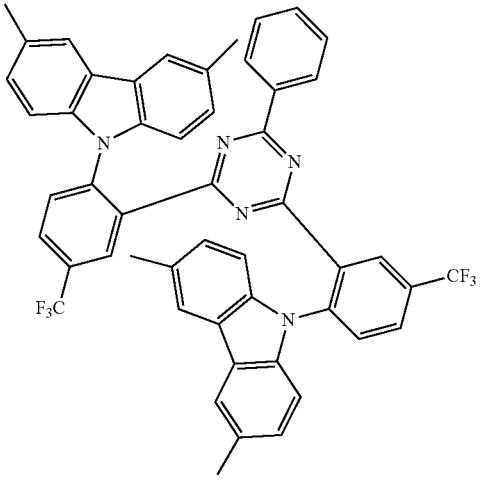
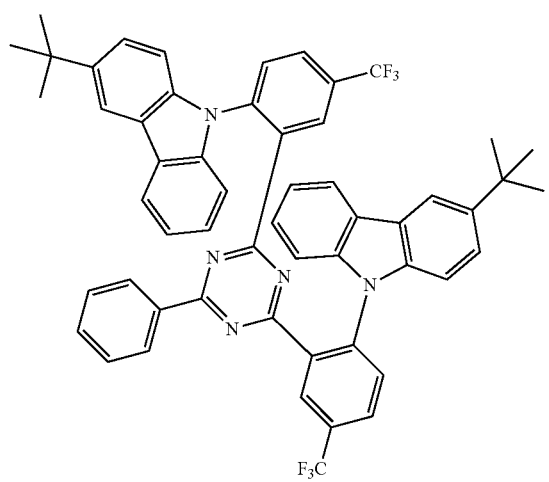
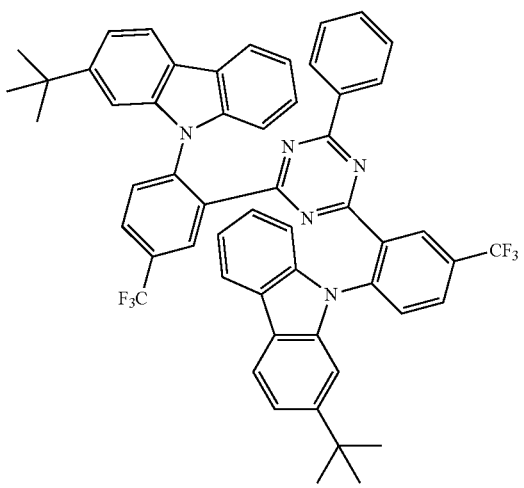
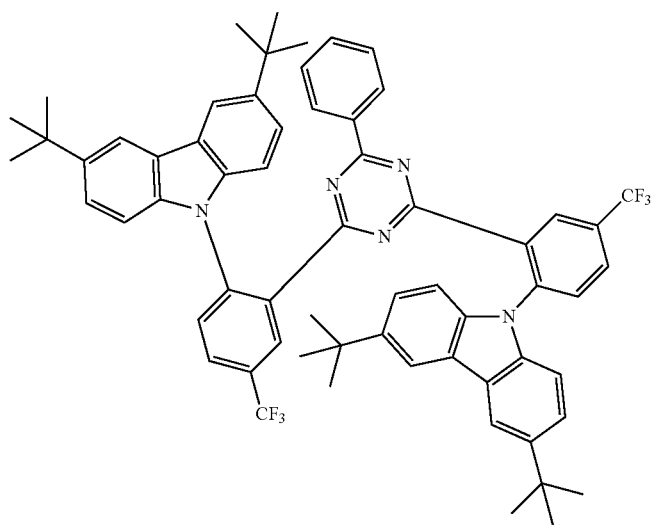

-continued
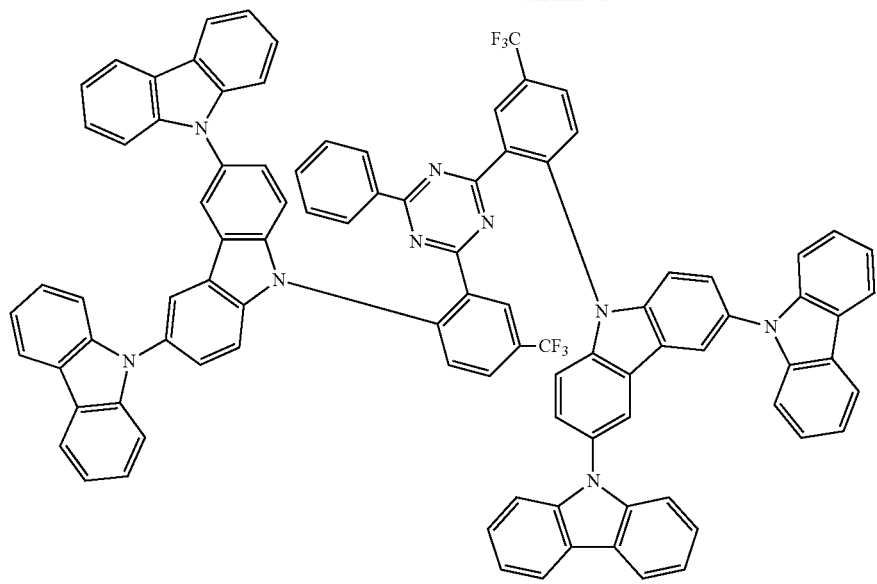
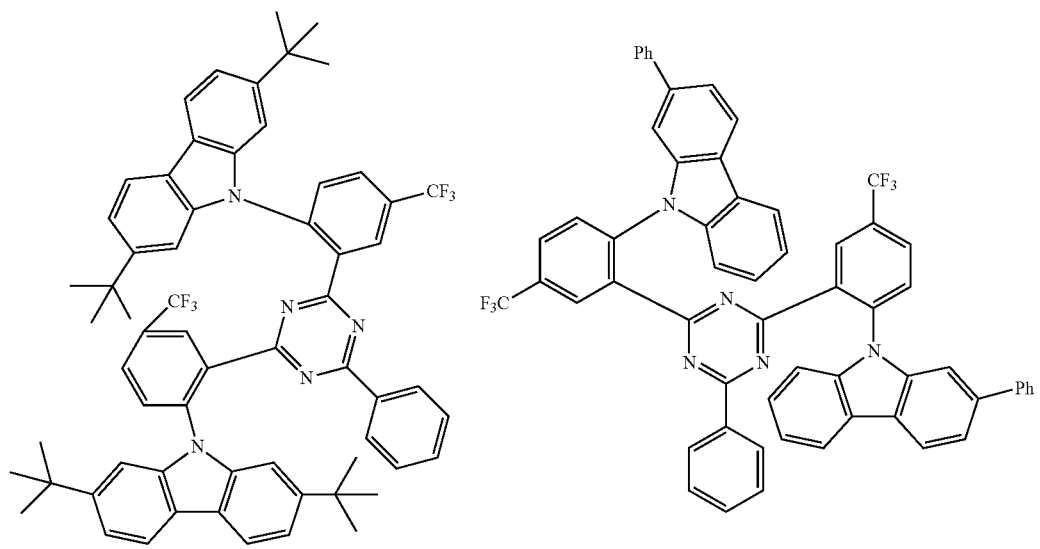
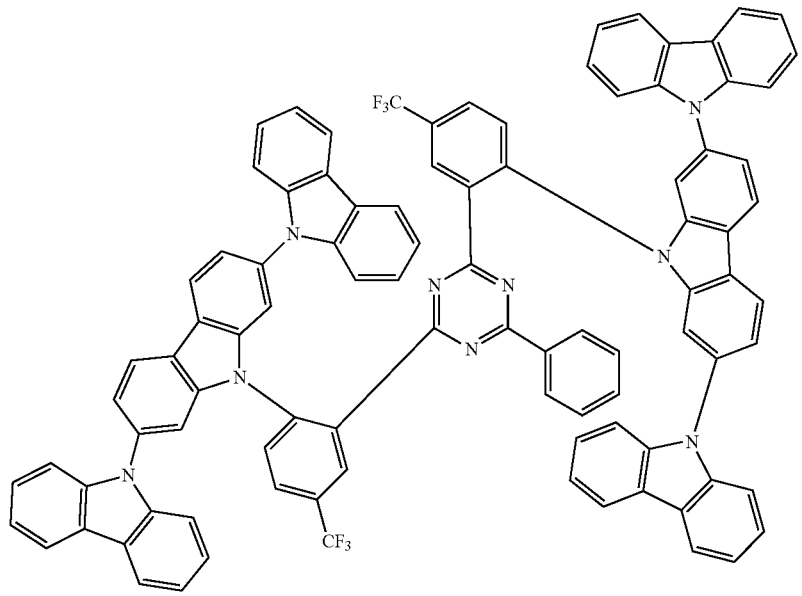

173 174
-continued
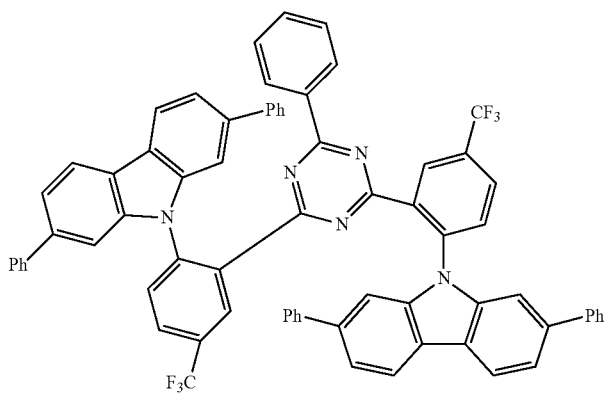
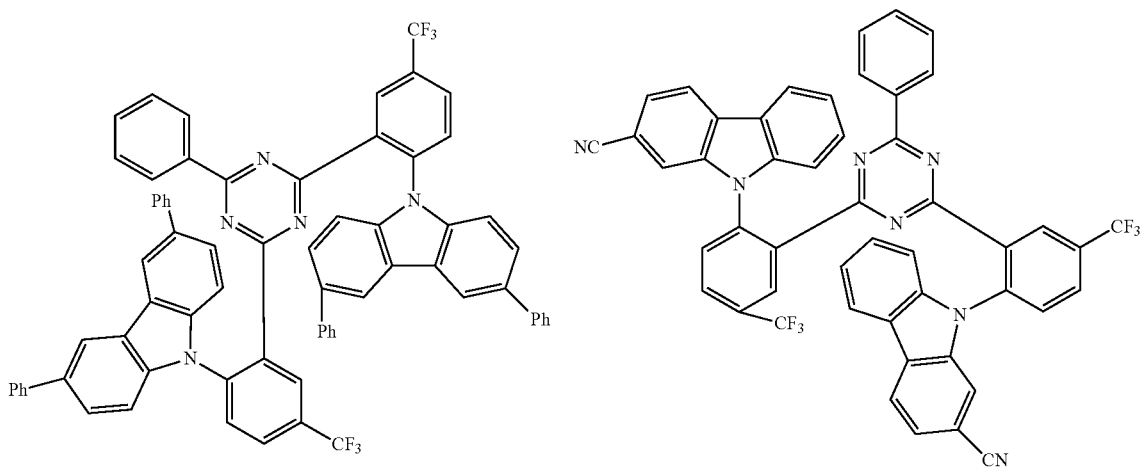
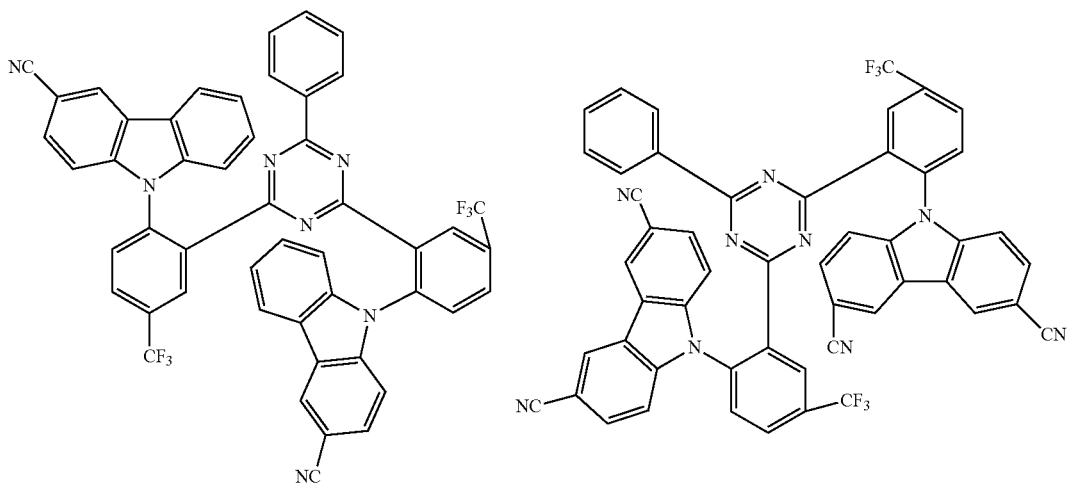

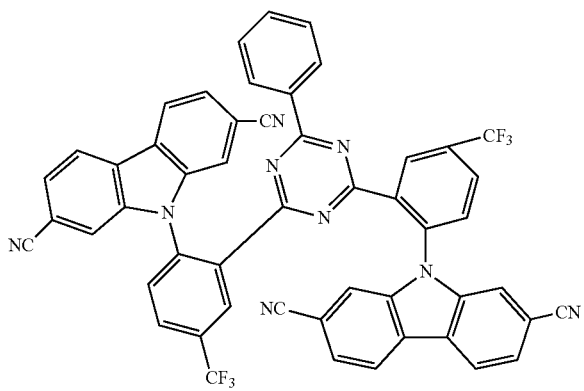
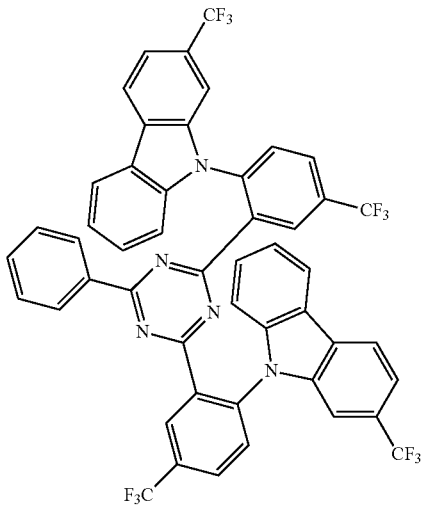
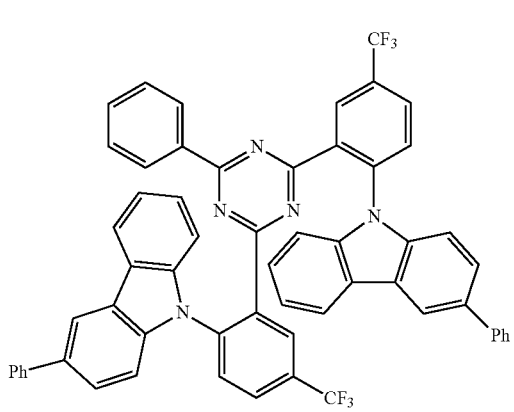
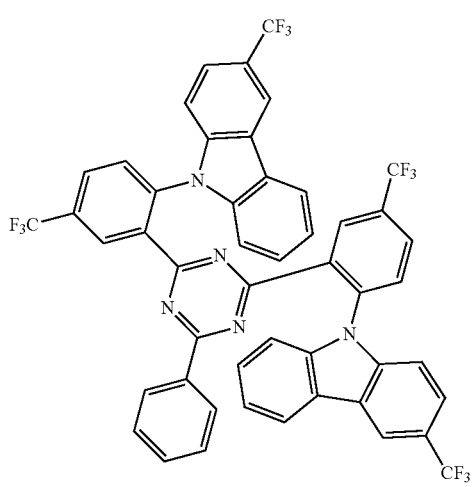
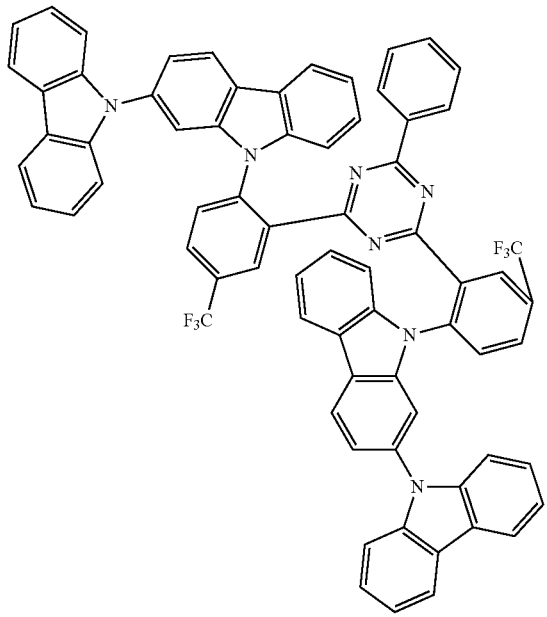

177
-continued
178
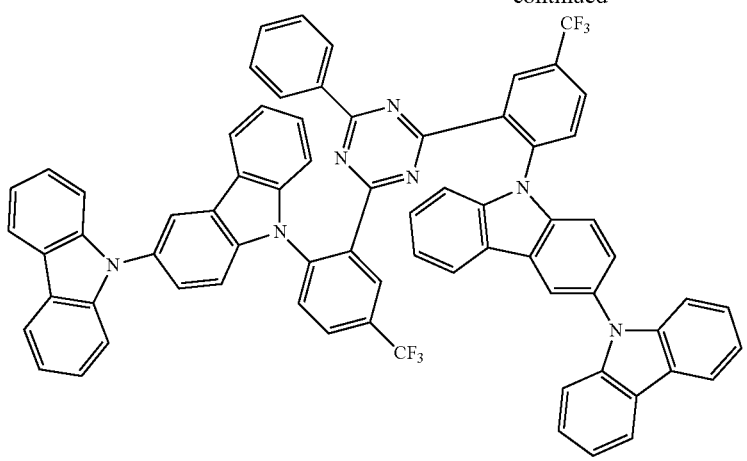
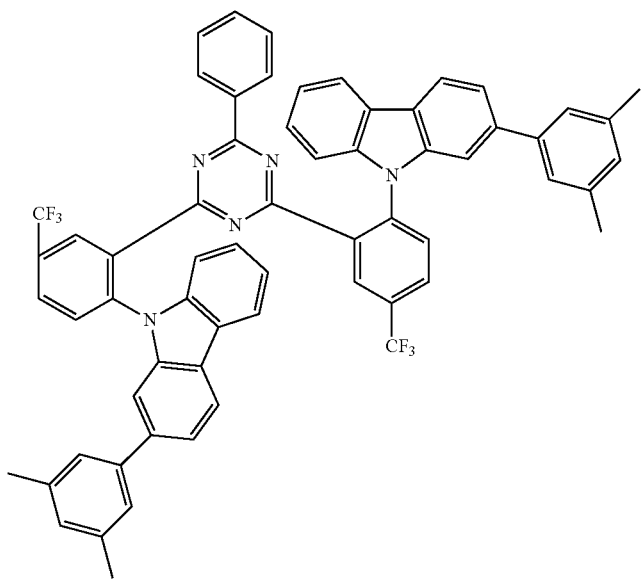
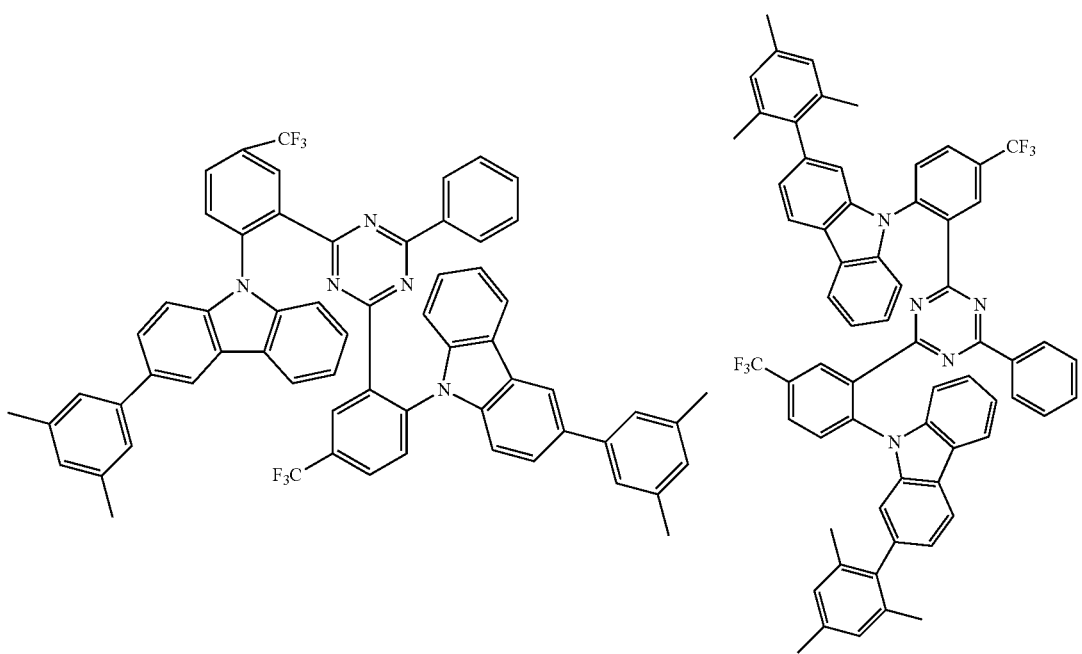

-continued
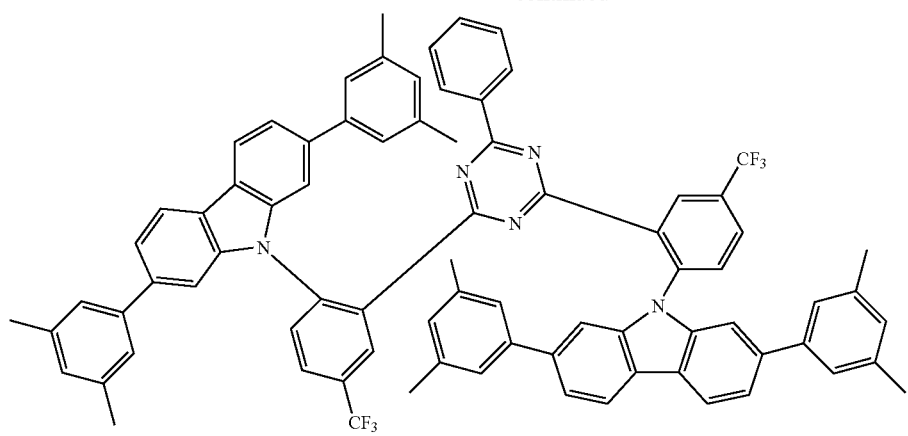
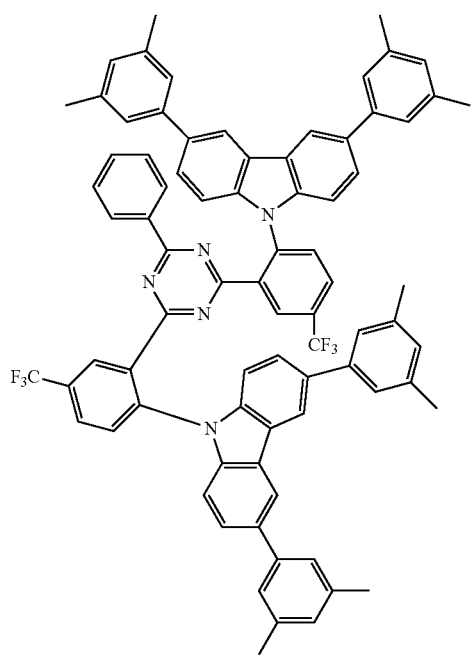
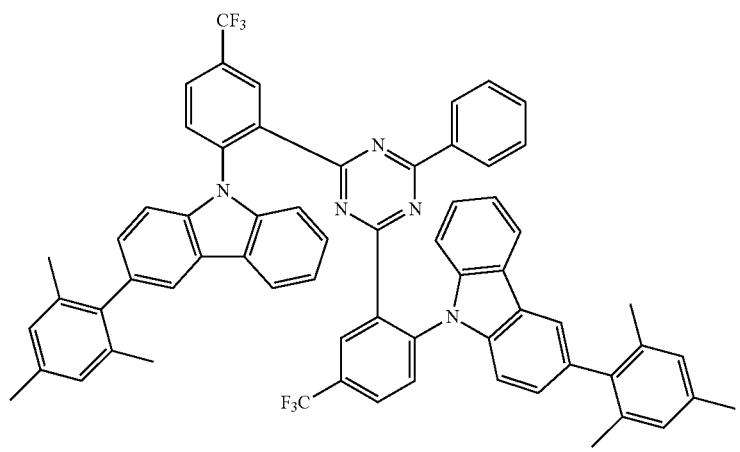

-continued
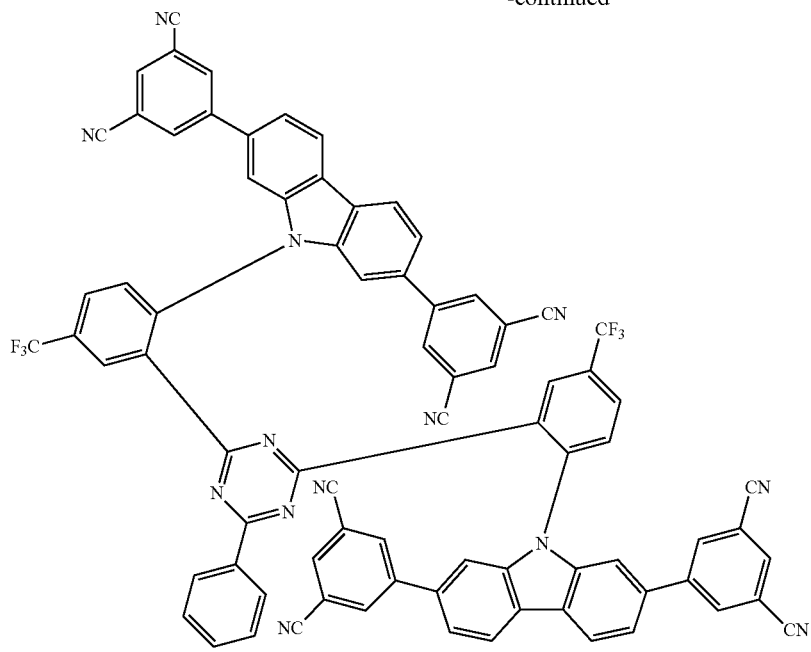
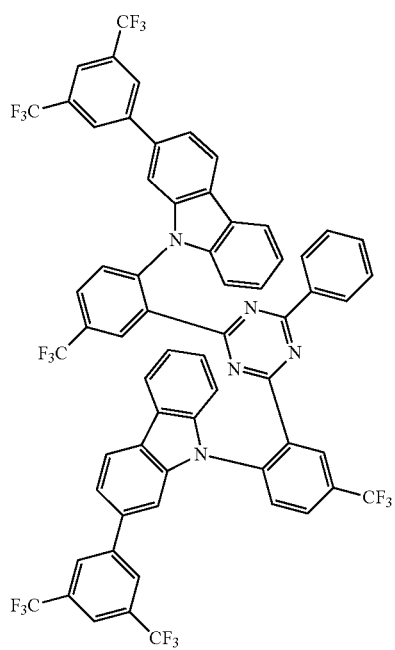

-continued
183
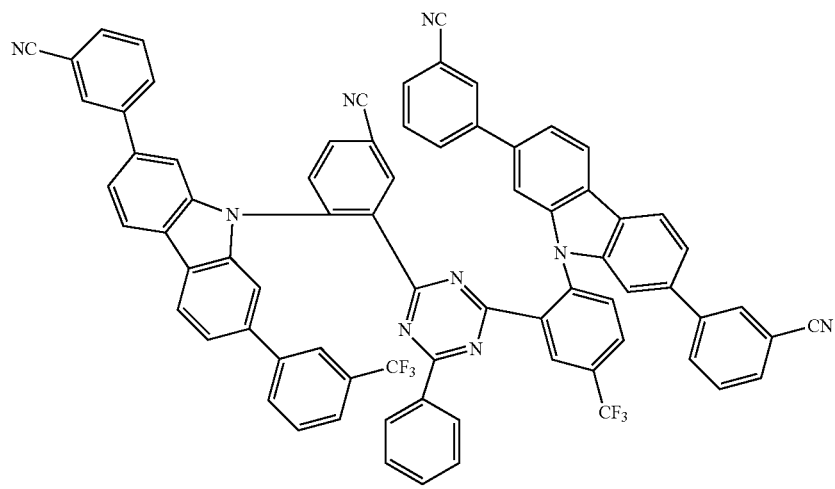
184
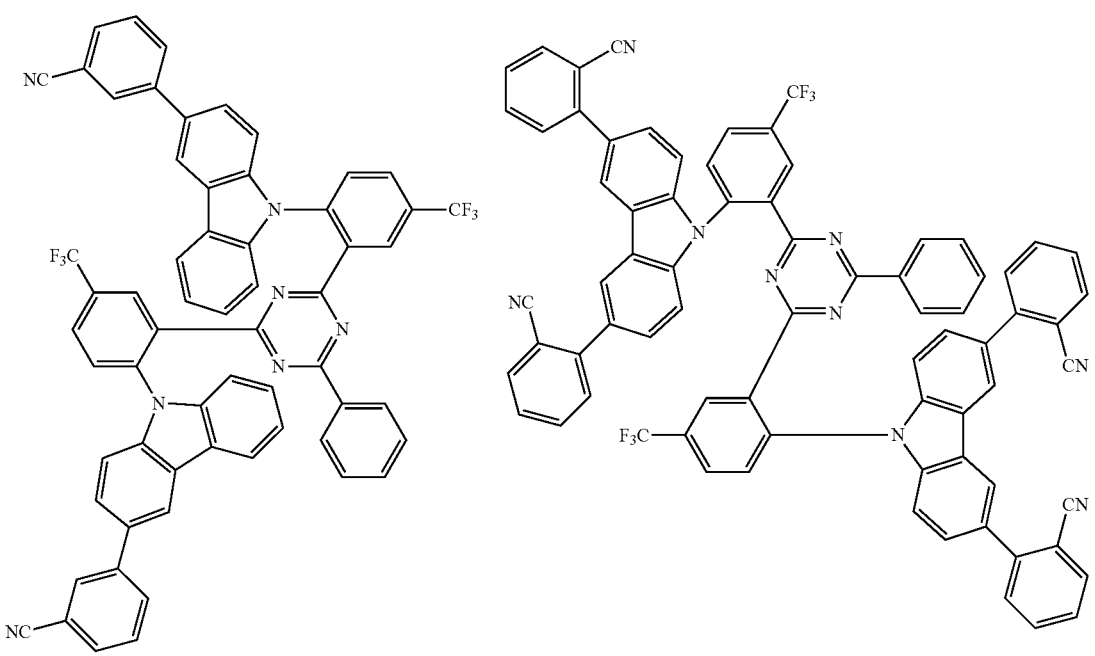

-continued
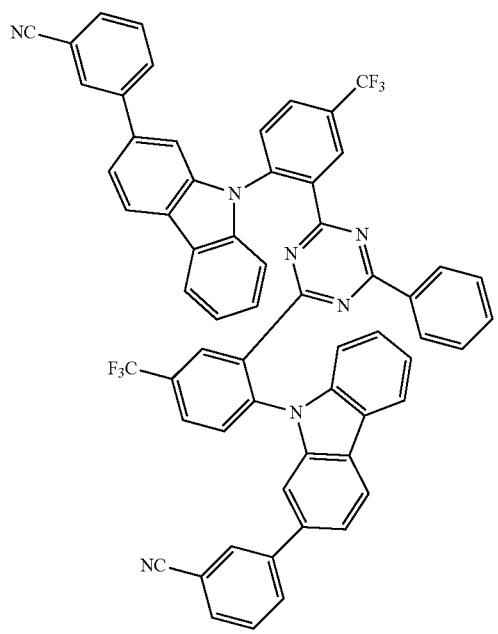
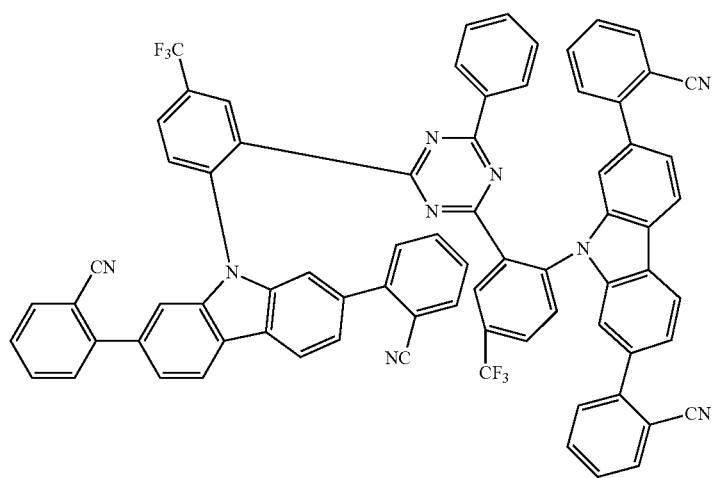
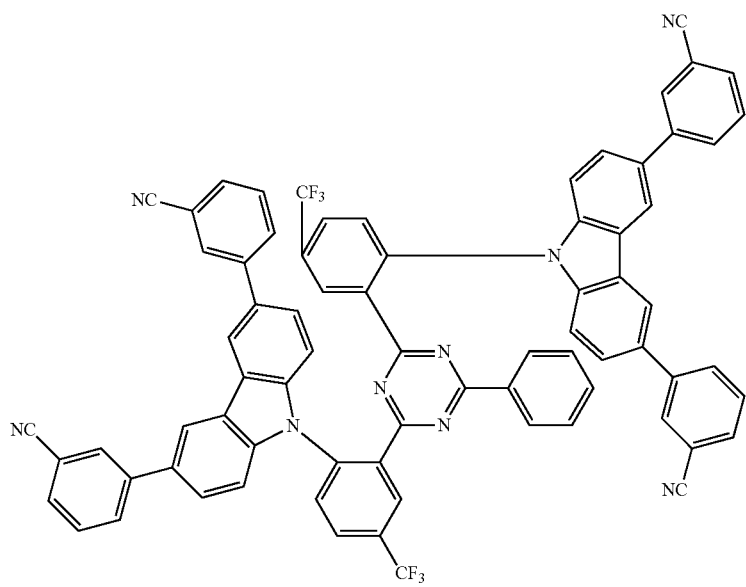

-continued
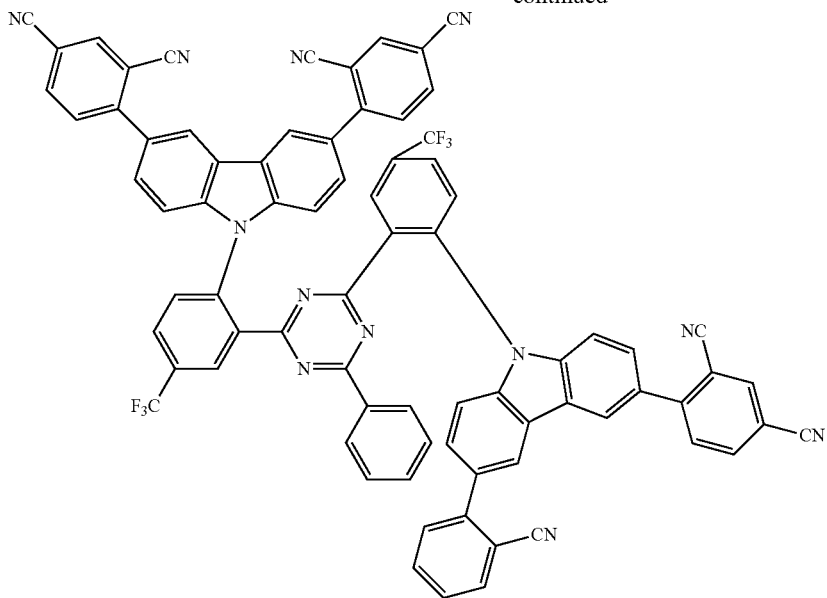
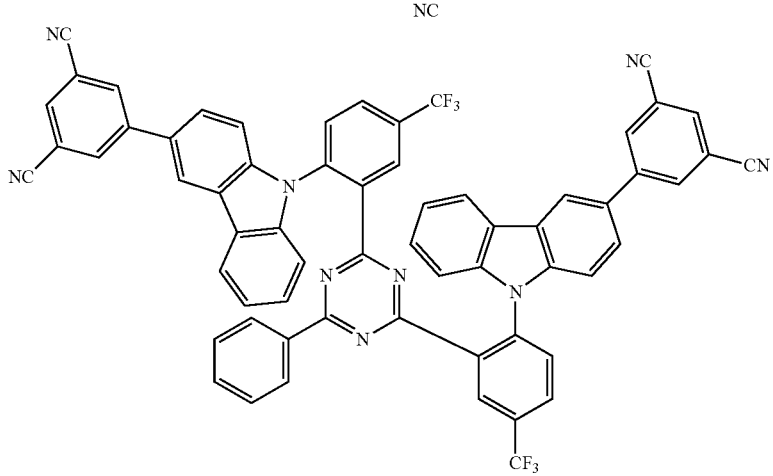
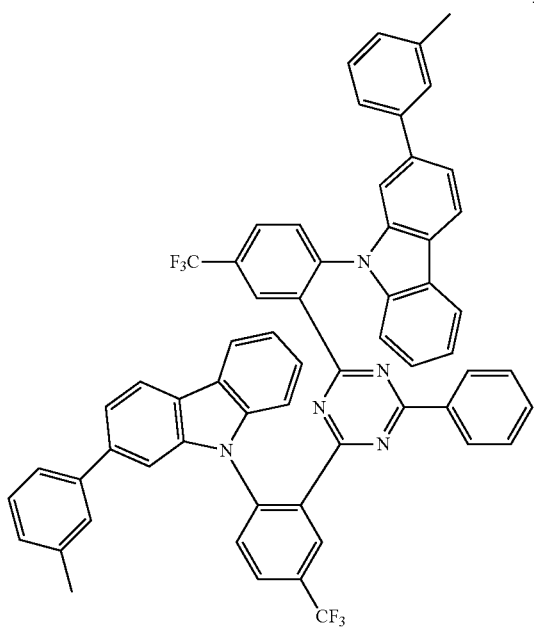

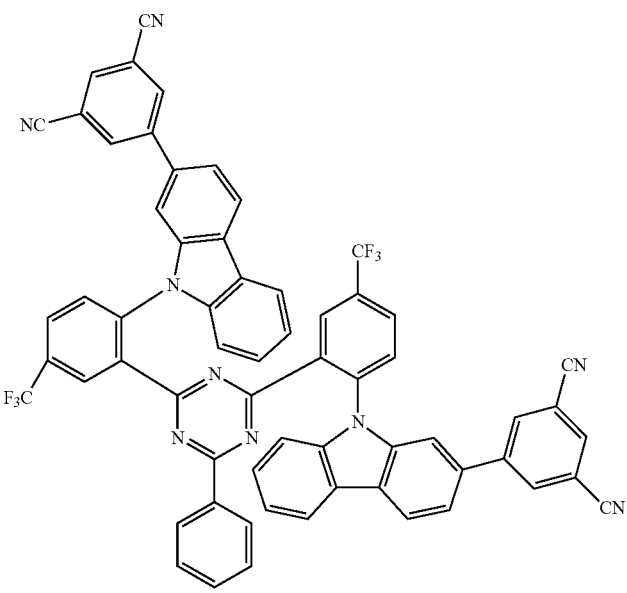 [SMILES: N#Cc1cc(C#N)cc(-c2ccc3c4ccccc4n(-c4ccc(C(F)(F)F)cc4-c4nc(-c5ccccc5)nc(-c5cc(C(F)(F)F)ccc5-n5c6ccccc6c6ccc(-c7cc(C#N)cc(C#N)c7)cc65)n4)c3c2)c1]
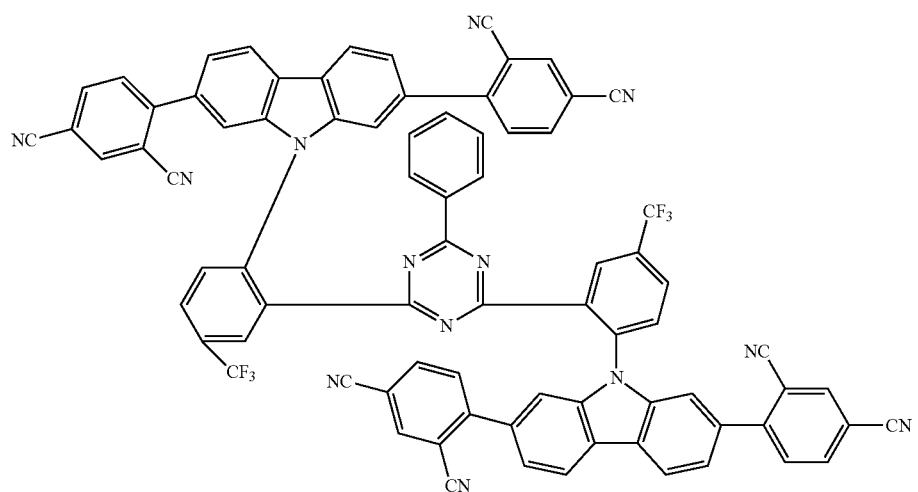
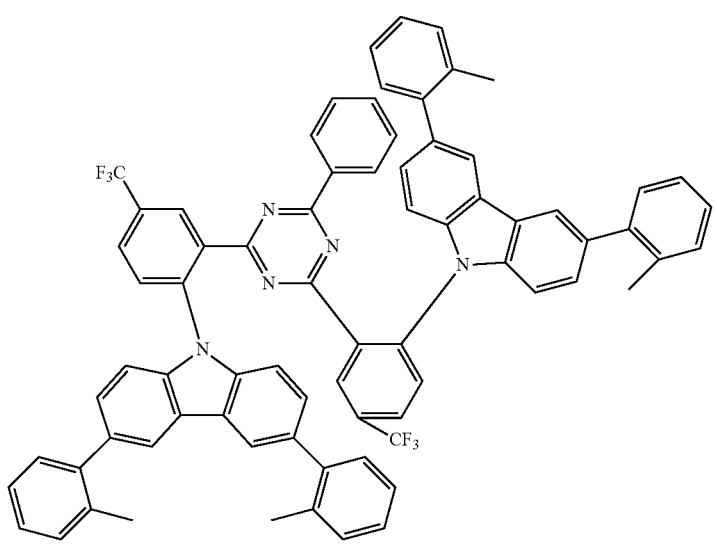

-continued
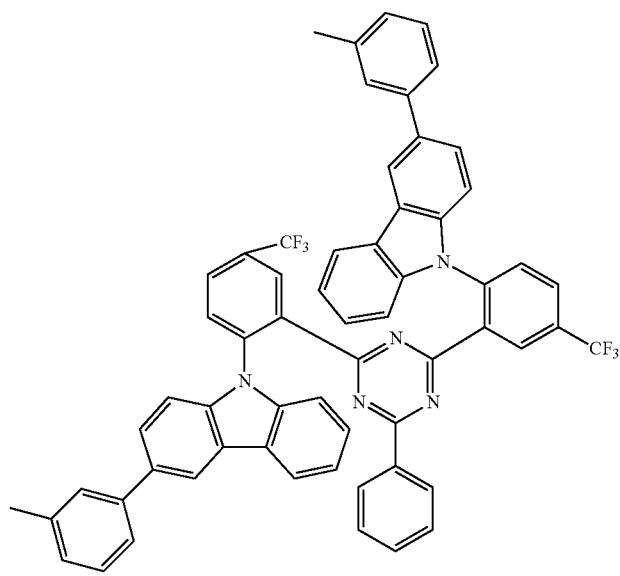
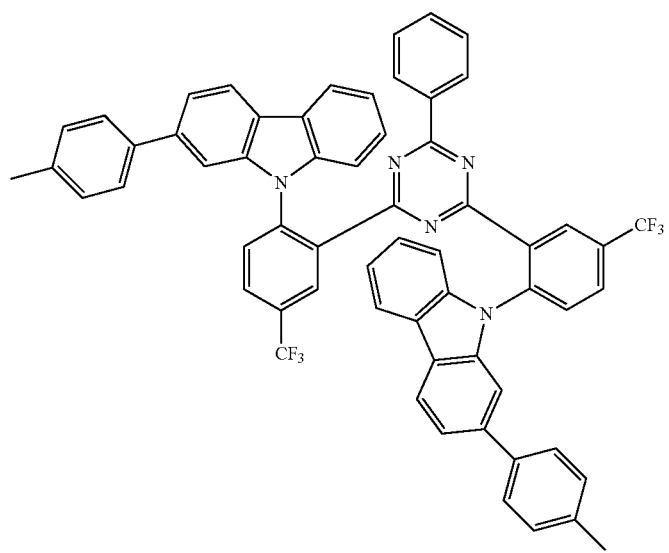

-continued
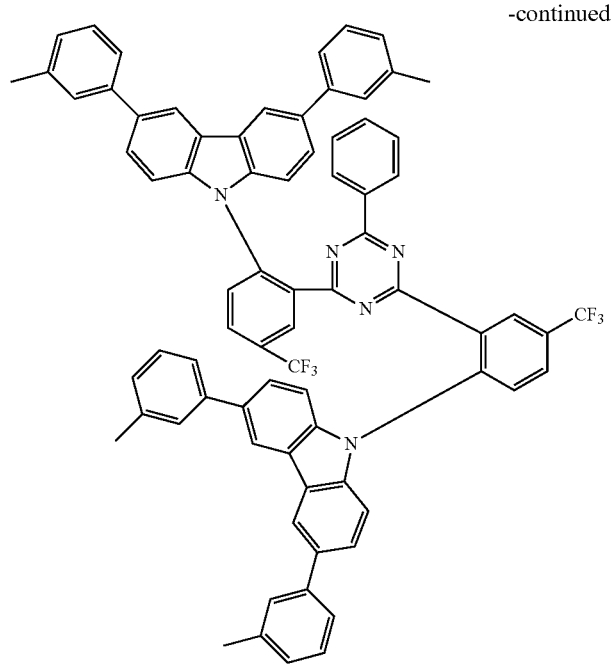
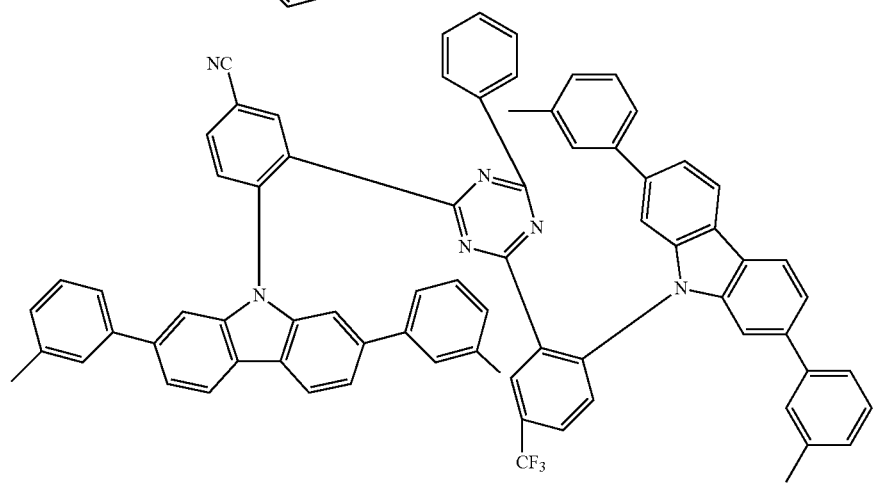
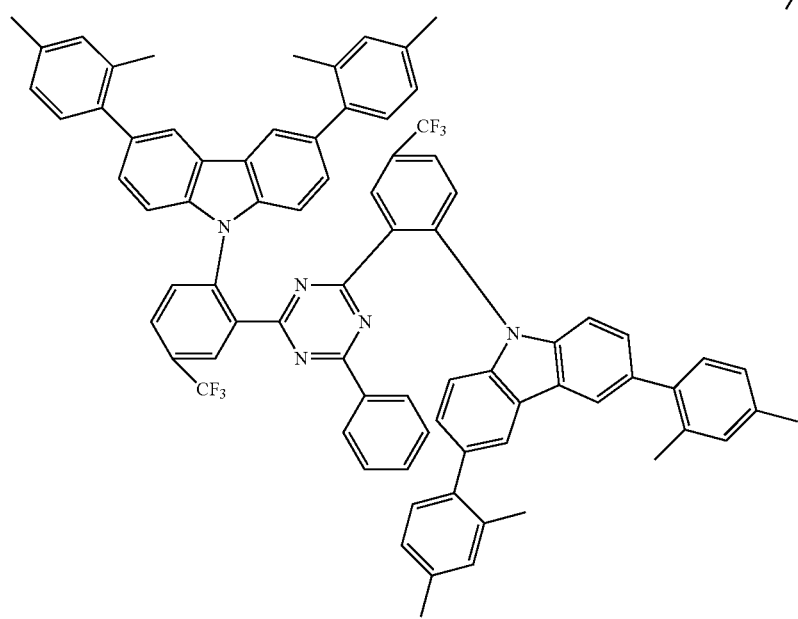

-continued
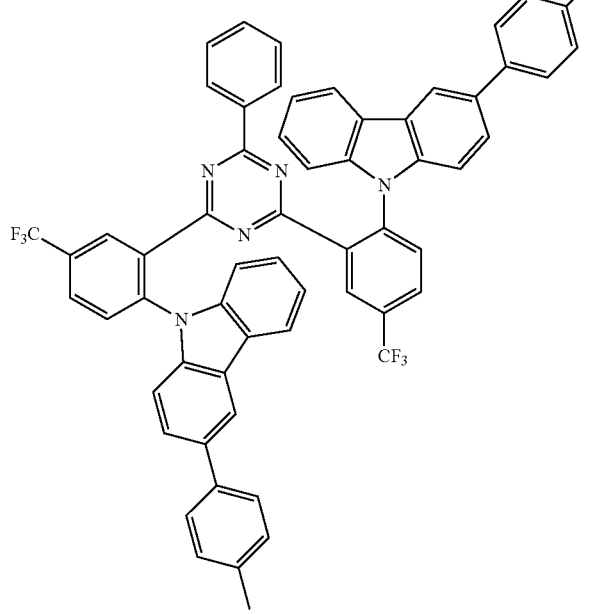
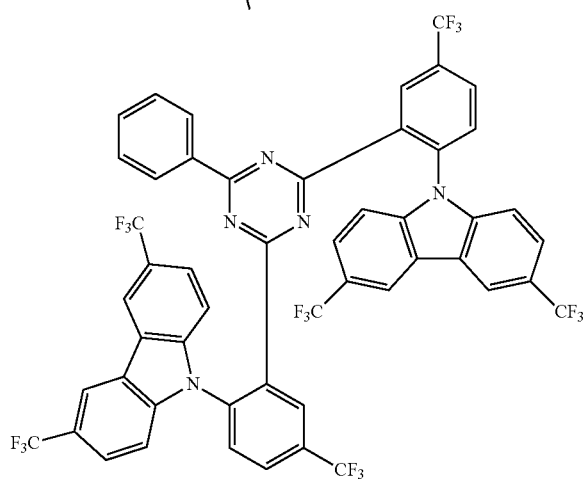
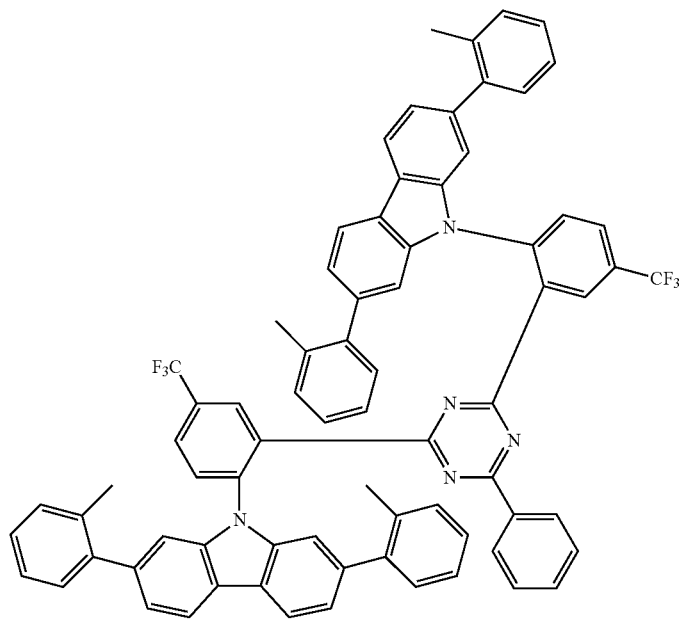

-continued
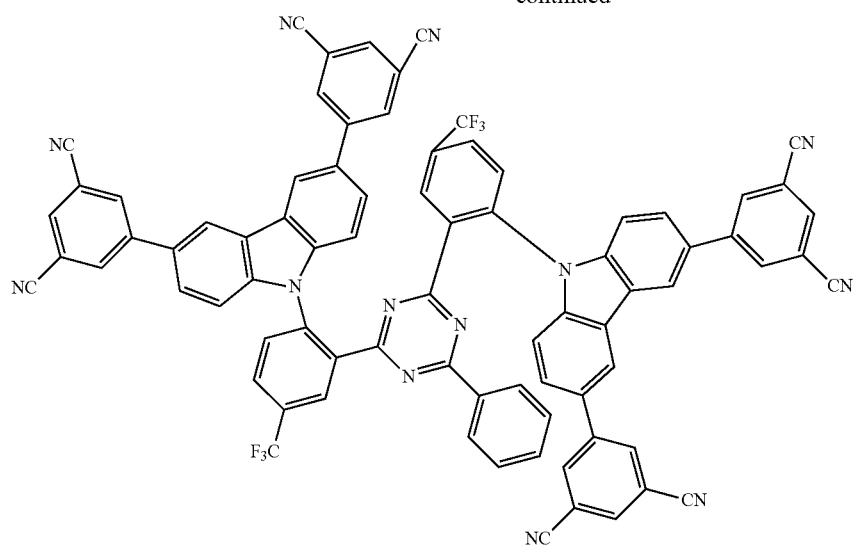
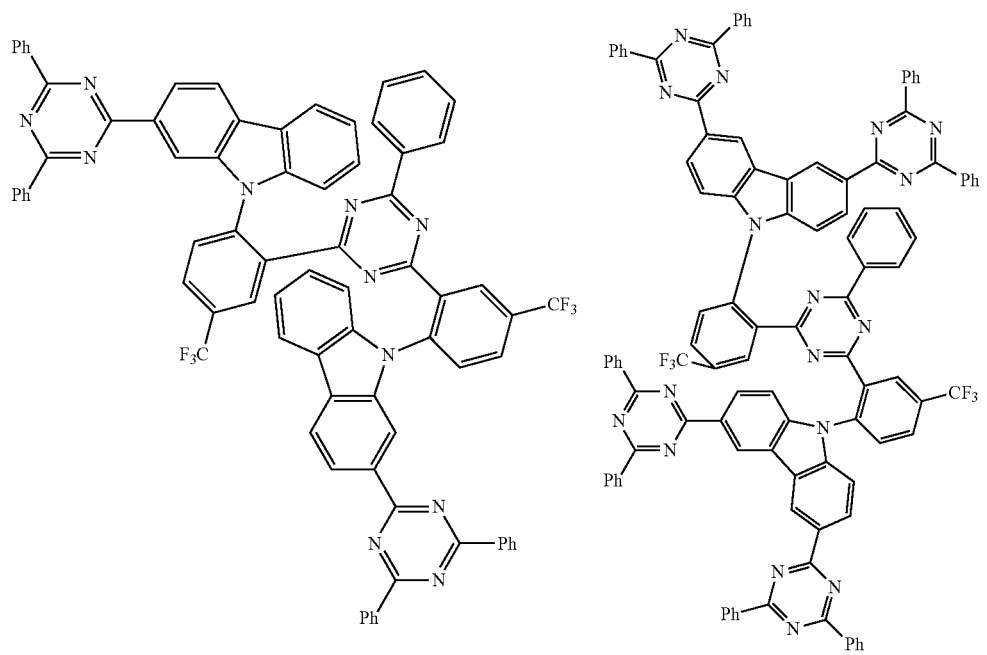

199 200
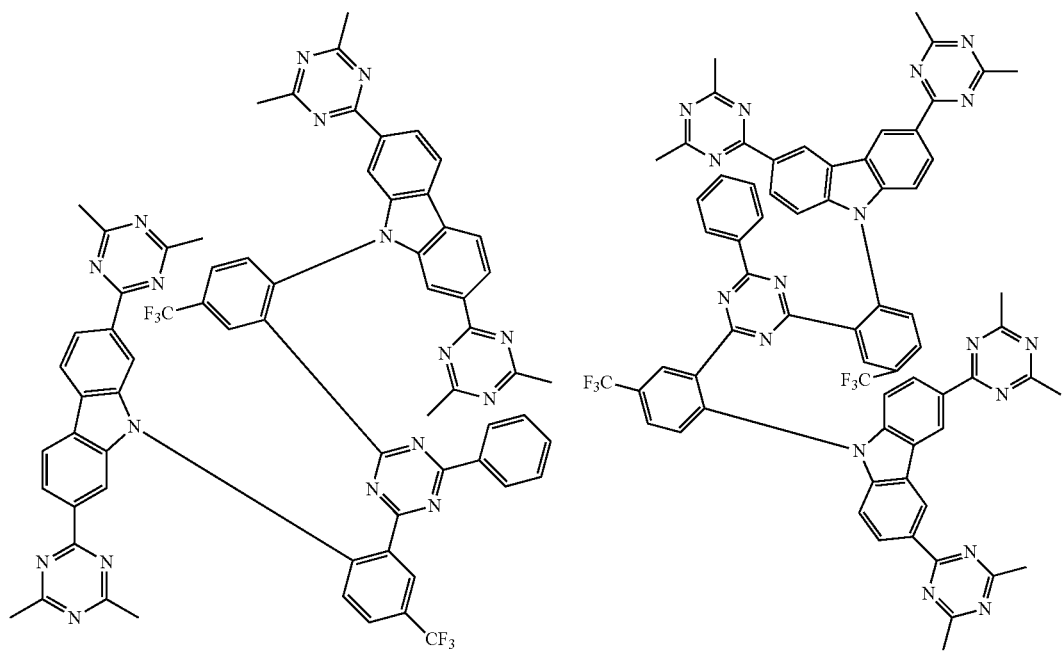
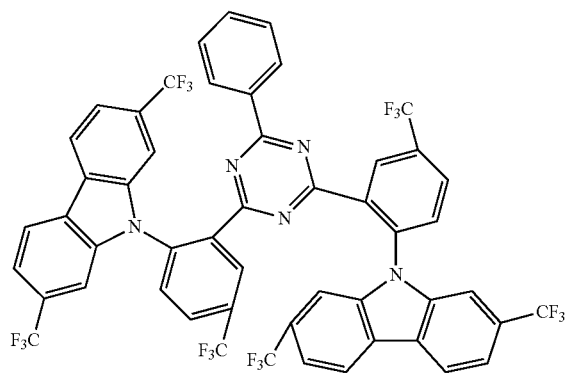
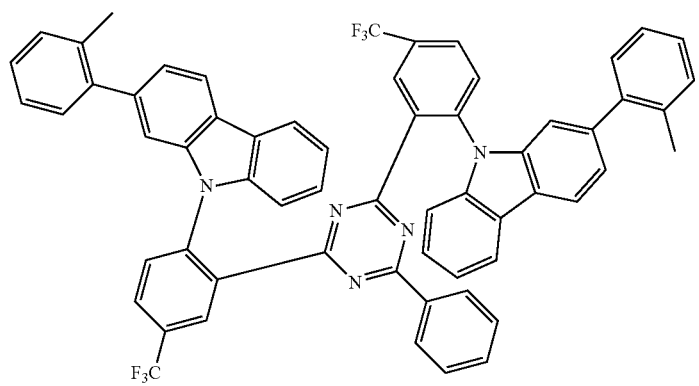

201
202
-continued
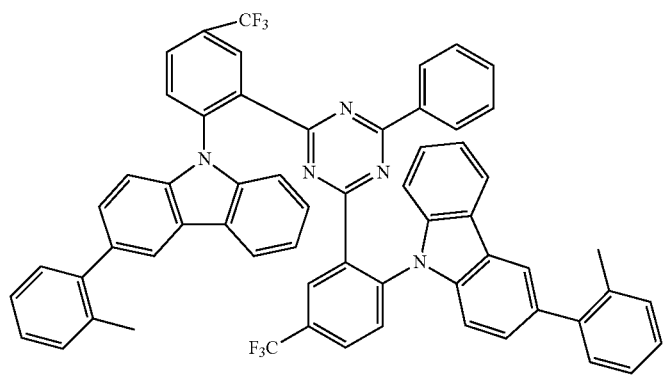
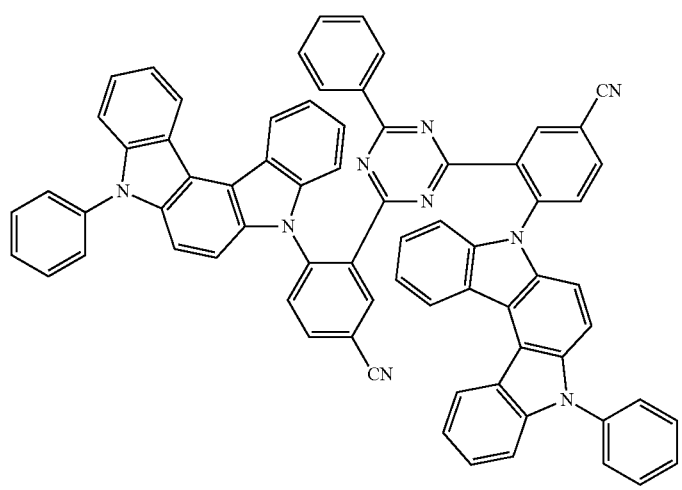
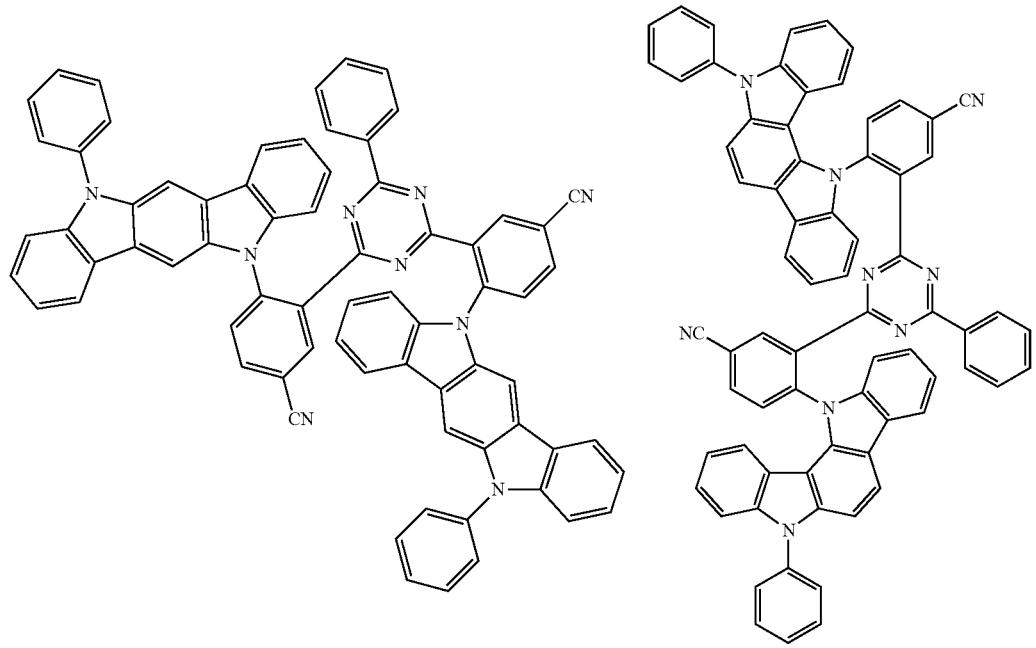

-continued
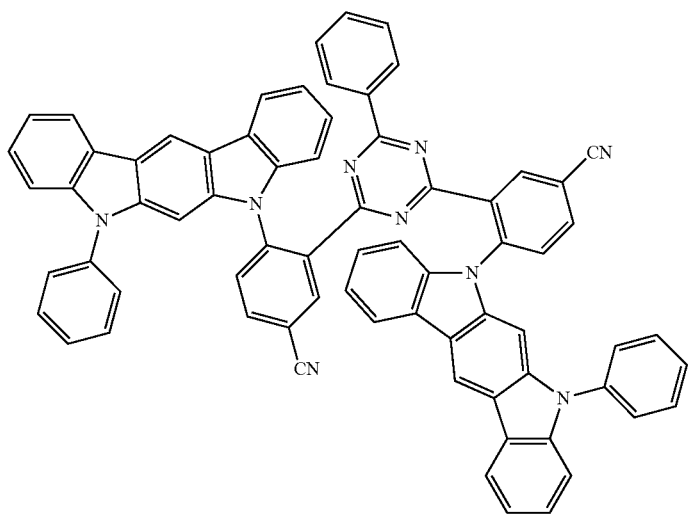
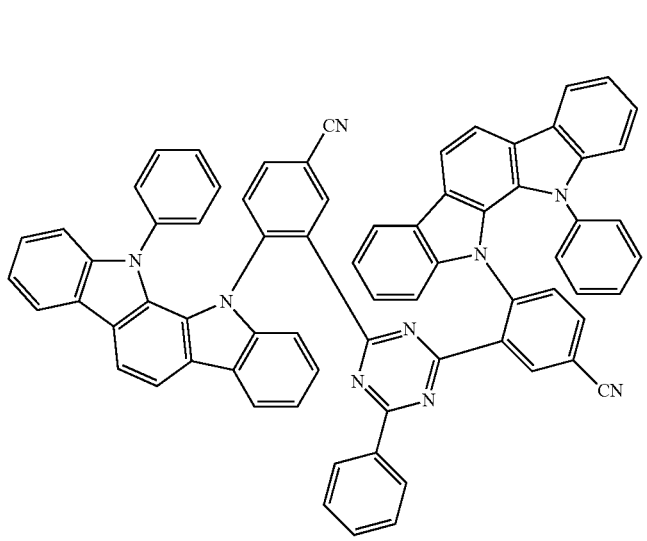
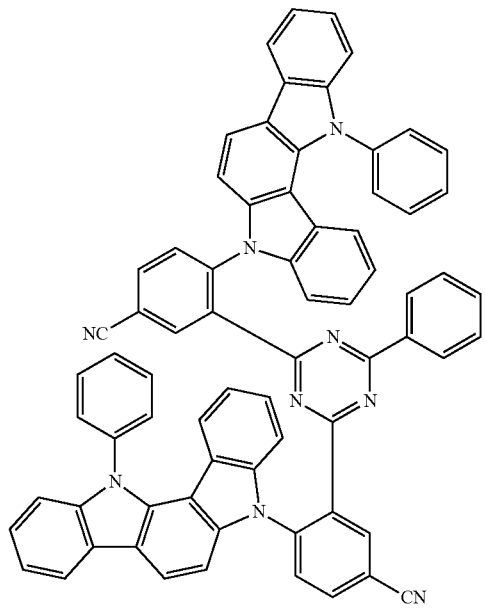
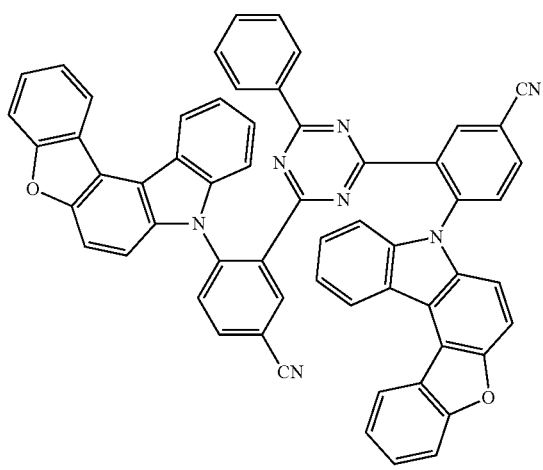

205
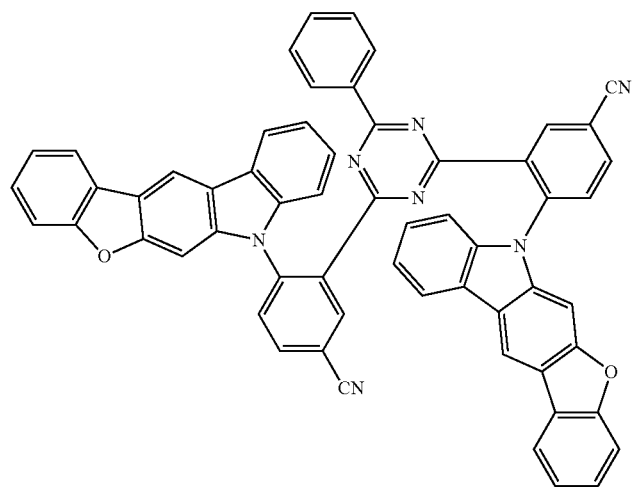
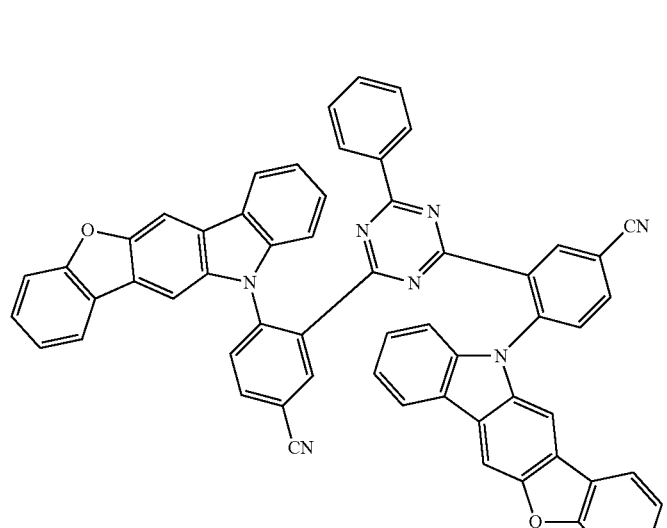
206
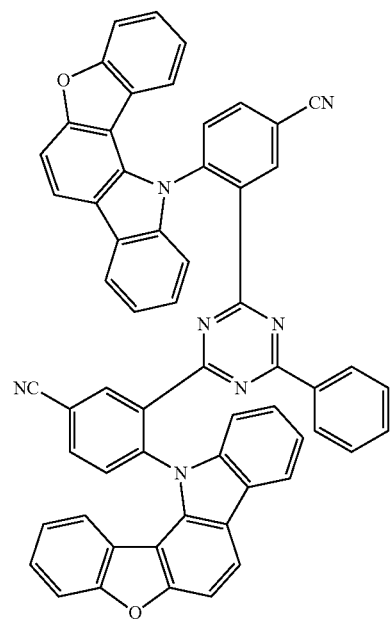
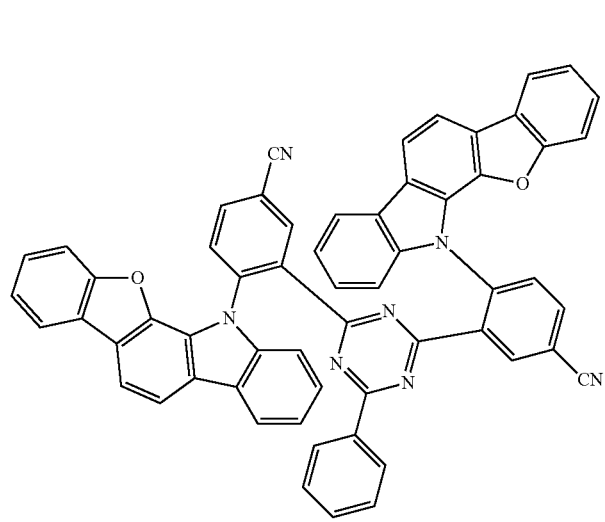
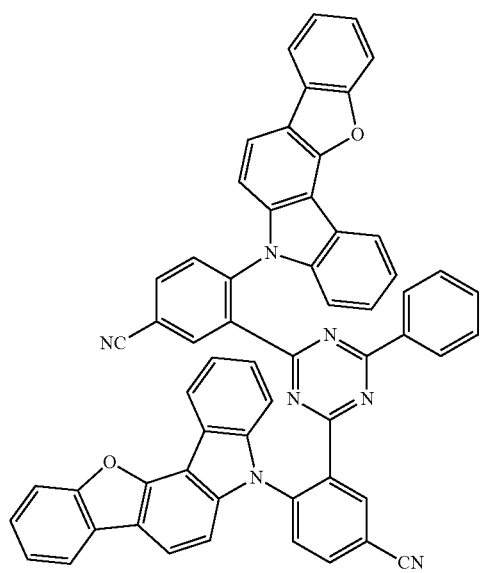

207
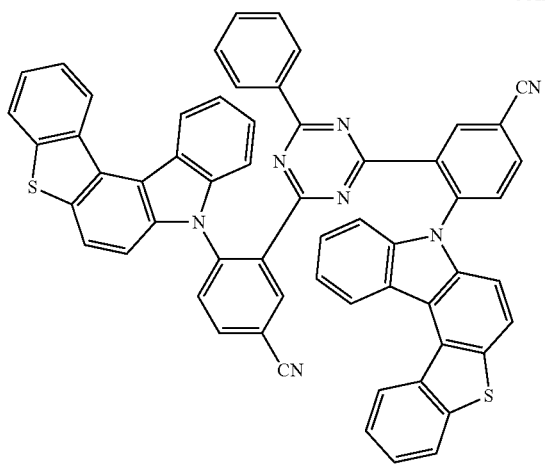
-continued
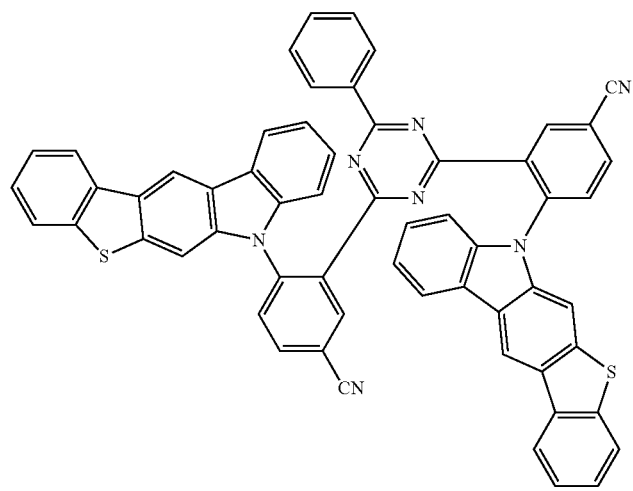
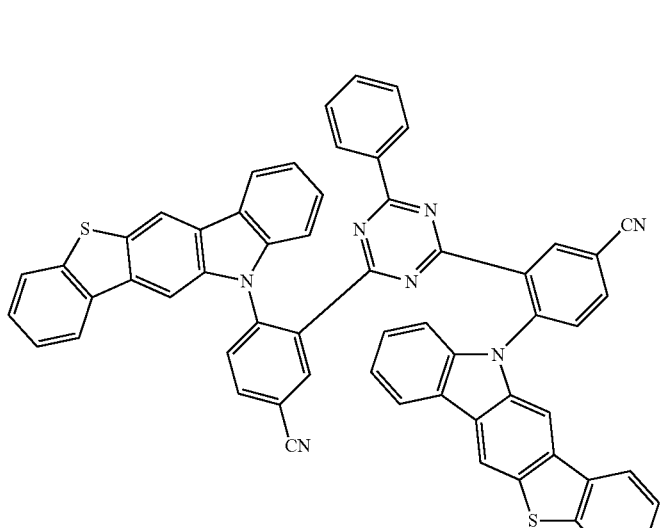
208
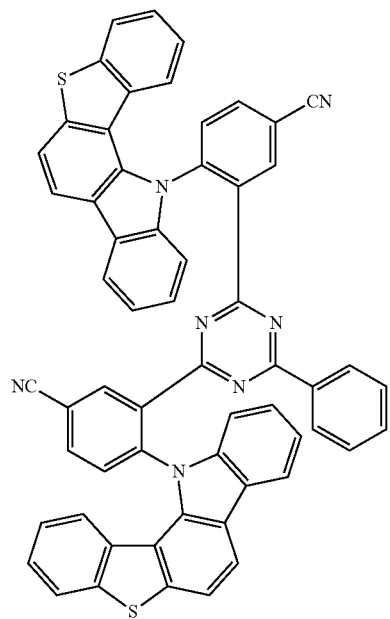

-continued
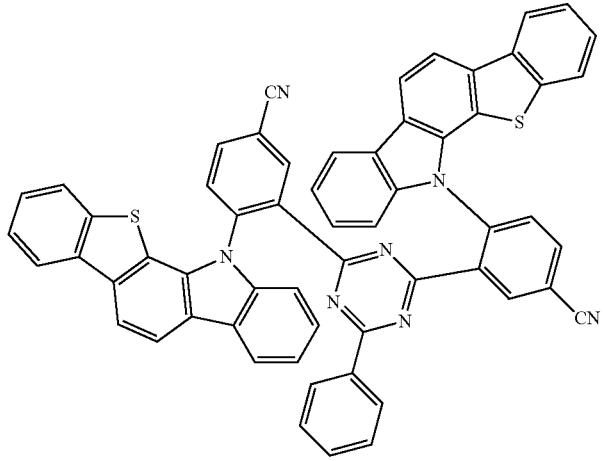
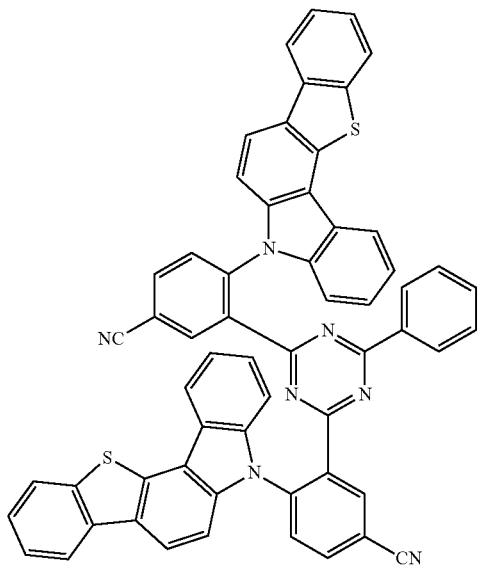
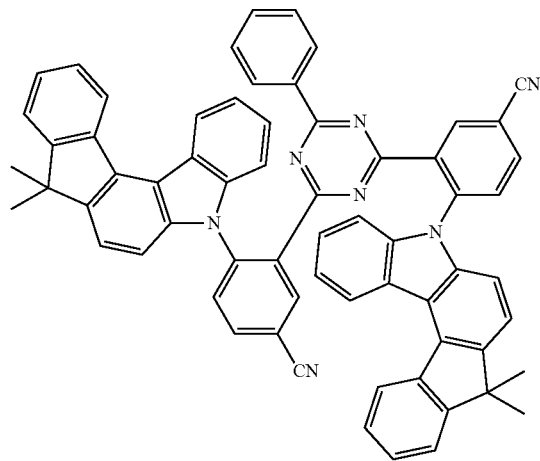
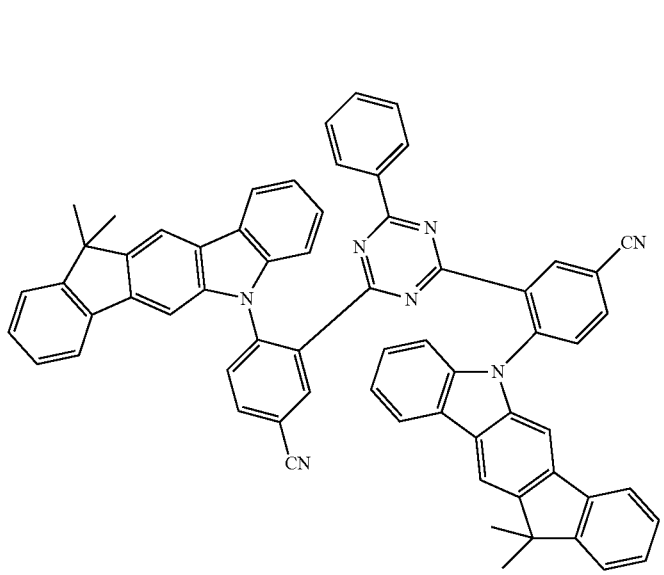
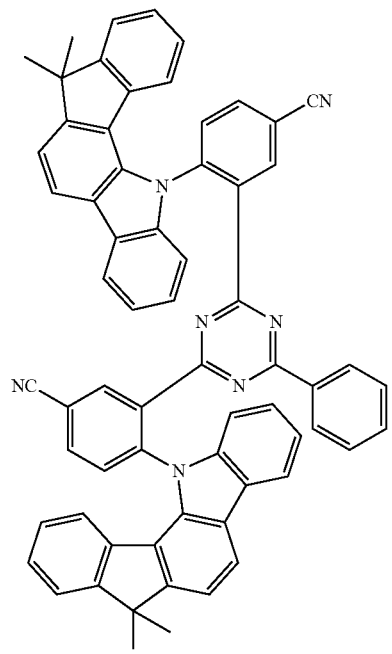

211
212
-continued
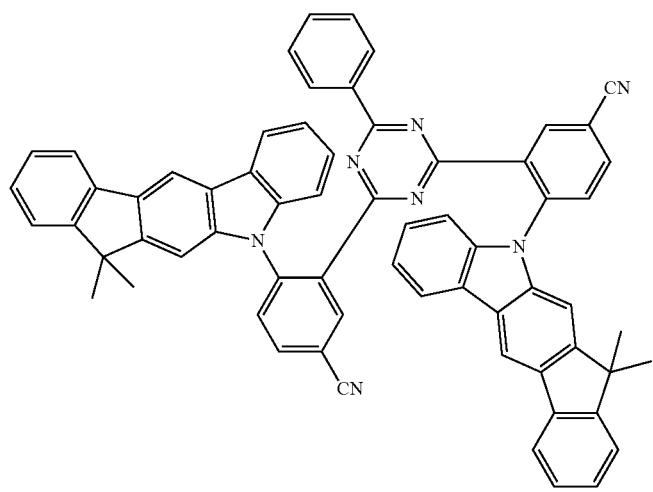
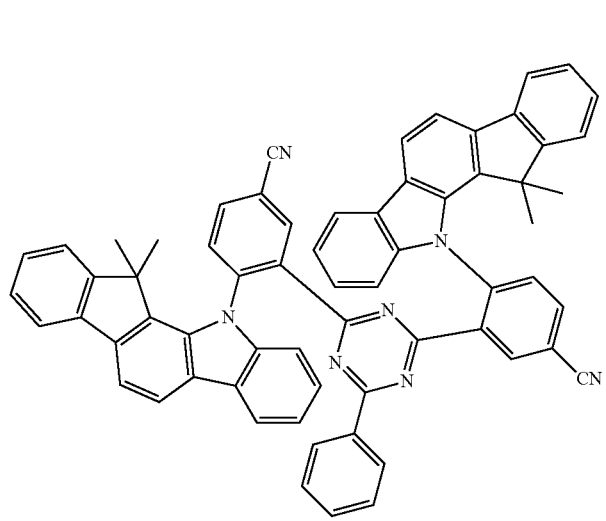
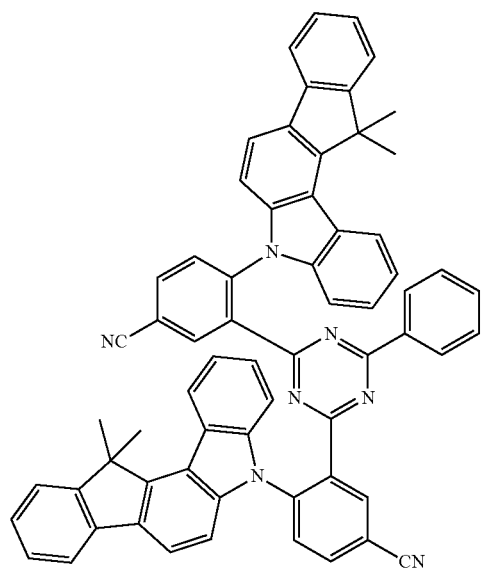
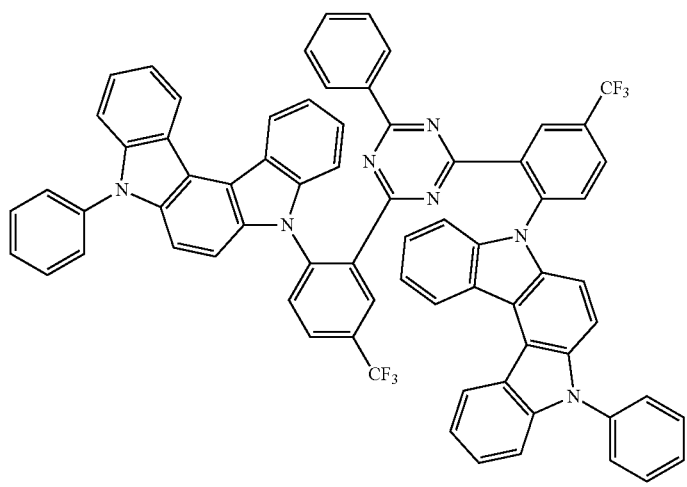

213
214
-continued
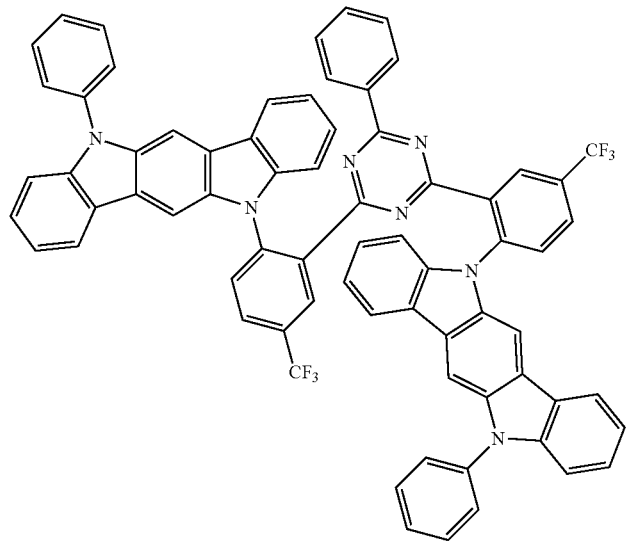
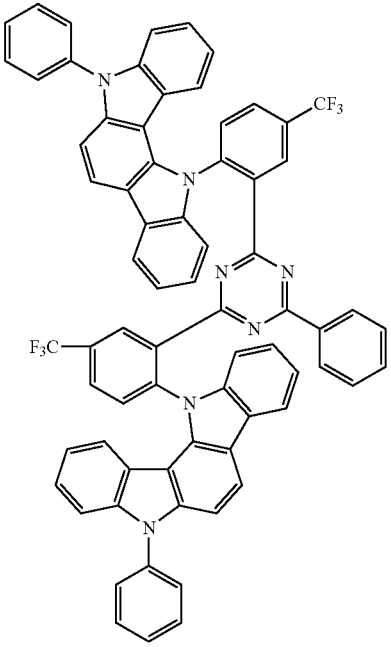
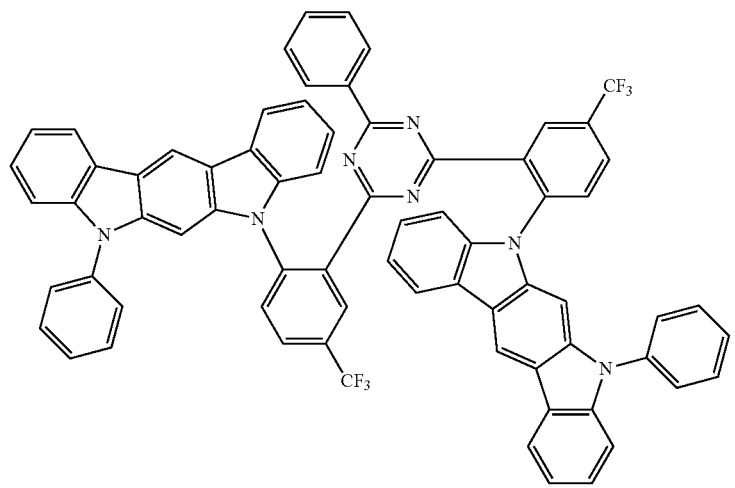
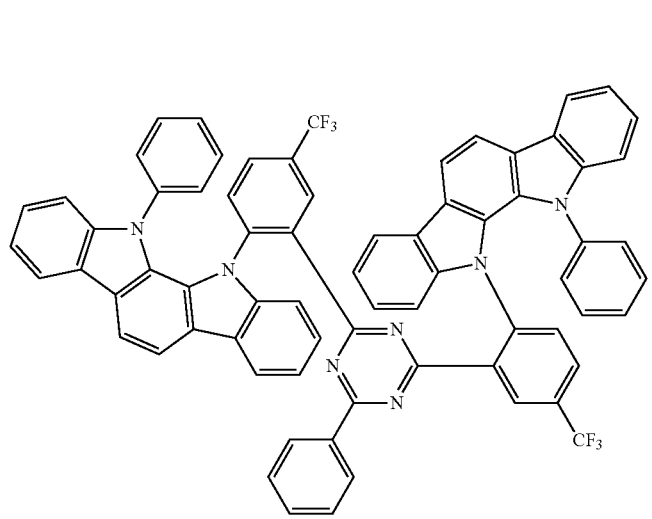
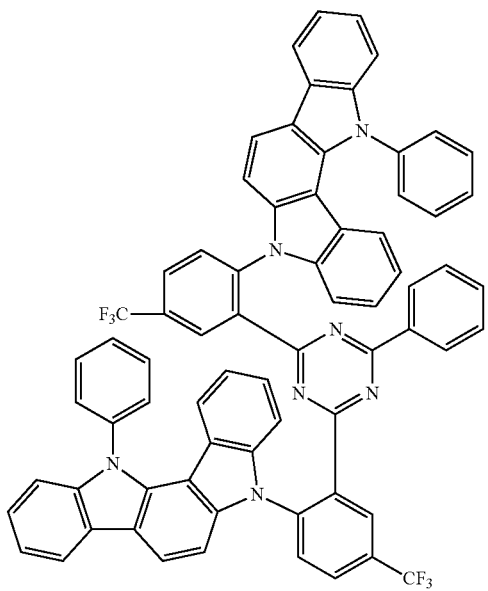

215
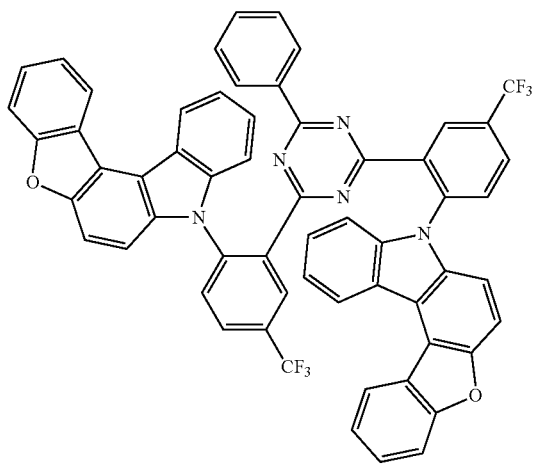
216
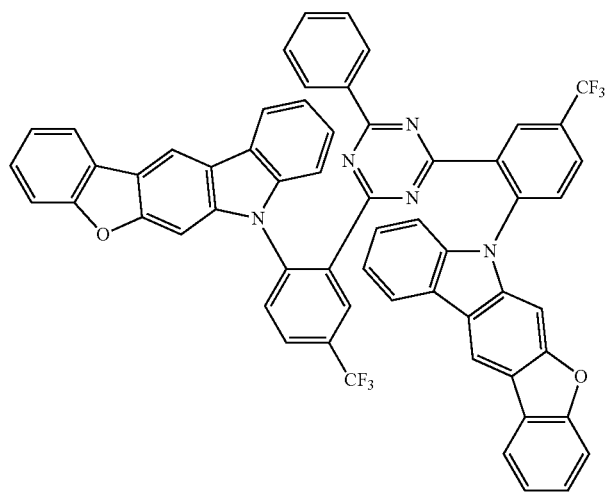
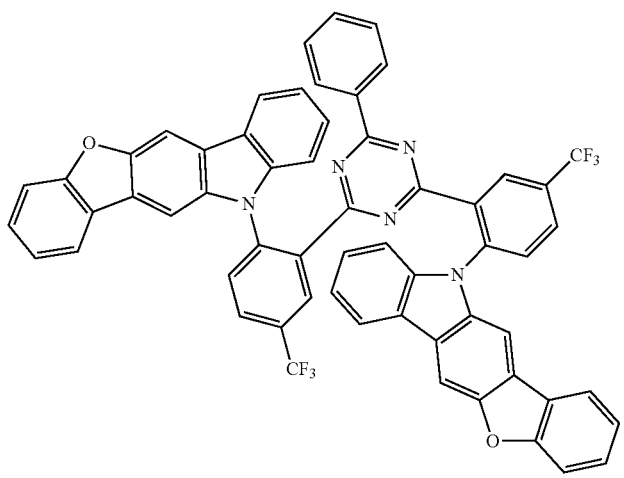
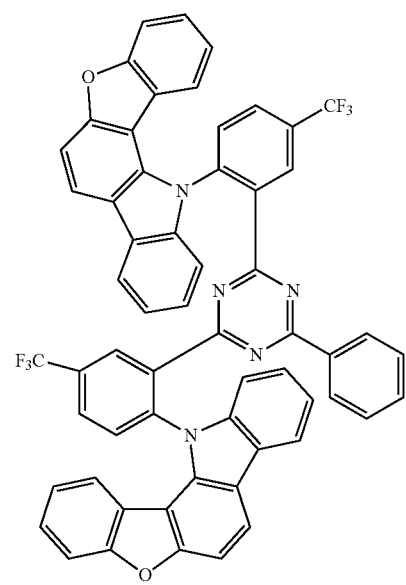
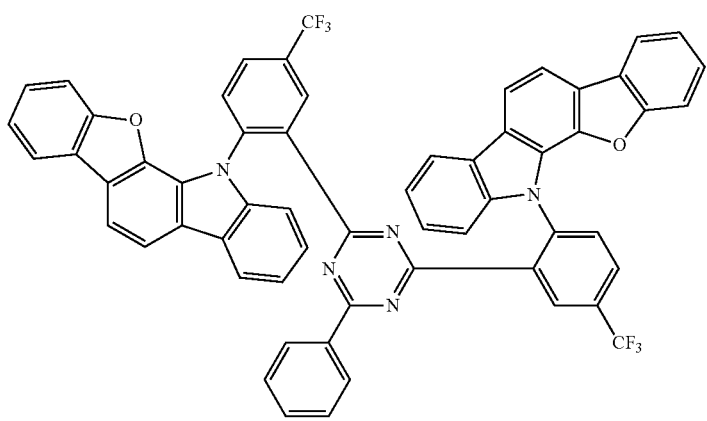

217
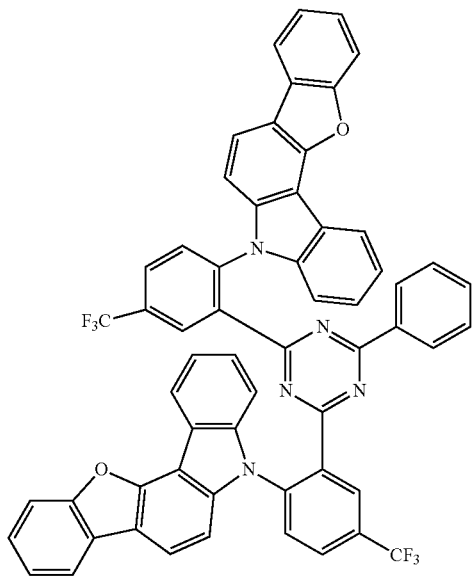 [SMILES: FC(F)(F)c1ccc(-n2c3ccccc3c3c4oc5ccccc5c4ccc32)c(-c2nc(-c3ccccc3)nc(-c3cc(C(F)(F)F)ccc3-n3c4ccccc4c4c5oc6ccccc6c5ccc43)n2)c1]
-continued
218
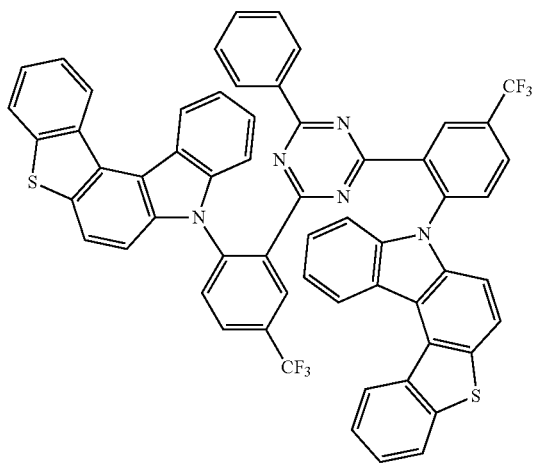
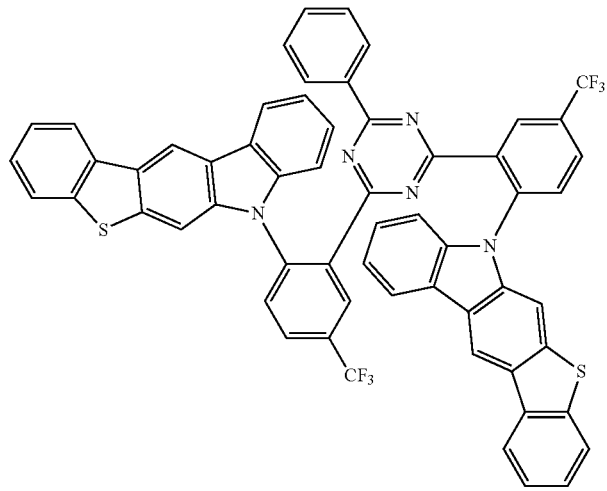
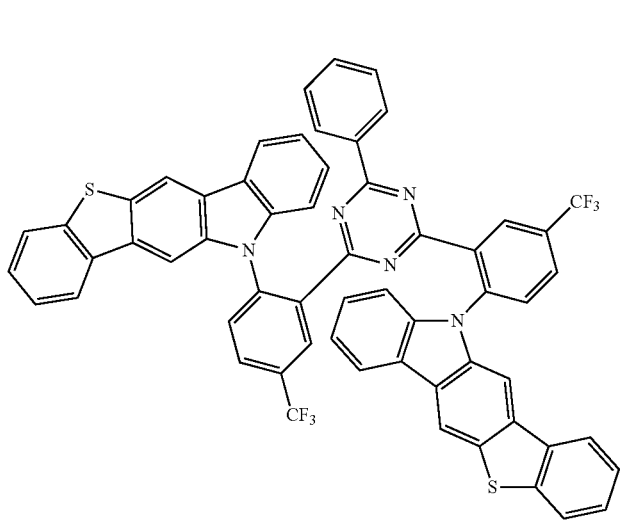
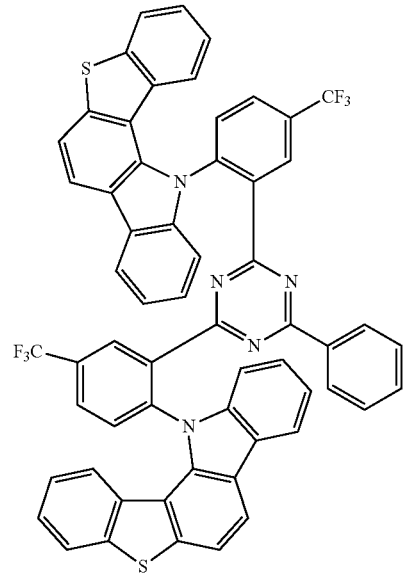

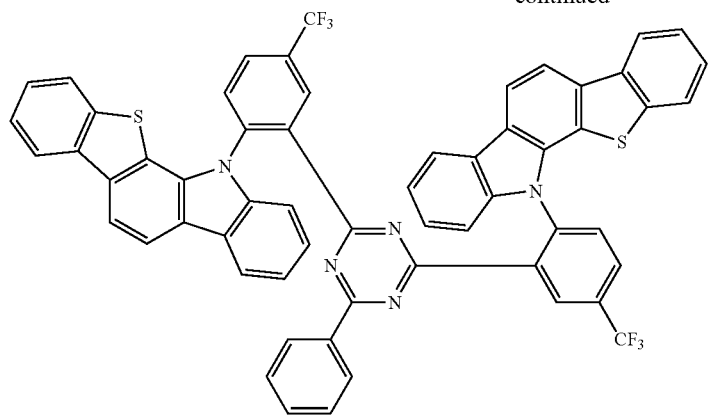
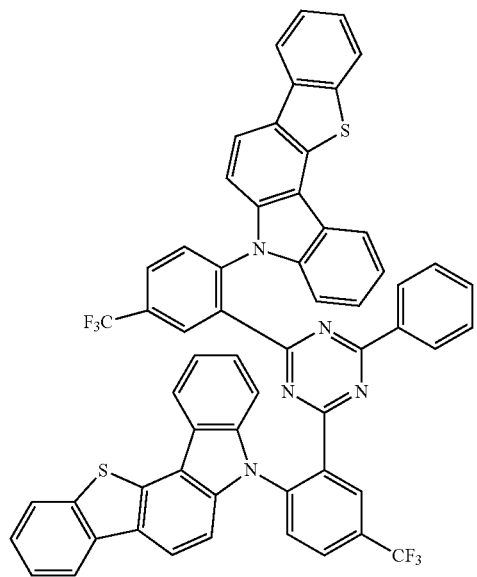 [SMILES: FC(F)(F)c1ccc(-n2c3ccccc3c3c4sc5ccccc5c4ccc32)c(-c2nc(-c3ccccc3)nc(-c3cc(C(F)(F)F)ccc3-n3c4ccccc4c4c5sc6ccccc6c5ccc43)n2)c1]
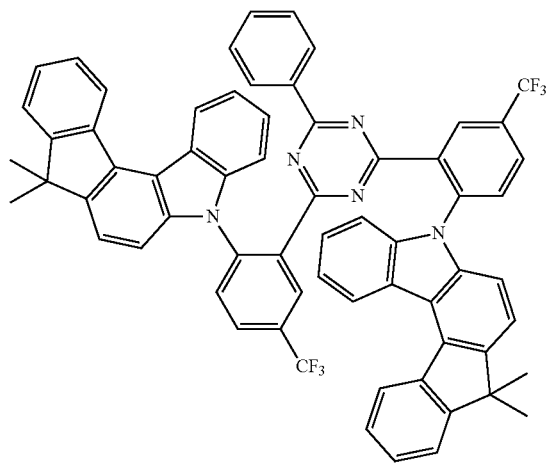

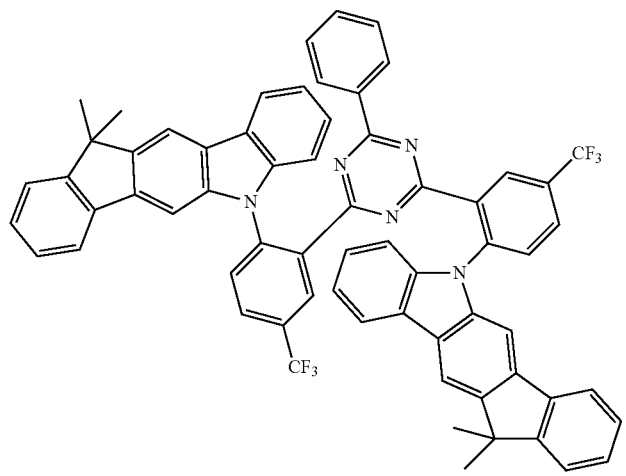
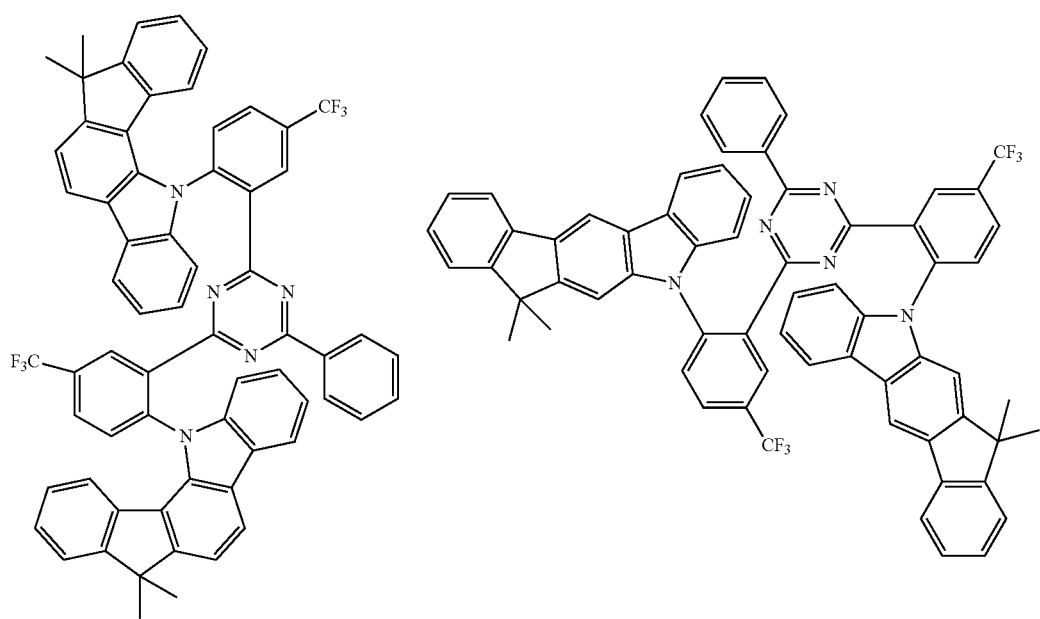
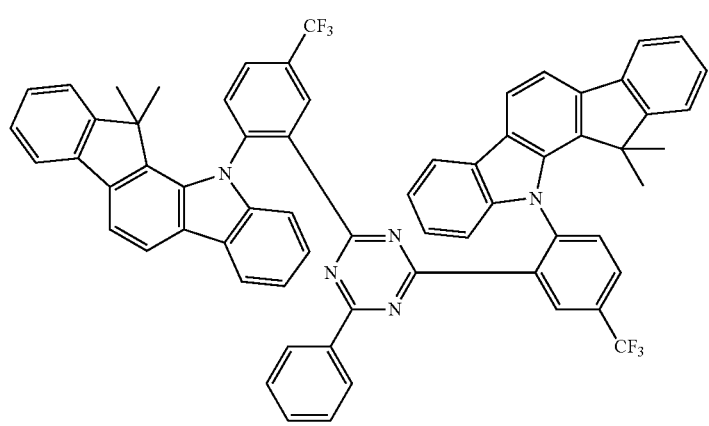

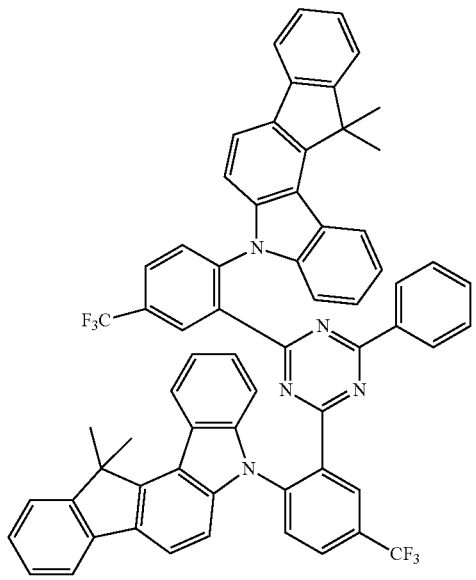

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

The invention claimed is:

1. An organic molecule, comprising:
a first chemical moiety comprising a structure of Formula I,

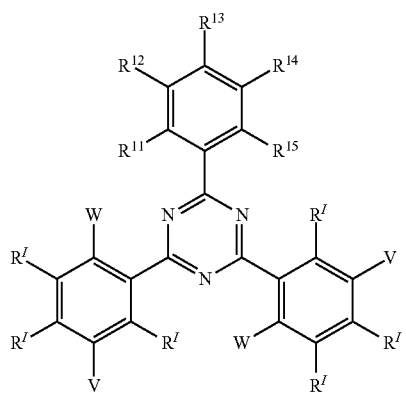

Formula I and
two second chemical moieties, each comprising a structure of Formula IIb or Formula IIc,

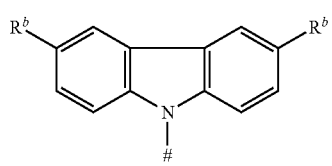

Formula IIb

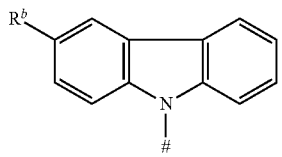

Formula IIc wherein the first chemical moiety is linked to the second chemical moiety via a single bond;
wherein # represents the binding site of the first chemical moiety to the second chemical moiety;
W is the bond linking the first chemical moiety to one of the two second chemical moieties;
V is CN;
$R^I$ is at each occurrence independently from another selected from the group consisting of:
hydrogen, deuterium,
$C_1$-$C_5$-alkyl, wherein one or more hydrogen atoms are optionally substituted by deuterium;
$C_2$-$C_8$-alkenyl, wherein one or more hydrogen atoms are optionally substituted by deuterium;
$C_2$-$C_8$-alkynyl, wherein one or more hydrogen atoms are optionally substituted by deuterium; and
$C_6$-$C_{18}$-aryl;
$R^{11}$, $R^{12}$, $R^{13}$, $R^{14}$ and $R^{15}$ is at each occurrence independently from another selected from the group consisting of
hydrogen, deuterium, CN, $CF_3$,
$C_1$-$C_5$-alkyl, wherein one or more hydrogen atoms are optionally substituted by deuterium;
$C_2$-$C_8$-alkenyl, wherein one or more hydrogen atoms are optionally substituted by deuterium;
$C_2$-$C_8$-alkynyl, wherein one or more hydrogen atoms are optionally substituted by deuterium; and
$C_6$-$C_{18}$-aryl;
$R^b$ is at each occurrence independently from another selected from the group consisting of:
$B(OR^5)_2$,
$C_1$-$C_{40}$-alkyl, which is substituted with at least one selected from the group consisting of deuterium, $N(R^6)_2$, $OR^6$, $Si(R^6)_3$, $B(OR^6)_2$, $OSO_2R^6$, $CF_3$, CN, F, Br, I, $C_1$-$C_{40}$-alkoxy, which is unsubstituted or substituted with one or more substituents $R^6$, $C_1$-$C_{40}$-thioalkoxy, which is unsubstituted or substituted with one or more substituents $R^6$, $C_2$-$C_{40}$-alkenyl, which is unsubstituted or substituted with one or more substituents $R^6$, $C_2$-$C_{40}$-alkynyl, which is unsubstituted or substituted with one or more substituents $R^6$, $C_6$-$C_{60}$-aryl, which is unsubstituted or substituted with one or more substituents $R^6$, and $C_3$-$C_{57}$-heteroaryl, which is unsubstituted or substituted with one or more substituents $R^6$ provided that $R^b$ is not a carbazolyl group, $C_1$-$C_{40}$-thioalkoxy, which is unsubstituted or substituted with at least one selected from the group consisting of hydrogen, deuterium, $N(R^6)_2$, $OR^6$, $Si(R^6)_3$, $B(OR^6)_2$, $OSO_2R^6$, $CF_3$, CN, F, Br, I, $C_1$-$C_{40}$-alkyl, which is unsubstituted or substituted with one or more substituents $R^6$, $C_1$-$C_{40}$-alkoxy, which is unsubstituted or substituted with one or more substituents $R^6$, $C_2$-$C_{40}$-alkenyl, which is unsubstituted or substituted with one or more substituents $R^6$, $C_2$-$C_{40}$-alkynyl, which is unsubstituted or substituted with one or more substituents $R^6$, $C_6$-$C_{60}$-aryl, which is unsubstituted or substituted with one or more substituents $R^6$, and $C_3$-$C_{57}$-heteroaryl, which is unsubstituted or substituted with one or more substituents $R^6$, $C_2$-$C_{40}$-alkenyl, which is unsubstituted or substituted with at least one selected from the group consisting of hydrogen, deuterium, $N(R^6)_2$, $OR^6$, $Si(R^6)_3$, $B(OR^6)_2$, $OSO_2R^6$, $CF_3$, CN, F, Br, I, $C_1$-$C_{40}$-alkyl, which is unsubstituted or substituted with one or more substituents $R^6$, $C_1$-$C_{40}$-alkoxy, which is unsubstituted or substituted with one or more substituents $R^6$, $C_1$-$C_{40}$-thioalkoxy, which is unsubstituted or substituted with one or more substituents $R^6$, $C_2$-$C_{40}$-alkynyl, which is unsubstituted or substituted with one or more substituents $R^6$, $C_6$-$C_{60}$-aryl, which is unsubstituted or substituted with one or more substituents $R^6$, and $C_3$-$C_{57}$-heteroaryl, which is unsubstituted or substituted with one or more substituents $R^6$, $C_2$-$C_{40}$-alkynyl, which is unsubstituted or substituted with at least one selected from the group consisting of hydrogen, deuterium, $N(R^6)_2$, $OR^6$, $Si(R^6)_3$, $B(OR^6)_2$, $OSO_2R^6$, $CF_3$, CN, F, Br, I, $C_1$-$C_{40}$-alkyl, which is unsubstituted or substituted with one or more substituents $R^6$, $C_1$-$C_{40}$-alkoxy, which is unsubstituted or substituted with one or more substituents $R^6$, $C_1$-$C_{40}$-thioalkoxy, which is unsubstituted or substituted with one or more substituents $R^6$, $C_2$-$C_{40}$-alkenyl, which is unsubstituted or substituted with one or more substituents $R^6$, $C_6$-$C_{60}$-aryl, which is unsubstituted or substituted with one or more substituents $R^6$, and $C_3$-$C_{57}$-heteroaryl, which is unsubstituted or substituted with one or more substituents $R^6$, and $C_3$-$C_{57}$-heteroaryl, which is unsubstituted or substituted with at least one selected from the group consisting of hydrogen, deuterium, $N(R^6)_2$, $OR^6$, $Si(R^6)_3$, $B(OR^6)_2$, $OSO_2R^6$, $CF_3$, CN, F, Br, I, $C_1$-$C_{40}$-alkyl, which is unsubstituted or substituted with one or more substituents $R^6$, $C_1$-$C_{40}$-alkoxy, which is unsubstituted or substituted with one or more substituents $R^6$, $C_1$-$C_{40}$-thioalkoxy, which is unsubstituted or substituted with one or more substituents $R^6$, $C_2$-$C_{40}$-alkenyl, which is unsubstituted or substituted with one or more substituents $R^6$, $C_2$-$C_{40}$-alkynyl, which is unsubstituted or substituted with one or more substituents $R^6$, and $C_6$-$C_{60}$-aryl, which is unsubstituted or substituted with one or more substituents $R^6$;

$R^5$ is at each occurrence independently from another selected from the group consisting of: hydrogen, deuterium, $N(R^6)_2$, $OR^6$, $Si(R^6)_3$, $B(OR^6)_2$, $OSO_2R^6$, $CF_3$, CN, F, Br, I, $C_1$-$C_{40}$-alkyl, which is unsubstituted or substituted with at least one selected from the group consisting of hydrogen, deuterium, OPh, $CF_3$, CN, F, $C_1$-$C_5$-alkoxy, which is unsubstituted or substituted by deuterium, CN, $CF_3$, or F, $C_1$-$C_5$-thioalkoxy, which is unsubstituted or substituted by deuterium, CN, $CF_3$, or F, $C_2$-$C_5$-alkenyl, which is unsubstituted or substituted by deuterium, CN, $CF_3$, or F, $C_2$-$C_5$-alkynyl, which is unsubstituted or substituted by deuterium, CN, $CF_3$, or F, $C_6$-$C_{18}$-aryl, which is unsubstituted or substituted by one or more $C_1$-$C_5$-alkyl substituents, $C_3$-$C_{17}$-heteroaryl, which is unsubstituted or substituted by one or more $C_1$-$C_5$-alkyl substituents, $N(C_6$-$C_{18}$-aryl$)_2$, $N(C_3$-$C_{17}$-heteroaryl$)_2$, and $N(C_3$-$C_{17}$-heteroaryl$)(C_6$-$C_{18}$-aryl), $C_1$-$C_{40}$-thioalkoxy, which is unsubstituted or substituted with at least one selected from the group consisting of hydrogen, deuterium, OPh, $CF_3$, CN, F, $C_1$-$C_{40}$-alkyl, which is unsubstituted or substituted by deuterium, CN, $CF_3$, or F, $C_1$-$C_5$-alkoxy, which is unsubstituted or substituted by deuterium, CN, $CF_3$, or F, $C_2$-$C_5$-alkenyl, which is unsubstituted or substituted by deuterium, CN, $CF_3$, or F, $C_2$-$C_5$-alkynyl, which is unsubstituted or substituted by deuterium, CN, $CF_3$, or F, $C_6$-$C_{18}$-aryl, which is unsubstituted or substituted by one or more $C_1$-$C_5$-alkyl substituents, $C_3$-$C_{17}$-heteroaryl, which is unsubstituted or substituted by one or more $C_1$-$C_5$-alkyl substituents, $N(C_6$-$C_{18}$-aryl$)_2$, $N(C_3$-$C_{17}$-heteroaryl$)_2$, and $N(C_3$-$C_{17}$-heteroaryl$)(C_6$-$C_{18}$-aryl), $C_2$-$C_{40}$-alkenyl, which is unsubstituted or substituted with at least one selected from the group consisting of hydrogen, deuterium, OPh, $CF_3$, CN, F, $C_1$-$C_{40}$-alkyl, which is unsubstituted or substituted by deuterium, CN, $CF_3$, or F, $C_1$-$C_5$-alkoxy, which is unsubstituted or substituted by deuterium, CN, $CF_3$, or F, $C_1$-$C_5$-thioalkoxy, which is unsubstituted or substituted by deuterium, CN, $CF_3$, or F, $C_2$-$C_5$-alkenyl, which is unsubstituted or substituted by deuterium, CN, $CF_3$, or F, $C_2$-$C_5$-alkynyl, which is unsubstituted or substituted by deuterium, CN, $CF_3$, or F, $C_6$-$C_{18}$-aryl, which is unsubstituted or substituted by one or more $C_1$-$C_5$-alkyl substituents, $C_3$-$C_{17}$-heteroaryl, which is unsubstituted or substituted by one or more $C_1$-$C_5$-alkyl substituents, $N(C_6$-$C_{18}$-aryl$)_2$, $N(C_3$-$C_{17}$-heteroaryl$)_2$, and $N(C_3$-$C_{17}$-heteroaryl$)(C_6$-$C_{18}$-aryl), $C_2$-$C_{40}$-alkynyl, which is unsubstituted or substituted with at least one selected from the group consisting of hydrogen, deuterium, OPh, $CF_3$, CN, F, $C_1$-$C_{40}$-alkyl, which is unsubstituted or substituted by deuterium, CN, $CF_3$, or F, $C_1$-$C_5$-alkoxy, which is unsubstituted or substituted by deuterium, CN, $CF_3$, or F, $C_1$-$C_5$-thioalkoxy, which is unsubstituted or substituted by deuterium, CN, $CF_3$, or F, $C_2$-$C_5$-alkenyl, which is unsubstituted or substituted by deuterium, CN, $CF_3$, or F, $C_2$-$C_5$-alkynyl, which is unsubstituted or substituted by deuterium, CN, $CF_3$, or F, $C_6$-$C_{18}$-aryl, which is unsubstituted or substituted by one or more $C_1$-$C_5$-alkyl substituents, $C_3$-$C_{17}$-heteroaryl, which is unsubstituted or substituted by one or more $C_1$-$C_5$-alkyl substituents, $N(C_6$-$C_{18}$-aryl$)_2$, $N(C_3$-$C_{17}$-heteroaryl$)_2$, and $N(C_3$-$C_{17}$-heteroaryl$)(C_6$-$C_{18}$-aryl), $C_6$-$C_{60}$-aryl, which is unsubstituted or substituted with at least one selected from the group consisting of hydrogen, deuterium, OPh, $CF_3$, CN, F, $C_1$-$C_{40}$-alkyl, which is unsubstituted or substituted by deuterium, CN, $CF_3$, or F, $C_1$-$C_5$-alkoxy, which is unsubstituted or substituted by deuterium, CN, $CF_3$, or F, $C_1$-$C_5$-thioalkoxy, which is unsubstituted or substituted by deuterium, CN, $CF_3$, or F, $C_2$-$C_5$-alkenyl, which is unsubstituted or substituted by deuterium, CN, $CF_3$, or F, $C_2$-$C_5$-alkynyl, which is unsubstituted or substituted by deuterium, CN, $CF_3$, or F, $C_3$-$C_{17}$-heteroaryl, which is unsubstituted or substituted by one or more $C_1$-$C_5$-alkyl substituents, $N(C_6$-$C_{18}$-aryl$)_2$, $N(C_3$-$C_{17}$-heteroaryl$)_2$, and $N(C_3$-$C_{17}$-heteroaryl)($C_6$-$C_{18}$-aryl); and $C_3$-$C_{57}$-heteroaryl, which is unsubstituted or substituted with at least one selected from the group consisting of hydrogen, deuterium, OPh, $CF_3$, CN, F, $C_1$-$C_{40}$-alkyl, which is unsubstituted or substituted by deuterium, CN, $CF_3$, or F, $C_1$-$C_5$-alkoxy, which is unsubstituted or substituted by deuterium, CN, $CF_3$, or F, $C_1$-$C_5$-thioalkoxy, which is unsubstituted or substituted by deuterium, CN, $CF_3$, or F, $C_2$-$C_5$-alkenyl, which is unsubstituted or substituted by deuterium, CN, $CF_3$, or F, $C_2$-$C_5$-alkynyl, which is unsubstituted or substituted by deuterium, CN, $CF_3$, or F, $C_6$-$C_{18}$-aryl, which is unsubstituted or substituted by one or more $C_1$-$C_5$-alkyl substituents, $N(C_6$-$C_{18}$-aryl$)_2$, $N(C_3$-$C_{17}$-heteroaryl$)_2$, and $N(C_3$-$C_{17}$-heteroaryl)($C_6$-$C_{18}$-aryl);

$R^6$ is at each occurrence independently from another selected from the group consisting of: hydrogen, deuterium, OPh, $CF_3$, CN, F, $C_1$-$C_5$-alkyl,
  wherein one or more hydrogen atoms are optionally, independently from each other substituted by deuterium, CN, $CF_3$, or F;

$C_1$-$C_5$-alkoxy,
  wherein one or more hydrogen atoms are optionally, independently from each other substituted by deuterium, CN, $CF_3$, or F;

$C_1$-$C_5$-thioalkoxy,
  wherein one or more hydrogen atoms are optionally, independently from each other substituted by deuterium, CN, $CF_3$, or F;

$C_2$-$C_5$-alkenyl,
  wherein one or more hydrogen atoms are optionally, independently from each other substituted by deuterium, CN, $CF_3$, or F;

$C_2$-$C_5$-alkynyl,
  wherein one or more hydrogen atoms are optionally, independently from each other substituted by deuterium, CN, $CF_3$, or F;

$C_6$-$C_{18}$-aryl,
  which is optionally substituted with one or more $C_1$-$C_5$-alkyl substituents;

$C_3$-$C_{17}$-heteroaryl,
  which is optionally substituted with one or more $C_1$-$C_5$-alkyl substituents;

$N(C_6$-$C_{18}$-aryl$)_2$;
$N(C_3$-$C_{17}$-heteroaryl$)_2$, and
$N(C_3$-$C_{17}$-heteroaryl)($C_6$-$C_{18}$-aryl);
wherein the substituents $R^5$ independently from each other optionally form a mono- or polycyclic, aliphatic, aromatic and/or benzo-fused ring system with one or more substituents $R^5$.

2. The organic molecule according to claim 1, wherein $R^I$, $R^{11}$, $R^{12}$, $R^{13}$, $R^{14}$, $R^{15}$ is at each occurrence independently from another selected from the group consisting of H, methyl and phenyl.

3. An organic molecule, comprising:
a first chemical moiety comprising a structure of Formula I,

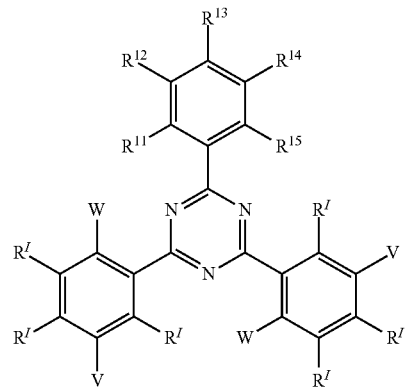

Formula I and
two second chemical moieties, each comprising a structure of Formula IIa',

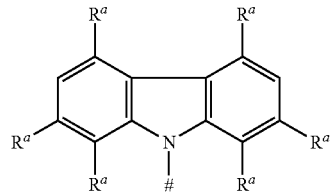

Formula IIa' wherein the first chemical moiety is linked to the second chemical moiety via a single bond;
wherein
represents the binding site of the first chemical moiety to the second chemical moiety;
W is the bond linking the first chemical moiety to one of the two second chemical moieties;
V is CN;
$R^I$ is at each occurrence independently from another selected from the group consisting of:
hydrogen, deuterium,
$C_1$-$C_5$-alkyl, wherein one or more hydrogen atoms are optionally substituted by deuterium;
$C_2$-$C_8$-alkenyl, wherein one or more hydrogen atoms are optionally substituted by deuterium;
$C_2$-$C_8$-alkynyl, wherein one or more hydrogen atoms are optionally substituted by deuterium; and
$C_6$-$C_{18}$-aryl;
$R^{11}$, $R^{12}$, $R^{13}$, $R^{14}$ and $R^{15}$ is at each occurrence independently from another selected from the group consisting of
hydrogen, deuterium, CN, $CF_3$,
$C_1$-$C_5$-alkyl, wherein one or more hydrogen atoms are optionally substituted by deuterium;
$C_2$-$C_8$-alkenyl, wherein one or more hydrogen atoms are optionally substituted by deuterium;

C$_2$-C$_8$-alkynyl, wherein one or more hydrogen atoms are optionally substituted by deuterium; and C$_6$-C$_{18}$-aryl;

R$^a$ is at each occurrence independently from another selected from the group consisting of: hydrogen, deuterium, B(OR$^5$)$_2$, OSO$_2$R$^5$, CF$_3$, Br, I, C$_1$-C$_{40}$-alkyl, which is substituted with at least one selected from the group consisting of deuterium, N(R$^6$)$_2$, OR$^6$, Si(R$^6$)$_3$, B(OR$^6$)$_2$, OSO$_2$R$^6$, CF$_3$, CN, F, Br, I, C$_1$-C$_{40}$-alkoxy, which is unsubstituted or substituted with one or more substituents R$^6$, C$_1$-C$_{40}$-thioalkoxy, which is unsubstituted or substituted with one or more substituents R$^6$, C$_2$-C$_{40}$-alkenyl, which is unsubstituted or substituted with one or more substituents R$^6$, C$_2$-C$_{40}$-alkynyl, which is unsubstituted or substituted with one or more substituents R$^6$, C$_6$-C$_{60}$-aryl, which is unsubstituted or substituted with one or more substituents R$^6$, and C$_3$-C$_{57}$-heteroaryl, which is unsubstituted or substituted with one or more substituents R$^6$ provided that R$^a$ is not a carbazolyl group, C$_1$-C$_{40}$-thioalkoxy, which is unsubstituted or substituted with at least one selected from the group consisting of hydrogen, deuterium, N(R$^6$)$_2$, OR$^6$, Si(R$^6$)$_3$, B(OR$^6$)$_2$, OSO$_2$R$^6$, CF$_3$, CN, F, Br, I, C$_1$-C$_{40}$-alkyl, which is unsubstituted or substituted with one or more substituents R$^6$, C$_1$-C$_{40}$-alkoxy, which is unsubstituted or substituted with one or more substituents R$^6$, C$_2$-C$_{40}$-alkenyl, which is unsubstituted or substituted with one or more substituents R$^6$, C$_2$-C$_{40}$-alkynyl, which is unsubstituted or substituted with one or more substituents R$^6$, C$_6$-C$_{60}$-aryl, which is unsubstituted or substituted with one or more substituents R$^6$, and C$_3$-C$_{57}$-heteroaryl, which is unsubstituted or substituted with one or more substituents R$^6$, and C$_2$-C$_{40}$-alkenyl, which is unsubstituted or substituted with at least one selected from the group consisting of hydrogen, deuterium, N(R$^6$)$_2$, OR$^6$, Si(R$^6$)$_3$, B(OR$^6$)$_2$, OSO$_2$R$^6$, CF$_3$, CN, F, Br, I, C$_1$-C$_{40}$-alkyl, which is unsubstituted or substituted with one or more substituents R$^6$, C$_1$-C$_{40}$-alkoxy, which is unsubstituted or substituted with one or more substituents R$^6$, C$_1$-C$_{40}$-thioalkoxy, which is unsubstituted or substituted with one or more substituents R$^6$, C$_2$-C$_{40}$-alkynyl, which is unsubstituted or substituted with one or more substituents R$^6$, C$_6$-C$_{60}$-aryl, which is unsubstituted or substituted with one or more substituents R$^6$, and C$_3$-C$_{57}$-heteroaryl, which is unsubstituted or substituted with one or more substituents R$^6$, C$_2$-C$_{40}$-alkynyl, which is unsubstituted or substituted with at least one selected from the group consisting of hydrogen, deuterium, N(R$^6$)$_2$, OR$^6$, Si(R$^6$)$_3$, B(OR$^6$)$_2$, OSO$_2$R$^6$, CF$_3$, CN, F, Br, I, C$_1$-C$_{40}$-alkyl, which is unsubstituted or substituted with one or more substituents R$^6$, C$_1$-C$_{40}$-alkoxy, which is unsubstituted or substituted with one or more substituents R$^6$, C$_1$-C$_{40}$-thioalkoxy, which is unsubstituted or substituted with one or more substituents R$^6$, C$_2$-C$_{40}$-alkenyl, which is unsubstituted or substituted with one or more substituents R$^6$, C$_6$-C$_{60}$-aryl, which is unsubstituted or substituted with one or more substituents R$^6$, and C$_3$-C$_{57}$-heteroaryl, which is unsubstituted or substituted with one or more substituents R$^6$, and C$_3$-C$_{57}$-heteroaryl, which is unsubstituted or substituted with at least one selected from the group consisting of hydrogen, deuterium, N(R$^6$)$_2$, OR$^6$, Si(R$^6$)$_3$, B(OR$^6$)$_2$, OSO$_2$R$^6$, CF$_3$, CN, F, Br, I, C$_1$-C$_{40}$-alkyl, which is unsubstituted or substituted with one or more substituents R$^6$, C$_1$-C$_{40}$-alkoxy, which is unsubstituted or substituted with one or more substituents R$^6$, C$_1$-C$_{40}$-thioalkoxy, which is unsubstituted or substituted with one or more substituents R$^6$, C$_2$-C$_{40}$-alkenyl, which is unsubstituted or substituted with one or more substituents R$^6$, C$_2$-C$_{40}$-alkynyl, which is unsubstituted or substituted with one or more substituents R$^6$, and C$_6$-C$_{60}$-aryl, which is unsubstituted or substituted with one or more substituents R$^6$;

wherein at least one of R$^a$ is not hydrogen;

R$^5$ is at each occurrence independently from another selected from the group consisting of: hydrogen, deuterium, N(R$^6$)$_2$, OR$^6$, Si(R$^6$)$_3$, B(OR$^6$)$_2$, OSO$_2$R$^6$, CF$_3$, CN, F, Br, I, C$_1$-C$_{40}$-alkyl, which is unsubstituted or substituted with at least one selected from the group consisting of hydrogen, deuterium, OPh, CF$_3$, CN, F, C$_1$-C$_5$-alkoxy, which is unsubstituted or substituted by deuterium, CN, CF$_3$, or F, C$_1$-C$_5$-thioalkoxy, which is unsubstituted or substituted by deuterium, CN, CF$_3$, or F, C$_2$-C$_5$-alkenyl, which is unsubstituted or substituted by deuterium, CN, CF$_3$, or F, C$_2$-C$_5$-alkynyl, which is unsubstituted or substituted by deuterium, CN, CF$_3$, or F, C$_6$-C$_{18}$-aryl, which is unsubstituted or substituted by one or more C$_1$-C$_5$-alkyl substituents, C$_3$-C$_{17}$-heteroaryl, which is unsubstituted or substituted by one or more C$_1$-C$_5$-alkyl substituents, N(C$_6$-C$_{18}$-aryl)$_2$, N(C$_3$-C$_{17}$-heteroaryl)$_2$, and N(C$_3$-C$_{17}$-heteroaryl)(C$_6$-C$_{18}$-aryl), and C$_1$-C$_{40}$-thioalkoxy, which is unsubstituted or substituted with at least one selected from the group consisting of hydrogen, deuterium, OPh, CF$_3$, CN, F, C$_1$-C$_{40}$-alkyl, which is unsubstituted or substituted by deuterium, CN, CF$_3$, or F, C$_1$-C$_5$-alkoxy, which is unsubstituted or substituted by deuterium, CN, CF$_3$, or F, C$_2$-C$_5$-alkenyl, which is unsubstituted or substituted by deuterium, CN, CF$_3$, or F, C$_2$-C$_5$-alkynyl, which is unsubstituted or substituted by deuterium, CN, CF$_3$, or F, C$_6$-C$_{18}$-aryl, which is unsubstituted or substituted by one or more C$_1$-C$_5$-alkyl substituents, C$_3$-C$_{17}$-heteroaryl, which is unsubstituted or substituted by one or more C$_1$-C$_5$-alkyl substituents, N(C$_6$-C$_{18}$-aryl)$_2$, N(C$_3$-C$_{17}$-heteroaryl)$_2$, and N(C$_3$-C$_{17}$-heteroaryl)(C$_6$-C$_{18}$-aryl), C$_2$-C$_{40}$-alkenyl, which is unsubstituted or substituted with at least one selected from the group consisting of hydrogen, deuterium, OPh, CF$_3$, CN, F, C$_1$-C$_{40}$-alkyl, which is unsubstituted or substituted by deuterium, CN, CF$_3$, or F, C$_1$-C$_5$-alkoxy, which is unsubstituted or substituted by deuterium, CN, CF$_3$, or F, C$_1$-C$_5$-thioalkoxy, which is unsubstituted or substituted by deuterium, CN, CF$_3$, or F, C$_2$-C$_5$-alkenyl, which is unsubstituted or substituted by deuterium, CN, CF$_3$, or F, C$_2$-C$_5$-alkynyl, which is unsubstituted or substituted by deuterium, CN, CF$_3$, or F, C$_6$-C$_{18}$-aryl, which is unsubstituted or substituted by one or more C$_1$-C$_5$-alkyl substituents, C$_3$-C$_{17}$-heteroaryl, which is unsubstituted or substituted by one or more C$_1$-C$_5$-alkyl substituents, N(C$_6$-C$_{18}$-aryl)$_2$, N(C$_3$-C$_{17}$-heteroaryl)$_2$, and N(C$_3$-C$_{17}$-heteroaryl)(C$_6$-C$_{18}$-aryl), C$_2$-C$_{40}$-alkynyl, which is unsubstituted or substituted with at least one selected from the group consisting of hydrogen, deuterium, OPh, CF$_3$, CN, F, C$_1$-C$_{40}$-alkyl, which is unsubstituted or substituted by deuterium, CN, CF$_3$, or F, C$_1$-C$_5$-alkoxy, which is unsubstituted or substituted by deuterium, CN, CF$_3$, or F, C$_1$-C$_5$-thioalkoxy, which is unsubstituted or substituted by deuterium, CN, CF$_3$, or F, C$_2$-C$_5$-alkenyl, which is unsubstituted or substituted by deuterium, CN, $CF_3$, or F, $C_2$-$C_5$-alkynyl, which is unsubstituted or substituted by deuterium, CN, $CF_3$, or F, $C_6$-$C_{18}$-aryl, which is unsubstituted or substituted by one or more $C_1$-$C_5$-alkyl substituents, $C_3$-$C_{17}$-heteroaryl, which is unsubstituted or substituted by one or more $C_1$-$C_5$-alkyl substituents, $N(C_6$-$C_{18}$-aryl$)_2$, $N(C_3$-$C_{17}$-heteroaryl$)_2$, and $N(C_3$-$C_{17}$-heteroaryl)($C_6$-$C_{18}$-aryl), $C_6$-$C_{60}$-aryl, which is unsubstituted or substituted with at least one selected from the group consisting of hydrogen, deuterium, OPh, $CF_3$, CN, F, $C_1$-$C_{40}$-alkyl, which is unsubstituted or substituted by deuterium, CN, $CF_3$, or F, $C_1$-$C_5$-alkoxy, which is unsubstituted or substituted by deuterium, CN, $CF_3$, or F, $C_1$-$C_5$-thioalkoxy, which is unsubstituted or substituted by deuterium, CN, $CF_3$, or F, $C_2$-$C_5$-alkenyl, which is unsubstituted or substituted by deuterium, CN, $CF_3$, or F, $C_2$-$C_5$-alkynyl, which is unsubstituted or substituted by deuterium, CN, $CF_3$, or F, $C_3$-$C_{17}$-heteroaryl, which is unsubstituted or substituted by one or more $C_1$-$C_5$-alkyl substituents, $N(C_6$-$C_{18}$-aryl$)_2$, $N(C_3$-$C_{17}$-heteroaryl$)_2$, and $N(C_3$-$C_{17}$-heteroaryl)($C_6$-$C_{18}$-aryl);

$C_3$-$C_{57}$-heteroaryl, which is unsubstituted or substituted with at least one selected from the group consisting of hydrogen, deuterium, OPh, $CF_3$, CN, F, $C_1$-$C_{40}$-alkyl, which is unsubstituted or substituted by deuterium, CN, $CF_3$, or F, $C_1$-$C_5$-alkoxy, which is unsubstituted or substituted by deuterium, CN, $CF_3$, or F, $C_1$-$C_5$-thioalkoxy, which is unsubstituted or substituted by deuterium, CN, $CF_3$, or F, $C_2$-$C_5$-alkenyl, which is unsubstituted or substituted by deuterium, CN, $CF_3$, or F, $C_2$-$C_5$-alkynyl, which is unsubstituted or substituted by deuterium, CN, $CF_3$, or F, $C_6$-$C_{18}$-aryl, which is unsubstituted or substituted by one or more $C_1$-$C_5$-alkyl substituents, $N(C_6$-$C_{18}$-aryl$)_2$, $N(C_3$-$C_{17}$-heteroaryl$)_2$, and $N(C_3$-$C_{17}$-heteroaryl)($C_6$-$C_{18}$-aryl);

$R^6$ is at each occurrence independently from another selected from the group consisting of: hydrogen, deuterium, OPh, $CF_3$, CN, F, $C_1$-$C_5$-alkyl,
  wherein one or more hydrogen atoms are optionally, independently from each other substituted by deuterium, CN, $CF_3$, or F;

$C_1$-$C_5$-alkoxy,
  wherein one or more hydrogen atoms are optionally, independently from each other substituted by deuterium, CN, $CF_3$, or F;

$C_1$-$C_5$-thioalkoxy,
  wherein one or more hydrogen atoms are optionally, independently from each other substituted by deuterium, CN, $CF_3$, or F;

$C_2$-$C_5$-alkenyl,
  wherein one or more hydrogen atoms are optionally, independently from each other substituted by deuterium, CN, $CF_3$, or F;

$C_2$-$C_5$-alkynyl,
  wherein one or more hydrogen atoms are optionally, independently from each other substituted by deuterium, CN, $CF_3$, or F;

$C_6$-$C_{18}$-aryl,
  which is optionally substituted with one or more $C_1$-$C_5$-alkyl substituents;

$C_3$-$C_{17}$-heteroaryl,
  which is optionally substituted with one or more $C_1$-$C_5$-alkyl substituents;

$N(C_6$-$C_{18}$-aryl$)_2$;
$N(C_3$-$C_{17}$-heteroaryl$)_2$, and
$N(C_3$-$C_{17}$-heteroaryl)($C_6$-$C_{18}$-aryl);

wherein the substituents $R^5$ independently from each other optionally form a mono- or polycyclic, aliphatic, aromatic and/or benzo-fused ring system with one or more substituents $R^5$ provided that substituents $R^a$ do not form a mono- or polycyclic, aliphatic, aromatic and/or benzo-fused ring system with one or more substituents $R^a$, wherein the organic molecule exhibits an emission maxima in the blue or sky-blue spectral range.

4. A method for preparing an organic molecule according to claim 1, wherein a $R^{11}$-$R^{15}$-substituted 2,4-dichloro-6-phenyltriazine is used as reactant.

5. A composition, comprising:
(a) at least one organic molecule according to claim 1, in the form of an emitter and/or a host, and
(b) one or more emitter and/or host materials, which differ from the organic molecule of claim 1, and
(c) optionally, one or more dyes and/or one or more solvents.

6. A composition, comprising:
(i) 1-50% by weight of one organic molecule according to claim 1;
(ii) 5-98% by weight of one host compound H;
(iii) 1-30% by weight of at least one further emitter molecule with a structure differing from the structure of the organic molecule according to claim 1; and
(iv) optionally, 0-94% by weight of at least one further host compound D with a structure differing from the structure of the organic molecules according to claim 1; and
(v) optionally, 0-94% by weight of a solvent.

7. An optoelectronic device, comprising an organic molecule according to claim 1.

8. An optoelectronic device, comprising:
a substrate,
an anode and
a cathode, wherein the anode or the cathode are disposed on the substrate, and
at least one light-emitting layer, which is arranged between the anode and the cathode and which comprises an organic molecule according to claim 1.

9. The optoelectronic device according to claim 8, in form of a device selected from the group consisting of: organic light-emitting diodes (OLEDS), light-emitting electrochemical cell, OLED-sensor, organic diode, organic solar cell, organic transistor, organic field-effect transistors, organic laser, and down-conversion element.

10. The optoelectronic device according to claim 7, wherein the organic molecule is one or more of a luminescent emitter, a host material, an electron transport material, a hole injection material and a hole blocking material.

11. A method for producing an optoelectronic device, wherein an organic molecule according to claim 1.

12. The method according to claim 11, comprising depositing the organic molecule by a vacuum evaporation method or from a solution.

13. An optoelectronic device, comprising an organic molecule according to claim 5.

14. An optoelectronic device comprising:
a substrate,
an anode and
a cathode, wherein the anode or the cathode are disposed on the substrate, and at least one light-emitting layer, which is arranged between the anode and the cathode and which comprises a composition according to claim 5.

15. A method for producing an optoelectronic device, wherein a composition according to claim 5 is deposited.

* * * * *